United States Patent
Ikenaka et al.

[11] Patent Number: 5,824,522
[45] Date of Patent: Oct. 20, 1998

[54] RECOMBINANT DECARBAMYLASES FOR PRODUCING D-α-AMINO ACIDS

[75] Inventors: Yasuhiro Ikenaka, Akashi; Hirokazu Nanba, Takasago; Masayuki Takano, Akashi; Kazuyoshi Yajima, Kobe; Yukio Yamada, Kakogawa; Satomi Takahashi, Kobe; Kazuma Okubo, Kakogawa; Kazuhiko Yamada, Akashi; Yoshiro Hiraishi, Himeji, all of Japan

[73] Assignee: Kanegafuchi Kagaku Kogyo Kabushiki Kaisha, Osaka-Fu, Japan

[21] Appl. No.: 294,871

[22] Filed: Aug. 22, 1994

Related U.S. Application Data

[63] Continuation-in-part of Ser. No. 971,758, Apr. 12, 1993, abandoned, Ser. No. 917,111, Aug. 7, 1992, Pat. No. 5,565,344, and Ser. No. 211,641, Apr. 11, 1994, abandoned.

[30] Foreign Application Priority Data

| Dec. 7, 1990 | [JP] | Japan | 2-400848 |
| Dec. 27, 1990 | [JP] | Japan | 2-407922 |
| Apr. 11, 1991 | [JP] | Japan | 3-078840 |
| Jun. 12, 1991 | [JP] | Japan | 3-140051 |
| Aug. 10, 1992 | [JP] | Japan | 4-212692 |
| Dec. 21, 1992 | [JP] | Japan | 4-340078 |

[51] Int. Cl.[6] .......................... C12P 13/04; C12N 11/00; C12N 9/14; C12N 1/20
[52] U.S. Cl. .................. 435/106; 435/69.1; 435/71.2; 435/172.3; 435/174; 435/176; 435/178; 435/180; 435/195; 435/227; 435/228; 435/252.3; 435/252.33; 435/252.34; 435/320.1; 435/849; 435/874
[58] Field of Search .................... 435/106, 195, 435/174, 176, 180, 181, 182, 172.3, 69.1, 71.2, 178, 227, 228, 252.3, 252.33, 252.34, 320.1, 849, 874

[56] References Cited

U.S. PATENT DOCUMENTS

| Re. 34,606 | 5/1994 | Estell et al. | 435/222 |
| 4,118,279 | 10/1978 | Determann et al. | 195/63 |
| 4,170,696 | 10/1979 | Hirohara et al. | 521/29 |
| 4,189,536 | 2/1980 | Green | 435/12 |
| 4,312,948 | 1/1982 | Olivieri et al. | 435/253 |
| 4,612,287 | 9/1986 | Coleman et al. | 435/172.5 |
| 4,666,840 | 5/1987 | Olivieri et al. | 435/106 |
| 5,108,914 | 4/1992 | Wagner et al. | 435/106 |

FOREIGN PATENT DOCUMENTS

| 515698 | 12/1992 | European Pat. Off. |
| 0 677 584 | 10/1995 | European Pat. Off. |
| 0 677 585 | 10/1995 | European Pat. Off. |
| 0018793 | 4/1982 | Japan . |
| 63-20520 | 8/1988 | Japan . |
| 1-320991 | 12/1989 | Japan . |
| 2042531 | 9/1980 | United Kingdom . |
| WO 94/00577 | 1/1994 | WIPO . |

*Primary Examiner*—David M. Naff
*Attorney, Agent, or Firm*—Foley & Lardner

[57] ABSTRACT

Decarbamylases are provided capable of producing D-α-amino acids by hydrolysis of N-carbamyl-D-α-amino acids. A source of the decarbamylases is recombinant microorganisms produced by gene manipulation methods. Decarbamylases having improved thermostability can be obtained in which amino acids at a thermostability-related site of a natural decarbamylase have been replaced with other amino acids by mutating a DNA fragment encoding the natural decarbamylase. Recombinant DNA is obtained from a vector DNA and a DNA fragment encoding a natural decarbamylase where the nucleic acid sequence encoding an amino acid at a thermostability-related site is replaced with a nucleic acid sequence encoding another amino acid. The recombinant DNA is used to produce transformants that produce thermostable decarbamylases. The decarbamylases may be immobilized in purified, partially-purified or crude form or in the form of decarbamylase-containing microbial cells on a support such as a polymer having ion exchange groups or covalent bonding groups. The presence of an antioxidant such as dithiothreitol results in an immobilized decarbamylase preparation that can be repeatedly used 30 times or more.

12 Claims, 11 Drawing Sheets

FIG. 5
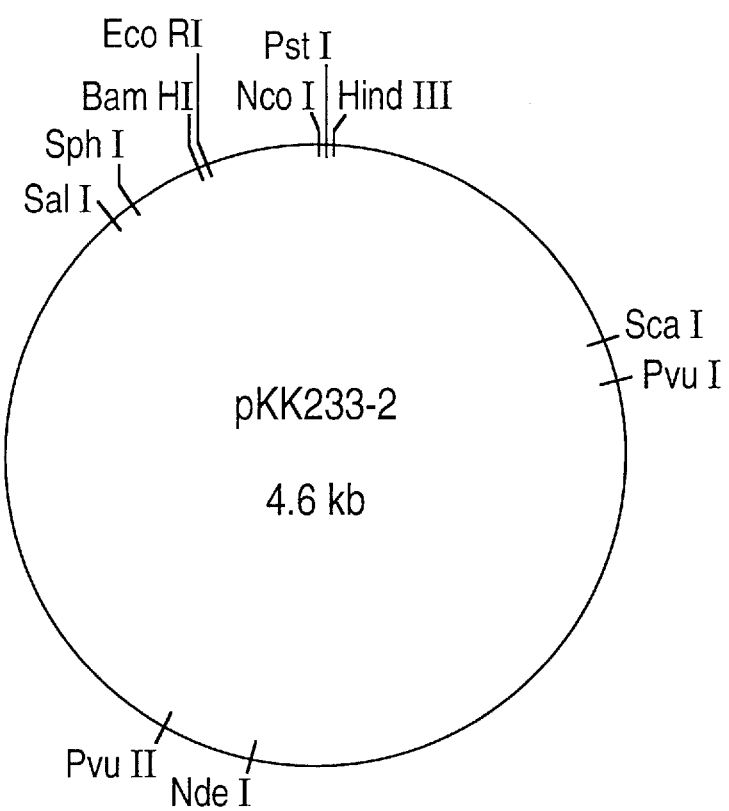
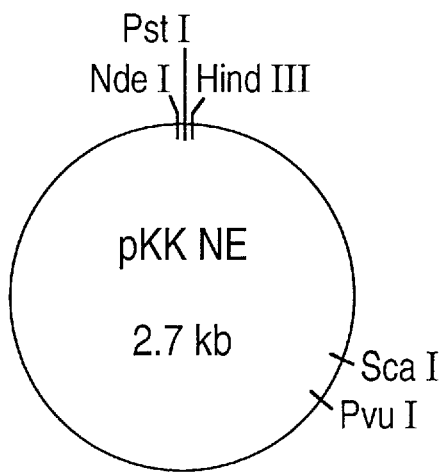

FIG. 6
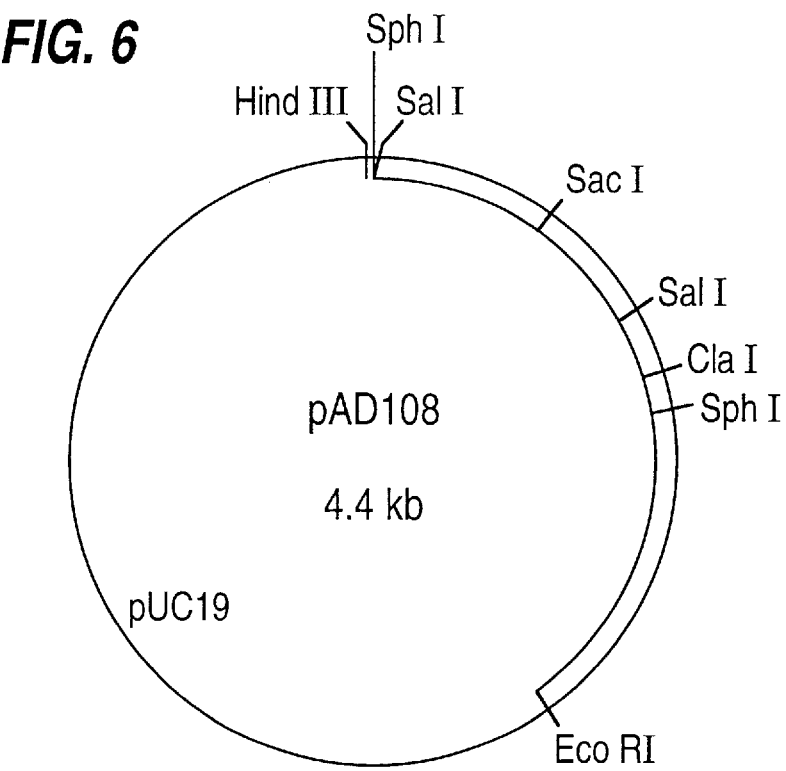
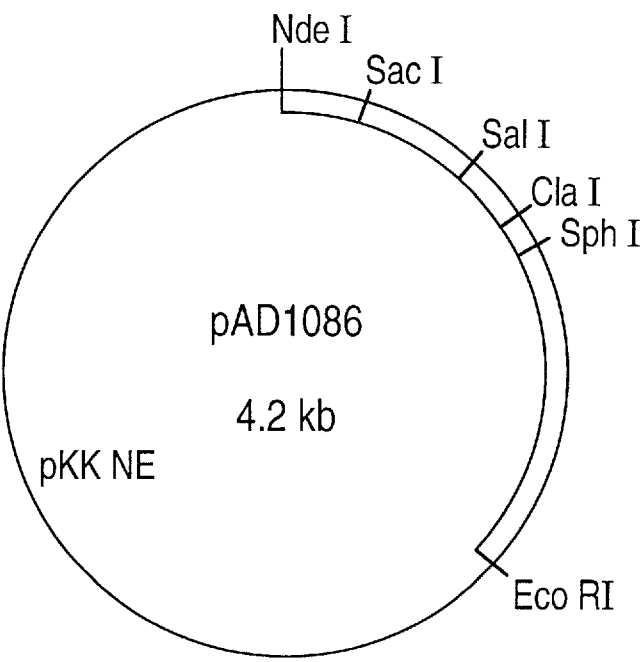

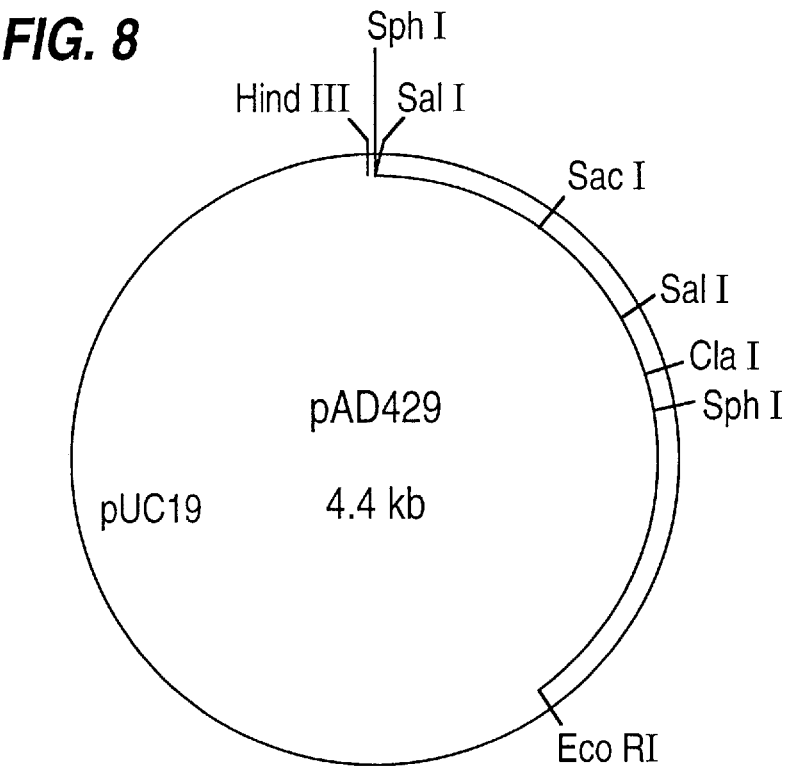
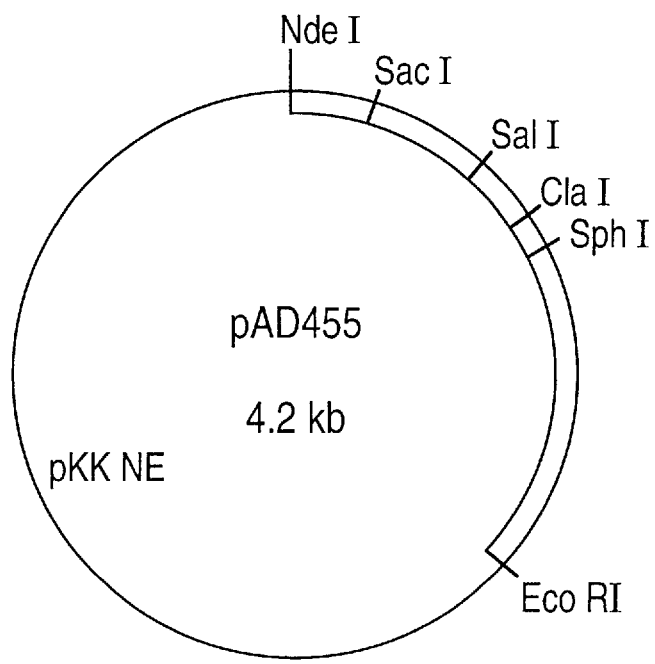
FIG. 8

RECOMBINANT DECARBAMYLASES FOR PRODUCING D-α-AMINO ACIDS

CROSS REFERENCE

This is a continuation-in-part application of application Ser. No. 07/971,758 filed Apr. 12, 1993, now abandoned; application Ser. No. 07/917,111 filed Aug. 7, 1992, now U.S. Pat. No. 5,565,344; and application Ser. No. 08/211,641 filed Apr. 11, 1994, now abandoned.

FIELD OF THE INVENTION

The present invention relates to an immobilized enzyme preparation having excellent repeated usability and a process for producing D-α-amino acids using the same. In particular, the immobilized enzyme preparation of the present invention serves for the production of D-α-amino acids Which are available as intermediate materials of antibiotics, such as D-(p-hydroxyphenyl)glycine used in the production of antibiotic amoxicillin.

PRIOR ART

It has already been known from JP-B 57-18793, JP-B 63-20520, JP-B 1-48758, etc., that there exist some enzymes (hereinafter referred to as "decarbamyases") capable of converting N-carbamyl-D-α-amino acid derivatives into D-α-amino acid.

With respect to the other numerous enzymes, it has already been known that the use of these enzymes or enzyme-producing cells in insolubilized or immobilized form makes it possible to prepare an enzyme reaction mixture having only a few impurities, which results in an easy recovery of the product, and also makes it possible to attain the repeated use of these enzymes, which is advantageous from the view point of cost recovery. Moreover, there has been obtained a good effect by the use in the production on an industrial scale.

In the case of a decarbamylase, however, the possibility of using this enzyme as an immobilized enzyme is generally suggested as a mode of use only in JP-B 63-20520, although there are some examples of using this enzyme in the form of whole cells, toluene-treated bacterial cells, acetone-treated powder of cells or cell-free extracts.

These examples of using a decarbamylase will cause a problem of how to maintain its enzyme activity, although it is exhibited. In particular, they fall behind in repeated use, and they cannot be repeatedly used on a commercial base.

OBJECTS OF THE INVENTION

The present invention is to obtain an immobilized enzyme preparation of decarbamylases with stability sufficient to withstand the repeated use and attempts to use it in the production on an industrial scale.

We have found that an antioxidant is effective for the stabilization of decarbamylases and that a repeatedly usable immobilized preparation of decarbamyases can be obtained by bringing the carbamylases into contact with a solid support in the presence thereof.

On the other hand, we have also found that the repeated usability of decarbamylases can be improve by increasing heat resistance of the enzymes and we have created decarbamylases having improved thermostability by replacing their amino acids at a thermostability-related site with other amino acids. Thus, the repeated usability is further improved by immoblizing such a thermostable decarbamylase together with an antioxidant. In addition, the repeated usability of an immobilized preparation can be further improved by immobilizing such a thermostable decarbamylase in the presence of an antioxidant and reacting the immobilized preparation with a N-carbamyl-D-α-amino acid.

BRIEF DESCRIPTION OF THE DRAWINGS

FIG. 5 shows restriction maps of plasmids pKK233–2and pKK NE.

FIG. 6 shows restriction maps of plasmids pAD108and pAD1086.

FIG. 8 shows restriction maps of plasmids pAD429and pAD455.

SUMMARY OF THE INVENTION

Figure 1:
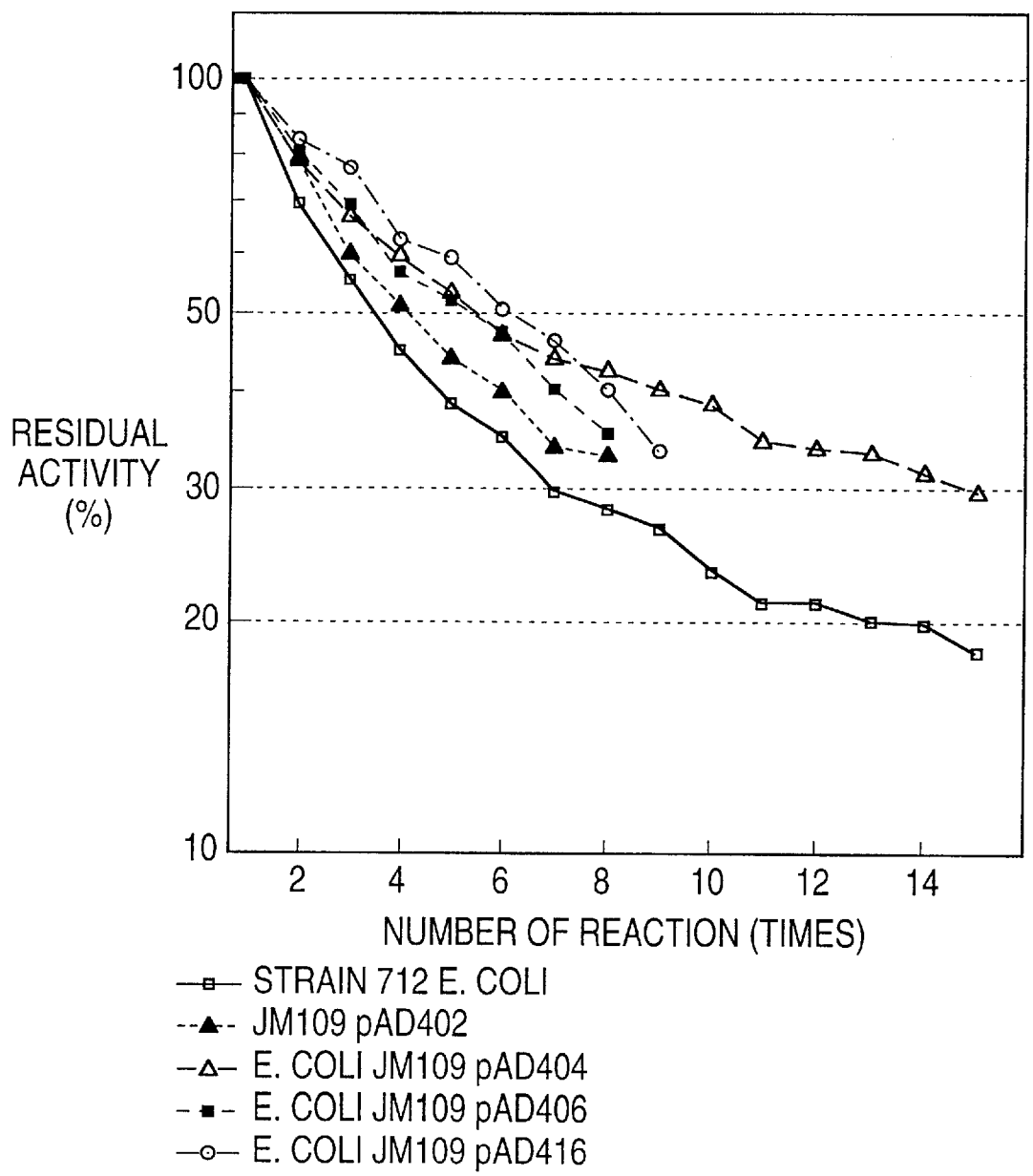
FIG. 1 is a graph illustrating the results of stability obtained by a repeated continuous test on the thermostability using a resin having immobilized thereon a decarbamylase improved in thermostability according to the present invention.

The present invention provides an enzyme capable of producing D-α-amino acids by hydrolysis of N-carbamyl-D-α-amino acids (decarbamylase); an immobilized enzyme preparation characterized in that it comprises an antioxidant and an appropriate support for immobilization; a process for producing the said immobilized enzyme preparation, characterized in that a decarbamylase is brought into contact with a support for immobilization in the presence of an antioxidant; and a process for producing D-α-amino acids, characterized in that the said immobilized enzyme preparation is allowed to act on N-carbamyl-D-α-amino acids.

DETAILED DESCRIPTION OF THE INVENTION

The decarbamylase used in the present invention may be any one of the enzymes having an action to remove an N-carbamyl group from N-carbamyl-D-α-ainino acids, and it may be either one having a stereospecific action on D-amino acids or one having an action on both of D- and L-amino acids. Usually, enzymes specific co D-amino acids are useful in many cases, though it depends upon a particular mode of use.

The enzyme source, such as animals, plants and microorganisms, is not particularly limited, with microorganisms being preferred for the production on an industrial scale. Examples of the microorganisms are naturally occurring microorganisms such as those belonging to the genus, e.g., Agrobacterium, Pseudomonas, Arthrobacter, Alkaligenes, Achromobacter, Moraxella, Paracoccus, Aerobacter, Aeromonas, Brevibacterium, Bacillus, Flavobacterium and Serratia, as disclosed in JP-B 57-18793, JP-B 63-20520 and JP-B 1-48758, and artificial microorganisms which, by gene manipulation methods, have been conferred with a given or enhanced ability to produce decarbamylases. Typical examples of these microorganisms are *Agrobacterium species* KNK 712 (FERM BP-1900) (SEQ ID No.: 1), *Pseudomonas sp.* KNK 003A (FERM BP-3181)(SEQ ID No.: C9, *Pseudomonas sp.* KNK505 (FERM BP-3182), *Escherichia coli* JM109 pAD108 (FERM BP-3184) and *Escherichia coli* JM109 pPD304 (FERM BP-3183).

Among these microorganisms, FERM BP-1900 and FERM BP-3184 produce an enzyme protein having the amino acid sequence consisting of Nos. 1 to 303 amino acids SEQ. ID No. 2 the accompanying Sequence Listings. FERM BP-3181and FERM BP-3183 produce an enzyme protein having the amino acid sequence consisting of Nos. 1 to 311 amino acids of SEQ ID No. 70 of the accompanying Sequence Listings. Any of them can be used as an enzyme source of the immobilized enzyme of the present invention.

In addition, decarbamylase in which amino acids at a thermostability-related site of natural decarbamylase have been replaced with other amino acids are disclosed in WO94/03613 (co-owned co-pending U.S. application Ser. filed Apr. 11, 1994U.S. application Ser. No. 08/211,641) and they are used for the immobilized preparation of the present invention. Decarbamylase having the amino acid sequences as shown in SEQ ID Nos. even-numbered SEQ IDs among SEQ ID Nos. 4 to 68 of the accompanying Sequence Listings correspond to such enzymes. These decarbamylases can be produced by mutating a DNA fragment encoding a natural decarbamylase as described in WO94/03613. A decarbamylase having improved thermostability is obtained by using the mutated DNA fragment, followed by analysis of its amino acid sequence to detect the amino acids at its thermostability-related site and recombination at the site with a base sequence for the amino acids. The resulting DNA is integrated in a suitable vector to obtain a recombinant DNA to obtain the desired following transformants.

*E. coli* JM109 pAD402 (FERM BP-3912), *E. coli* JM109pAD404 (FERM BP-3913), *E. coli* JM109 pAD406 (FERM BP-3914), *E. coli* JM1109 pAD416 (FERM BP-3915), *E. coli* JM109 pAD428, *E. coli* JM109 pAD429 (FERM BP-4035), *E. coli* JM109 pAD431, *E. coli* JM109 pAD434, *E. coli* JM109 pAD435, *E. coli* JM109 pAD439, *E. coli* JM109 pAD441, *E. coli* JM109 pAD445, *E. coli*JM109 pAD447, *E. coli* JM109 pAD448, *E. coli* JM109 pAD450, *E. coli* JM109 pAD421, *E. coli* JM109 pAD422, *E. coli* JM109pAD423, *E. coli* JM109 pAD424 (FERM BP-4034), *E. coli* JM109pAD425, *E. coli* JM109 pAD426, *E. coli* JM109 pAD427, *E. coli*JM109 pAD451, *E. coli* JM109 pAD452, *E. coli* JM109 pAD453, *E. coli* JM109 pAD461, *E. coli* JM109 pAD454, *E. coli* JM109pAD455 (FERM BP-4036), *E. coli* JM109 pAD456, *E. coli* JM109pAD468, *E. coli* JM109 pAD469, *E. coli* JM109 pAD470, and *E. coli* HB101 pNT4553 (FERM BP-4368).

The decarbamylases having improved thermostability can be obtained by using these transformants.

In the present invention, the said decarbamylase may be present in the immobilized enzyme preparation, as a purified enzyme, a partially-purified enzyme or a crude enzyme, or in some cases, as it is in the form of bacterial cells. As long as this enzyme is under such conditions that it can exhibit the decarbamyl activity, there is no need to be concerned with its form or the presence of contaminants.

As the antioxidant, dithiothreitol, 2-mercaptoethanol, L-cysteine hydrochloride, cysteamine hydrochloride, dithioerythritol, mixtures of dithiothreitol and dithioerythritol, or reduced-type glutathione can be used.

The support used for immobilization may vary depending upon the mode of decarbamylase immobilization; in cases where crude enzyme solutions such as cell-free extracts or partially-purified enzyme solutions obtained by fractionation with ammonium sulfate are subjected to immobilization, a polymer support having ion exchange groups or covalent-bonding groups can be used.

As the polymer support having ion exchange groups, an anionic exchange resin such as a series of Duolite (registered trade mark) A and Amberlite IRA (registered trade mark), having primary, secondary, tertiary and quaternary amines as exchange groups, or a polystylene resin having diethanol-type functional groups, such as Diaion EX, can be used.

As those having covalent-bonding groups, a substituted polymethacrylate polymer having aldehydes as bonding groups, or high-density almina covered with a polyethyleneimine/glutaraldehyde composite can be used.

Moreover, for immobilization of whole cells such as viable bacterial cells or dried bacterial cells, a polymer such as polyacrylamide, polyurethane and calcium alginate, or a porous material such as pumice and almina, can be used.

The immobilized enzyme preparation of the present invention can Le produced as follows.

First, a culture of microorganisms is prepared, and bacterial cells are collected therefrom. Then, a cell-free extract is prepared by ultrasonic disruption, mechanical disruption (e.g., homogenizer), enzyme treatment or the like. In this case, an antioxidant is allowed to exist at a concentration of 0.1 to 20 mM, usually about 5 mM.

For the partial purification of an enzyme from the cell-free extract, any means usually used by those skilled in the art is employed. For example, nucleic acids are precipitated by addition of protamine sulfate in a ⅕ to 1/10 quantity to the amount of proteins, and after heating at 50° to 60° C. for about 20 minutes, heat-unstable proteins are precipitated by cooling to 4° C., after which the nucleic acids and the heat-unstable protein s are removed by centrifugation. Further, fractionation with ammonium sulfate is conducted, if necessary, to obtain an enzyme solution to be brought into contact with a support. During this step, an antioxidant is used at a concentration of 0.1 to 20 mM, usually about 5 mM.

The support whose exchange groups have been activated with saline and then equilibrated in a buffer containing 0.1 to 20 mM, usually about 5 mM, of antioxidant is used. The support and the enzyme solution are brought into contact with each other in the presence of an antioxidant at a concentration of 0.1 to 20 mM, usually about 5 mM, followed by stirring at 40° to 300° C., preferably 25° C. After the amount of enzyme adsorbed reaches the desired amount (usually after 8 to 48 hours), the support is removed by filtration and treated with a cross-linking agent to attain the stability of enzymes by insolubilization. As the cross-linking agent, for example, those known in the art can be used, such as not greater than 1% (preferably 0.2%) glutaraldehyde. It is also preferred that an antioxidant is used at a concentration of 0.1 to 20 mM during this step. The cross-linked, immobilized enzyme preparation is washed with distilled water or a buffer (preferably containing an antioxidant), and stored under moist conditions in a sealed vessel at low temperatures (about 4° C.).

It is preferred that all procedures are conducted, if possible, in an atmosphere of an inert gas such as nitrogen. The amount of enzyme to be loaded, although it may vary depending upon the degree of purification of the enzyme, is usually in the range of 10 to 80 units/g of support (wherein one unit of decarbamylase refers to the amount of enzyme required to convert 1 µmol of N-carbamy-D-(p-hydroxyphenyl)glycine into D-(p-hydroxyphenyl)glycine within one minute). It is preferred that an antioxidant is included in the immobilized enzyme preparation at an amount of 5 to 10 mg/g of the preparation.

Then, the following will describe the process for producing D-α-amino acids from N-carbamyl-D-α-amino acids by use of an immobilized preparation of decarbamylases.

The reaction is conducted in the presence of an antioxidant, and it can be expressed by the reaction scheme:

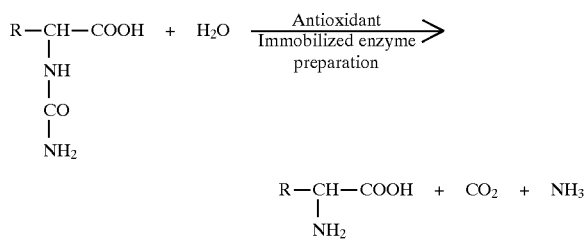

wherein R is $C_1$–$C_4$ alkyl optionally substituted with a group such as hydroxy, alkylthio, carboxy, amino or amide; $C_7$–$C_8$ aralkyl (e.g., benzyl, phenethyl) having an aromatic ring optionally substituted with a group such as hydroxy; or phenyl optionally substituted with hydroxy or halogen.

The amount of antioxidant is in the range of 0.1 to 20 mM, preferably 2.0 to 5.0 mM.

The concentration of N-carbamyl-D-α-amino acid as a reaction substrate is selected in the range of 1 to 25 w/v%, and preferably used at 3 to 15 w/v%. The amount of immobilized enzyme preparation used is selected in the range of 10 to 20 units per substrate, and preferably used at 15units/g of substrate, for those containing 10 to 80 units/g of support. The reaction is conducted, while controlling the pH in the range of pH 6.5 to 8.0, usually to pH 7.0. The temperature, although it may vary depending upon the kind of enzyme, is generally in the range of 30° to 60° C.; in particular, higher temperatures can be employed for heat resistant enzymes. The reaction is conducted by a column technique or by suspension in a reaction vessel; in the latter case, batch reaction is usually conducted for a period of reaction time in the range of about 6 to 48 hours per batch. The immobilized enzyme preparation of the present invention is quite stable; for example, it exhibited almost no decrease in its activity, even if used 15 times or more, and the repeated use at 30 times or more was made possible.

Preferably, the atmosphere in the reaction vessel is replaced by an inert gas with no oxygen remaining.

The present invention will be explained in more detail by way of the following Examples, which are only illustrative and not to be construed to limit the scope thereof.

EXAMPLE 1

A decarbamylase was produced by bacterial fermentation using the following procedures.

Medium ingredients:

| | |
|---|---|
| Sucrose | 300 g |
| Urea | 25.5 g |
| $KH_2PO_4$ | 30 g |
| $Na_2HPO_4$ | 30 g |
| $MgSO_4.7H_2O$ | 15 g |
| $MnCl_2.4H_2O$ | 150 mg |
| Yeast extract | 75 g |
| N-carbamyl-D-phenylglycine | 15 g |
| Anti-foaming agent | 15 g |

First, 15 liters of fermentation medium containing these ingredients were provided and adjusted to pH 7.0. This medium was placed in a fermentation bath of 18 liters in volume and sterilized by autoclaving at 121° C. for 30 minutes. Then, a solution of urea and a solution of N-carbamyl-D-pheniylglycine were independently subjected to the removal of bacteria through a millipore filter, and each of these solutions was added in 500-ml portions to the fermentation bath under sterile conditions.

The fermentation bath was inoculated with a seed culture of *Agrobacterium species* KNK712 (FERM BP-1900) grown at 30° C. for 30 hours in the same medium but containing no N-carbamyl-D-phenylglycine. During the fermentation, temperature was maintained at 33° C. and aeration was performed. The pH was controlled to 7.0 using sulfuric acid and sodium hydroxide solutions.

After the fermentation for 30 hours, the cells were collected by centrifugation. This cell precipitate was resuspended in 1.5 liters of 0.2 M phosphate buffer (pH 7.0), to which dithiothreitol was added to give a concentration of 5 mM, followed by ultrasonic treatment to discharge a decarbamylase into the solution.

The partial purification of enzymes was conducted as follows.

First, 76 ml of 3% aqueous protamine sulfate was gradually added with stirring, thereby precipitating nucleic acids. The enzyme solution was heat treated at 50° C. for 20minutes, followed by cooling to 4° C. After allowed to stand overnight at 4° C., the nucleic acids, as well as proteins, were precipitated, and the cell debris was removed by centrifugation. This preparation was assayed to determine its decarbamyl activity. To 1% N-carbamyl-D-phenylglycine/ 0.2 M phosphate buffer (pH 7.0), the enzyme preparation was added, and the reaction was allowed to proceed under the conditions at 40° C., after which the formation of D-phenylglycine was examined.

On the other hand, to this enzyme preparation, dithiothreitol was added to give a concentration of 5 mM, and the mixture was subjected to fractionation with ammonium sulfate. Ammonium sulfate was added in small portions with ice-cooling and stirring, thereby precipitating proteins. Active fractions at 15% to 35% of saturation with ammonium sulfate were collected and dissolved in 100 ml of phosphate buffer (pH 7.0), after which the same activity assay as above was conducted.

EXAMPLE 2

Each sample of three kinds of anion exchange resins purchased from commercial sources (Duolite, Amberlite and Diaion) was washed in 1M NaCl for 1 hour, and equilibrated overnight in 0.2 M phosphate buffer containing 5 mM of dithiothreitol. The equilibrated resins were filtered and stored until they were required for use. The partially-purified enzyme prepared as described in Example 1 was used for immobilization. The enzyme of Example 1 after the heat treatment and that after the fractionation with ammonium sulfate at the respective amounts of 5 ml and 10 ml per 1 g (wet weight) of resin (10 to 80 units/g of resin) were mixed with each of the resins at 25° C. for 24 hours, thereby allowing the enzymes to be adsorbed thereon. These enzyme-resin composites were filtered and treated with 1% glutaraldehyde at pH 7.0. After one hour, the resin samples were filtered once again, and washed three times with distilled water. Finally, the enzyme-resin composites were washed with 0.2 M phosphate buffer (pH 7.0), and stored as they remained wet in separate sealed vessels containing $N_2$ gas at 4° C.

Each of the enzyme-resin composites produced by this process was assayed to determine its activities as described in Example 1. The specific activities obtained from a series of commercially available ion exchange resins treated by this method are shown in Table 1.

TABLE 1

| Resin | Support | Functional group | Partially-purified enzyme | Specific activity |
|---|---|---|---|---|
| Duolite | Phenolform-aldehyde | Secondary amine | A | 10.0 |
|  |  |  | B | 80.2 |
| Amberlite | Polystyrene | Tertiary amine | A | 7.3 |
|  |  |  | B | 52.2 |
| Diaion | Polystyrene | Diethanol-type | A | 12.2 |
|  |  |  | B | 69.9 |

A. Enzyme after heat treatment
B. Enzyme after fractionation with ammonium sulfate
Specific activity: units/g of resin The resins Duolite and Amberlite are products available from Rohm & Haas, Co., USA, and the resin Diaion is a product available from Mitsubishi Chemical Industries, Ltd., Japan.

EXAMPLE 3

First, 100 ml of the partially-purified enzyme solution after the heat treatment (activity; 2.5 units/ml) prepared in Example 1 was added to 15 g of the resin Duolite A-568. This mixture was moderately stirred at 25° C. for 24hours, thereby allowing the enzyme decarbamylase to be adsorbed thereon. Then, the enzyme-resin composite was separated by filtration, and stirred in 0.2% glutaraldehyde solution (pH 7.0) containing 5 mM dithiothreitol for 1hour. The mixture was washed three times with distilled water, and finally washed with 0.2 M phosphate buffer (pH 7.0). This enzyme-resin was stored as it remained wet in a sealed vessel at 4° C. On the other hand, 30 ml of the enzyme solution after the fractionation with ammonium sulfate (activity: 9.3 units/ml) was added to 3 g of the resin Duolite A-568, and then treated in the same manner as described above. The immobilized enzyme solutions were assayed as described in Example 1, and their specific activities were 9.8 units/g and 70 units/g of resin, respectively.

To 100 ml of distilled water in a vessel equipped with a jacket, 10 9 of N-carbamyl-D-hydroxyphenylglycine and 8 mg of dithiothreitol (giving a concentration of 0.5 mM) were added, and the pH was adjusted to 7.0 by addition of 10 N NaOH with stirring. While blowing nitrogen gas thereinto, the temperature was controlled to 40° C. After this system was equilibrated, the reaction was conducted by addition of 147 units of the enzyme-resin composite (15 g). During this step, the mixture was adjusted to pH 7.0 by addition of a hydrochloric acid solution. After 24 hours, the yield of D-hydroxyphenyl-glycine was determined by HPLC to be 97%. It was found that the product produced by this process can be isolated by a conventional technique and it has high optical purity. On the other hand, for the enzyme-resin after the fractionation with ammonium sulfate, 15 g of N-carbamyl-D-hydroxyphenyl-glycine and 8 mg of dithiothreitol were added to 100 ml of distilled water in a vessel equipped with a jacket, followed by the same treatment, and the reaction was conducted in the same manner as described above, by addition of 210 units, i.e., 3 g of the enzyme-resin, resulting in a product having high optical purity.

The enzyme-resin used in this process was recycled 30 times by sucking out a solution of D-hydroxyphenyl-glycine after the completion of the reaction, while paying attention to maintain the enzyme in the atmosphere of nitrogen, and then newly setting, in place of that solution, a suspension of the substrate which had been equilibrated in advance. Throughout these cycles, the degree of conversion into D-hydroxyphenyl-glycine was 95% or more.

EXAMPLE 4

In the medium as described in Example 1, *Pseudomonas sp.* KNK003A (FERM BP-3181) was grown, and the cells harvested from 9 liters of fermentation broth by centrifugation. These cells were resuspended in 300 ml of 0.2 M Tris/HCl buffer (pH 7.0), and dithiothreitol was added to give a concentration of 5 mM, followed by ultrasonic treatment to discharge a decarbamylase into the solution. Then, 20 ml of 3% aqueous protamine sulfate was gradually added thereto with stirring, thereby precipitating nucleic acids. The enzyme solution was heat treated at 65° C. for 20 minutes, and then cooled to 4° C. After being stored overnight at 4° C., the nucleic acids, as well as proteins, were precipitated, and the cell debris was removed by centrifugation. Then, 100 ml of this partially-purified enzyme solution after the heat treatment (activity: 0.06units/ml) was added to 10 g of the resin Duolite A-568.This mixture was stirred at 25° C. for 24 hours, thereby allowing the decarbamylase to be adsorbed on the support. The enzyme-resin composite was removed by filtration, and cross-linked by moderately stirring in 0.2% glutaraldehyde solution (pH 7.0) containing 5 mM dithiothreitol for 1hour. The mixture was washed three times with distilled water, and finally washed with 0.2 M Tris/HCl buffer (pH 7.0). The specific activity thereof was 0.38 units/g of resin, and the activity in the case where N-carbamyl-D-alanine was used as a substrate was 4.2 units/g.

EXAMPLE 5

Using 5 g of the enzyme-resin produced by the process as described in Example 4, 2 g of N-carbamyl-D-alanine was hydrolyzed in 40 ml of distilled water containing 0.5 mM dithiothreitol. The hydrolysis was conducted at 45° C., at pH 6.7 to 7.0, for 24 hours, while blowing $N_2$ into this mixture to exclude oxygen therefrom. The yield of D-alanine after completion of the reaction was determined to be 96.5%.

Then, the hydrolysis of 5% N-carbamyl-D-alanine was conducted 35 times to give an average yield of 96.1%.

EXAMPLE 6

First, 1 g of the enzyme-resin produced by the process as described in Example 4 was charged into a column, and 2% N-carbamyl-D-(p-hydroxyphenyl)glycine solution containing 1 mM antioxidant was applied to the above column for continuous hydrolysis. As the antioxidant, dithiothreitol, L-cysteine hydrochloride or cysteamine hydrochloride was used, and the continuous reaction was conducted at an application speed of 1 ml/min., at 40° C. under $N_2$ sealing for 4 days. The results are shown in Table 2.

With the use of these antioxidants, the degree of enzyme deactivation for 4 days was suppressed to 30% to 35%, whereas the enzyme deactivation of 80% or more was found when no antioxidant was used.

TABLE 2

| Antioxidant | Ratio of remaining enzyme activity (%) after | | | |
|---|---|---|---|---|
| | 1 day | 2 days | 3 days | 4 days |
| Dithiothreitol | 80 | 70 | 68 | 65 |
| L-cysteine hydrochloride | 78 | 71 | 68 | 66 |
| Cysteamine hydrochloride | 78 | 75 | 73 | 68 |
| Dithioerythritol | 78 | 72 | 68 | — |
| No addition | 50 | 29 | 20 | 14 |

EXAMPLE 7

Preparation of immobilized D-N-carbamoyl-α-amino acid amidohydrolase

After harvesting 200 ml of a culture solution of *E. coli* JM109 pAD108, the solution was washed with 0.1 M KPB (pH 7.0) and suspended in 20 ml of 0.1 M KPB (pH 7.0), followed by ultrasonication of the bacterial cells. This suspension of disintegrated bacterial cells was subjected to centrifugation at 12000 rpm for 20 minutes to give the supernatant as a crude enzyme solution. To this crude enzyme solution, 2 g of an anion exchange resin Duolite A568equilibrated with 0.1 M KPB (pH 7.)) was added, and stirred at 4° C. for 15 hours to make the enzyme adsorbed thereon. To this solution, glutaraldehyde was added to have a final concentration of 0.1%, and stirred for 1 hour, followed by cross-linking treatment, after which the resin was collected by filtration and washed with 0.1 M KPB, resulting in 2 g of immobilized D-N-carbamoyl-α-amino acid amidohydrolase.

Conversion of D-N-carbamoyl-parahydroxyphenyl-glycine into D-parahydroxyphenylglicne with immobilized enzyme Two grams of the above-obtained immobilized D-Ncarbamoyl-α-amino acid amidohydrolase was added to 100 ml of 2% D-N-carbamoyl-parahydroxyphenylglycine and 0.1 M KPB (pH 7.0), and stirred at 40° C. for 20 hours, while maintaining the pH at 7.0 by addition of 1 N HCl, thereby causing reaction. After the reaction, the mixture was allowed to stand, and the reaction mixture was collected by suction. Conc. HCl was added to the reaction mixture to adjust to pH to 2.7, followed by adsorption on a cation exchange resin IR-120B ($H^+$type) and elution with 5% $NH_4OH$. Then, the eluate was desalinized with IRC-84 ($H^+$type) and decolorized with an AF resin. The decolorized solution was concentrated to allow crystallization, and the deposited crystals were recrystallized from water to give 1.5 g of D-paraphydroxyphenylglycine.

EXAMPLE 8

*E. coli* JM109 pAD108 (FERM BP-3184) was cultivated in 1 liter of 2YT medium (16 g/l of bactotrypton (Difco Co.), 10 g/l of bacto yesat extract (Difco Co.), and 5 g/l of NaCl) containing 50 μg/ml of ampicilline and 1 mm of IPTG. After harvesting the bacterial cells, they were washed with 0.1 M KPB (pH 7.0) and suspended in 100 ml of 0.1 M KPB (pH 7.) and 5 mM dithiothreitol (DTT) and sonicated to disintegrated bacterial cells. This suspension of disintegared bacterial cells was centrifuged at 12000 rpm for 20 minutes to give the supernatant as a crude enzyme solution. To 45 ml of the crude enzyme solution, 7.7 g of an anion exchange resin Duolite A-568 equilibrated with the same buffer as that used for disintegration of bacterial cells and the mixture was stirred at 4° C. for 20 hours to adsorb the enzyme thereon and washed three times with the same buffer. To the resin which adsorbed the enzyme were added 5-fold volume of 0.1% glutaraldehyde in 0.1 M KPB (pH 7.0) and stirred at 4° C. for 10 minutes to conduct cross-linking treatment. The resin was collected and washed three times with 0.1 M KPB (pH 7.0) and 10 mM DTT to obtain 7.7 g of immobilized D-N-carbamoyl-α-amino acid hydrolase.

EXAMPLE 9

TABLE 3

| Mutant | E. coli JM109 pAD402 | E. coli JM109 pAD404 | E. coli JM109 pAD406 | E. coli JM109 pAD416 | E. coli JM109 pAD108 |
|---|---|---|---|---|---|
| Activity (u/g resin) | 12.4 | 9.4 | 10.0 | 14.6 | 9.6 |

EXAMPLE 10

Repeated continuous reaction using immobilized decarbamylase

The mutant decarbamylase improved in thermostability was evaluated by the repeated continuous reaction using the immobilized enzyme-containing resin as obtained in Example 9.The reaction was effected (100 ml of reaction mixture) using 50 units of the immobilized decarbamylase and 3% carbamyl-D-HPG as the substrate at 40° C. with stirring under a stream of nitrogen gas while the pH was adjusted to 7.0. The sample was taken for the activity measurement after 10 and 60 minutes, and the reaction was continued for 23.5 hours in total. The reaction mixture was removed by suction, after which another fresh reaction mixture was charged and allowed to react in the same manner as described above; such an operation was repeated 15 times, and the change in the activity of the immobilized decarbamylase was examined. The results are shown in FIG. 1. All the decarbamylases improved in thermostability were found to have improved stabilities when used in the reaction as the immobilized enzyme-containing resin, as compared with those before the mutagenesis.

EXAMPLE 11

Figure 2:
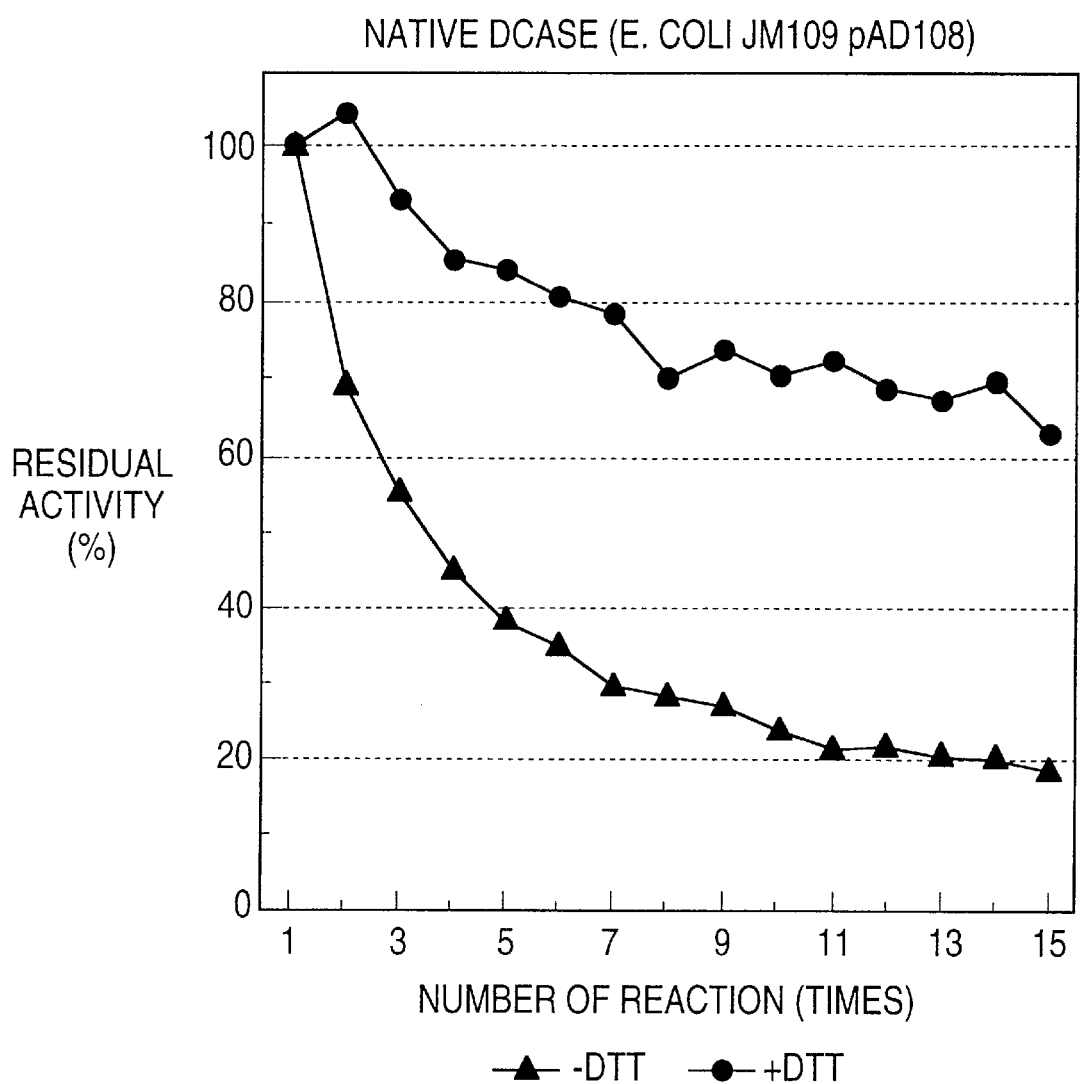
FIG. 2 is a graph illustrating the results of stability obtained by repeated continuous test on thermostability using a native decarbamylase with or without addition of dithiothreitol (DTT).
Figure 3:
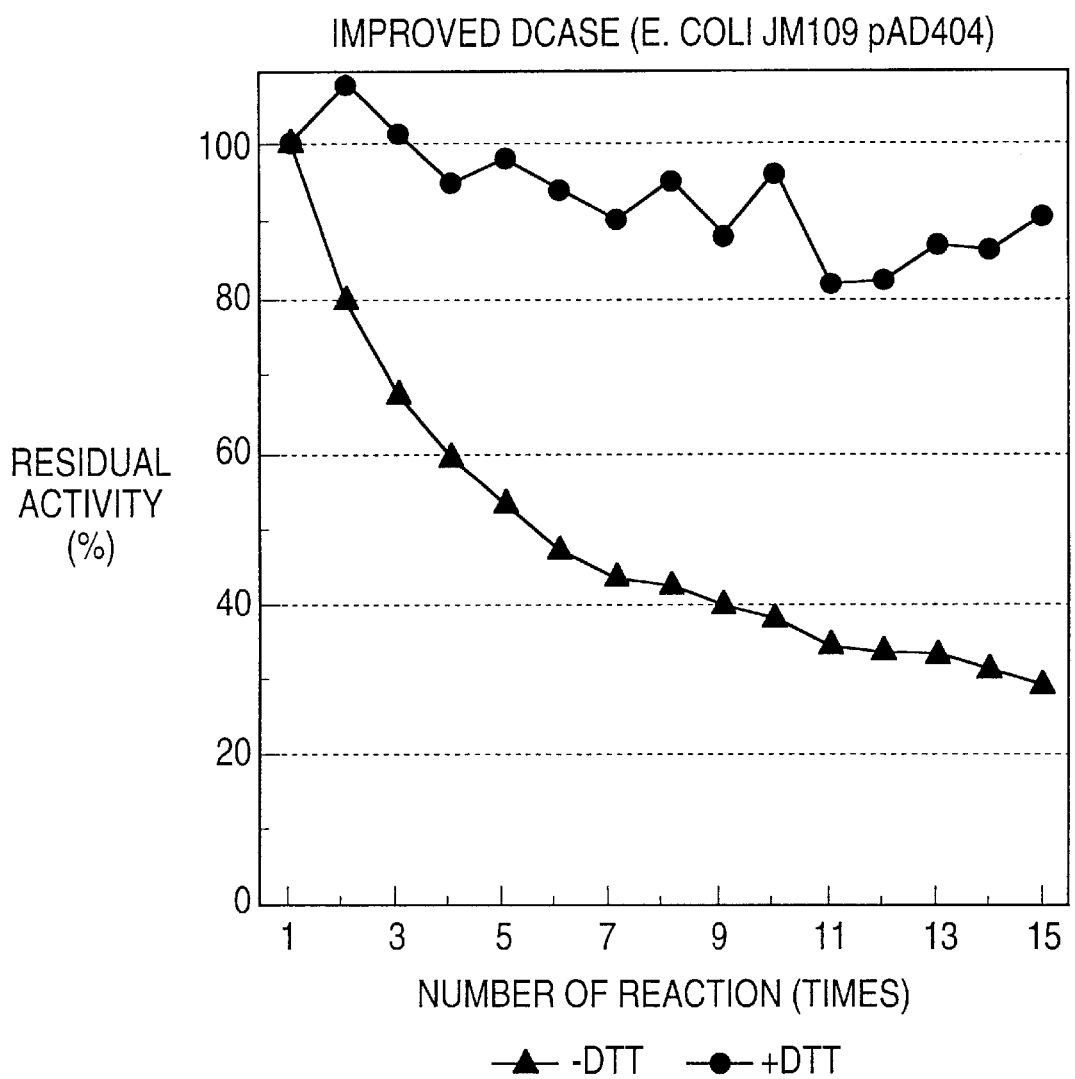
FIG. 3 is a graph illustrating the results of stability obtained by repeated continuous test on thermostability using a decarbamylase improved in thermostability according to the present invention with or without addition of DTT.
Figure 4:
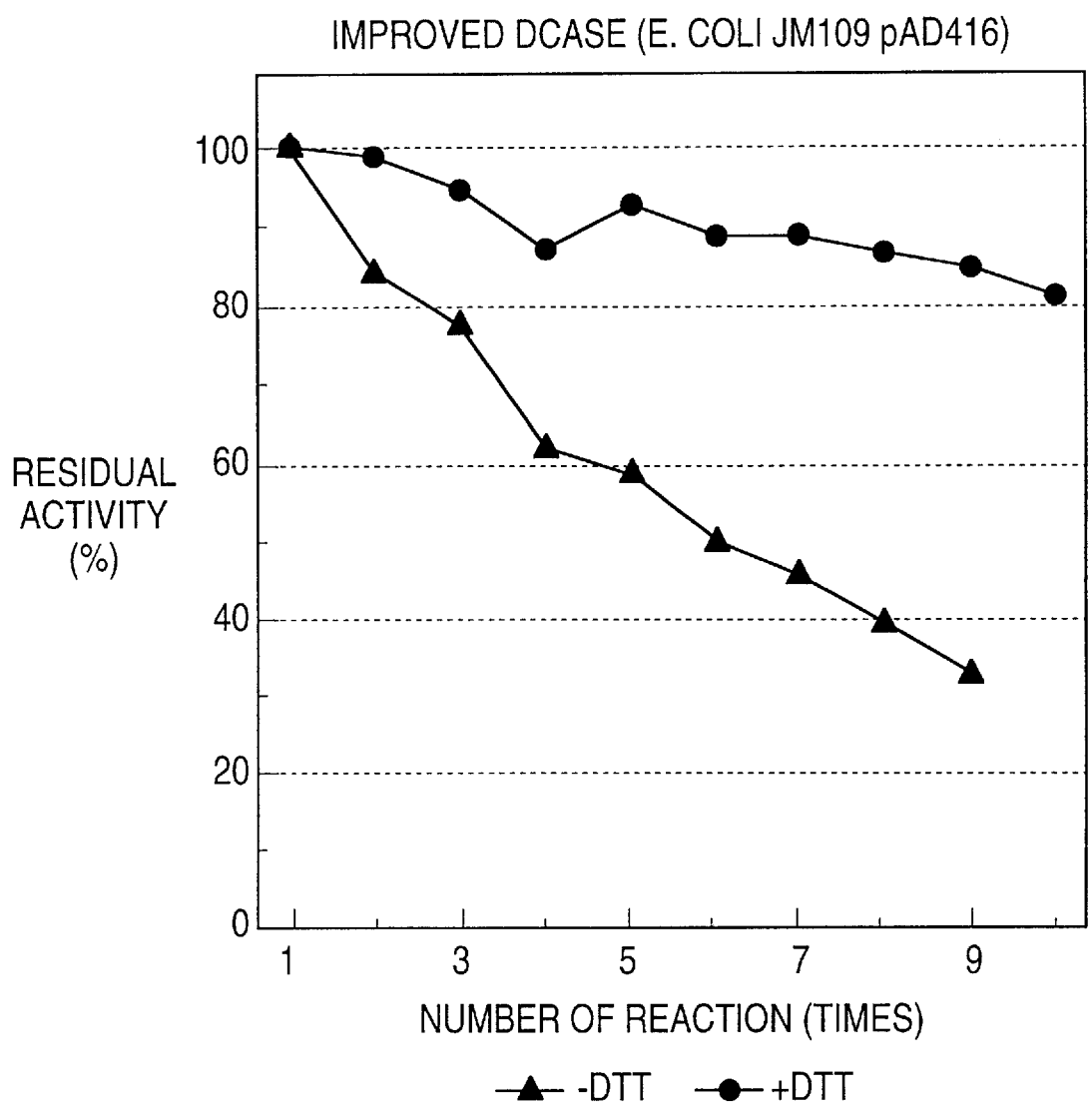
FIG. 4 is a graph illustrating the results of stability obtained by repeated continuous test on thermostability using another decarbamylase improved in thermostability according to the present invention with or without addition of DTT.

The repeated continuous reaction using the immobilized decarbamylase as described in Example 10 was carried out with addition of 5 mM DTT to the substrate. The results are shown FIGS. 2, 3 and 4. For comparison, the results of Example 10 are also shown in the drawings.

As seen from these drawings, when the antioxidant was added to the repeated continuous reaction, the decrease in activity of the immobilized enzyme was remarkably prevented.

EXAMPLE 12

Analysis of DNA base sequence for the gene of decarbamylase enzyme derived from *Agrobacterium species*KNK 712 (FERM BP-1900) and amino acid sequence.

The plasmid pAD 108 containing the gene of a decarbamylase derived from *Agrobacterium species*KNK 712 (FERM BP-1900) was digested with restriction endonucleases EcoRI and HindIII (manufactured by Takara Shuzo Co., Ltd.), and a 1.8 kb DNA fragment was separated for preparation by agarose gel electrophoresis. This fragment was digested with various restriction endonucleases, and ligated with T4-DNA ligase (manufactured by Takara Shuzo Co., Ltd.) to M13mp18 or M13mp19, after which *Escherichia coli* JM 109 was infected therewith, resulting in the formation of a plaque. This single plaque was inoculated into 1.5 ml of 2YT medium (16 g/l of bactotrypton (Difco Co.), 10 g/l of yeast extract (Difco Co.), and 5 g/l of NaCl) into which 1% JM 109 had been inoculated, and subjected to shaking culture at 37° C. for 5hours. After centrifugation, 200 μl of 20% polyethylene-glycol 6000 and 25 M NaCl solution were added to the supernatant, and allowed to stand at room temperature for 15minutes, after which phage particles were recovered as a precipitate by centrifugation. This was dissolved in 100 μl of TE solution [10 mM Tris HCl (pH 8.0), 1 mM EDTA], and extracted with 50 μl of phenol (saturated with TE solution), after which 10 μl of 3 M sodium acetate solution and 250 μl of ethanol were added and allowed to stand overnight at −20° C., followed by centrifugation. After drying, the precipitate was dissolved in 50 μl of TE solution. Then, 7 μl of this solution was used for reaction, electrophoresis, and autoradiography with the aid of a DNA sequence kit (manufactured by United States Biochemical Corp.) using SEQUENASE (registered trade mark) ver. 2, according to its instruction manual. From the results obtained, the DNA base sequence of decarbamylase gene for the strain KNK 712 was determined. Furthermore, the amino acid sequence (SEQ ID No.was determined based on the DNA base sequence (SEQ ID No.: 1 in the accompanying Sequence Listing).

EXAMPLE 13

Analysis of DNA base sequence for the gene of decarbamylase derived from *Pseudomonas sp.* KNK 003A (FERM BP-3181) and amino acid sequence The plasmid pPD 304 containing carbamylase gene derived from the strain KNK 003A was digested with restriction endonucleases BamHI and HindIII (manufactured by Takara Shuzo Co., Ltd.), and a 1.8 kb DNA fragment was separated for preparation by agarose gel electrophoresis. This fragment was digested with various restriction endonucleases, and ligated with T4-DNA ligase (Takara Shuzo Co., Ltd.) to M13mp18 or M13mp19, after which *Escherichia coli* JM 109 was infected therewith, resulting in the formation of a plaque. This single plaque was inoculated into 1.5 ml of 2YT medium (16 g/l bactotrypton (Difco Co.), 10 g/l yeast extract (Difco Co.), and 5 g/l NaCl) into which 1% JM 109 had been inoculated, and subjected to shaking culture at 37° C. for 5 hours. After centrifugation, 200μl of 20% polyethyleneglycol 6000. and 25 M NaCl solution were added to the supernatant, and allowed to stand at room temperature for 15 minutes, after which phage particles were recovered as a precipitate by centrifugation. This was dissolved in 100 μl of TE solution [10 mM Tris HCl (pH 8.0), 1 mM EDTA], and extracted with 50 μl of phenol (saturated with TE solution), after which 10 μl of 3M sodium acetate solution and 250 μl of ethanol were added thereto, and allowed to stand overnight at −20° C., followed by centrifugation. After drying, the precipitate was dissolved in 50 μl of TE solution. Then, 7 μl of this solution was used for reaction, electrophoresis, and autoradiography with the aid of a DNA sequence kit (manufactured by United States Biochemical Corp.) using SEQUENASE (registered trade mark) ver. 2, according to its instruction mannual. From the results obtained, the DNA base sequence of decarbamylase gene derived from the strain KNK 003A was determined. Furthermore, the amino acid sequence (SEQ ID No.: 70 was determined based on the DNA sequence (SEQ ID No. 69 in the accompanying Sequence Listing).

EXAMPLE 14

Purification of decarbamylase derived from *Agrobacterium species* KNK 712 (FERM BP-1900) *Agrobacterium species* KNK 712 (FERM BP-1900) was cultivated in the medium of Table 3 at 33° C. for 25 hours.

TABLE 3

| | |
|---|---|
| Glycerin | 25 g |
| Sucrose | 5 g |
| KH$_2$PO$_4$ | 5 g |
| Na$_2$HPO$_4$ | 5 g |
| MgSO$_4$.7H$_2$O | 1 g |
| MnCl$_2$.4H$_2$O | 10 mg |
| Yeast extract | 4 g |
| Urea | 2 g |
| D-N-carbamoyl-P-hydroxyphenylglycine | 1 g |

Water was added to the volume of 1 liter (pH 6.5).

Twenty one liters of this culture solution were harvested and the bacterial cells were ultrasonicated. after removal of the residue by centrifugation, nucleic acids were removed by protamine sulfate treatment (0.1 mg/mg of protein). The centrifuged supernatant was subjected to heat treatment at 50° C. for 20 minutes, and after removal of the precipitate, protein was precipitated by addition of ammonium sulfate, and a protein fraction having activity and being precipitated with 15% to 35% saturated ammonium sulfate was recovered. This fraction was dissolved and subjected to HPLC using DEAE-5pw column (manufactured by Toso Co., Ltd.), followed by elution with a concentration gradient of NaCl and recovered active fractions. At this stage, in comparison with a suspension of disintegrated bacterial cells, there was about 20-fold increase in the specific activity of decarbamylase. When this fraction was analyzed by SDS-polyacrylamide gel electrophoresis, this decarbamylase migrated near to the position corresponding to the molecular weight of about 35,000.

EXAMPLE 15

Purification of decarbamylase derived from *Pseudomonas sp.* KNK 003A (FERM BP-3181)

*Pseudomonas sp.* KNK 003A (FERM BP-3181) was cultivated in the medium of Table 4 at 45° C. for 3 days.

TABLE 4

| | |
|---|---|
| Glycerin | 10 g |
| Glucose | 5 g |
| KH$_2$PO$_4$ | 3.5 g |
| Na$_2$HPO$_4$ | 3.5 g |
| MgSO$_4$.7H$_2$O | 0.5 g |
| MnCl$_2$.4H$_2$O | 20 mg |
| FeSO$_4$ | 10 mg |
| CaCO$_3$ | 1 g |
| Meat extract | 2 g |
| Yeast extract | 2 g |
| Polypeptone | 2 g |
| D-N-carbamoylalanine | 1 g |

Water was added to the volume of 1 liter (pH 7.0).

Twenty six liters of this culture solution were harvested, and in the same manner as described in Example 13, the following operations were conducted: ultrasonication of the bacterial cells; removal of nucleic acids by protamine sulfate treatment; heat treatment (65° C., 20 min); fractionation by ammonium sulfate precipitation (separation of protein fractions having decarbamylase activity and being precipitated with 50% to 70% saturated ammonium sulfate); and HPLC using DEAE-5pw column. These active fractions was allowed to adsorb in a Biogel-HT (Bio-Rad Laboratories Co., Ltd.) column, and eluted with a concentration gradient of ammonium sulfate, after which the active fractions were concentrated and subjected to gel filtration using a Sephacryl S-300 (Pharmacia LKB Biotechnology Co., Ltd.) column.

Then, when isoelectric focusing (pH 4 to 6.5) was conducted, the above decarbamylase migrated near to the position at pH 5.7, and the gel of this band portion having activity was cut out, from which protein was extracted. At this stage, in comparison with a suspension of the disintegrated bacterial cells, there was about 100-fold increase in the specific activity of decarbamylase. When this sample was analyzed by SDS-polyacrylamide gel electrophoresis, decarbamylase migrated near to the position corresponding to the molecular weight of about 38,000. Moreover, when this sample was subjected to gel filtration using a Sephacryl S-200 column, it was eluted at the position corresponding to the molecular weight of about 67,000.

EXAMPLE 16

Mutagenesis of *Agrobacterium radiobacter* KNK712decarbamylase gene with hydroxylamine Plasmid pAD108 having a KNK712 decarbamylase gene was digested with restriction enzymes HindIII and EcoRI, which was mixed and ligated with the digest of an M13mp18 doublestranded DNA with HIndIII and EcoRI. This was transformed into *E. coli* JM109, which was mixed with 2 ml of H top agar medium (10 g/l bactotrypton, 8 g/l NaCl, 8 g/l bactoagar) containing 100 mM isopropyl-β-D-thiogalactopyranoside (IPTG) and 0.2% 5-bromo-4-chloro-3-indolyl-β-D-galactoside (X-Gal) added both in an amount of 40 μl, and then plated on an H agar plate (10 g/l bactotrypton, 8 g/l NaCl, 12 g/l bactoagar), followed by incubation at 37° C. and separation of a white plaque. This recombinant phage was cultured on 100 ml of 2YT medium (16 g/l bactotrypton, 10 g/l bactoyeast extract, 5 g/l NaCi), and a PEG-NaCl (20% polyethylene glycol 6000, 2.5 M NaCl) solution was added to the supernatant at a 1/5 volume, so that phage particles were precipitated and collected by centrifugation. These recombinant phage particles were treated in $NH_2OH$ having a final concentration of 0.25 M (pH 6.0) at 37° C. for 1 to 8 hours. The phage particles were precipitated with a PEG-NaCl solution, and then dissolved in sterilized water, with which *E. coli* JM109 was infected. The microorganism was cultured on 800 ml of 2YT medium, and a double-stranded DNA having some mutation was prepared by the alkaline-SDS method and CsCl ultracentrifugation method. This was digested with HindIII and EcoRI, and then incorporated into pUC19, which was transformed into *E. coli* JM109, and then plated on a 2YT agar plate containing 50 μg/ml ampicillin. Thus, about 15,000 *E. coli* transformants each having a mutant decarbamylase gene were obtained.

EXAMPLE 17

Mutagenesis of *Agrobacterium radiobacter* KNK712 decarbamylase gene with nitrous acid The recombinant phage. particles obtained by incorporating a KNK712 decarbamylase gene into M13mp18 as prepared in Example 1 were cultured on 800 ml of 2YT medium for preparation, and then subjected to phenol extraction and ethanol precipitation, which afforded a single-stranded phage DNA. This single-stranded DNA was treated with $NaNO_2$ having a final concentration of 0.9 M (pH 4.3) at 25° C. for 30 minutes, allowing a gene to cause some mutation. This was made into a double-stranded form by the use of Sequenase$^R$ ver. 2.0 (United States Biochemical) and AMV reverse transcriptase (Life Science). This was digested with restriction enzymes HindIII and EcoRI, and incorporated into pUC19, which was transformed into *E. coli* JM109 and then plated on a 2YT plate (containing ampicillin). Thus, about 7600 *E. coli* transformants each having a mutant decarbamylase gene were obtained.

EXAMPLE 18

Screening of decarbamylase-producing strain improved in thermostability

The colony of the *E. coli* transformants each having a mutant decarbamylase gene on the plate were replicated onto a filter paper (Toyo Roshi, 5C, φ83 mm), which was soaked with 1.5 ml of lytic solution (20 mM Tris·HCl (pH 7.5), 10 mM EDTA, 2 mg/ml lysozyme, 1% Triton X-100), followed by a reaction at 37° C. for 30 minutes, washing with water and drying. This filter paper was immersed in hot water at 65° C. for thermal treatment, and after drying, it was soaked with 1 ml of color development reaction solution (30 mM K-phosphate buffer (pH 7.4), 0.3% carbamyl-D-phenylglycine, 0.25% phenol, 10 mg/ml D-amino acid oxidase (Sigma), 2.36 μg/ml peroxidase (derived from horseradish, CALZYME Lab.), 0.1 mg/ml 4-aminoantipyrine), followed by a reaction at 37° C. for 30 minutes. Colonies corresponding to the red-color developed spots were separated, as the strain improved in thermostability, from the original plate.

From 27,000 mutants as prepared by mutagenesis with hydroxylamine in Example 16 and 7600 mutants as prepared by mutagenesis with nitrous acid in Example 17, twelve and seven mutants improved in thermostability were obtained, respectively.

EXAMPLE 19

Gene analysis of decarbamylase improved in thermostability

The gene analysis was conducted for the mutant decarbamylase improved in thermostability, to presume the mutation sites of the decarbamylase protein. The plasmid having a gene for the decarbamylase improved in thermostability was reacted in a programmable incubator (ASTEC, model PC-700) using Taq Dye Deoxy ™Terminator Cycle Sequencing Kit (Applied Biosystems), followed by removal of excess Dye Deoxy using Bio Spin 30 (BIO-RAD). This sample was subjected to electrophoresis and data analysis with DNA sequencer model 373A (Applied Biosystems). As the result, the mutation sites were found as shown in Table 5. In every cases, the thermostability was improved by one amino acid mutation.

TABLE 5

| Mutant | | Thermostable temperature(°C.) | DNA mutation | Amino acid mutation |
|---|---|---|---|---|
| (712) *Escherichia coli* | | 61.8 | none | none |
| JM109 | pAD402 | 67.3 | 401 C→T | 57 His→Tvr |
| JMJ09 | pAD404 | 68.0 | 840 C→T | 203 Pro→Leu |

TABLE 5-continued

| Mutant | | Thermostable temperature(°C.) | DNA mutation | Amino acid mutation |
|---|---|---|---|---|
| JMJ09 | pAD406 | 66.5 | 839 C→T | 203 Pro→Ser |
| JMJ09 | pAD416 | 71.4 | 939 T→C | 236 Val→Ala |

The thermostable temperature in Table 5 is the temperature at which 50% of the activity is lost in the heat treatment for 10 minutes.

EXAMPLE 20

Amino acid replacement at thermostability-related sites

Various amino acids were substituted for three sites found to be related to thermostability, i.e., histidine which is 57-amino acid, proline which is 203-amino acid, and valine which is 236-amino acid, to prepare various derivatives. The preparation of these derivatives was conducted by the use of a method utilizing polymerase chain reaction (PCR) (W. Ito, et al., Gene, 102, 67–70 (1991)). For each of the thermostability-related sites, various synthetic primers were prepared with a mixed solution of A, T, G and C by the DNA synthesizer model 391 (Applied Biosystems), said primers having about 10-base sequence portions which were the same as the complimentary gene sequences on both sides of the gene portion corresponding to the amino acid at each site and also having any combination of A, T, G and C in the 3-base portion corresponding to the amino acid to be replaced, so that any kind of amino acid was incorporated into this 3-base portion after the replacement. With the use of pAD108 as the template, and using this primer and M13RV primer (Takara Shuzo), the PCR was effected by the programmable incubator model PC700(ASTEC). A DNA fragment containing the full-length decarbamylase gene fragment (1785 bases) and short-length sequences on both sides and having a mutation at every HindIII restriction sites so as not to be cleaved was prepared by the PCR reaction using pAD108 and MUTF3 and M13M4primers (both, Takara Shuzo). These two kinds of PCR products were mixed together, and heated at 94° C. for 10 minutes, after which the mixture was gradually cooled for annealing, which afforded a combined form of these two kinds of DNAs. Using Taq DNA polymerase, single-stranded DNA portions were made into double-stranded forms. Using this DNA and M13M4and M13RV primers, the PCR reaction was effected, and the DNA produced was simultaneously digested with HindIII and EcoRI. The digest was ligated with pUC19 which had been digested in the same manner as described above, and transformed into E. coli. According to the method as described in Example 18, only the strains improved in thermostability were screened, and it was found that derivatives having a substitution of leucine for 57-histidine, derivatives having a substitution of asparagine, glutamic acid, threonine, alanine, isoleucine or histidine for 203-proline, and derivatives having a substitution of threonine or serine for 236-valine had improved thermostability, as shown in Tables 6 and 7.

TABLE 6

| Mutant | | Thermostable temperature (°C.) | DNA mutation | Amino acid mutation |
|---|---|---|---|---|
| (712) Escherichia coli | | 61.8 | none | none |
| JM109 | pAD434 | 67.5 | 402 A→T 403 T→A | 57 His→Leu |
| JM109 | pAD435 | 67.0 | 402 A→T | 57 His→Leu |
| JM109 | pAD431 | 67.0 | 839 C→A 840 C→A 841 T→C | 203 Pro→Asn |
| JM109 | pAD429 | 70.0 | 839 C→G 840 C→A 841 T→A | 203 Pro→Glu |
| JM109 | pAD445 | 67.5 | 839 C→A 841 T→C | 203 Pro→Thr |
| JM109 | pAD468 | 67.7 | 839 C→C | 203 Pro→Ala |
| JMI09 | pAD469 | 67.2 | 839 C→A 840 C→T | 203 Pro→Ile |
| JM109 | pAD470 | 65.2 | 840 C→A | 203 Pro→His |

TABLE 7

| Mutant | | Thermostable temperature (°C.) | DNA mutation | Amino acid mutation |
|---|---|---|---|---|
| (712) Escherichia Coli | | 61.8 | none | none |
| JM109 | pAD428 | 70.0 | 939 T→C 940 G→C | 236 Val→Ala |
| JM109 | pAD439 | 71.5 | 939 T→C 940 G→T | 236 Val→Ala |
| JM109 | pAD441 | 71.5 | 938 G→A 939 T→G 940 G→T | 236 Val→Ser |
| JM109 | pAD447 | 72.0 | 938 G→T 939 T→C 940 G→A | 236 Val→Ser |
| JM109 | pAD448 | 72.0 | 938 G→T 939 T→C | 236 Val→Ser |
| JM109 | pAD450 | 69.5 | 938 C→A 939 C→C | 236 Val→Thr |

EXAMPLE 21

Multiple mutation at thermostability-related site

Derivatives (multiple mutants) having a combination of two or three amino acid mutations which had been found to improve the thermostability, at three sites which had been found to be related to the thermostability, i.e., histidine which is 57-amino acid, proline which is 203-amino acid, and valine which is 236-amino acid, were prepared as follows.

The multiple mutants were prepared by replacing the mutation-free DNA fragments of a native gene with the restriction enzyme-digested DNA fragments each containing some mutation site of a mutant decarbamylase gene which had been improved in thermostability by a single amino acid substitution, as obtained in Example 18 or 20. First, because pAD108, pAD402 and other plasmids, which had the same restriction sites, each have two SalI and two SphI restriction sites for use in the replacement of the above-described DNA fragments, it is necessary to make these sites into a single restriction site. Therefore, as a new vector for gene incorporation, pKK NE was prepared, into which a decarbamylase gene fragment was incorporated, thereby constructing an expression vector to be used for the DNA fragment replacement.

Plasmid pKK NE was prepared as follows. Plasmid pKK233-2 (Pharmacia) shown in FIG. 5 was digested with EcoRI and NdeI, and subjected to agarose gel electrophoresis to separate a 2.7-kb DNA fragment, after which the cohesive end of the DNA fragment was changed to the blunt end with a DNA blunting kit (Takara Shuzo), followed by ligation and transformation into *E. coli* JM109.

Figure 7:
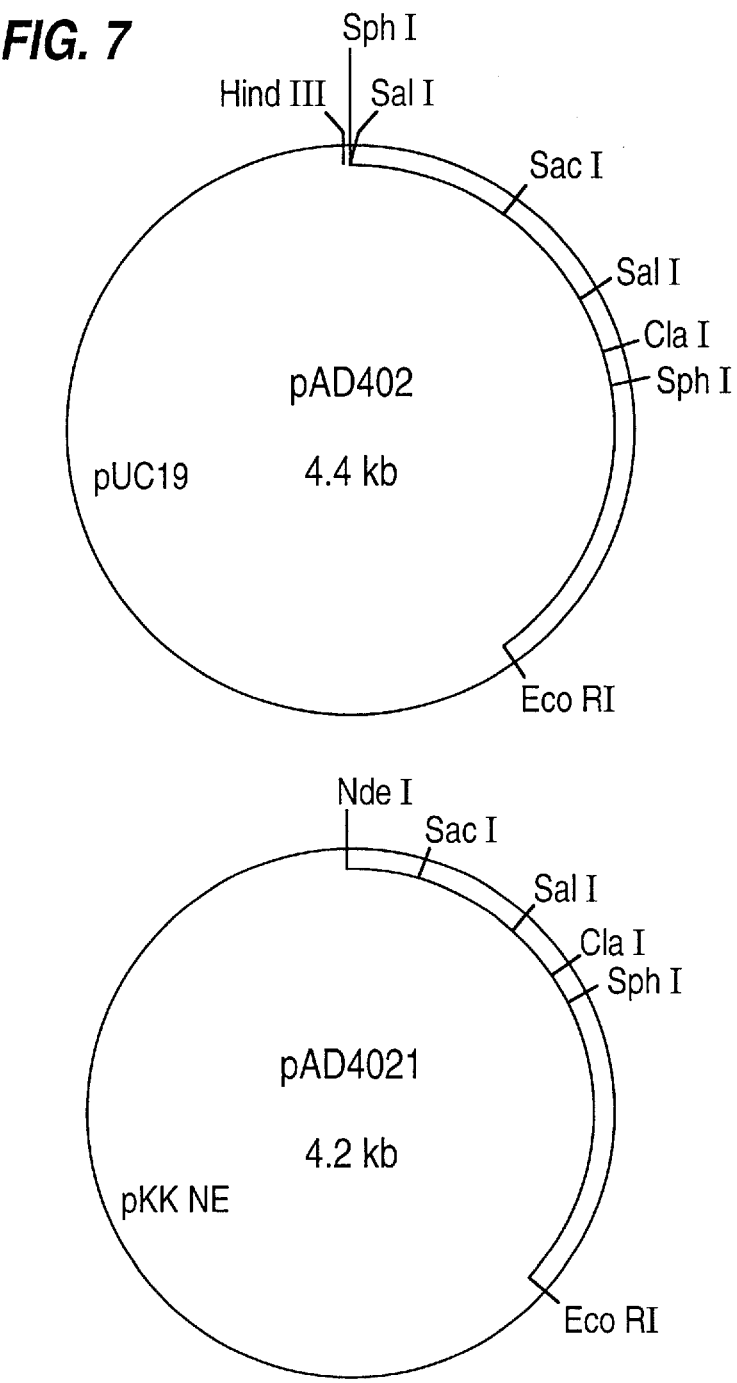
FIG. 7 shows restriction maps of plasmids pAD402and pAD4021.

The NcoI restriction site of the vector thus prepared was changed to the NdeI restriction site using the PCR method. The resulting plasmid was digested with HindIII, and the cohesive end thereof was changed to the blunt end, followed by ligation with pEcoRI linker (Takara Shuzo), which afforded pKK NE as shown in FIG. 5. Next, into the initiation codon portion of the decarbamylase gene in plasmid pAD108 or pAD402, the NdeI restriction site was generated by the PCR method. The resulting NdeI-EcoRI DNA fragment of 1.6 kb was then incorporated into pKK NE, which afforded expression vectors pAD1086 (derived from pAD108; shown in FIG. 6) and pAD4021 (derived from pAD402; shown in FIG. 7).

The 57-amino acid mutation is positioned on the NdeI-SacI DNA fragment of about 190 bp; the 203-amino acid mutation on the SalI-ClaI DNA fragment of about 170 bp (this DNA fragment is hereinafter referred to as fragment A); and the 236-amino acid mutation on the ClaI-SphI DNA fragment of about 75 bp (hereinafter referred to as fragment B). Therefore, fragment A of pAD4021 was removed, into which site the same fragment of pAD404 or pAD406 was incorporated, resulting in pAD421 or pAD422, respectively. Also, fragment B of pAD1086, pAD4021, pAD421 or pAD422 was replaced with the same fragment of pAD416, resulting in pAD4161, pAD423, pAD426 or pAD427, respectively. Further, fragment A of pAD4161 was replaced with the same fragment of pAD404, pAD406 or pAD429, resulting in pAD424, pAD425 or pAD461, respectively; fragment A of pAD402 or pAD423 was replaced with the same fragment of pAD429, resulting in pAD451 or pAD455 (shown in FIG. 8), respectively; fragment B of pAD402, pAD429 (shown in FIG. 8), pAD451 or pAD421 was replaced with the same fragment of pAD447, resulting in pAD452, pAD453, pAD454 or pAD456, respectively.

The expression vectors prepared in the above-described manner were separately transformed into *E. coli* JM109, from which the extracts of disrupted bacterial cells were prepared and examined for the thermostability.

As shown in Tables 8 and 9, for the multiple mutants, it was found that the thermostability was additively improved according to the degree of an improvement in the thermostability attained by a single mutation. For the decarbamylase produced by *E. coli* JM109 pAD455 (FERM PB-4036) having highest thermostability, it was found that the thermostability was improved even by about 19° C., as compared with the decarbamylase before the mutagenesis.

TABLE 8

| Mutant | | Amino acid mutation | Thermostable temperature (°C.) |
|---|---|---|---|
| (712) *Escherichia coli* | | none | 61.8 |
| JM109 | pAD421 | 57 His→Tyr 203 Pro→Leu | 71.5 |
| JM109 | pAD422 | 57 His→Tyr 203 Pro→Ser | 70.0 |
| JM109 | pAD423 | 57 His→Tyr 236 Val→Ala | 75.4 |

TABLE 8-continued

| Mutant | | Amino acid mutation | Thermostable temperature (°C.) |
|---|---|---|---|
| JM109 | pAD424 | 203 Pro→Leu 236 Val→Ala | 77.5 |
| JM109 | pAD425 | 203 Pro→Ser 236 Val→Ala | 75.9 |
| JM109 | pAD426 | 57 His→Tyr 203 Pro→Leu 236 Val→Ala | 78.8 |
| JM109 | pAD427 | 57 His→Tyr 203 Pro→Ser 236 Val→Ala | 77.8 |

TABLE 9

| Mutant | | Amino acid mutation | Thermostable temperature (°C.) |
|---|---|---|---|
| (712) *Escherichia coli* | | none | 61.8 |
| JM109 | pAD451 | 57 His→Tyr 203 Pro→Glu | 74.0 |
| JM109 | pAD452 | 57 His→Tyr 236 Val→Ser | 75.3 |
| JM109 | pAD453 | 203 Pro→Glu 236 Val→Ser | 76.0 |
| JM109 | pAD461 | 203 Pro→Glu 236 Val→Ala | 79.0 |
| JM109 | pAD454 | 57 His→Tyr 203 Pro→Glu 236 Val→Ser | 80.4 |
| JM109 | pAD455 | 57 His→Tyr 203 Pro→Glu 236 Val→Ala | 80.8 |
| JM109 | pAD456 | 57 His→Tyr 203 Pro→Leu 236 Val→Ser | 78.5 |

EXAMPLE 22

Figure 9:
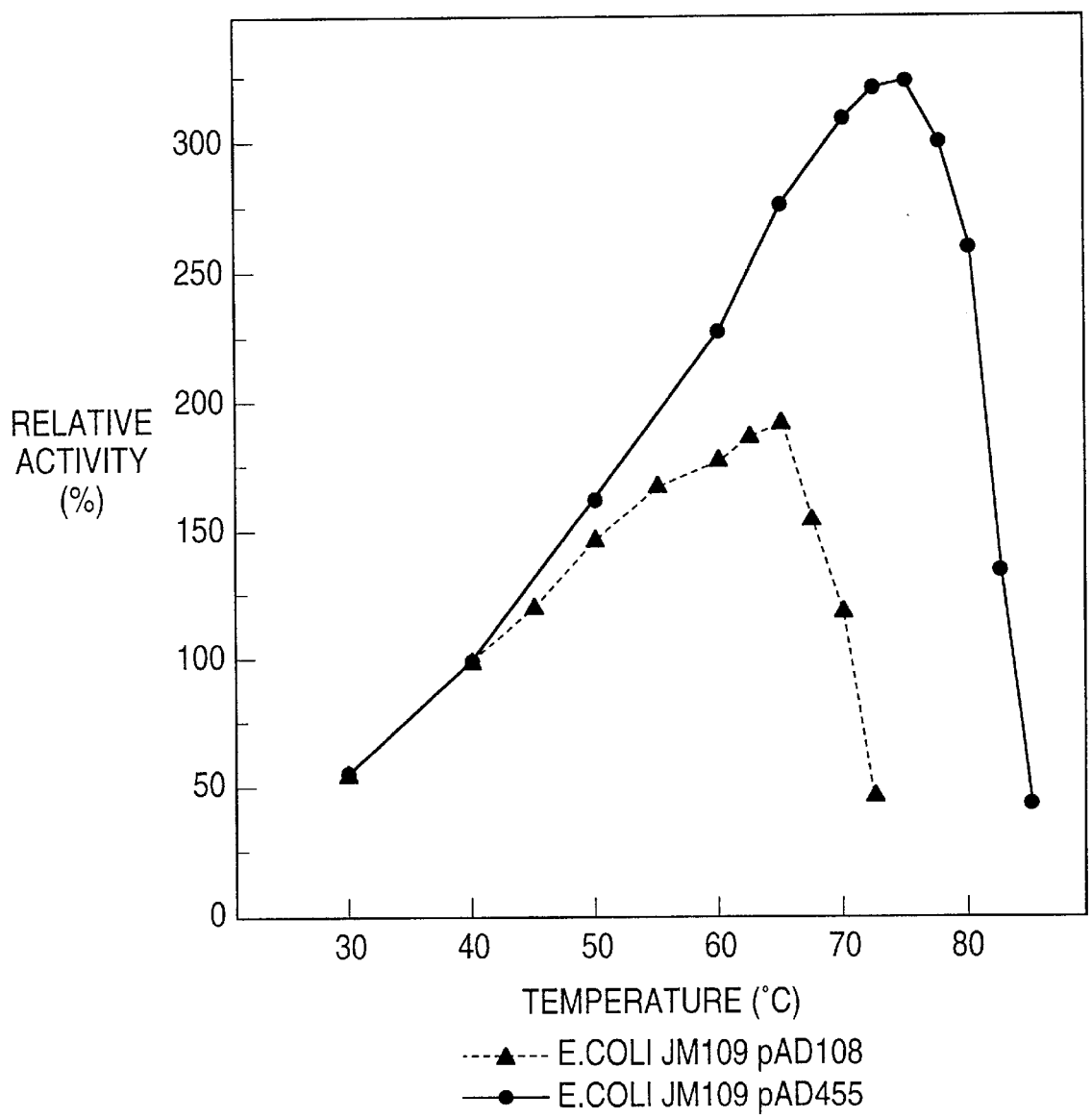
FIG. 9 is a graph illustrating the relationship between the reaction temperature of decarbamylases and their activity.

Reaction temperature characteristics of decarbamylase improved in thermostability A shaken culture containing a thermostability-improved decarbamylase-producing strain, *E coli* JM109 pAD108 (FERM BP-3184) or *E. coli* JM109 pAD455 (FERM BP-4036), was prepared in 10 ml of 2YT medium and incubated overnight. After harvested, the bacterial cells were washed with 0.1 M K-phosphate buffer (pH 7.0), and then suspended in 1 ml of the same buffer, after which the suspension was disrupted with an ultrasonic disrupting apparatus (Tomy Seiko, model UR-20P) and the residue was removed by centrifugation to yield a clude enzyme solution. This crude enzyme solution was 10-fold diluted with a solution obtained by the addition of 5 mM dithiothreitol to the same buffer. Several 1 ml substrate solutions (1% carbamyl-D-p-hydroxyphenylglycine, 0.1% K-phosphate buffer (pH 6.5)) were kept at various temperatures of 30° C. to 85° C. for 3 minutes, respectively, to which 100 µl of the diluted crude enzyme solution (or when the temperature was in the range of 50° C. to 80° C. for higher thermostability (the temperature was in the range of 50° C. to 65° C. for the crude enzyme solution of *E. coli* JM109 pAD108), 100 µl of the enzyme solution which had been further 2- to 3-fold diluted) was added, followed by a reaction at the respective temperatures for 20 minutes. Then, the reaction was allowed to stop by adding 250 µl of 20% trichloroacetic acid solution, followed by centrifugation, after which the supernatant was analyzed by high performance liquid chromatography (Nakalai tesque, Cosmosil 5C18-AR column). Taking the activity at 40° C. as 100%, the relative activity at each temperature is shown in FIG. 9. As can be seen from FIG. 9, the enzyme produced by *E. coli* JM109 pAD455 exhibits the highest activity at a temperature around 75° C. and has extremely improved stability, indicating that it was improved into an enzyme capable of acting at higher temperatures, as compared with the enzyme produced by *E. coli* JM109 pAD108.

EXAMPLE 23 pH stability of decarbamylase improved in thermostability

Figure 10:
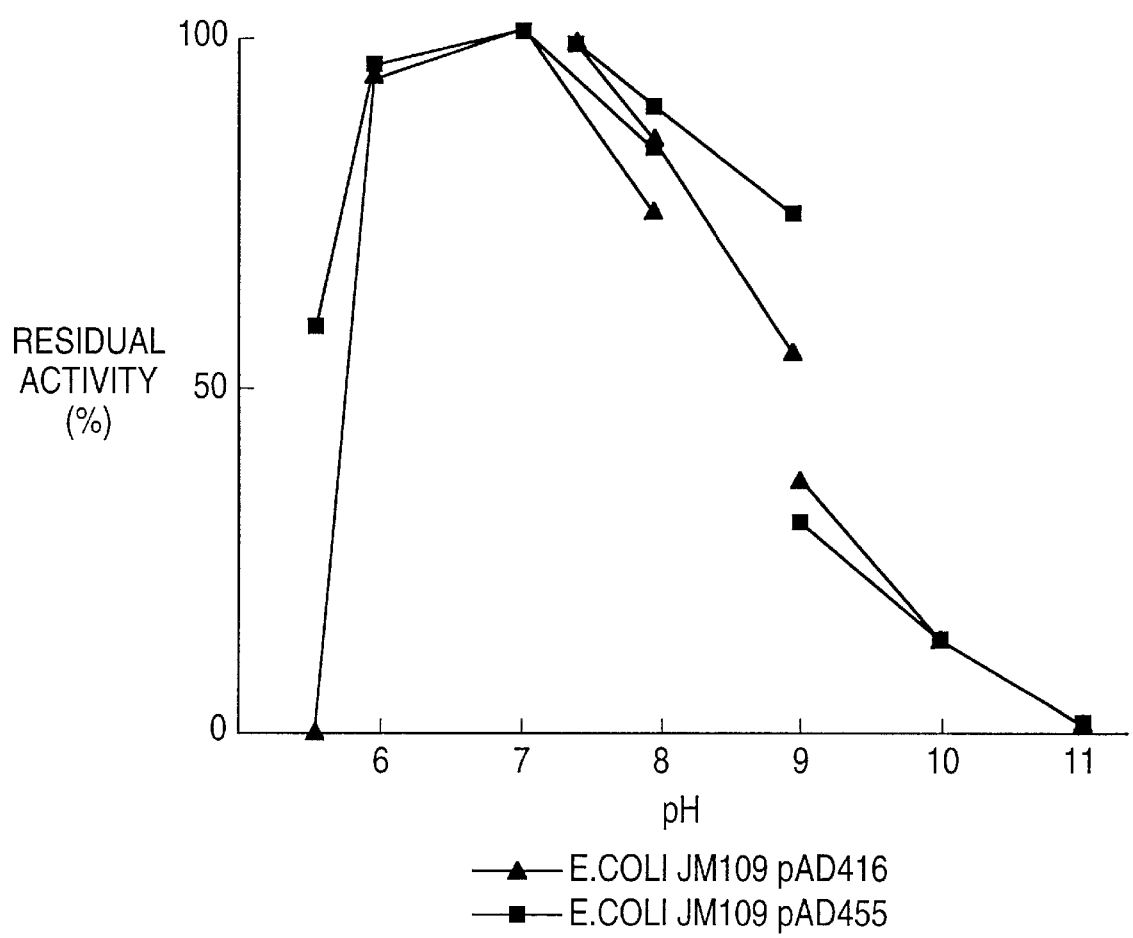
FIG. 10 is a graph illustrating the stability against pH of decarbamylases.

A shaken culture containing a thermostability-improved decarbamylase-producing strain, *E. coli* JM109 pAD416 (FERM BP-3915) or *E. coli* JM109 pAD455 (FERM BP-4036), was prepared in 10 ml of 2YT medium and incubated overnight. After harvested, the bacterial cells were washed with 10 mM K-phosphate buffer (pH 7.0; containing 0.5 mM dithiothreitol), and suspended in 1 ml of the same buffer, after which the suspension was disrupted with a small-sized ultrasonic disrupting apparatus and the residue was removed by centrifugation to yield a clude enzyme solution. Various buffers for the respective pHs were prepared from 0.1 M K-phosphate buffer (pH 5.5, 6, 7, 8), Tris-HCl buffer (pH 7.5, 8, 9) and sodium carbonate buffer (pH 9, 10, 11). To 800 μl of each of these buffers, 200 μl of the crude enzyme solution was added, and the mixture was incubated at 40° C. for 12.5 hours. Then, 100 μl of the mixture was added to 1 ml of substrate solution (1% carbamyl-D-p-hydroxyphenylglycine, 0.1% K-phosphate buffer (pH 7.0)), followed by a reaction at 40° C., after which the reaction mixture was analyzed in the same manner as described in Example 22. Taking the activity at pH 7.0 as 100%, the relative activity of the treated sample at each pH is shown in Fig.10.

EXAMPLE 24

According to the same manner, an immobilized enzyme-resin preparation was prepared from *E. coli* HB101pNT4553 and the effect of an antioxidant on the stability of the enzyme was tested. The immobilized enzyme-resin preparation was suspended in 0.1 M KPB (pH 7.0) containing 5mM of DTT, reduced glutathione or cysteamine hydrochloride. As a control, the immobilized enzyme-resin preparation was also suspended in 0.1 M KPB to which no antioxidant was added. After removing the solution, the preparation was packed with a plastic film and stored at 5° C. On the 7th, 13th and 28th days, a sample was taken out and its decarbamylase activity was determined and the relative activity (the ratio (%) of the activity to the activity before storage) was calculated. The results are shown in FIG. 11.

Figure 11:
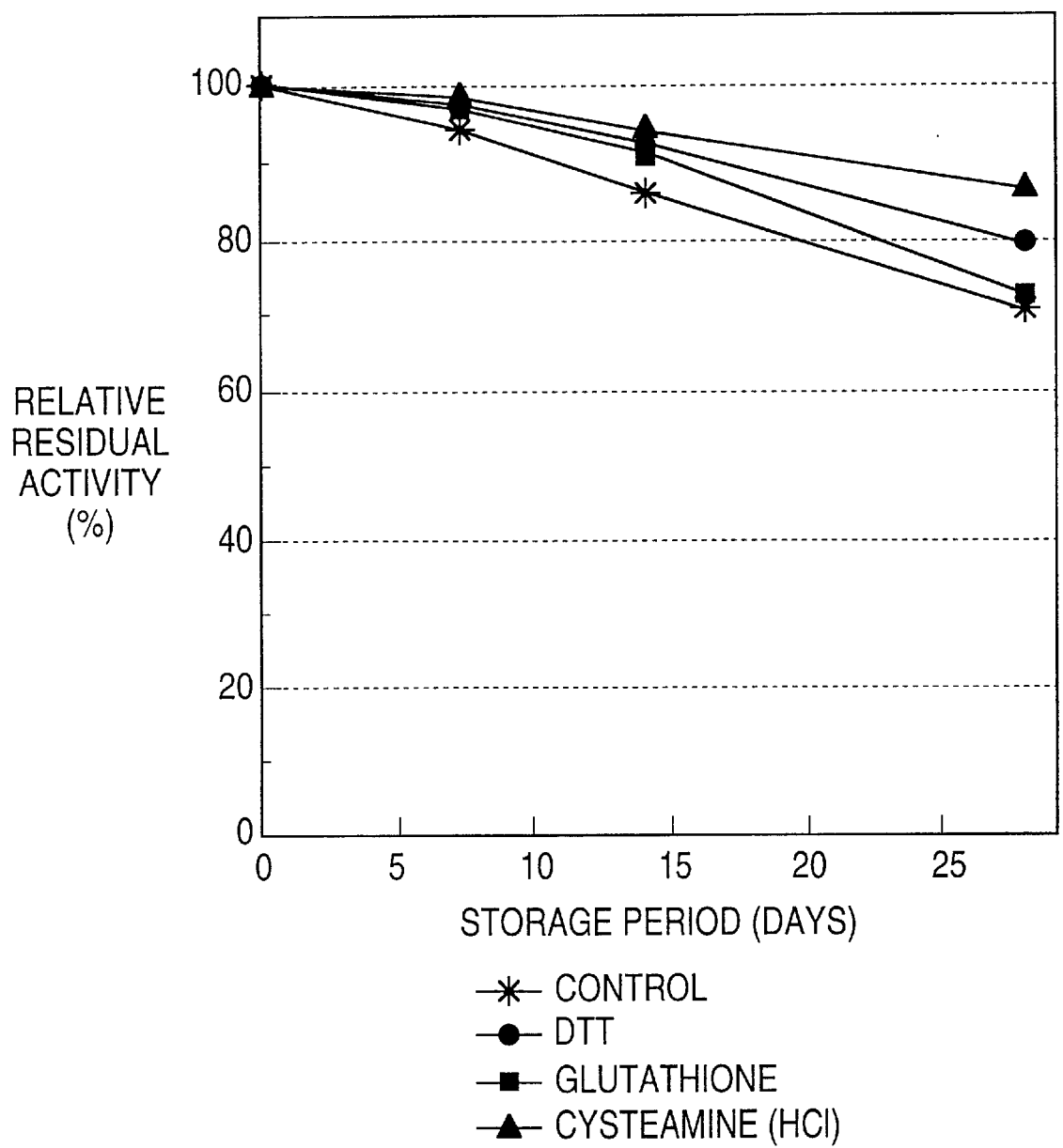
FIG. 11 is a graph illustrating the relationship between the activity of decarbamylase and the prior to storage.

As seen from FIG. 11, the storage stability of the enzyme is clearly improved by addition of the antioxidant upon storage.

As described above, according to the present invention, there is provided an immobilized preparation of decarbamylases capable of producing D-α-amino acids which are important as intermediate materials of antibiotics and the like. The use of this preparation makes possible the repeated use at 30 times or more, which gives the expectation of using it in the production on an industrial scale.

What is claimed is:

1. A decarbamylase having improved thermostability wherein said decarbamylase comprises an amino acid sequence as shown in the even-numbered SEQ IDs selected from the group consisting of SEQ ID Nos. 4 to 68.

2. A decarbamylase according to claim 1, wherein said decarbamylase is produced by a microorganism transformed with a DNA sequence encoding said decarbamylase wherein said DNA sequence is derived from *Pseudomonas species* KNK003A (FERM BP3181) or *Agrobacterium species* KNK712 (FERM BP-1900), said DNA sequence being modified to encode a decarbamylase having an amino acid sequence which differs from native decarbamylase by at least one amino acid among amino acids at one or more thermostability-related sites so as to permit improved thermostability and repeated usability of said decarbamylase; said microorganism being *E. coli* JM109 pAD402 (FERM BP-3912), *E. coli* JM109 pAD404(FERM BP-3913), *E. coli* JM109 pAD406 (FERM BP-3914), *E. coli*JM109 pAD416 (FERM BP-3915), *E. coli* JM109 pAD429 (FERM BP-4035),*E. coli* JM109 pAD424 (FERM BP-4034),*E. coli* JM109 pAD455 (FERM BP-4036) or *E. coli* HB101 pNT4553 (FERM BP-4368).

3. An immobilized enzyme preparation comprising:
the decarbamylase of claim 2;
5 to 10 mg of at least one antioxidant selected from the group consisting of dithiothreitol, 2-mercaptoethanol, L-cystein hydrochloride, cysteamine hydrochloride, dithioerythritol and reduced glutathione per 1 g of the immobilized enzyme preparation; and
a support for immobilization which is an anion exchange resin,
wherein said immobilized enzyme can be used repeatedly at 30 times or more for converting a renewed N-carbamyl-D-α-amino acid into D-α-amino acid.

4. A process for preparing a D-α-amino acid comprising reacting the decarbamylase of claim 3 with an N-carbamyl-D-α-amino acid and repeatedly at 30 times or more reacting said decarbamylase with a renewed N-carbamyl-D-α-amino acid.

5. An immobilized enzyme preparation which comprises the decarbamylase of claim 1
5 to 10 mg of at least one antioxidant selected from the group consisting of dithiothreitol, 2-mercaptoethanol, L-cystein hydrochloride, cysteamine hydrochloride, dithioerythritol and reduced glutathione for each 1 g of the immobilized enzyme preparation; and an anion exchange resin as a supporting material for immobilization, wherein said immobilized enzyme can be used repeatedly at 30 times or more for converting a renewed N-carbamyl-D-α-amino acid into D-α-amino acid.

6. A process for preparing a D-α-amino acid comprising reacting the decarbamylase of claim 5 with an N-carbamyl-D-α-amino acid; and repeatedly at 30 times or more reacting said decarbamylase with a renewed N-carbamyl-D-α-amino acid.

7. A decarbamylase having an amino acid sequence of amino acids No. 1 to No. 311 of SEQ ID 70.

8. A decarbamylase according to claim 7 capable of producing D-μ-amino acids by removing the carbamoyl group of corresponding N-carbamyl-D-μ-amino acids, wherein said decarbamylase is produced by a microorganism transformed with a DNA sequence encoding said decarbamylase wherein said DNA sequence is derived from *Pseudomonas species* KNK003A (FERM BP3181) and wherein said microorganism is *Escherichia coli* JM109pPD304 (FERM BP-3183).

9. An immobilized enzyme preparation comprising:

the decarbamylase of claim 8;

5 to 10 mg of at least one antioxidant selected from the group consisting of dithiothreitol, 2-mercaptoethanol, L-cystein hydrochloride, cysteamine hydrochloride, dithioerythritol and reduced glutathione per 1 g of the immobilized enzyme preparation; and a support for immobilization which is an anion exchange resin, wherein said immobilized enzyme can be used repeatedly at 30 times or more for converting a renewed N-carbamyl-D-α-amino acid into D-α-amino acid.

10. A process for preparing a D-α-amino acid comprising reacting the decarbamylase of claim 9 with an N-carbamyl-D-α-amino acid; and repeatedly at 30 times or more reacting said decarbamylase with a renewed N-carbamyl-D-α-amino acid.

11. An immobilized enzyme preparation comprising:

the decarbamylase of claim 7;

5 to 10 mg of at least one antioxidant selected from the group consisting of dithiothreitol, 2-mercaptoethanol, L-cystein hydrochloride, cysteamine hydrochloride, dithioerythritol and reduced glutathione per 1 g of the immobilized enzyme preparation; and a support for immobilization which is an anion exchange resin, wherein said immobilized enzyme can be used repeatedly at 30 times or more for converting a renewed N-carbamyl-D-α-amino acid into D-α-amino acid.

12. A process for preparing a D-α-amino acid comprising reacting the decarbamylase of claim 11 with an N-carbamyl-D-α-amino acid; and repeatedly at 30 times or more reacting said decarbamylase with a renewed N-carbamyl-D-α-amino acid.

* * * * *

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: KNK712 (FERM BP- 1900)

( i x ) FEATURE:
        ( A ) NAME/KEY: CDS
        ( B ) LOCATION: 233..1144

( x i ) SEQUENCE DESCRIPTION: SEQ ID NO:1:

```
GTCGACGGCG  GGCTCGCGCG  AGAGCTTGTC  AAGCAGCGCA  AATTCCGGTT  CCGCTCCGGT         60

TGACAGATCA  AAAATTTTAC  GCCTGTTATT  GTCGTGCTGC  ATGTAATATT  TCGTACTTTA        120

TGTAGAATTT  GCATTGCGCC  GCGAGTCACA  AAGCCGGTTT  TCGGCGATGT  GTTTCACAAC        180

GTTTTCCCGG  CCGCTGGGCC  GGACATCACC  TAGGAAGGAG  CAGAGGTTCA  TG ACA            235
                                                            Thr
                                                             1

CGT CAG ATG ATA CTT GCA GTG GGA CAA CAA GGT CCG ATC GCG CGC GCG              283
Arg Gln Met Ile Leu Ala Val Gly Gln Gln Gly Pro Ile Ala Arg Ala
      5              10              15
```

| | | | | | | | | | | | | | | | | |
|---|---|---|---|---|---|---|---|---|---|---|---|---|---|---|---|---|
| GAG | ACA | CGC | GAA | CAG | GTC | GTC | GTT | CGT | CTT | CTC | GAC | ATG | CTG | ACG | AAA | 331 |
| Glu | Thr | Arg | Glu | Gln | Val | Val | Val | Arg | Leu | Leu | Asp | Met | Leu | Thr | Lys | |
| | | 20 | | | | 25 | | | | | 30 | | | | | |
| GCC | GCG | AGC | CGG | GGC | GCG | AAT | TTC | ATT | GTC | TTC | CCC | GAA | CTC | GCG | CTT | 379 |
| Ala | Ala | Ser | Arg | Gly | Ala | Asn | Phe | Ile | Val | Phe | Pro | Glu | Leu | Ala | Leu | |
| | | 35 | | | | 40 | | | | | 45 | | | | | |
| ACG | ACC | TTC | TTC | CCG | CGC | TGG | CAT | TTC | ACC | GAC | GAG | GCC | GAG | CTC | GAT | 427 |
| Thr | Thr | Phe | Phe | Pro | Arg | Trp | His | Phe | Thr | Asp | Glu | Ala | Glu | Leu | Asp | |
| 50 | | | | | 55 | | | | | 60 | | | | | 65 | |
| AGC | TTC | TAT | GAG | ACC | GAA | ATG | CCC | GGC | CCG | GTG | GTC | CGT | CCA | CTC | TTT | 475 |
| Ser | Phe | Tyr | Glu | Thr | Glu | Met | Pro | Gly | Pro | Val | Val | Arg | Pro | Leu | Phe | |
| | | | | 70 | | | | | 75 | | | | | 80 | | |
| GAG | AAG | GCC | GCG | GAA | CTC | GGG | ATC | GGC | TTC | AAT | CTG | GGC | TAC | GCT | GAA | 523 |
| Glu | Lys | Ala | Ala | Glu | Leu | Gly | Ile | Gly | Phe | Asn | Leu | Gly | Tyr | Ala | Glu | |
| | | | 85 | | | | | 90 | | | | | 95 | | | |
| CTC | GTC | GTC | GAA | GGC | GGC | GTC | AAG | CGT | CGC | TTC | AAC | ACG | TCC | ATT | TTG | 571 |
| Leu | Val | Val | Glu | Gly | Gly | Val | Lys | Arg | Arg | Phe | Asn | Thr | Ser | Ile | Leu | |
| | | | 100 | | | | | 105 | | | | | 110 | | | |
| GTG | GAT | AAG | TCA | GGC | AAG | ATC | GTC | GGC | AAG | TAT | CGT | AAG | ATC | CAT | TTG | 619 |
| Val | Asp | Lys | Ser | Gly | Lys | Ile | Val | Gly | Lys | Tyr | Arg | Lys | Ile | His | Leu | |
| | | 115 | | | | 120 | | | | | 125 | | | | | |
| CCG | GGT | CAC | AAG | GAG | TAC | GAG | GCC | TAC | CGG | CCG | TTC | CAG | CAT | CTT | GAA | 667 |
| Pro | Gly | His | Lys | Glu | Tyr | Glu | Ala | Tyr | Arg | Pro | Phe | Gln | His | Leu | Glu | |
| 130 | | | | | 135 | | | | | 140 | | | | | 145 | |
| AAG | CGT | TAT | TTC | GAG | CCG | GGC | GAT | CTC | GGC | TTC | CCG | GTC | TAT | GAC | GTC | 715 |
| Lys | Arg | Tyr | Phe | Glu | Pro | Gly | Asp | Leu | Gly | Phe | Pro | Val | Tyr | Asp | Val | |
| | | | | 150 | | | | | 155 | | | | | 160 | | |
| GAC | GCC | GCG | AAA | ATG | GGG | ATG | TTC | ATC | TGC | AAC | GAT | CGC | CGC | TGG | CCT | 763 |
| Asp | Ala | Ala | Lys | Met | Gly | Met | Phe | Ile | Cys | Asn | Asp | Arg | Arg | Trp | Pro | |
| | | | 165 | | | | | 170 | | | | | 175 | | | |
| GAA | GCC | TGG | CGG | GTG | ATG | GGC | CTC | AGG | GGC | GCC | GAG | ATC | ATC | TGC | GGC | 811 |
| Glu | Ala | Trp | Arg | Val | Met | Gly | Leu | Arg | Gly | Ala | Glu | Ile | Ile | Cys | Gly | |
| | | 180 | | | | 185 | | | | | 190 | | | | | |
| GGC | TAC | AAC | ACG | CCG | ACC | CAC | AAT | CCC | CCT | GTT | CCC | CAG | CAC | GAC | CAC | 859 |
| Gly | Tyr | Asn | Thr | Pro | Thr | His | Asn | Pro | Pro | Val | Pro | Gln | His | Asp | His | |
| | 195 | | | | | 200 | | | | | 205 | | | | | |
| CTG | ACG | TCC | TTC | CAC | CAT | CTC | CTA | TCG | ATG | CAG | GCC | GGG | TCT | TAT | CAG | 907 |
| Leu | Thr | Ser | Phe | His | His | Leu | Leu | Ser | Met | Gln | Ala | Gly | Ser | Tyr | Gln | |
| 210 | | | | | 215 | | | | | 220 | | | | | 225 | |
| AAC | GGG | GCC | TGG | TCC | GCG | GCC | GCG | GGC | AAG | GTG | GGC | ATG | GAG | GAG | AAC | 955 |
| Asn | Gly | Ala | Trp | Ser | Ala | Ala | Ala | Gly | Lys | Val | Gly | Met | Glu | Glu | Asn | |
| | | | | 230 | | | | | 235 | | | | | 240 | | |
| TGC | ATG | CTG | CTC | GGC | CAC | TCC | TGC | ATC | GTG | GCG | CCG | ACC | GGG | GAA | ATC | 1003 |
| Cys | Met | Leu | Leu | Gly | His | Ser | Cys | Ile | Val | Ala | Pro | Thr | Gly | Glu | Ile | |
| | | | 245 | | | | | 250 | | | | | 255 | | | |
| GTC | GCT | CTC | ACT | ACG | ACG | CTG | GAA | GAC | GAG | GTG | ATC | ACC | GCC | GCC | GTC | 1051 |
| Val | Ala | Leu | Thr | Thr | Thr | Leu | Glu | Asp | Glu | Val | Ile | Thr | Ala | Ala | Val | |
| | | | 260 | | | | | 265 | | | | | 270 | | | |
| GAT | CTC | GAT | CGC | TGC | CGG | GAA | CTG | CGT | GAA | CAC | ATC | TTC | AAC | TTC | AAG | 1099 |
| Asp | Leu | Asp | Arg | Cys | Arg | Glu | Leu | Arg | Glu | His | Ile | Phe | Asn | Phe | Lys | |
| | 275 | | | | | 280 | | | | | 285 | | | | | |
| CAG | CAT | CGT | CAG | CCC | CAG | CAC | TAT | GGT | CTG | ATC | GCG | GAA | CTC | TGAGGTTGCC | | 1151 |
| Gln | His | Arg | Gln | Pro | Gln | His | Tyr | Gly | Leu | Ile | Ala | Glu | Leu | | | |
| 290 | | | | | 295 | | | | | 300 | | | | | | |
| GAAAAGCATG | | TGTGTCGTTG | | TTCTCGGCGC | | CTGGGTCACA | | TCCAGGCGCG | | CCAGGGTGAC | | | | | | 1211 |
| GCTGGTGGAA | | TAGTACCACG | | ACCGCTTCAG | | GGCGATCCGC | | AAGGAGATGC | | GGGTCGCCGG | | | | | | 1271 |
| AGCGGCAAAG | | CCCGACATTC | | GTTTCGCACC | | GACGGCCGTC | | GTGAACTCGA | | CAGTCCGCGA | | | | | | 1331 |
| GAAGGGCGTA | | TTGCGCGGCC | | TGGACCTGTA | | CGTGGAACTG | | TAGCCCATAT | | ATAGATTTCC | | | | | | 1391 |

```
AAAGAGTTTC  GGCGAGGCGC  GGCGCGCCTA  GCCCCATGTG  AGCGAGAACC  GTGCCCAGAT    1451

CAAAGAATGA  GACCGACGCG  CCGGCCGCGG  CAAAGGATGA  TCCTCAGGGT  CGGATCTATC    1511

GCTCCGCCCT  GAAGCAGGAG  GGCGCACGCT  GGCTGCTGAC  GGCGGAGGAA  GGGTTGCTGG    1571

CAAAGCCCAA  GCCGCCCGGC  CTTGTTCCGG  CACTTGAGAA  TGCGATCGCC  ATCGTCGATT    1631

ACATCAACGG  TACACCGCCC  CATATCGCGT  CCCTGGCGGA  GCTTTCAACG  ACGCTCGGGA    1691

TATCCAAGAG  CCACTGTCAC  TCCATCCTCA  AGACGCTGAC  GCATTTCGGC  TGGCTGAAAT    1751

TCGACAATCG  CTCAAAGAGC  TACGAGCTGA  ATTC                                  1785
```

(2) INFORMATION FOR SEQ ID NO:2:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:2:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
            35                  40                  45

Leu Thr Thr Phe Phe Pro Arg Trp His Phe Thr Asp Glu Ala Glu Leu
    50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
               100                 105                 110

Leu Val Asp Lys Ser Gly Lys Ile Val Gly Lys Tyr Arg Lys Ile His
           115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Pro Val Pro Gln His Asp
           195                 200                 205

His Leu Thr Ser Phe His His Leu Leu Ser Met Gln Ala Gly Ser Tyr
    210                 215                 220

Gln Asn Gly Ala Trp Ser Ala Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285
```

| Lys | Gln | His | Arg | Gln | Pro | Gln | His | Tyr | Gly | Leu | Ile | Ala | Glu | Leu |
|-----|-----|-----|-----|-----|-----|-----|-----|-----|-----|-----|-----|-----|-----|-----|
|     |     |     |     | 290 |     |     |     | 295 |     |     |     | 300 |     |     |

(2) INFORMATION FOR SEQ ID NO:3:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (vi) ORIGINAL SOURCE:
        (B) STRAIN: JM109 pAD402 (FERM BP- 3912)

(ix) FEATURE:
        (A) NAME/KEY: CDS
        (B) LOCATION: 233..1144

(xi) SEQUENCE DESCRIPTION: SEQ ID NO:3:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                         Thr
                                                          1
```

| CGT | CAG | ATG | ATA | CTT | GCA | GTG | GGA | CAA | CAA | GGT | CCG | ATC | GCG | CGC | GCG | 283 |
|-----|-----|-----|-----|-----|-----|-----|-----|-----|-----|-----|-----|-----|-----|-----|-----|-----|
| Arg | Gln | Met | Ile | Leu | Ala | Val | Gly | Gln | Gln | Gly | Pro | Ile | Ala | Arg | Ala |     |
|     |     |     |   5 |     |     |     |     |  10 |     |     |     |     |  15 |     |     |     |

| GAG | ACA | CGC | GAA | CAG | GTC | GTC | GTT | CGT | CTT | CTC | GAC | ATG | CTG | ACG | AAA | 331 |
|-----|-----|-----|-----|-----|-----|-----|-----|-----|-----|-----|-----|-----|-----|-----|-----|-----|
| Glu | Thr | Arg | Glu | Gln | Val | Val | Val | Arg | Leu | Leu | Asp | Met | Leu | Thr | Lys |     |
|     |     |  20 |     |     |     |     |  25 |     |     |     |     |  30 |     |     |     |     |

| GCC | GCG | AGC | CGG | GGC | GCG | AAT | TTC | ATT | GTC | TTC | CCC | GAA | CTC | GCG | CTT | 379 |
|-----|-----|-----|-----|-----|-----|-----|-----|-----|-----|-----|-----|-----|-----|-----|-----|-----|
| Ala | Ala | Ser | Arg | Gly | Ala | Asn | Phe | Ile | Val | Phe | Pro | Glu | Leu | Ala | Leu |     |
|     |     |  35 |     |     |     |     |  40 |     |     |     |     |  45 |     |     |     |     |

| ACG | ACC | TTC | TTC | CCG | CGC | TGG | TAT | TTC | ACC | GAC | GAG | GCC | GAG | CTC | GAT | 427 |
|-----|-----|-----|-----|-----|-----|-----|-----|-----|-----|-----|-----|-----|-----|-----|-----|-----|
| Thr | Thr | Phe | Phe | Pro | Arg | Trp | Tyr | Phe | Thr | Asp | Glu | Ala | Glu | Leu | Asp |     |
|  50 |     |     |     |     |  55 |     |     |     |     |  60 |     |     |     |     |  65 |     |

| AGC | TTC | TAT | GAG | ACC | GAA | ATG | CCC | GGC | CCG | GTG | GTC | CGT | CCA | CTC | TTT | 475 |
|-----|-----|-----|-----|-----|-----|-----|-----|-----|-----|-----|-----|-----|-----|-----|-----|-----|
| Ser | Phe | Tyr | Glu | Thr | Glu | Met | Pro | Gly | Pro | Val | Val | Arg | Pro | Leu | Phe |     |
|     |     |     |     |  70 |     |     |     |     |  75 |     |     |     |     |  80 |     |     |

| GAG | AAG | GCC | GCG | GAA | CTC | GGG | ATC | GGC | TTC | AAT | CTG | GGC | TAC | GCT | GAA | 523 |
|-----|-----|-----|-----|-----|-----|-----|-----|-----|-----|-----|-----|-----|-----|-----|-----|-----|
| Glu | Lys | Ala | Ala | Glu | Leu | Gly | Ile | Gly | Phe | Asn | Leu | Gly | Tyr | Ala | Glu |     |
|     |     |     |     |  85 |     |     |     |     |  90 |     |     |     |     |  95 |     |     |

| CTC | GTC | GTC | GAA | GGC | GGC | GTC | AAG | CGT | CGC | TTC | AAC | ACG | TCC | ATT | TTG | 571 |
|-----|-----|-----|-----|-----|-----|-----|-----|-----|-----|-----|-----|-----|-----|-----|-----|-----|
| Leu | Val | Val | Glu | Gly | Gly | Val | Lys | Arg | Arg | Phe | Asn | Thr | Ser | Ile | Leu |     |
|     |     | 100 |     |     |     |     | 105 |     |     |     |     | 110 |     |     |     |     |

| GTG | GAT | AAG | TCA | GGC | AAG | ATC | GTC | GGC | AAG | TAT | CGT | AAG | ATC | CAT | TTG | 619 |
|-----|-----|-----|-----|-----|-----|-----|-----|-----|-----|-----|-----|-----|-----|-----|-----|-----|
| Val | Asp | Lys | Ser | Gly | Lys | Ile | Val | Gly | Lys | Tyr | Arg | Lys | Ile | His | Leu |     |
|     |     | 115 |     |     |     |     | 120 |     |     |     |     | 125 |     |     |     |     |

| CCG | GGT | CAC | AAG | GAG | TAC | GAG | GCC | TAC | CGG | CCG | TTC | CAG | CAT | CTT | GAA | 667 |
|-----|-----|-----|-----|-----|-----|-----|-----|-----|-----|-----|-----|-----|-----|-----|-----|-----|
| Pro | Gly | His | Lys | Glu | Tyr | Glu | Ala | Tyr | Arg | Pro | Phe | Gln | His | Leu | Glu |     |
| 130 |     |     |     |     | 135 |     |     |     |     | 140 |     |     |     |     | 145 |     |

| AAG | CGT | TAT | TTC | GAG | CCG | GGC | GAT | CTC | GGC | TTC | CCG | GTC | TAT | GAC | GTT | 715 |
|-----|-----|-----|-----|-----|-----|-----|-----|-----|-----|-----|-----|-----|-----|-----|-----|-----|
| Lys | Arg | Tyr | Phe | Glu | Pro | Gly | Asp | Leu | Gly | Phe | Pro | Val | Tyr | Asp | Val |     |
|     |     |     |     | 150 |     |     |     |     | 155 |     |     |     |     | 160 |     |     |

| GAC | GCC | GCG | AAA | ATG | GGG | ATG | TTC | ATC | TGC | AAC | GAT | CGC | CGC | TGG | CCT | 763 |
|-----|-----|-----|-----|-----|-----|-----|-----|-----|-----|-----|-----|-----|-----|-----|-----|-----|
| Asp | Ala | Ala | Lys | Met | Gly | Met | Phe | Ile | Cys | Asn | Asp | Arg | Arg | Trp | Pro |     |
|     |     |     | 165 |     |     |     |     | 170 |     |     |     |     | 175 |     |     |     |

| GAA | GCC | TGG | CGG | GTG | ATG | GGC | CTC | AGG | GGC | GCC | GAG | ATC | ATC | TGC | GGC | 811 |
|-----|-----|-----|-----|-----|-----|-----|-----|-----|-----|-----|-----|-----|-----|-----|-----|-----|
| Glu | Ala | Trp | Arg | Val | Met | Gly | Leu | Arg | Gly | Ala | Glu | Ile | Ile | Cys | Gly |     |
|     |     |     | 180 |     |     |     |     | 185 |     |     |     |     | 190 |     |     |     |

```
GGC  TAC  AAC  ACG  CCG  ACC  CAC  AAT  CCC  CCT  GTT  CCC  CAG  CAC  GAC  CAC     859
Gly  Tyr  Asn  Thr  Pro  Thr  His  Asn  Pro  Pro  Val  Pro  Gln  His  Asp  His
     195                      200                 205

CTG  ACG  TCC  TTC  CAC  CAT  CTC  CTA  TCG  ATG  CAG  GCC  GGG  TCT  TAT  CAG     907
Leu  Thr  Ser  Phe  His  His  Leu  Leu  Ser  Met  Gln  Ala  Gly  Ser  Tyr  Gln
210                      215                 220                           225

AAC  GGG  GCC  TGG  TCC  GCG  GCC  GCG  GGC  AAG  GTG  GGC  ATG  GAG  GAG  AAC     955
Asn  Gly  Ala  Trp  Ser  Ala  Ala  Ala  Gly  Lys  Val  Gly  Met  Glu  Glu  Asn
               230                      235                      240

TGC  ATG  CTG  CTC  GGC  CAC  TCC  TGC  ATC  GTG  GCG  CCG  ACC  GGG  GAA  ATC    1003
Cys  Met  Leu  Leu  Gly  His  Ser  Cys  Ile  Val  Ala  Pro  Thr  Gly  Glu  Ile
               245                      250                      255

GTC  GCT  CTC  ACT  ACG  ACG  CTG  GAA  GAC  GAG  GTG  ATC  ACC  GCC  GCC  GTC    1051
Val  Ala  Leu  Thr  Thr  Thr  Leu  Glu  Asp  Glu  Val  Ile  Thr  Ala  Ala  Val
               260                      265                      270

GAT  CTC  GAT  CGC  TGC  CGG  GAA  CTG  CGT  GAA  CAC  ATC  TTC  AAC  TTC  AAG    1099
Asp  Leu  Asp  Arg  Cys  Arg  Glu  Leu  Arg  Glu  His  Ile  Phe  Asn  Phe  Lys
     275                      280                 285

CAG  CAT  CGT  CAG  CCC  CAG  CAC  TAT  GGT  CTG  ATC  GCG  GAA  CTC  TGAGGTTGCC  1151
Gln  His  Arg  Gln  Pro  Gln  His  Tyr  Gly  Leu  Ile  Ala  Glu  Leu
290                      295                 300

GAAAAGCATG  TGTGTCGTTG  TTCTCGGCGC  CTGGGTCACA  TCCAGGCGCG  CCAGGGTGAC           1211

GCTGGTGGAA  TAGTACCACG  ACCGCTTCAG  GGCGATCCGC  AAGGAGATGC  GGGTCGCCGG           1271

AGCGGCAAAG  CCCGACATTC  GTTTCGCACC  GACGGCCGTC  GTGAACTCGA  CAGTCCGCGA           1331

GAAGGGCGTA  TTGCGCGGCC  TGGACCTGTA  CGTGGAACTG  TAGCCCATAT  ATAGATTTCC           1391

AAAGAGTTTC  GGCGAGGCGC  GGCGCGCCTA  GCCCATGTG   AGCGAGAACC  GTGCCCAGAT           1451

CAAAGAATGA  GACCGACGCG  CCGGCCGCGG  CAAAGGATGA  TCCTCAGGGT  CGGATCTATC           1511

GCTCCGCCCT  GAAGCAGGAG  GGCGCACGCT  GGCTGCTGAC  GGCGGAGGAA  GGGTTGCTGG           1571

CAAAGCCCAA  GCCGCCCGGC  CTTGTTCCGG  CACTTGAGAA  TGCGATCGCC  ATCGTCGATT           1631

ACATCAACGG  TACACCGCCC  CATATCGCGT  CCCTGGCGGA  GCTTTCAACG  ACGCTCGGGA           1691

TATCCAAGAG  CCACTGTCAC  TCCATCCTCA  AGACGCTGAC  GCATTTCGGC  TGGCTGAAAT           1751

TCGACAATCG  CTCAAAGAGC  TACGAGCTGA  ATTC                                        1785
```

( 2 ) INFORMATION FOR SEQ ID NO:4:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Thr  Arg  Gln  Met  Ile  Leu  Ala  Val  Gly  Gln  Gln  Gly  Pro  Ile  Ala  Arg
  1                 5                      10                      15

Ala  Glu  Thr  Arg  Glu  Gln  Val  Val  Arg  Leu  Leu  Asp  Met  Leu  Thr
               20                 25                      30

Lys  Ala  Ala  Ser  Arg  Gly  Ala  Asn  Phe  Ile  Val  Phe  Pro  Glu  Leu  Ala
               35                      40                 45

Leu  Thr  Thr  Phe  Phe  Pro  Arg  Trp  Tyr  Phe  Thr  Asp  Glu  Ala  Glu  Leu
     50                      55                 60

Asp  Ser  Phe  Tyr  Glu  Thr  Glu  Met  Pro  Gly  Pro  Val  Val  Arg  Pro  Leu
 65                      70                 75                           80

Phe  Glu  Lys  Ala  Ala  Glu  Leu  Gly  Ile  Gly  Phe  Asn  Leu  Gly  Tyr  Ala
                    85                 90                      95
```

| | | | | | | | | | | | | | | |
|---|---|---|---|---|---|---|---|---|---|---|---|---|---|---|
| Glu | Leu | Val | Val | Glu | Gly | Gly | Val | Lys | Arg | Arg | Phe | Asn | Thr | Ser | Ile |
| | | | 100 | | | | | 105 | | | | | 110 | | |
| Leu | Val | Asp | Lys | Ser | Gly | Lys | Ile | Val | Gly | Lys | Tyr | Arg | Lys | Ile | His |
| | | | 115 | | | | 120 | | | | | 125 | | | |
| Leu | Pro | Gly | His | Lys | Glu | Tyr | Glu | Ala | Tyr | Arg | Pro | Phe | Gln | His | Leu |
| | | 130 | | | | | 135 | | | | | 140 | | | |
| Glu | Lys | Arg | Tyr | Phe | Glu | Pro | Gly | Asp | Leu | Gly | Phe | Pro | Val | Tyr | Asp |
| 145 | | | | | 150 | | | | | 155 | | | | | 160 |
| Val | Asp | Ala | Ala | Lys | Met | Gly | Met | Phe | Ile | Cys | Asn | Asp | Arg | Arg | Trp |
| | | | | 165 | | | | | 170 | | | | | 175 | |
| Pro | Glu | Ala | Trp | Arg | Val | Met | Gly | Leu | Arg | Gly | Ala | Glu | Ile | Ile | Cys |
| | | | | 180 | | | | | 185 | | | | | 190 | |
| Gly | Gly | Tyr | Asn | Thr | Pro | Thr | His | Asn | Pro | Pro | Val | Pro | Gln | His | Asp |
| | | | 195 | | | | | 200 | | | | | 205 | | |
| His | Leu | Thr | Ser | Phe | His | His | Leu | Leu | Ser | Met | Gln | Ala | Gly | Ser | Tyr |
| | | 210 | | | | | 215 | | | | | 220 | | | |
| Gln | Asn | Gly | Ala | Trp | Ser | Ala | Ala | Ala | Gly | Lys | Val | Gly | Met | Glu | Glu |
| 225 | | | | | 230 | | | | | 235 | | | | | 240 |
| Asn | Cys | Met | Leu | Leu | Gly | His | Ser | Cys | Ile | Val | Ala | Pro | Thr | Gly | Glu |
| | | | | 245 | | | | | 250 | | | | | 255 | |
| Ile | Val | Ala | Leu | Thr | Thr | Thr | Leu | Glu | Asp | Glu | Val | Ile | Thr | Ala | Ala |
| | | | | 260 | | | | | 265 | | | | | 270 | |
| Val | Asp | Leu | Asp | Arg | Cys | Arg | Glu | Leu | Arg | Glu | His | Ile | Phe | Asn | Phe |
| | | | 275 | | | | | 280 | | | | | 285 | | |
| Lys | Gln | His | Arg | Gln | Pro | Gln | His | Tyr | Gly | Leu | Ile | Ala | Glu | Leu | |
| | | | 290 | | | | | 295 | | | | | 300 | | |

( 2 ) INFORMATION FOR SEQ ID NO:5:

( i ) SEQUENCE CHARACTERISTICS:
( A ) LENGTH: 1785 base pairs
( B ) TYPE: nucleic acid
( C ) STRANDEDNESS: double
( D ) TOPOLOGY: linear ( v i ) ORIGINAL SOURCE:
( B ) STRAIN: JM109 pAD404 (FERM BP- 3913)

( i x ) FEATURE:
( A ) NAME/KEY: CDS
( B ) LOCATION: 233..1144

( x i ) SEQUENCE DESCRIPTION: SEQ ID NO:5:

```
GTCGACGGCG  GGCTCGCGCG  AGAGCTTGTC  AAGCAGCGCA  AATTCCGGTT  CCGCTCCGGT        60

TGACAGATCA  AAAATTTTAC  GCCTGTTATT  GTCGTGCTGC  ATGTAATATT  TCGTACTTTA       120

TGTAGAATTT  GCATTGCGCC  GCGAGTCACA  AAGCCGGTTT  TCGGCGATGT  GTTTCACAAC       180

GTTTTCCCGG  CCGCTGGGCC  GGACATCACC  TAGGAAGGAG  CAGAGGTTCA TG  ACA            235
                                                             Thr
                                                              1
```

| | | | | | | | | | | | | | | | | |
|---|---|---|---|---|---|---|---|---|---|---|---|---|---|---|---|---|
| CGT | CAG | ATG | ATA | CTT | GCA | GTG | GGA | CAA | CAA | GGT | CCG | ATC | GCG | CGC | GCG | 283 |
| Arg | Gln | Met | Ile | Leu | Ala | Val | Gly | Gln | Gln | Gly | Pro | Ile | Ala | Arg | Ala | |
| | | | | 5 | | | | | 10 | | | | | 15 | | |
| GAG | ACA | CGC | GAA | CAG | GTC | GTC | GTT | CGT | CTT | CTC | GAC | ATG | CTG | ACG | AAA | 331 |
| Glu | Thr | Arg | Glu | Gln | Val | Val | Val | Arg | Leu | Leu | Asp | Met | Leu | Thr | Lys | |
| | | 20 | | | | | 25 | | | | | 30 | | | | |
| GCC | GCG | AGC | CGG | GGC | GCG | AAT | TTC | ATT | GTC | TTC | CCC | GAA | CTC | GCG | CTT | 379 |
| Ala | Ala | Ser | Arg | Gly | Ala | Asn | Phe | Ile | Val | Phe | Pro | Glu | Leu | Ala | Leu | |
| | | 35 | | | | | 40 | | | | | 45 | | | | |
| ACG | ACC | TTC | TTC | CCG | CGC | TGG | CAT | TTC | ACC | GAC | GAG | GCC | GAG | CTC | GAT | 427 |

| | | | | | | | | | | | | | | | |
|---|---|---|---|---|---|---|---|---|---|---|---|---|---|---|---|
| Thr | Thr | Phe | Phe | Pro | Arg | Trp | His | Phe | Thr | Asp | Glu | Ala | Glu | Leu | Asp |
| 50 | | | | 55 | | | | | 60 | | | | | 65 | |

| AGC | TTC | TAT | GAG | ACC | GAA | ATG | CCC | GGC | CCG | GTG | GTC | CGT | CCA | CTC | TTT | 475 |
|---|---|---|---|---|---|---|---|---|---|---|---|---|---|---|---|---|
| Ser | Phe | Tyr | Glu | Thr | Glu | Met | Pro | Gly | Pro | Val | Val | Arg | Pro | Leu | Phe | |
| | | | | 70 | | | | | 75 | | | | | 80 | | |

| GAG | AAG | GCC | GCG | GAA | CTC | GGG | ATC | GGC | TTC | AAT | CTG | GGC | TAC | GCT | GAA | 523 |
|---|---|---|---|---|---|---|---|---|---|---|---|---|---|---|---|---|
| Glu | Lys | Ala | Ala | Glu | Leu | Gly | Ile | Gly | Phe | Asn | Leu | Gly | Tyr | Ala | Glu | |
| | | | | 85 | | | | | 90 | | | | | 95 | | |

| CTC | GTC | GTC | GAA | GGC | GGC | GTC | AAG | CGT | CGC | TTC | AAC | ACG | TCC | ATT | TTG | 571 |
|---|---|---|---|---|---|---|---|---|---|---|---|---|---|---|---|---|
| Leu | Val | Val | Glu | Gly | Gly | Val | Lys | Arg | Arg | Phe | Asn | Thr | Ser | Ile | Leu | |
| | | | | 100 | | | | | 105 | | | | | 110 | | |

| GTG | GAT | AAG | TCA | GGC | AAG | ATC | GTC | GGC | AAG | TAT | CGT | AAG | ATC | CAT | TTG | 619 |
|---|---|---|---|---|---|---|---|---|---|---|---|---|---|---|---|---|
| Val | Asp | Lys | Ser | Gly | Lys | Ile | Val | Gly | Lys | Tyr | Arg | Lys | Ile | His | Leu | |
| | | | | 115 | | | | | 120 | | | | | 125 | | |

| CCG | GGT | CAC | AAG | GAG | TAC | GAG | GCC | TAC | CGG | CCG | TTC | CAG | CAT | CTT | GAA | 667 |
|---|---|---|---|---|---|---|---|---|---|---|---|---|---|---|---|---|
| Pro | Gly | His | Lys | Glu | Tyr | Glu | Ala | Tyr | Arg | Pro | Phe | Gln | His | Leu | Glu | |
| 130 | | | | | 135 | | | | | 140 | | | | | 145 | |

| AAG | CGT | TAT | TTC | GAG | CCG | GGC | GAT | CTC | GGC | TTC | CCG | GTC | TAT | GAC | GTC | 715 |
|---|---|---|---|---|---|---|---|---|---|---|---|---|---|---|---|---|
| Lys | Arg | Tyr | Phe | Glu | Pro | Gly | Asp | Leu | Gly | Phe | Pro | Val | Tyr | Asp | Val | |
| | | | | 150 | | | | | 155 | | | | | 160 | | |

| GAC | GCC | GCG | AAA | ATG | GGG | ATG | TTC | ATC | TGC | AAC | GAT | CGC | CGC | TGG | CCT | 763 |
|---|---|---|---|---|---|---|---|---|---|---|---|---|---|---|---|---|
| Asp | Ala | Ala | Lys | Met | Gly | Met | Phe | Ile | Cys | Asn | Asp | Arg | Arg | Trp | Pro | |
| | | | | 165 | | | | | 170 | | | | | 175 | | |

| GAA | GCC | TGG | CGG | GTG | ATG | GGC | CTC | AGG | GGC | GCC | GAG | ATC | ATC | TGC | GGC | 811 |
|---|---|---|---|---|---|---|---|---|---|---|---|---|---|---|---|---|
| Glu | Ala | Trp | Arg | Val | Met | Gly | Leu | Arg | Gly | Ala | Glu | Ile | Ile | Cys | Gly | |
| | | | | 180 | | | | | 185 | | | | | 190 | | |

| GGC | TAC | AAC | ACG | CCG | ACC | CAC | AAT | CCC | CTT | GTT | CCC | CAG | CAC | GAC | CAC | 859 |
|---|---|---|---|---|---|---|---|---|---|---|---|---|---|---|---|---|
| Gly | Tyr | Asn | Thr | Pro | Thr | His | Asn | Pro | Leu | Val | Pro | Gln | His | Asp | His | |
| | | | | 195 | | | | | 200 | | | | | 205 | | |

| CTG | ACG | TCC | TTC | CAC | CAT | CTC | CTA | TCG | ATG | CAG | GCC | GGG | TCT | TAT | CAG | 907 |
|---|---|---|---|---|---|---|---|---|---|---|---|---|---|---|---|---|
| Leu | Thr | Ser | Phe | His | His | Leu | Leu | Ser | Met | Gln | Ala | Gly | Ser | Tyr | Gln | |
| 210 | | | | | 215 | | | | | 220 | | | | | 225 | |

| AAC | GGG | GCC | TGG | TCC | GCG | GCC | GCG | GGC | AAG | GTG | GGC | ATG | GAG | GAG | AAC | 955 |
|---|---|---|---|---|---|---|---|---|---|---|---|---|---|---|---|---|
| Asn | Gly | Ala | Trp | Ser | Ala | Ala | Ala | Gly | Lys | Val | Gly | Met | Glu | Glu | Asn | |
| | | | | 230 | | | | | 235 | | | | | 240 | | |

| TGC | ATG | CTG | CTC | GGC | CAC | TCC | TGC | ATC | GTG | GCG | CCG | ACC | GGG | GAA | ATC | 1003 |
|---|---|---|---|---|---|---|---|---|---|---|---|---|---|---|---|---|
| Cys | Met | Leu | Leu | Gly | His | Ser | Cys | Ile | Val | Ala | Pro | Thr | Gly | Glu | Ile | |
| | | | | 245 | | | | | 250 | | | | | 255 | | |

| GTC | GCT | CTC | ACT | ACG | ACG | CTG | GAA | GAC | GAG | GTG | ATC | ACC | GCC | GCC | GTC | 1051 |
|---|---|---|---|---|---|---|---|---|---|---|---|---|---|---|---|---|
| Val | Ala | Leu | Thr | Thr | Thr | Leu | Glu | Asp | Glu | Val | Ile | Thr | Ala | Ala | Val | |
| | | | | 260 | | | | | 265 | | | | | 270 | | |

| GAT | CTC | GAT | CGC | TGC | CGG | GAA | CTG | CGT | GAA | CAC | ATC | TTC | AAC | TTC | AAG | 1099 |
|---|---|---|---|---|---|---|---|---|---|---|---|---|---|---|---|---|
| Asp | Leu | Asp | Arg | Cys | Arg | Glu | Leu | Arg | Glu | His | Ile | Phe | Asn | Phe | Lys | |
| | | | | 275 | | | | | 280 | | | | | 285 | | |

| CAG | CAT | CGT | CAG | CCC | CAG | CAC | TAT | GGT | CTG | ATC | GCG | GAA | CTC | TGAGGTTGCC | | 1151 |
|---|---|---|---|---|---|---|---|---|---|---|---|---|---|---|---|---|
| Gln | His | Arg | Gln | Pro | Gln | His | Tyr | Gly | Leu | Ile | Ala | Glu | Leu | | | |
| 290 | | | | | 295 | | | | | 300 | | | | | | |

| GAAAAGCATG | TGTGTCGTTG | TTCTCGGCGC | CTGGGTCACA | TCCAGGCGCG | CCAGGGTGAC | 1211 |
|---|---|---|---|---|---|---|
| GCTGGTGGAA | TAGTACCACG | ACCGCTTCAG | GGCGATCCGC | AAGGAGATGC | GGGTCGCCGG | 1271 |
| AGCGGCAAAG | CCCGACATTC | GTTTCGCACC | GACGGCCGTC | GTGAACTCGA | CAGTCCGCGA | 1331 |
| GAAGGGCGTA | TTGCGCGGCC | TGGACCTGTA | CGTGGAACTG | TAGCCCATAT | ATAGATTTCC | 1391 |
| AAAGAGTTTC | GGCGAGGCGC | GGCGCGCCTA | GCCCCATGTG | AGCGAGAACC | GTGCCCAGAT | 1451 |
| CAAAGAATGA | GACCGACGCG | CCGGCCGCGG | CAAAGGATGA | TCCTCAGGGT | CGGATCTATC | 1511 |
| GCTCCGCCCT | GAAGCAGGAG | GGCGCACGCT | GGCTGCTGAC | GGCGGAGGAA | GGGTTGCTGG | 1571 |
| CAAAGCCCAA | GCCGCCCGGC | CTTGTTCCGG | CACTTGAGAA | TGCGATCGCC | ATCGTCGATT | 1631 |
| ACATCAACGG | TACACCGCCC | CATATCGCGT | CCCTGGCGGA | GCTTTCAACG | ACGCTCGGGA | 1691 |

TATCCAAGAG CCACTGTCAC TCCATCCTCA AGACGCTGAC GCATTTCGGC TGGCTGAAAT    1751

TCGACAATCG CTCAAAGAGC TACGAGCTGA ATTC    1785

( 2 ) INFORMATION FOR SEQ ID NO:6:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Thr  Arg  Gln  Met  Ile  Leu  Ala  Val  Gly  Gln  Gln  Gly  Pro  Ile  Ala  Arg
 1              5                        10                       15
Ala  Glu  Thr  Arg  Glu  Gln  Val  Val  Arg  Leu  Leu  Asp  Met  Leu  Thr
              20                       25                       30
Lys  Ala  Ala  Ser  Arg  Gly  Ala  Asn  Phe  Ile  Val  Phe  Pro  Glu  Leu  Ala
              35                       40                       45
Leu  Thr  Thr  Phe  Phe  Pro  Arg  Trp  His  Phe  Thr  Asp  Glu  Ala  Glu  Leu
       50                       55                       60
Asp  Ser  Phe  Tyr  Glu  Thr  Glu  Met  Pro  Gly  Pro  Val  Val  Arg  Pro  Leu
 65                       70                       75                       80
Phe  Glu  Lys  Ala  Ala  Glu  Leu  Gly  Ile  Gly  Phe  Asn  Leu  Gly  Tyr  Ala
                   85                       90                       95
Glu  Leu  Val  Val  Glu  Gly  Gly  Val  Lys  Arg  Arg  Phe  Asn  Thr  Ser  Ile
                  100                      105                     110
Leu  Val  Asp  Lys  Ser  Gly  Lys  Ile  Val  Gly  Lys  Tyr  Arg  Lys  Ile  His
             115                      120                      125
Leu  Pro  Gly  His  Lys  Glu  Tyr  Glu  Ala  Tyr  Arg  Pro  Phe  Gln  His  Leu
     130                      135                      140
Glu  Lys  Arg  Tyr  Phe  Glu  Pro  Gly  Asp  Leu  Gly  Phe  Pro  Val  Tyr  Asp
145                      150                      155                      160
Val  Asp  Ala  Ala  Lys  Met  Gly  Met  Phe  Ile  Cys  Asn  Asp  Arg  Arg  Trp
                  165                      170                      175
Pro  Glu  Ala  Trp  Arg  Val  Met  Gly  Leu  Arg  Gly  Ala  Glu  Ile  Ile  Cys
                  180                      185                      190
Gly  Gly  Tyr  Asn  Thr  Pro  Thr  His  Asn  Pro  Leu  Val  Pro  Gln  His  Asp
             195                      200                      205
His  Leu  Thr  Ser  Phe  His  His  Leu  Leu  Ser  Met  Gln  Ala  Gly  Ser  Tyr
     210                      215                      220
Gln  Asn  Gly  Ala  Trp  Ser  Ala  Ala  Ala  Gly  Lys  Val  Gly  Met  Glu  Glu
225                      230                      235                      240
Asn  Cys  Met  Leu  Leu  Gly  His  Ser  Cys  Ile  Val  Ala  Pro  Thr  Gly  Glu
                  245                      250                      255
Ile  Val  Ala  Leu  Thr  Thr  Thr  Leu  Glu  Asp  Glu  Val  Ile  Thr  Ala  Ala
             260                      265                      270
Val  Asp  Leu  Asp  Arg  Cys  Arg  Glu  Leu  Arg  Glu  His  Ile  Phe  Asn  Phe
             275                      280                      285
Lys  Gln  His  Arg  Gln  Pro  Gln  His  Tyr  Gly  Leu  Ile  Ala  Glu  Leu
     290                      295                      300
```

( 2 ) INFORMATION FOR SEQ ID NO:7:

( i ) SEQUENCE CHARACTERISTICS:
        ( A ) LENGTH: 1785 base pairs
        ( B ) TYPE: nucleic acid (C) STRANDEDNESS: double
(D) TOPOLOGY: linear (vi) ORIGINAL SOURCE:
(B) STRAIN: JM109 pAD406 (FERM BP- 3914)

(ix) FEATURE:
(A) NAME/KEY: CDS
(B) LOCATION: 233..1144

(xi) SEQUENCE DESCRIPTION: SEQ ID NO:7:

```
GTCGACGGCG GGCTCGCGCG AGAGCTTGTC AAGCAGCGCA AATTCCGGTT CCGCTCCGGT         60

TGACAGATCA AAAATTTTAC GCCTGTTATT GTCGTGCTGC ATGTAATATT TCGTACTTTA        120

TGTAGAATTT GCATTGCGCC GCGAGTCACA AAGCCGGTTT TCGGCGATGT GTTTCACAAC        180

GTTTTCCCGG CCGCTGGGCC GGACATCACC TAGGAAGGAG CAGAGGTTCA TG ACA           235
                                                         Thr
                                                          1
```

| | | | | | | | | | | | | | | | | |
|---|---|---|---|---|---|---|---|---|---|---|---|---|---|---|---|---|
| CGT | CAG | ATG | ATA | CTT | GCA | GTG | GGA | CAA | CAA | GGT | CCG | ATC | GCG | CGC | GCG | 283 |
| Arg | Gln | Met | Ile | Leu | Ala | Val | Gly | Gln | Gln | Gly | Pro | Ile | Ala | Arg | Ala | |
| | | | 5 | | | | | 10 | | | | | 15 | | | |
| GAG | ACA | CGC | GAA | CAG | GTC | GTC | GTT | CGT | CTT | CTC | GAC | ATG | CTG | ACG | AAA | 331 |
| Glu | Thr | Arg | Glu | Gln | Val | Val | Val | Arg | Leu | Leu | Asp | Met | Leu | Thr | Lys | |
| | | 20 | | | | | 25 | | | | | 30 | | | | |
| GCC | GCG | AGC | CGG | GGC | GCG | AAT | TTC | ATT | GTC | TTC | CCC | GAA | CTC | GCG | CTT | 379 |
| Ala | Ala | Ser | Arg | Gly | Ala | Asn | Phe | Ile | Val | Phe | Pro | Glu | Leu | Ala | Leu | |
| | 35 | | | | | 40 | | | | | 45 | | | | | |
| ACG | ACC | TTC | TTC | CCG | CGC | TGG | CAT | TTC | ACC | GAC | GAG | GCC | GAG | CTC | GAT | 427 |
| Thr | Thr | Phe | Phe | Pro | Arg | Trp | His | Phe | Thr | Asp | Glu | Ala | Glu | Leu | Asp | |
| 50 | | | | | 55 | | | | | 60 | | | | | 65 | |
| AGC | TTC | TAT | GAG | ACC | GAA | ATG | CCC | GGC | CCG | GTG | GTC | CGT | CCA | CTC | TTT | 475 |
| Ser | Phe | Tyr | Glu | Thr | Glu | Met | Pro | Gly | Pro | Val | Val | Arg | Pro | Leu | Phe | |
| | | | | 70 | | | | | 75 | | | | | 80 | | |
| GAG | AAG | GCC | GCG | GAA | CTC | GGG | ATC | GGC | TTC | AAT | CTG | GGC | TAC | GCT | GAA | 523 |
| Glu | Lys | Ala | Ala | Glu | Leu | Gly | Ile | Gly | Phe | Asn | Leu | Gly | Tyr | Ala | Glu | |
| | | | | 85 | | | | | 90 | | | | | 95 | | |
| CTC | GTC | GTC | GAA | GGC | GGC | GTC | AAG | CGT | CGC | TTC | AAC | ACG | TCC | ATT | TTG | 571 |
| Leu | Val | Val | Glu | Gly | Gly | Val | Lys | Arg | Arg | Phe | Asn | Thr | Ser | Ile | Leu | |
| | | 100 | | | | | 105 | | | | | 110 | | | | |
| GTG | GAT | AAG | TCA | GGC | AAG | ATC | GTC | GGC | AAG | TAT | CGT | AAG | ATC | CAT | TTG | 619 |
| Val | Asp | Lys | Ser | Gly | Lys | Ile | Val | Gly | Lys | Tyr | Arg | Lys | Ile | His | Leu | |
| | 115 | | | | | 120 | | | | | 125 | | | | | |
| CCG | GGT | CAC | AAG | GAG | TAC | GAG | GCC | TAC | CGG | CCG | TTC | CAG | CAT | CTT | GAA | 667 |
| Pro | Gly | His | Lys | Glu | Tyr | Glu | Ala | Tyr | Arg | Pro | Phe | Gln | His | Leu | Glu | |
| 130 | | | | | 135 | | | | | 140 | | | | | 145 | |
| AAG | CGT | TAT | TTC | GAG | CCG | GGC | GAT | CTC | GGC | TTC | CCG | GTC | TAT | GAC | GTC | 715 |
| Lys | Arg | Tyr | Phe | Glu | Pro | Gly | Asp | Leu | Gly | Phe | Pro | Val | Tyr | Asp | Val | |
| | | | | 150 | | | | | 155 | | | | | 160 | | |
| GAC | GCC | GCG | AAA | ATG | GGG | ATG | TTC | ATC | TGC | AAC | GAT | CGC | CGC | TGG | CCT | 763 |
| Asp | Ala | Ala | Lys | Met | Gly | Met | Phe | Ile | Cys | Asn | Asp | Arg | Arg | Trp | Pro | |
| | | | 165 | | | | | 170 | | | | | 175 | | | |
| GAA | GCC | TGG | CGG | GTG | ATG | GGC | CTC | AGG | GGC | GCC | GAG | ATC | ATC | TGC | GGC | 811 |
| Glu | Ala | Trp | Arg | Val | Met | Gly | Leu | Arg | Gly | Ala | Glu | Ile | Ile | Cys | Gly | |
| | | 180 | | | | | 185 | | | | | 190 | | | | |
| GGC | TAC | AAC | ACG | CCG | ACC | CAC | AAT | CCC | TCT | GTT | CCC | CAG | CAC | GAC | CAC | 859 |
| Gly | Tyr | Asn | Thr | Pro | Thr | His | Asn | Pro | Ser | Val | Pro | Gln | His | Asp | His | |
| | 195 | | | | | 200 | | | | | 205 | | | | | |
| CTG | ACG | TCC | TTC | CAC | CAT | CTC | CTA | TCG | ATG | CAG | GCC | GGG | TCT | TAT | CAG | 907 |
| Leu | Thr | Ser | Phe | His | His | Leu | Leu | Ser | Met | Gln | Ala | Gly | Ser | Tyr | Gln | |
| 210 | | | | | 215 | | | | | 220 | | | | | 225 | |
| AAC | GGG | GCC | TGG | TCC | GCG | GCC | GCG | GGC | AAG | GTG | GGC | ATG | GAG | GAG | AAC | 955 |
| Asn | Gly | Ala | Trp | Ser | Ala | Ala | Ala | Gly | Lys | Val | Gly | Met | Glu | Glu | Asn | |

|  |  |  |  |  |  |  |  |  |  |  |  |  |  |  |  |
|---|---|---|---|---|---|---|---|---|---|---|---|---|---|---|---|
|  |  |  | 230 |  |  |  |  | 235 |  |  |  |  | 240 |  |  |
| TGC | ATG | CTG | CTC | GGC | CAC | TCC | TGC | ATC | GTG | GCG | CCG | ACC | GGG | GAA | ATC | 1003 |
| Cys | Met | Leu | Leu | Gly | His | Ser | Cys | Ile | Val | Ala | Pro | Thr | Gly | Glu | Ile |  |
|  |  |  | 245 |  |  |  |  | 250 |  |  |  |  | 255 |  |  |
| GTC | GCT | CTC | ACT | ACG | ACG | CTG | GAA | GAC | GAG | GTG | ATC | ACC | GCC | GCC | GTC | 1051 |
| Val | Ala | Leu | Thr | Thr | Thr | Leu | Glu | Asp | Glu | Val | Ile | Thr | Ala | Ala | Val |  |
|  |  |  | 260 |  |  |  |  | 265 |  |  |  |  | 270 |  |  |
| GAT | CTC | GAT | CGC | TGC | CGG | GAA | CTG | CGT | GAA | CAC | ATC | TTC | AAC | TTC | AAG | 1099 |
| Asp | Leu | Asp | Arg | Cys | Arg | Glu | Leu | Arg | Glu | His | Ile | Phe | Asn | Phe | Lys |  |
|  |  |  | 275 |  |  |  |  | 280 |  |  |  |  | 285 |  |  |
| CAG | CAT | CGT | CAG | CCC | CAG | CAC | TAT | GGT | CTG | ATC | GCG | GAA | CTC | TGAGGTTGCC |  | 1151 |
| Gln | His | Arg | Gln | Pro | Gln | His | Tyr | Gly | Leu | Ile | Ala | Glu | Leu |  |  |  |
| 290 |  |  |  |  | 295 |  |  |  |  | 300 |  |  |  |  |  |  |

| GAAAAGCATG | TGTGTCGTTG | TTCTCGGCGC | CTGGGTCACA | TCCAGGCGCG | CCAGGGTGAC | 1211 |
| GCTGGTGGAA | TAGTACCACG | ACCGCTTCAG | GGCGATCCGC | AAGGAGATGC | GGGTCGCCGG | 1271 |
| AGCGGCAAAG | CCCGACATTC | GTTTCGCACC | GACGGCCGTC | GTGAACTCGA | CAGTCCGCGA | 1331 |
| GAAGGGCGTA | TTGCGCGGCC | TGGACCTGTA | CGTGGAACTG | TAGCCCATAT | ATAGATTTCC | 1391 |
| AAAGAGTTTC | GGCGAGGCGC | GGCGCGCCTA | GCCCCATGTG | AGCGAGAACC | GTGCCCAGAT | 1451 |
| CAAAGAATGA | GACCGACGCG | CCGGCCGCGG | CAAAGGATGA | TCCTCAGGGT | CGGATCTATC | 1511 |
| GCTCCGCCCT | GAAGCAGGAG | GGCGCACGCT | GGCTGCTGAC | GGCGGAGGAA | GGGTTGCTGG | 1571 |
| CAAAGCCCAA | GCCGCCCGGC | CTTGTTCCGG | CACTTGAGAA | TGCGATCGCC | ATCGTCGATT | 1631 |
| ACATCAACGG | TACACCGCCC | CATATCGCGT | CCCTGGCGGA | GCTTTCAACG | ACGCTCGGGA | 1691 |
| TATCCAAGAG | CCACTGTCAC | TCCATCCTCA | AGACGCTGAC | GCATTTCGGC | TGGCTGAAAT | 1751 |
| TCGACAATCG | CTCAAAGAGC | TACGAGCTGA | ATTC |  |  | 1785 |

( 2 ) INFORMATION FOR SEQ ID NO:8:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Thr | Arg | Gln | Met | Ile | Leu | Ala | Val | Gly | Gln | Gln | Gly | Pro | Ile | Ala | Arg |
|---|---|---|---|---|---|---|---|---|---|---|---|---|---|---|---|
| 1 |  |  |  | 5 |  |  |  |  | 10 |  |  |  |  | 15 |  |
| Ala | Glu | Thr | Arg | Glu | Gln | Val | Val | Arg | Leu | Leu | Asp | Met | Leu | Thr |  |
|  |  |  | 20 |  |  |  | 25 |  |  |  |  | 30 |  |  |  |
| Lys | Ala | Ala | Ser | Arg | Gly | Ala | Asn | Phe | Ile | Val | Phe | Pro | Glu | Leu | Ala |
|  |  | 35 |  |  |  |  | 40 |  |  |  |  | 45 |  |  |  |
| Leu | Thr | Thr | Phe | Phe | Pro | Arg | Trp | His | Phe | Thr | Asp | Glu | Ala | Glu | Leu |
|  | 50 |  |  |  |  | 55 |  |  |  |  | 60 |  |  |  |  |
| Asp | Ser | Phe | Tyr | Glu | Thr | Glu | Met | Pro | Gly | Pro | Val | Val | Arg | Pro | Leu |
| 65 |  |  |  |  | 70 |  |  |  |  | 75 |  |  |  |  | 80 |
| Phe | Glu | Lys | Ala | Ala | Glu | Leu | Gly | Ile | Gly | Phe | Asn | Leu | Gly | Tyr | Ala |
|  |  |  |  | 85 |  |  |  |  | 90 |  |  |  |  | 95 |  |
| Glu | Leu | Val | Val | Glu | Gly | Gly | Val | Lys | Arg | Arg | Phe | Asn | Thr | Ser | Ile |
|  |  |  |  | 100 |  |  |  |  | 105 |  |  |  |  | 110 |  |
| Leu | Val | Asp | Lys | Ser | Gly | Lys | Ile | Val | Gly | Lys | Tyr | Arg | Lys | Ile | His |
|  |  |  | 115 |  |  |  |  | 120 |  |  |  |  | 125 |  |  |
| Leu | Pro | Gly | His | Lys | Glu | Tyr | Glu | Ala | Tyr | Arg | Pro | Phe | Gln | His | Leu |
|  |  | 130 |  |  |  |  | 135 |  |  |  |  | 140 |  |  |  |
| Glu | Lys | Arg | Tyr | Phe | Glu | Pro | Gly | Asp | Leu | Gly | Phe | Pro | Val | Tyr | Asp |

| | | | | | | | | | | | | | | | |
|---|---|---|---|---|---|---|---|---|---|---|---|---|---|---|---|
|145| | | | |150| | | | |155| | | | |160|

Val Asp Ala Ala Lys Met Gly Met Phe Ile Cys Asn Asp Arg Arg Trp
              165                 170                 175

Pro Glu Ala Trp Arg Val Met Gly Leu Arg Gly Ala Glu Ile Ile Cys
              180                 185                 190

Gly Gly Tyr Asn Thr Pro Thr His Asn Pro Ser Val Pro Gln His Asp
              195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
              245                 250                 255

Ile Val Ala Leu Thr Thr Thr Leu Glu Asp Val Ile Thr Ala Ala
              260                 265                 270

Val Asp Leu Asp Arg Cys Arg Glu Leu Arg Glu His Ile Phe Asn Phe
              275                 280                 285

Lys Gln His Arg Gln Pro Gln His Tyr Gly Leu Ile Ala Glu Leu
    290                 295                 300

( 2 ) INFORMATION FOR SEQ ID NO:9:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD416 (FERM BP- 3915)

( i x ) FEATURE:
        ( A ) NAME/KEY: CDS
        ( B ) LOCATION: 233..1144

( x i ) SEQUENCE DESCRIPTION: SEQ ID NO:9:

GTCGACGGCG GGCTCGCGCG AGAGCTTGTC AAGCAGCGCA AATTCCGGTT CCGCTCCGGT    60

TGACAGATCA AAAATTTTAC GCCTGTTATT GTCGTGCTGC ATGTAATATT TCGTACTTTA   120

TGTAGAATTT GCATTGCGCC GCGAGTCACA AAGCCGGTTT TCGGCGATGT GTTTCACAAC   180

GTTTTCCCGG CCGCTGGGCC GGACATCACC TAGGAAGGAG CAGAGGTTCA TG ACA    235
                                                                                                          Thr
                                                                                                           1

CGT CAG ATG ATA CTT GCA GTG GGA CAA CAA GGT CCG ATC GCG CGC GCG   283
Arg Gln Met Ile Leu Ala Val Gly Gln Gln Gly Pro Ile Ala Arg Ala
               5                          10                    15

GAG ACA CGC GAA CAG GTC GTC GTT CGT CTT CTC GAC ATG CTG ACG AAA   331
Glu Thr Arg Glu Gln Val Val Val Arg Leu Leu Asp Met Leu Thr Lys
             20                        25                      30

GCC GCG AGC CGG GGC GCG AAT TTC ATT GTC TTC CCC GAA CTC GCG CTT   379
Ala Ala Ser Arg Gly Ala Asn Phe Ile Val Phe Pro Glu Leu Ala Leu
         35                      40                      45

ACG ACC TTC TTC CCG CGC TGG CAT TTC ACC GAC GAG GCC GAG CTC GAT   427
Thr Thr Phe Phe Pro Arg Trp His Phe Thr Asp Glu Ala Glu Leu Asp
50                          55                      60                    65

AGC TTC TAT GAG ACC GAA ATG CCC GGC CCG GTG GTC CGT CCA CTC TTT   475
Ser Phe Tyr Glu Thr Glu Met Pro Gly Pro Val Val Arg Pro Leu Phe
                      70                      75                    80

GAG AAG GCC GCG GAA CTC GGG ATC GGC TTC AAT CTG GGC TAC GCT GAA   523
Glu Lys Ala Ala Glu Leu Gly Ile Gly Phe Asn Leu Gly Tyr Ala Glu
         85                      90                      95

```
CTC  GTC  GTC  GAA  GGC  GGC  GTC  AAG  CGT  CGC  TTC  AAC  ACG  TCC  ATT  TTG          571
Leu  Val  Val  Glu  Gly  Gly  Val  Lys  Arg  Arg  Phe  Asn  Thr  Ser  Ile  Leu
          100                      105                      110

GTG  GAT  AAG  TCA  GGC  AAG  ATC  GTC  GGC  AAG  TAT  CGT  AAG  ATC  CAT  TTG          619
Val  Asp  Lys  Ser  Gly  Lys  Ile  Val  Gly  Lys  Tyr  Arg  Lys  Ile  His  Leu
          115                      120                      125

CCG  GGT  CAC  AAG  GAG  TAC  GAG  GCC  TAC  CGG  CCG  TTC  CAG  CAT  CTT  GAA          667
Pro  Gly  His  Lys  Glu  Tyr  Glu  Ala  Tyr  Arg  Pro  Phe  Gln  His  Leu  Glu
130                      135                      140                      145

AAG  CGT  TAT  TTC  GAG  CCG  GGC  GAT  CTC  GGC  TTC  CCG  GTC  TAT  GAC  GTC          715
Lys  Arg  Tyr  Phe  Glu  Pro  Gly  Asp  Leu  Gly  Phe  Pro  Val  Tyr  Asp  Val
          150                      155                      160

GAC  GCC  GCG  AAA  ATG  GGG  ATG  TTC  ATC  TGC  AAC  GAT  CGC  CGC  TGG  CCT          763
Asp  Ala  Ala  Lys  Met  Gly  Met  Phe  Ile  Cys  Asn  Asp  Arg  Arg  Trp  Pro
          165                      170                      175

GAA  GCC  TGG  CGG  GTG  ATG  GGC  CTC  AGG  GGC  GCC  GAG  ATC  ATC  TGC  GGC          811
Glu  Ala  Trp  Arg  Val  Met  Gly  Leu  Arg  Gly  Ala  Glu  Ile  Ile  Cys  Gly
          180                      185                      190

GGC  TAC  AAC  ACG  CCG  ACC  CAC  AAT  CCC  CCT  GTT  CCC  CAG  CAC  GAC  CAC          859
Gly  Tyr  Asn  Thr  Pro  Thr  His  Asn  Pro  Pro  Val  Pro  Gln  His  Asp  His
          195                      200                      205

CTG  ACG  TCC  TTC  CAC  CAT  CTC  CTA  TCG  ATG  CAG  GCC  GGG  TCT  TAT  CAG          907
Leu  Thr  Ser  Phe  His  His  Leu  Leu  Ser  Met  Gln  Ala  Gly  Ser  Tyr  Gln
210                      215                      220                      225

AAC  GGG  GCC  TGG  TCC  GCG  GCC  GCG  GGC  AAG  GCG  GGC  ATG  GAG  GAG  AAC          955
Asn  Gly  Ala  Trp  Ser  Ala  Ala  Ala  Gly  Lys  Ala  Gly  Met  Glu  Glu  Asn
          230                      235                      240

TGC  ATG  CTG  CTC  GGC  CAC  TCC  TGC  ATC  GTG  GCG  CCG  ACC  GGG  GAA  ATC         1003
Cys  Met  Leu  Leu  Gly  His  Ser  Cys  Ile  Val  Ala  Pro  Thr  Gly  Glu  Ile
          245                      250                      255

GTC  GCT  CTC  ACT  ACG  ACG  CTG  GAA  GAC  GAG  GTG  ATC  ACC  GCC  GCC  GTC         1051
Val  Ala  Leu  Thr  Thr  Thr  Leu  Glu  Asp  Glu  Val  Ile  Thr  Ala  Ala  Val
          260                      265                      270

GAT  CTC  GAT  CGC  TGC  CGG  GAA  CTG  CGT  GAA  CAC  ATC  TTC  AAC  TTC  AAG         1099
Asp  Leu  Asp  Arg  Cys  Arg  Glu  Leu  Arg  Glu  His  Ile  Phe  Asn  Phe  Lys
          275                      280                      285

CAG  CAT  CGT  CAG  CCC  CAG  CAC  TAT  GGT  CTG  ATC  GCG  GAA  CTC  TGAGGTTGCC        1151
Gln  His  Arg  Gln  Pro  Gln  His  Tyr  Gly  Leu  Ile  Ala  Glu  Leu
290                      295                      300

GAAAAGCATG  TGTGTCGTTG  TTCTCGGCGC  CTGGGTCACA  TCCAGGCGCG  CCAGGGTGAC           1211

GCTGGTGGAA  TAGTACCACG  ACCGCTTCAG  GGCGATCCGC  AAGGAGATGC  GGGTCGCCGG           1271

AGCGGCAAAG  CCCGACATTC  GTTTCGCACC  GACGGCCGTC  GTGAACTCGA  CAGTCCGCGA           1331

GAAGGGCGTA  TTGCGCGGCC  TGGACCTGTA  CGTGGAACTG  TAGCCCATAT  ATAGATTTCC           1391

AAAGAGTTTC  GGCGAGGCGC  GGCGCGCCTA  GCCCCATGTG  AGCGAGAACC  GTGCCCAGAT           1451

CAAAGAATGA  GACCGACGCG  CCGGCCGCGG  CAAAGGATGA  TCCTCAGGGT  CGGATCTATC           1511

GCTCCGCCCT  GAAGCAGGAG  GGCGCACGCT  GGCTGCTGAC  GGCGGAGGAA  GGGTTGCTGG           1571

CAAAGCCCAA  GCCGCCCGGC  CTTGTTCCGG  CACTTGAGAA  TGCGATCGCC  ATCGTCGATT           1631

ACATCAACGG  TACACCGCCC  CATATCGCGT  CCCTGGCGGA  GCTTTCAACG  ACGCTCGGGA           1691

TATCCAAGAG  CCACTGTCAC  TCCATCCTCA  AGACGCTGAC  GCATTTCGGC  TGGCTGAAAT           1751

TCGACAATCG  CTCAAAGAGC  TACGAGCTGA  ATTC                                        1785
```

( 2 ) INFORMATION FOR SEQ ID NO:10:

( i ) SEQUENCE CHARACTERISTICS:
    ( A ) LENGTH: 303 amino acids (B) TYPE: amino acid
(D) TOPOLOGY: linear (i i) MOLECULE TYPE: protein (x i) SEQUENCE DESCRIPTION: SEQ ID NO:10:

| Thr | Arg | Gln | Met | Ile | Leu | Ala | Val | Gly | Gln | Gln | Gly | Pro | Ile | Ala | Arg |
|---|---|---|---|---|---|---|---|---|---|---|---|---|---|---|---|
| 1 | | | | 5 | | | | | 10 | | | | | 15 | |

| Ala | Glu | Thr | Arg | Glu | Gln | Val | Val | Val | Arg | Leu | Leu | Asp | Met | Leu | Thr |
|---|---|---|---|---|---|---|---|---|---|---|---|---|---|---|---|
| | | | 20 | | | | | 25 | | | | | 30 | | |

| Lys | Ala | Ala | Ser | Arg | Gly | Ala | Asn | Phe | Ile | Val | Phe | Pro | Glu | Leu | Ala |
|---|---|---|---|---|---|---|---|---|---|---|---|---|---|---|---|
| | | 35 | | | | | 40 | | | | | 45 | | | |

| Leu | Thr | Thr | Phe | Phe | Pro | Arg | Trp | His | Phe | Thr | Asp | Glu | Ala | Glu | Leu |
|---|---|---|---|---|---|---|---|---|---|---|---|---|---|---|---|
| | 50 | | | | | 55 | | | | | 60 | | | | |

| Asp | Ser | Phe | Tyr | Glu | Thr | Glu | Met | Pro | Gly | Pro | Val | Val | Arg | Pro | Leu |
|---|---|---|---|---|---|---|---|---|---|---|---|---|---|---|---|
| 65 | | | | | 70 | | | | | 75 | | | | | 80 |

| Phe | Glu | Lys | Ala | Ala | Glu | Leu | Gly | Ile | Gly | Phe | Asn | Leu | Gly | Tyr | Ala |
|---|---|---|---|---|---|---|---|---|---|---|---|---|---|---|---|
| | | | | 85 | | | | | 90 | | | | | 95 | |

| Glu | Leu | Val | Val | Glu | Gly | Gly | Val | Lys | Arg | Arg | Phe | Asn | Thr | Ser | Ile |
|---|---|---|---|---|---|---|---|---|---|---|---|---|---|---|---|
| | | | 100 | | | | | 105 | | | | | 110 | | |

| Leu | Val | Asp | Lys | Ser | Gly | Lys | Ile | Val | Gly | Lys | Tyr | Arg | Lys | Ile | His |
|---|---|---|---|---|---|---|---|---|---|---|---|---|---|---|---|
| | | 115 | | | | | 120 | | | | | 125 | | | |

| Leu | Pro | Gly | His | Lys | Glu | Tyr | Glu | Ala | Tyr | Arg | Pro | Phe | Gln | His | Leu |
|---|---|---|---|---|---|---|---|---|---|---|---|---|---|---|---|
| | 130 | | | | | 135 | | | | | 140 | | | | |

| Glu | Lys | Arg | Tyr | Phe | Glu | Pro | Gly | Asp | Leu | Gly | Phe | Pro | Val | Tyr | Asp |
|---|---|---|---|---|---|---|---|---|---|---|---|---|---|---|---|
| 145 | | | | | 150 | | | | | 155 | | | | | 160 |

| Val | Asp | Ala | Ala | Lys | Met | Gly | Met | Phe | Ile | Cys | Asn | Asp | Arg | Arg | Trp |
|---|---|---|---|---|---|---|---|---|---|---|---|---|---|---|---|
| | | | | 165 | | | | | 170 | | | | | 175 | |

| Pro | Glu | Ala | Trp | Arg | Val | Met | Gly | Leu | Arg | Gly | Ala | Glu | Ile | Ile | Cys |
|---|---|---|---|---|---|---|---|---|---|---|---|---|---|---|---|
| | | | 180 | | | | | 185 | | | | | 190 | | |

| Gly | Gly | Tyr | Asn | Thr | Pro | Thr | His | Asn | Pro | Pro | Val | Pro | Gln | His | Asp |
|---|---|---|---|---|---|---|---|---|---|---|---|---|---|---|---|
| | | 195 | | | | | 200 | | | | | 205 | | | |

| His | Leu | Thr | Ser | Phe | His | His | Leu | Leu | Ser | Met | Gln | Ala | Gly | Ser | Tyr |
|---|---|---|---|---|---|---|---|---|---|---|---|---|---|---|---|
| | 210 | | | | | 215 | | | | | 220 | | | | |

| Gln | Asn | Gly | Ala | Trp | Ser | Ala | Ala | Ala | Gly | Lys | Ala | Gly | Met | Glu | Glu |
|---|---|---|---|---|---|---|---|---|---|---|---|---|---|---|---|
| 225 | | | | | 230 | | | | | 235 | | | | | 240 |

| Asn | Cys | Met | Leu | Leu | Gly | His | Ser | Cys | Ile | Val | Ala | Pro | Thr | Gly | Glu |
|---|---|---|---|---|---|---|---|---|---|---|---|---|---|---|---|
| | | | | 245 | | | | | 250 | | | | | 255 | |

| Ile | Val | Ala | Leu | Thr | Thr | Thr | Leu | Glu | Asp | Glu | Val | Ile | Thr | Ala | Ala |
|---|---|---|---|---|---|---|---|---|---|---|---|---|---|---|---|
| | | | 260 | | | | | 265 | | | | | 270 | | |

| Val | Asp | Leu | Asp | Arg | Cys | Arg | Glu | Leu | Arg | Glu | His | Ile | Phe | Asn | Phe |
|---|---|---|---|---|---|---|---|---|---|---|---|---|---|---|---|
| | | 275 | | | | | 280 | | | | | 285 | | | |

| Lys | Gln | His | Arg | Gln | Pro | Gln | His | Tyr | Gly | Leu | Ile | Ala | Glu | Leu |
|---|---|---|---|---|---|---|---|---|---|---|---|---|---|---|
| | 290 | | | | | 295 | | | | | 300 | | | |

(2) INFORMATION FOR SEQ ID NO:11:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (v i) ORIGINAL SOURCE:
        (B) STRAIN: JM109 pAD428

(i x) FEATURE:
        (A) NAME/KEY: CDS
        (B) LOCATION: 233..1144

( x i ) SEQUENCE DESCRIPTION: SEQ ID NO:11:

```
GTCGACGGCG GGCTCGCGCG AGAGCTTGTC AAGCAGCGCA AATTCCGGTT CCGCTCCGGT        60

TGACAGATCA AAAATTTTAC GCCTGTTATT GTCGTGCTGC ATGTAATATT TCGTACTTTA       120

TGTAGAATTT GCATTGCGCC GCGAGTCACA AAGCCGGTTT TCGGCGATGT GTTTCACAAC       180

GTTTTCCCGG CCGCTGGGCC GGACATCACC TAGGAAGGAG CAGAGGTTCA TG ACA           235
                                                        Thr
                                                         1

CGT CAG ATG ATA CTT GCA GTG GGA CAA CAA GGT CCG ATC GCG CGC GCG        283
Arg Gln Met Ile Leu Ala Val Gly Gln Gln Gly Pro Ile Ala Arg Ala
             5                  10                  15

GAG ACA CGC GAA CAG GTC GTC GTT CGT CTT CTC GAC ATG CTG ACG AAA        331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT        379
Ala Ala Ser Arg Gly Ala Asn Phe Ile Val Phe Pro Glu Leu Ala Leu
     35                  40                  45

ACG ACC TTC TTC CCG CGC TGG CAT TTC ACC GAC GAG GCC GAG CTC GAT        427
Thr Thr Phe Phe Pro Arg Trp His Phe Thr Asp Glu Ala Glu Leu Asp
 50              55                  60                      65

AGC TTC TAT GAG ACC GAA ATG CCC GGC CCG GTG GTC CGT CCA CTC TTT        475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA        523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG        571
Leu Val Val Glu Gly Gly Val Lys Arg Arg Phe Asn Thr Ser Ile Leu
             100                 105                 110

GTG GAT AAG TCA GGC AAG ATC GTC GGC AAG TAT CGT AAG ATC CAT TTG        619
Val Asp Lys Ser Gly Lys Ile Val Gly Lys Tyr Arg Lys Ile His Leu
     115                 120                 125

CCG GGT CAC AAG GAG TAC GAG GCC TAC CGG CCG TTC CAG CAT CTT GAA        667
Pro Gly His Lys Glu Tyr Glu Ala Tyr Arg Pro Phe Gln His Leu Glu
130             135                 140                     145

AAG CGT TAT TTC GAG CCG GGC GAT CTC GGC TTC CCG GTC TAT GAC GTC        715
Lys Arg Tyr Phe Glu Pro Gly Asp Leu Gly Phe Pro Val Tyr Asp Val
                 150                 155                 160

GAC GCC GCG AAA ATG GGG ATG TTC ATC TGC AAC GAT CGC CGC TGG CCT        763
Asp Ala Ala Lys Met Gly Met Phe Ile Cys Asn Asp Arg Arg Trp Pro
             165                 170                 175

GAA GCC TGG CGG GTG ATG GGC CTC AGG GGC GCC GAG ATC ATC TGC GGC        811
Glu Ala Trp Arg Val Met Gly Leu Arg Gly Ala Glu Ile Ile Cys Gly
             180                 185                 190

GGC TAC AAC ACG CCG ACC CAC AAT CCC CCT GTT CCC CAG CAC GAC CAC        859
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG        907
Leu Thr Ser Phe His His Leu Leu Ser Met Gln Ala Gly Ser Tyr Gln
210             215                 220                     225

AAC GGG GCC TGG TCC GCG GCC GCG GGC AAG GCC GGC ATG GAG GAG AAC        955
Asn Gly Ala Trp Ser Ala Ala Ala Gly Lys Ala Gly Met Glu Glu Asn
                 230                 235                 240

TGC ATG CTG CTC GGC CAC TCC TGC ATC GTG GCG CCG ACC GGG GAA ATC       1003
Cys Met Leu Leu Gly His Ser Cys Ile Val Ala Pro Thr Gly Glu Ile
             245                 250                 255

GTC GCT CTC ACT ACG ACG CTG GAA GAC GAG GTG ATC ACC GCC GCC GTC       1051
Val Ala Leu Thr Thr Thr Leu Glu Asp Glu Val Ile Thr Ala Ala Val
             260                 265                 270
```

```
GAT  CTC  GAT  CGC  TGC  CGG  GAA  CTG  CGT  GAA  CAC  ATC  TTC  AAC  TTC  AAG              1099
Asp  Leu  Asp  Arg  Cys  Arg  Glu  Leu  Arg  Glu  His  Ile  Phe  Asn  Phe  Lys
     275                 280                      285

CAG  CAT  CGT  CAG  CCC  CAG  CAC  TAT  GGT  CTG  ATC  GCG  GAA  CTC  TGAGGTTGCC            1151
Gln  His  Arg  Gln  Pro  Gln  His  Tyr  Gly  Leu  Ile  Ala  Glu  Leu
290                      295                      300

GAAAAGCATG  TGTGTCGTTG  TTCTCGGCGC  TGGGTCACA  TCCAGGCGCG  CCAGGGTGAC                       1211
GCTGGTGGAA  TAGTACCACG  ACCGCTTCAG  GGCGATCCGC  AAGGAGATGC  GGGTCGCCGG                       1271
AGCGGCAAAG  CCCGACATTC  GTTTCGCACC  GACGGCCGTC  GTGAACTCGA  CAGTCCGCGA                       1331
GAAGGGCGTA  TTGCGCGGCC  TGGACCTGTA  CGTGGAACTG  TAGCCCATAT  ATAGATTTCC                       1391
AAAGAGTTTC  GGCGAGGCGC  GGCGCGCCTA  GCCCCATGTG  AGCGAGAACC  GTGCCCAGAT                       1451
CAAAGAATGA  GACCGACGCG  CCGGCCGCGG  CAAAGGATGA  TCCTCAGGGT  CGGATCTATC                       1511
GCTCCGCCCT  GAAGCAGGAG  GGCGCACGCT  GGCTGCTGAC  GGCGGAGGAA  GGGTTGCTGG                       1571
CAAAGCCCAA  GCCGCCCGGC  CTTGTTCCGG  CACTTGAGAA  TGCGATCGCC  ATCGTCGATT                       1631
ACATCAACGG  TACACCGCCC  CATATCGCGT  CCCTGGCGGA  GCTTTCAACG  ACGCTCGGGA                       1691
TATCCAAGAG  CCACTGTCAC  TCCATCCTCA  AGACGCTGAC  GCATTTCGGC  TGGCTGAAAT                       1751
TCGACAATCG  CTCAAGAGC  TACGAGCTGA  ATTC                                                     1785
```

(2) INFORMATION FOR SEQ ID NO:12:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:12:

```
Thr  Arg  Gln  Met  Ile  Leu  Ala  Val  Gly  Gln  Gln  Gly  Pro  Ile  Ala  Arg
  1                   5                        10                       15

Ala  Glu  Thr  Arg  Glu  Gln  Val  Val  Arg  Leu  Leu  Asp  Met  Leu  Thr
               20                       25                       30

Lys  Ala  Ala  Ser  Arg  Gly  Ala  Asn  Phe  Ile  Val  Phe  Pro  Glu  Leu  Ala
               35                       40                       45

Leu  Thr  Thr  Phe  Phe  Pro  Arg  Trp  His  Phe  Thr  Asp  Glu  Ala  Glu  Leu
      50                        55                       60

Asp  Ser  Phe  Tyr  Glu  Thr  Glu  Met  Pro  Gly  Pro  Val  Val  Arg  Pro  Leu
 65                         70                       75                        80

Phe  Glu  Lys  Ala  Ala  Glu  Leu  Gly  Ile  Gly  Phe  Asn  Leu  Gly  Tyr  Ala
                    85                        90                       95

Glu  Leu  Val  Val  Glu  Gly  Gly  Val  Lys  Arg  Arg  Phe  Asn  Thr  Ser  Ile
                    100                       105                      110

Leu  Val  Asp  Lys  Ser  Gly  Lys  Ile  Val  Gly  Lys  Tyr  Arg  Lys  Ile  His
               115                       120                      125

Leu  Pro  Gly  His  Lys  Glu  Tyr  Glu  Ala  Tyr  Arg  Pro  Phe  Gln  His  Leu
      130                       135                      140

Glu  Lys  Arg  Tyr  Phe  Glu  Pro  Gly  Asp  Leu  Gly  Phe  Pro  Val  Tyr  Asp
145                       150                      155                       160

Val  Asp  Ala  Ala  Lys  Met  Gly  Met  Phe  Ile  Cys  Asn  Asp  Arg  Arg  Trp
                    165                       170                      175

Pro  Glu  Ala  Trp  Arg  Val  Met  Gly  Leu  Arg  Gly  Ala  Glu  Ile  Ile  Cys
                    180                       185                      190

Gly  Gly  Tyr  Asn  Thr  Pro  Thr  His  Asn  Pro  Pro  Val  Pro  Gln  His  Asp
               195                       200                      205
```

| His | Leu | Thr | Ser | Phe | His | His | Leu | Leu | Ser | Met | Gln | Ala | Gly | Ser | Tyr |
| | 210 | | | | | 215 | | | | | 220 | | | | |

| Gln | Asn | Gly | Ala | Trp | Ser | Ala | Ala | Ala | Gly | Lys | Ala | Gly | Met | Glu | Glu |
| 225 | | | | | 230 | | | | | 235 | | | | | 240 |

| Asn | Cys | Met | Leu | Leu | Gly | His | Ser | Cys | Ile | Val | Ala | Pro | Thr | Gly | Glu |
| | | | | 245 | | | | | 250 | | | | | 255 | |

| Ile | Val | Ala | Leu | Thr | Thr | Thr | Leu | Glu | Asp | Glu | Val | Ile | Thr | Ala | Ala |
| | | | 260 | | | | | 265 | | | | | 270 | | |

| Val | Asp | Leu | Asp | Arg | Cys | Arg | Glu | Leu | Arg | Glu | His | Ile | Phe | Asn | Phe |
| | | 275 | | | | | 280 | | | | | 285 | | | |

| Lys | Gln | His | Arg | Gln | Pro | Gln | His | Tyr | Gly | Leu | Ile | Ala | Glu | Leu | |
| | 290 | | | | | 295 | | | | | 300 | | | | |

( 2 ) INFORMATION FOR SEQ ID NO:13:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD429

( i x ) FEATURE:
        ( A ) NAME/KEY: CDS
        ( B ) LOCATION: 233..1144

( x i ) SEQUENCE DESCRIPTION: SEQ ID NO:13:

```
GTCGACGGCG GGCTCGCGCG AGAGCTTGTC AAGCAGCGCA AATTCCGGTT CCGCTCCGGT        60

TGACAGATCA AAAATTTTAC GCCTGTTATT GTCGTGCTGC ATGTAATATT TCGTACTTTA       120

TGTAGAATTT GCATTGCGCC GCGAGTCACA AAGCCGGTTT TCGGCGATGT GTTTCACAAC       180

GTTTTCCCGG CCGCTGGGCC GGACATCACC TAGGAAGGAG CAGAGGTTCA TG ACA           235
                                                       Thr
                                                        1
```

| CGT | CAG | ATG | ATA | CTT | GCA | GTG | GGA | CAA | CAA | GGT | CCG | ATC | GCG | CGC | GCG | 283 |
| Arg | Gln | Met | Ile | Leu | Ala | Val | Gly | Gln | Gln | Gly | Pro | Ile | Ala | Arg | Ala | |
| | | | 5 | | | | | 10 | | | | | 15 | | | |

| GAG | ACA | CGC | GAA | CAG | GTC | GTC | GTT | CGT | CTT | CTC | GAC | ATG | CTG | ACG | AAA | 331 |
| Glu | Thr | Arg | Glu | Gln | Val | Val | Val | Arg | Leu | Leu | Asp | Met | Leu | Thr | Lys | |
| | | 20 | | | | | 25 | | | | | 30 | | | | |

| GCC | GCG | AGC | CGG | GGC | GCG | AAT | TTC | ATT | GTC | TTC | CCC | GAA | CTC | GCG | CTT | 379 |
| Ala | Ala | Ser | Arg | Gly | Ala | Asn | Phe | Ile | Val | Phe | Pro | Glu | Leu | Ala | Leu | |
| | | 35 | | | | 40 | | | | | 45 | | | | | |

| ACG | ACC | TTC | TTC | CCG | CGC | TGG | CAT | TTC | ACC | GAC | GAG | GCC | GAG | CTC | GAT | 427 |
| Thr | Thr | Phe | Phe | Pro | Arg | Trp | His | Phe | Thr | Asp | Glu | Ala | Glu | Leu | Asp | |
| 50 | | | | | 55 | | | | | 60 | | | | | 65 | |

| AGC | TTC | TAT | GAG | ACC | GAA | ATG | CCC | GGC | CCG | GTG | GTC | CGT | CCA | CTC | TTT | 475 |
| Ser | Phe | Tyr | Glu | Thr | Glu | Met | Pro | Gly | Pro | Val | Val | Arg | Pro | Leu | Phe | |
| | | | | 70 | | | | | 75 | | | | | 80 | | |

| GAG | AAG | GCC | GCG | GAA | CTC | GGG | ATC | GGC | TTC | AAT | CTG | GGC | TAC | GCT | GAA | 523 |
| Glu | Lys | Ala | Ala | Glu | Leu | Gly | Ile | Gly | Phe | Asn | Leu | Gly | Tyr | Ala | Glu | |
| | | | 85 | | | | | 90 | | | | | 95 | | | |

| CTC | GTC | GTC | GAA | GGC | GGC | GTC | AAG | CGT | GCC | TTC | AAC | ACG | TCC | ATT | TTG | 571 |
| Leu | Val | Val | Glu | Gly | Gly | Val | Lys | Arg | Ala | Phe | Asn | Thr | Ser | Ile | Leu | |
| | | 100 | | | | | 105 | | | | | 110 | | | | |

| GTG | GAT | AAG | TCA | GGC | AAG | ATC | GTC | GGC | AAG | TAT | CGT | AAG | ATC | CAT | TTG | 619 |
| Val | Asp | Lys | Ser | Gly | Lys | Ile | Val | Gly | Lys | Tyr | Arg | Lys | Ile | His | Leu | |
| | 115 | | | | | 120 | | | | | 125 | | | | | |

| CCG | GGT | CAC | AAG | GAG | TAC | GAG | GCC | TAC | CGG | CCG | TTC | CAG | CAT | CTT | GAA | 667 |

```
Pro  Gly  His  Lys  Glu  Tyr  Glu  Ala  Tyr  Arg  Pro  Phe  Gln  His  Leu  Glu
130            135                      140                      145

AAG  CGT  TAT  TTC  GAG  CCG  GGC  GAT  CTC  GGC  TTC  CCG  GTC  TAT  GAC  GTC        715
Lys  Arg  Tyr  Phe  Glu  Pro  Gly  Asp  Leu  Gly  Phe  Pro  Val  Tyr  Asp  Val
               150                      155                      160

GAC  GCC  GCG  AAA  ATG  GGG  ATG  TTC  ATC  TGC  AAC  GAT  CGC  CGC  TGG  CCT        763
Asp  Ala  Ala  Lys  Met  Gly  Met  Phe  Ile  Cys  Asn  Asp  Arg  Arg  Trp  Pro
               165                      170                      175

GAA  GCC  TGG  CGG  GTG  ATG  GGC  CTC  AGG  GGC  GCC  GAG  ATC  ATC  TGC  GGC        811
Glu  Ala  Trp  Arg  Val  Met  Gly  Leu  Arg  Gly  Ala  Glu  Ile  Ile  Cys  Gly
               180                      185                      190

GGC  TAC  AAC  ACG  CCG  ACC  CAC  AAT  CCC  GAA  GTT  CCC  CAG  CAC  GAC  CAC        859
Gly  Tyr  Asn  Thr  Pro  Thr  His  Asn  Pro  Glu  Val  Pro  Gln  His  Asp  His
     195                      200                      205

CTG  ACG  TCC  TTC  CAC  CAT  CTC  CTA  TCG  ATG  CAG  GCC  GGG  TCT  TAT  CAG        907
Leu  Thr  Ser  Phe  His  His  Leu  Leu  Ser  Met  Gln  Ala  Gly  Ser  Tyr  Gln
210                      215                      220                      225

AAC  GGG  GCC  TGG  TCC  GCG  GCC  GCG  GGC  AAG  GTG  GGC  ATG  GAG  GAG  AAC        955
Asn  Gly  Ala  Trp  Ser  Ala  Ala  Ala  Gly  Lys  Val  Gly  Met  Glu  Glu  Asn
               230                      235                      240

TGC  ATG  CTG  CTC  GGC  CAC  TCC  TGC  ATC  GTG  GCG  CCG  ACC  GGG  GAA  ATC       1003
Cys  Met  Leu  Leu  Gly  His  Ser  Cys  Ile  Val  Ala  Pro  Thr  Gly  Glu  Ile
               245                      250                      255

GTC  GCT  CTC  ACT  ACG  ACG  CTG  GAA  GAC  GAG  GTG  ATC  ACC  GCC  GCC  GTC       1051
Val  Ala  Leu  Thr  Thr  Thr  Leu  Glu  Asp  Glu  Val  Ile  Thr  Ala  Ala  Val
               260                      265                      270

GAT  CTC  GAT  CGC  TGC  CGG  GAA  CTG  CGT  GAA  CAC  ATC  TTC  AAC  TTC  AAG       1099
Asp  Leu  Asp  Arg  Cys  Arg  Glu  Leu  Arg  Glu  His  Ile  Phe  Asn  Phe  Lys
     275                      280                      285

CAG  CAT  CGT  CAG  CCC  CAG  CAC  TAT  GGT  CTG  ATC  GCG  GAA  CTC  TGAGGTTGCC     1151
Gln  His  Arg  Gln  Pro  Gln  His  Tyr  Gly  Leu  Ile  Ala  Glu  Leu
290                      295                      300

GAAAAGCATG  TGTGTCGTTG  TTCTCGGCGC  CTGGGTCACA  TCCAGGCGCG  CCAGGGTGAC              1211

GCTGGTGGAA  TAGTACCACG  ACCGCTTCAG  GGCGATCCGC  AAGGAGATGC  GGGTCGCCGG              1271

AGCGGCAAAG  CCCGACATTC  GTTTCGCACC  GACGGCCGTC  GTGAACTCGA  CAGTCCGCGA              1331

GAAGGGCGTA  TTGCGCGGCC  TGGACCTGTA  CGTGGAACTG  TAGCCCATAT  ATAGATTTCC              1391

AAAGAGTTTC  GGCGAGGCGC  GGCGCGCCTA  GCCCCATGTG  AGCGAGAACC  GTGCCCAGAT              1451

CAAAGAATGA  GACCGACGCG  CCGGCCGCGG  CAAAGGATGA  TCCTCAGGGT  CGGATCTATC              1511

GCTCCGCCCT  GAAGCAGGAG  GGCGCACGCT  GGCTGCTGAC  GGCGGAGGAA  GGGTTGCTGG              1571

CAAAGCCCAA  GCCGCCCGGC  CTTGTTCCGG  CACTTGAGAA  TGCGATCGCC  ATCGTCGATT              1631

ACATCAACGG  TACACCGCCC  CATATCGCGT  CCCTGGCGGA  GCTTTCAACG  ACGCTCGGGA              1691

TATCCAAGAG  CCACTGTCAC  TCCATCCTCA  AGACGCTGAC  GCATTTCGGC  TGGCTGAAAT              1751

TCGACAATCG  CTCAAAGAGC  TACGAGCTGA  ATTC                                            1785
```

( 2 ) INFORMATION FOR SEQ ID NO:14:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Thr  Arg  Gln  Met  Ile  Leu  Ala  Val  Gly  Gln  Gln  Gly  Pro  Ile  Ala  Arg
1              5                        10                       15
```

| Ala | Glu | Thr | Arg | Glu | Gln | Val | Val | Arg | Leu | Leu | Asp | Met | Leu | Thr |
|-----|-----|-----|-----|-----|-----|-----|-----|-----|-----|-----|-----|-----|-----|-----|
|     |     |     | 20  |     |     |     | 25  |     |     |     | 30  |     |     |     |

| Lys | Ala | Ala | Ser | Arg | Gly | Ala | Asn | Phe | Ile | Val | Phe | Pro | Glu | Leu | Ala |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Leu | Thr | Thr | Phe | Phe | Pro | Arg | Trp | His | Phe | Thr | Asp | Glu | Ala | Glu | Leu |
|-----|-----|-----|-----|-----|-----|-----|-----|-----|-----|-----|-----|-----|-----|-----|-----|
|     | 50  |     |     |     |     | 55  |     |     |     |     |     | 60  |     |     |     |

| Asp | Ser | Phe | Tyr | Glu | Thr | Glu | Met | Pro | Gly | Pro | Val | Val | Arg | Pro | Leu |
|-----|-----|-----|-----|-----|-----|-----|-----|-----|-----|-----|-----|-----|-----|-----|-----|
| 65  |     |     |     |     | 70  |     |     |     |     |     | 75  |     |     |     | 80  |

| Phe | Glu | Lys | Ala | Ala | Glu | Leu | Gly | Ile | Gly | Phe | Asn | Leu | Gly | Tyr | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Glu | Leu | Val | Val | Glu | Gly | Gly | Val | Lys | Arg | Arg | Phe | Asn | Thr | Ser | Ile |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Val | Asp | Lys | Ser | Gly | Lys | Ile | Val | Gly | Lys | Tyr | Arg | Lys | Ile | His |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Leu | Pro | Gly | His | Lys | Glu | Tyr | Glu | Ala | Tyr | Arg | Pro | Phe | Gln | His | Leu |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Glu | Lys | Arg | Tyr | Phe | Glu | Pro | Gly | Asp | Leu | Gly | Phe | Pro | Val | Tyr | Asp |
|-----|-----|-----|-----|-----|-----|-----|-----|-----|-----|-----|-----|-----|-----|-----|-----|
| 145 |     |     |     |     |     | 150 |     |     |     |     | 155 |     |     |     | 160 |

| Val | Asp | Ala | Ala | Lys | Met | Gly | Met | Phe | Ile | Cys | Asn | Asp | Arg | Arg | Trp |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Pro | Glu | Ala | Trp | Arg | Val | Met | Gly | Leu | Arg | Gly | Ala | Glu | Ile | Ile | Cys |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Gly | Gly | Tyr | Asn | Thr | Pro | Thr | His | Asn | Pro | Glu | Val | Pro | Gln | His | Asp |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| His | Leu | Thr | Ser | Phe | His | His | Leu | Leu | Ser | Met | Gln | Ala | Gly | Ser | Tyr |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gln | Asn | Gly | Ala | Trp | Ser | Ala | Ala | Ala | Gly | Lys | Val | Gly | Met | Glu | Glu |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Asn | Cys | Met | Leu | Leu | Gly | His | Ser | Cys | Ile | Val | Ala | Pro | Thr | Gly | Glu |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ile | Val | Ala | Leu | Thr | Thr | Thr | Leu | Glu | Asp | Glu | Val | Ile | Thr | Ala | Ala |
|-----|-----|-----|-----|-----|-----|-----|-----|-----|-----|-----|-----|-----|-----|-----|-----|
|     |     |     |     | 260 |     |     |     |     | 265 |     |     |     |     | 270 |     |

| Val | Asp | Leu | Asp | Arg | Cys | Arg | Glu | Leu | Arg | Glu | His | Ile | Phe | Asn | Phe |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Lys | Gln | His | Arg | Gln | Pro | Gln | His | Tyr | Gly | Leu | Ile | Ala | Glu | Leu |
|-----|-----|-----|-----|-----|-----|-----|-----|-----|-----|-----|-----|-----|-----|-----|
|     | 290 |     |     |     |     | 295 |     |     |     |     | 300 |     |     |     |

( 2 ) INFORMATION FOR SEQ ID NO:15:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD431

( i x ) FEATURE:
        ( A ) NAME/KEY: CDS
        ( B ) LOCATION: 233..1144

( x i ) SEQUENCE DESCRIPTION: SEQ ID NO:15:

```
GTCGACGGCG GGCTCGCGCG AGAGCTTGTC AAGCAGCGCA AATTCCGGTT CCGCTCCGGT        60

TGACAGATCA AAAATTTTAC GCCTGTTATT GTCGTGCTGC ATGTAATATT TCGTACTTTA       120

TGTAGAATTT GCATTGCGCC GCGAGTCACA AAGCCGGTTT TCGGCGATGT GTTTCACAAC       180

GTTTTCCCGG CCGCTGGGCC GGACATCACC TAGGAAGGAG CAGAGGTTCA TG ACA           235
                                                         Thr
```

-continued

```
                                                                      1
CGT CAG ATG ATA CTT GCA GTG GGA CAA CAA GGT CCG ATC GCG CGC GCG       283
Arg Gln Met Ile Leu Ala Val Gly Gln Gln Gly Pro Ile Ala Arg Ala
             5                   10                  15

GAG ACA CGC GAA CAG GTC GTC GTT CGT CTT CTC GAC ATG CTG ACG AAA       331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT       379
Ala Ala Ser Arg Gly Ala Asn Phe Ile Val Phe Pro Glu Leu Ala Leu
         35                  40                  45

ACG ACC TTC TTC CCG CGC TGG CAT TTC ACC GAC GAG GCC GAG CTC GAT       427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT       475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA       523
Glu Lys Ala Ala Glu Leu Gly Ile Gly Phe Asn Leu Gly Tyr Ala Glu
                 85                  90                  95

CTC GTC GTC GAA GGC GGC GTC AAG CGT CGC TTC AAC ACG TCC ATT TTG       571
Leu Val Val Glu Gly Gly Val Lys Arg Arg Phe Asn Thr Ser Ile Leu
            100                 105                 110

GTG GAT AAG TCA GGC AAG ATC GTC GGC AAG TAT CGT AAG ATC CAT TTG       619
Val Asp Lys Ser Gly Lys Ile Val Gly Lys Tyr Arg Lys Ile His Leu
            115                 120                 125

CCG GGT CAC AAG GAG TAC GAG GCC TAC CGG CCG TTC CAG CAT CTT GAA       667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC       715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT       763
Asp Ala Ala Lys Met Gly Met Phe Ile Cys Asn Asp Arg Arg Trp Pro
                165                 170                 175

GAA GCC TGG CGG GTG ATG GGC CTC AGG GGC GCC GAG ATC ATC TGC GGC       811
Glu Ala Trp Arg Val Met Gly Leu Arg Gly Ala Glu Ile Ile Cys Gly
            180                 185                 190

GGC TAC AAC ACG CCG ACC CAC AAT CCC AAC GTT CCC CAG CAC GAC CAC       859
Gly Tyr Asn Thr Pro Thr His Asn Pro Asn Val Pro Gln His Asp His
        195                 200                 205

CTG ACG TCC TTC CAC CAT CTC CTA TCG ATG CAG GCC GGG TCT TAT CAG       907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC       955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC       1003
Cys Met Leu Leu Gly His Ser Cys Ile Val Ala Pro Thr Gly Glu Ile
                245                 250                 255

GTC GCT CTC ACT ACG ACG CTG GAA GAC GAG GTG ATC ACC GCC GCC GTC       1051
Val Ala Leu Thr Thr Thr Leu Glu Asp Glu Val Ile Thr Ala Ala Val
            260                 265                 270

GAT CTC GAT CGC TGC CGG GAA CTG CGT GAA CAC ATC TTC AAC TTC AAG       1099
Asp Leu Asp Arg Cys Arg Glu Leu Arg Glu His Ile Phe Asn Phe Lys
        275                 280                 285

CAG CAT CGT CAG CCC CAG CAC TAT GGT CTG ATC GCG GAA CTC TGAGGTGCC    1151
Gln His Arg Gln Pro Gln His Tyr Gly Leu Ile Ala Glu Leu
290                 295                 300

GAAAAGCATG TGTGTCGTTG TTCTCGGCGC CTGGGTCACA TCCAGGCGCG CCAGGGTGAC    1211
```

-continued

```
GCTGGTGGAA  TAGTACCACG  ACCGCTTCAG  GGCGATCCGC  AAGGAGATGC  GGGTCGCCGG  1271
AGCGGCAAAG  CCCGACATTC  GTTTCGCACC  GACGGCCGTC  GTGAACTCGA  CAGTCCGCGA  1331
GAAGGGCGTA  TTGCGCGGCC  TGGACCTGTA  CGTGGAACTG  TAGCCCATAT  ATAGATTTCC  1391
AAAGAGTTTC  GGCGAGGCGC  GGCGCGCCTA  GCCCCATGTG  AGCGAGAACC  GTGCCCAGAT  1451
CAAAGAATGA  GACCGACGCG  CCGGCCGCGG  CAAAGGATGA  TCCTCAGGGT  CGGATCTATC  1511
GCTCCGCCCT  GAAGCAGGAG  GGCGCACGCT  GGCTGCTGAC  GGCGGAGGAA  GGGTTGCTGG  1571
CAAAGCCCAA  GCCGCCCGGC  CTTGTTCCGG  CACTTGAGAA  TGCGATCGCC  ATCGTCGATT  1631
ACATCAACGG  TACACCGCCC  CATATCGCGT  CCCTGGCGGA  GCTTTCAACG  ACGCTCGGGA  1691
TATCCAAGAG  CCACTGTCAC  TCCATCCTCA  AGACGCTGAC  GCATTTCGGC  TGGCTGAAAT  1751
TCGACAATCG  CTCAAAGAGC  TACGAGCTGA  ATTC                                1785
```

( 2 ) INFORMATION FOR SEQ ID NO:16:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Thr  Arg  Gln  Met  Ile  Leu  Ala  Val  Gly  Gln  Gln  Gly  Pro  Ile  Ala  Arg
 1                    5                         10                        15
Ala  Glu  Thr  Arg  Glu  Gln  Val  Val  Arg  Leu  Leu  Asp  Met  Leu  Thr
           20                        25                        30
Lys  Ala  Ala  Ser  Arg  Gly  Ala  Asn  Phe  Ile  Val  Phe  Pro  Glu  Leu  Ala
                35                        40                        45
Leu  Thr  Thr  Phe  Phe  Pro  Arg  Trp  His  Phe  Thr  Asp  Glu  Ala  Glu  Leu
      50                        55                        60
Asp  Ser  Phe  Tyr  Glu  Thr  Glu  Met  Pro  Gly  Pro  Val  Val  Arg  Pro  Leu
 65                        70                        75                   80
Phe  Glu  Lys  Ala  Ala  Glu  Leu  Gly  Ile  Gly  Phe  Asn  Leu  Gly  Tyr  Ala
                     85                        90                        95
Glu  Leu  Val  Val  Glu  Gly  Gly  Val  Lys  Arg  Arg  Phe  Asn  Thr  Ser  Ile
                100                       105                       110
Leu  Val  Asp  Lys  Ser  Gly  Lys  Ile  Val  Gly  Lys  Tyr  Arg  Lys  Ile  His
                115                       120                       125
Leu  Pro  Gly  His  Lys  Glu  Tyr  Glu  Ala  Tyr  Arg  Pro  Phe  Gln  His  Leu
           130                       135                       140
Glu  Lys  Arg  Tyr  Phe  Glu  Pro  Gly  Asp  Leu  Gly  Phe  Pro  Val  Tyr  Asp
145                       150                       155                  160
Val  Asp  Ala  Ala  Lys  Met  Gly  Met  Phe  Ile  Cys  Asn  Asp  Arg  Arg  Trp
                     165                       170                       175
Pro  Glu  Ala  Trp  Arg  Val  Met  Gly  Leu  Arg  Gly  Ala  Glu  Ile  Ile  Cys
                180                       185                       190
Gly  Gly  Tyr  Asn  Thr  Pro  Thr  His  Asn  Pro  Asn  Val  Pro  Gln  His  Asp
           195                       200                       205
His  Leu  Thr  Ser  Phe  His  His  Leu  Leu  Ser  Met  Gln  Ala  Gly  Ser  Tyr
      210                       215                       220
Gln  Asn  Gly  Ala  Trp  Ser  Ala  Ala  Ala  Gly  Lys  Val  Gly  Met  Glu  Glu
225                       230                       235                  240
Asn  Cys  Met  Leu  Leu  Gly  His  Ser  Cys  Ile  Val  Ala  Pro  Thr  Gly  Glu
                     245                       250                       255
```

```
Ile  Val  Ala  Leu  Thr  Thr  Thr  Leu  Glu  Asp  Glu  Val  Ile  Thr  Ala  Ala
               260                      265                     270

Val  Asp  Leu  Asp  Arg  Cys  Arg  Glu  Leu  Arg  Glu  His  Ile  Phe  Asn  Phe
               275                      280                     285

Lys  Gln  His  Arg  Gln  Pro  Gln  His  Tyr  Gly  Leu  Ile  Ala  Glu  Leu
               290                      295                     300
```

( 2 ) INFORMATION FOR SEQ ID NO:17:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD434

( i x ) FEATURE:
        ( A ) NAME/KEY: CDS
        ( B ) LOCATION: 233..1144

( x i ) SEQUENCE DESCRIPTION: SEQ ID NO:17:

```
GTCGACGGCG  GGCTCGCGCG  AGAGCTTGTC  AAGCAGCGCA  AATTCCGGTT  CCGCTCCGGT      60

TGACAGATCA  AAAATTTTAC  GCCTGTTATT  GTCGTGCTGC  ATGTAATATT  TCGTACTTTA     120

TGTAGAATTT  GCATTGCGCC  GCGAGTCACA  AAGCCGGTTT  TCGGCGATGT  GTTTCACAAC     180

GTTTTCCCGG  CCGCTGGGCC  GGACATCACC  TAGGAAGGAG  CAGAGGTTCA  TG  ACA        235
                                                               Thr
                                                                1

CGT  CAG  ATG  ATA  CTT  GCA  GTG  GGA  CAA  CAA  GGT  CCG  ATC  GCG  CGC  GCG    283
Arg  Gln  Met  Ile  Leu  Ala  Val  Gly  Gln  Gln  Gly  Pro  Ile  Ala  Arg  Ala
               5                        10                      15

GAG  ACA  CGC  GAA  CAG  GTC  GTC  GTT  CGT  CTT  CTC  GAC  ATG  CTG  ACG  AAA    331
Glu  Thr  Arg  Glu  Gln  Val  Val  Val  Arg  Leu  Leu  Asp  Met  Leu  Thr  Lys
               20                       25                      30

GCC  GCG  AGC  CGG  GGC  GCG  AAT  TTC  ATT  GTC  TTC  CCC  GAA  CTC  GCG  CTT    379
Ala  Ala  Ser  Arg  Gly  Ala  Asn  Phe  Ile  Val  Phe  Pro  Glu  Leu  Ala  Leu
          35                        40                      45

ACG  ACC  TTC  TTC  CCG  CGC  TGG  CTA  TTC  ACC  GAC  GAG  GCC  GAG  CTC  GAT    427
Thr  Thr  Phe  Phe  Pro  Arg  Trp  Leu  Phe  Thr  Asp  Glu  Ala  Glu  Leu  Asp
50                       55                      60                      65

AGC  TTC  TAT  GAG  ACC  GAA  ATG  CCC  GGC  CCG  GTG  GTC  CGT  CCA  CTC  TTT    475
Ser  Phe  Tyr  Glu  Thr  Glu  Met  Pro  Gly  Pro  Val  Val  Arg  Pro  Leu  Phe
               70                       75                      80

GAG  AAG  GCC  GCG  GAA  CTC  GGG  ATC  GGC  TTC  AAT  CTG  GGC  TAC  GCT  GAA    523
Glu  Lys  Ala  Ala  Glu  Leu  Gly  Ile  Gly  Phe  Asn  Leu  Gly  Tyr  Ala  Glu
          85                        90                      95

CTC  GTC  GTC  GAA  GGC  GGC  GTC  AAG  CGT  CGC  TTC  AAC  ACG  TCC  ATT  TTG    571
Leu  Val  Val  Glu  Gly  Gly  Val  Lys  Arg  Arg  Phe  Asn  Thr  Ser  Ile  Leu
          100                       105                     110

GTG  GAT  AAG  TCA  GGC  AAG  ATC  GTC  GGC  AAG  TAT  CGT  AAG  ATC  CAT  TTG    619
Val  Asp  Lys  Ser  Gly  Lys  Ile  Val  Gly  Lys  Tyr  Arg  Lys  Ile  His  Leu
          115                       120                     125

CCG  GGT  CAC  AAG  GAG  TAC  GAG  GCC  TAC  CGG  CCG  TTC  CAG  CAT  CTT  GAA    667
Pro  Gly  His  Lys  Glu  Tyr  Glu  Ala  Tyr  Arg  Pro  Phe  Gln  His  Leu  Glu
130                      135                     140                     145

AAG  CGT  TAT  TTC  GAG  CCG  GGC  GAT  CTC  GGC  TTC  CCG  GTC  TAT  GAC  GTC    715
Lys  Arg  Tyr  Phe  Glu  Pro  Gly  Asp  Leu  Gly  Phe  Pro  Val  Tyr  Asp  Val
               150                      155                     160

GAC  GCC  GCG  AAA  ATG  GGG  ATG  TTC  ATC  TGC  AAC  GAT  CGC  CGC  TGG  CCT    763
Asp  Ala  Ala  Lys  Met  Gly  Met  Phe  Ile  Cys  Asn  Asp  Arg  Arg  Trp  Pro
               165                      170                     175
```

```
GAA  GCC  TGG  CGG  GTG  ATG  GGC  CTC  AGG  GGC  GCC  GAG  ATC  ATC  TGC  GGC     811
Glu  Ala  Trp  Arg  Val  Met  Gly  Leu  Arg  Gly  Ala  Glu  Ile  Ile  Cys  Gly
          180                      185                      190

GGC  TAC  AAC  ACG  CCG  ACC  CAC  AAT  CCC  CCT  GTT  CCC  CAG  CAC  GAC  CAC     859
Gly  Tyr  Asn  Thr  Pro  Thr  His  Asn  Pro  Pro  Val  Pro  Gln  His  Asp  His
     195                      200                      205

CTG  ACG  TCC  TTC  CAC  CAT  CTC  CTA  TCG  ATG  CAG  GCC  GGG  TCT  TAT  CAG     907
Leu  Thr  Ser  Phe  His  His  Leu  Leu  Ser  Met  Gln  Ala  Gly  Ser  Tyr  Gln
210                           215                      220                      225

AAC  GGG  GCC  TGG  TCC  GCG  GCC  GCG  GGC  AAG  GTG  GGC  ATG  GAG  GAG  AAC     955
Asn  Gly  Ala  Trp  Ser  Ala  Ala  Ala  Gly  Lys  Val  Gly  Met  Glu  Glu  Asn
                    230                      235                      240

TGC  ATG  CTG  CTC  GGC  CAC  TCC  TGC  ATC  GTG  GCG  CCG  ACC  GGG  GAA  ATC    1003
Cys  Met  Leu  Leu  Gly  His  Ser  Cys  Ile  Val  Ala  Pro  Thr  Gly  Glu  Ile
               245                      250                      255

GTC  GCT  CTC  ACT  ACG  ACG  CTG  GAA  GAC  GAG  GTG  ATC  ACC  GCC  GCC  GTC    1051
Val  Ala  Leu  Thr  Thr  Thr  Leu  Glu  Asp  Glu  Val  Ile  Thr  Ala  Ala  Val
               260                      265                      270

GAT  CTC  GAT  CGC  TGC  CGG  GAA  CTG  CGT  GAA  CAC  ATC  TTC  AAC  TTC  AAG    1099
Asp  Leu  Asp  Arg  Cys  Arg  Glu  Leu  Arg  Glu  His  Ile  Phe  Asn  Phe  Lys
          275                      280                      285

CAG  CAT  CGT  CAG  CCC  CAG  CAC  TAT  GGT  CTG  ATC  GCG  GAA  CTC  TGAGGTTGCC  1151
Gln  His  Arg  Gln  Pro  Gln  His  Tyr  Gly  Leu  Ile  Ala  Glu  Leu
290                      295                      300

GAAAAGCATG  TGTGTCGTTG  TTCTCGGCGC  TGGGTCACA   TCCAGGCGCG  CCAGGGTGAC           1211

GCTGGTGGAA  TAGTACCACG  ACCGCTTCAG  GGCGATCCGC  AAGGAGATGC  GGGTCGCCGG           1271

AGCGGCAAAG  CCCGACATTC  GTTTCGCACC  GACGGCCGTC  GTGAACTCGA  CAGTCCGCGA           1331

GAAGGGCGTA  TTGCGCGGCC  TGGACCTGTA  CGTGGAACTG  TAGCCCATAT  ATAGATTTCC           1391

AAAGAGTTTC  GGCGAGGCGC  GGCGCGCCTA  GCCCCATGTG  AGCGAGAACC  GTGCCCAGAT           1451

CAAAGAATGA  GACCGACGCG  CCGGCCGCGG  CAAAGGATGA  TCCTCAGGGT  CGGATCTATC           1511

GCTCCGCCCT  GAAGCAGGAG  GGCGCACGCT  GGCTGCTGAC  GGCGGAGGAA  GGGTTGCTGG           1571

CAAAGCCCAA  GCCGCCCGGC  CTTGTTCCGG  CACTTGAGAA  TGCGATCGCC  ATCGTCGATT           1631

ACATCAACGG  TACACCGCCC  CATATCGCGT  CCCTGGCGGA  GCTTTCAACG  ACGCTCGGGA           1691

TATCCAAGAG  CCACTGTCAC  TCCATCCTCA  AGACGCTGAC  GCATTTCGGC  TGGCTGAAAT           1751

TCGACAATCG  CTCAAAGAGC  TACGAGCTGA  ATTC                                        1785
```

( 2 ) INFORMATION FOR SEQ ID NO:18:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Thr  Arg  Gln  Met  Ile  Leu  Ala  Val  Gly  Gln  Gln  Gly  Pro  Ile  Ala  Arg
 1                  5                     10                       15

Ala  Glu  Thr  Arg  Glu  Gln  Val  Val  Arg  Leu  Leu  Asp  Met  Leu  Thr
               20                   25                  30

Lys  Ala  Ala  Ser  Arg  Gly  Ala  Asn  Phe  Ile  Val  Phe  Pro  Glu  Leu  Ala
               35                  40                       45

Leu  Thr  Thr  Phe  Phe  Pro  Arg  Trp  Leu  Phe  Thr  Asp  Glu  Ala  Glu  Leu
      50                       55                  60

Asp  Ser  Phe  Tyr  Glu  Thr  Glu  Met  Pro  Gly  Pro  Val  Val  Arg  Pro  Leu
```

|       |       |       |       | 65    |       |       |       |       | 70    |       |       |       |       | 75    |       |       |       |       | 80    |
|-------|-------|-------|-------|-------|-------|-------|-------|-------|-------|-------|-------|-------|-------|-------|-------|-------|-------|-------|-------|

Phe Glu Lys Ala Ala Glu Leu Gly Ile Gly Phe Asn Leu Gly Tyr Ala
                    85                     90                 95

Glu Leu Val Val Glu Gly Gly Val Lys Arg Arg Phe Asn Thr Ser Ile
                100             105                 110

Leu Val Asp Lys Ser Gly Lys Ile Val Gly Lys Tyr Arg Lys Ile His
            115                 120             125

Leu Pro Gly His Lys Glu Tyr Glu Ala Tyr Arg Pro Phe Gln His Leu
    130                 135             140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165             170                 175

Pro Glu Ala Trp Arg Val Met Gly Leu Arg Gly Ala Glu Ile Ile Cys
            180                 185             190

Gly Gly Tyr Asn Thr Pro Thr His Asn Pro Pro Val Pro Gln His Asp
        195             200             205

His Leu Thr Ser Phe His His Leu Leu Ser Met Gln Ala Gly Ser Tyr
    210                 215             220

Gln Asn Gly Ala Trp Ser Ala Ala Ala Gly Lys Val Gly Met Glu Glu
225             230             235                 240

Asn Cys Met Leu Leu Gly His Ser Cys Ile Val Ala Pro Thr Gly Glu
            245             250             255

Ile Val Ala Leu Thr Thr Thr Leu Glu Asp Glu Val Ile Thr Ala Ala
            260             265             270

Val Asp Leu Asp Arg Cys Arg Glu Leu Arg Glu His Ile Phe Asn Phe
            275             280             285

Lys Gln His Arg Gln Pro Gln His Tyr Gly Leu Ile Ala Glu Leu
    290             295             300

(2) INFORMATION FOR SEQ ID NO:19:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (vi) ORIGINAL SOURCE:
        (B) STRAIN: JM109 pAD435

(ix) FEATURE:
        (A) NAME/KEY: CDS
        (B) LOCATION: 233..1144

(xi) SEQUENCE DESCRIPTION: SEQ ID NO:19:

```
GTCGACGGCG  GGCTCGCGCG  AGAGCTTGTC  AAGCAGCGCA  AATTCCGGTT  CCGCTCCGGT       60

TGACAGATCA  AAAATTTTAC  GCCTGTTATT  GTCGTGCTGC  ATGTAATATT  TCGTACTTTA      120

TGTAGAATTT  GCATTGCGCC  GCGAGTCACA  AAGCCGGTTT  TCGGCGATGT  GTTTCACAAC      180

GTTTTCCCGG  CCGCTGGGCC  GGACATCACC  TAGGAAGGAG  CAGAGGTTCA  TG ACA          235
                                                              Thr
                                                              1

CGT CAG ATG ATA CTT GCA GTG GGA CAA CAA GGT CCG ATC GCG CGC GCG            283
Arg Gln Met Ile Leu Ala Val Gly Gln Gln Gly Pro Ile Ala Arg Ala
            5                   10                  15

GAG ACA CGC GAA CAG GTC GTC GTT CGT CTT CTC GAC ATG CTG ACG AAA            331
Glu Thr Arg Glu Gln Val Val Val Arg Leu Leu Asp Met Leu Thr Lys
        20                  25                  30
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GCC | GCG | AGC | CGG | GGC | GCG | AAT | TTC | ATT | GTC | TTC | CCC | GAA | CTC | GCG | CTT | 379  |
| Ala | Ala | Ser | Arg | Gly | Ala | Asn | Phe | Ile | Val | Phe | Pro | Glu | Leu | Ala | Leu |      |
|     |     | 35  |     |     |     | 40  |     |     |     |     | 45  |     |     |     |     |      |
| ACG | ACC | TTC | TTC | CCG | CGC | TGG | CTT | TTC | ACC | GAC | GAG | GCC | GAG | CTC | GAT | 427  |
| Thr | Thr | Phe | Phe | Pro | Arg | Trp | Leu | Phe | Thr | Asp | Glu | Ala | Glu | Leu | Asp |      |
| 50  |     |     |     |     | 55  |     |     |     |     | 60  |     |     |     |     | 65  |      |
| AGC | TTC | TAT | GAG | ACC | GAA | ATG | CCC | GGC | CCG | GTG | GTC | CGT | CCA | CTC | TTT | 475  |
| Ser | Phe | Tyr | Glu | Thr | Glu | Met | Pro | Gly | Pro | Val | Val | Arg | Pro | Leu | Phe |      |
|     |     |     |     | 70  |     |     |     |     | 75  |     |     |     |     | 80  |     |      |
| GAG | AAG | GCC | GCG | GAA | CTC | GGG | ATC | GGC | TTC | AAT | CTG | GGC | TAC | GCT | GAA | 523  |
| Glu | Lys | Ala | Ala | Glu | Leu | Gly | Ile | Gly | Phe | Asn | Leu | Gly | Tyr | Ala | Glu |      |
|     |     |     | 85  |     |     |     |     | 90  |     |     |     |     | 95  |     |     |      |
| CTC | GTC | GTC | GAA | GGC | GGC | GTC | AAG | CGT | CGC | TTC | AAC | ACG | TCC | ATT | TTG | 571  |
| Leu | Val | Val | Glu | Gly | Gly | Val | Lys | Arg | Arg | Phe | Asn | Thr | Ser | Ile | Leu |      |
|     |     | 100 |     |     |     |     | 105 |     |     |     |     | 110 |     |     |     |      |
| GTG | GAT | AAG | TCA | GGC | AAG | ATC | GTC | GGC | AAG | TAT | CGT | AAG | ATC | CAT | TTG | 619  |
| Val | Asp | Lys | Ser | Gly | Lys | Ile | Val | Gly | Lys | Tyr | Arg | Lys | Ile | His | Leu |      |
|     | 115 |     |     |     |     | 120 |     |     |     |     | 125 |     |     |     |     |      |
| CCG | GGT | CAC | AAG | GAG | TAC | GAG | GCC | TAC | CGG | CCG | TTC | CAG | CAT | CTT | GAA | 667  |
| Pro | Gly | His | Lys | Glu | Tyr | Glu | Ala | Tyr | Arg | Pro | Phe | Gln | His | Leu | Glu |      |
| 130 |     |     |     |     | 135 |     |     |     |     | 140 |     |     |     |     | 145 |      |
| AAG | CGT | TAT | TTC | GAG | CCG | GGC | GAT | CTC | GGC | TTC | CCG | GTC | TAT | GAC | GTC | 715  |
| Lys | Arg | Tyr | Phe | Glu | Pro | Gly | Asp | Leu | Gly | Phe | Pro | Val | Tyr | Asp | Val |      |
|     |     |     |     | 150 |     |     |     |     | 155 |     |     |     |     | 160 |     |      |
| GAC | GCC | GCG | AAA | ATG | GGG | ATG | TTC | ATC | TGC | AAC | GAT | CGC | CGC | TGG | CCT | 763  |
| Asp | Ala | Ala | Lys | Met | Gly | Met | Phe | Ile | Cys | Asn | Asp | Arg | Arg | Trp | Pro |      |
|     |     |     | 165 |     |     |     |     | 170 |     |     |     |     | 175 |     |     |      |
| GAA | GCC | TGG | CGG | GTG | ATG | GGC | CTC | AGG | GGC | GCC | GAG | ATC | ATC | TGC | GGC | 811  |
| Glu | Ala | Trp | Arg | Val | Met | Gly | Leu | Arg | Gly | Ala | Glu | Ile | Ile | Cys | Gly |      |
|     |     | 180 |     |     |     |     | 185 |     |     |     |     | 190 |     |     |     |      |
| GGC | TAC | AAC | ACG | CCG | ACC | CAC | AAT | CCC | CCT | GTT | CCC | CAG | CAC | GAC | CAC | 859  |
| Gly | Tyr | Asn | Thr | Pro | Thr | His | Asn | Pro | Pro | Val | Pro | Gln | His | Asp | His |      |
|     | 195 |     |     |     |     | 200 |     |     |     |     | 205 |     |     |     |     |      |
| CTG | ACG | TCC | TTC | CAC | CAT | CTC | CTA | TCG | ATG | CAG | GCC | GGG | TCT | TAT | CAG | 907  |
| Leu | Thr | Ser | Phe | His | His | Leu | Leu | Ser | Met | Gln | Ala | Gly | Ser | Tyr | Gln |      |
| 210 |     |     |     |     | 215 |     |     |     |     | 220 |     |     |     |     | 225 |      |
| AAC | GGG | GCC | TGG | TCC | GCG | GCC | GCG | GGC | AAG | GTG | GGC | ATG | GAG | GAG | AAC | 955  |
| Asn | Gly | Ala | Trp | Ser | Ala | Ala | Ala | Gly | Lys | Val | Gly | Met | Glu | Glu | Asn |      |
|     |     |     |     | 230 |     |     |     |     | 235 |     |     |     |     | 240 |     |      |
| TGC | ATG | CTG | CTC | GGC | CAC | TCC | TGC | ATC | GTG | GCG | CCG | ACC | GGG | GAA | ATC | 1003 |
| Cys | Met | Leu | Leu | Gly | His | Ser | Cys | Ile | Val | Ala | Pro | Thr | Gly | Glu | Ile |      |
|     |     |     | 245 |     |     |     |     | 250 |     |     |     |     | 255 |     |     |      |
| GTC | GCT | CTC | ACT | ACG | ACG | CTG | GAA | GAC | GAG | GTG | ATC | ACC | GCC | GCC | GTC | 1051 |
| Val | Ala | Leu | Thr | Thr | Thr | Leu | Glu | Asp | Glu | Val | Ile | Thr | Ala | Ala | Val |      |
|     |     | 260 |     |     |     |     | 265 |     |     |     |     | 270 |     |     |     |      |
| GAT | CTC | GAT | CGC | TGC | CGG | GAA | CTG | CGT | GAA | CAC | ATC | TTC | AAC | TTC | AAG | 1099 |
| Asp | Leu | Asp | Arg | Cys | Arg | Glu | Leu | Arg | Glu | His | Ile | Phe | Asn | Phe | Lys |      |
|     | 275 |     |     |     |     | 280 |     |     |     |     | 285 |     |     |     |     |      |
| CAG | CAT | CGT | CAG | CCC | CAG | CAC | TAT | GGT | CTG | ATC | GCG | GAA | CTC | TGAGGTTGCC |     | 1151 |
| Gln | His | Arg | Gln | Pro | Gln | His | Tyr | Gly | Leu | Ile | Ala | Glu | Leu |     |     |      |
| 290 |     |     |     |     | 295 |     |     |     | 300 |     |     |     |     |     |     |      |

```
GAAAAGCATG TGTGTCGTTG TTCTCGGCGC CTGGGTCACA TCCAGGCGCG CCAGGGTGAC   1211

GCTGGTGGAA TAGTACCACG ACCGCTTCAG GGCGATCCGC AAGGAGATGC GGGTCGCCGG   1271

AGCGGCAAAG CCCGACATTC GTTTCGCACC GACGGCCGTC GTGAACTCGA CAGTCCGCGA   1331

GAAGGGCGTA TTGCGCGGCC TGGACCTGTA CGTGGAACTG TAGCCCATAT ATAGATTTCC   1391

AAAGAGTTTC GGCGAGGCGC GGCGCGCCTA GCCCCATGTG AGCGAGAACC GTGCCCAGAT   1451

CAAAGAATGA GACCGACGCG CCGGCCGCGG CAAAGGATGA TCCTCAGGGT CGGATCTATC   1511
```

```
GCTCCGCCCT  GAAGCAGGAG  GGCGCACGCT  GGCTGCTGAC  GGCGGAGGAA  GGGTTGCTGG    1571

CAAAGCCCAA  GCCGCCCGGC  CTTGTTCCGG  CACTTGAGAA  TGCGATCGCC  ATCGTCGATT    1631

ACATCAACGG  TACACCGCCC  CATATCGCGT  CCCTGGCGGA  GCTTTCAACG  ACGCTCGGGA    1691

TATCCAAGAG  CCACTGTCAC  TCCATCCTCA  AGACGCTGAC  GCATTTCGGC  TGGCTGAAAT    1751

TCGACAATCG  CTCAAAGAGC  TACGAGCTGA  ATTC                                  1785
```

( 2 ) INFORMATION FOR SEQ ID NO:20:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Thr  Arg  Gln  Met  Ile  Leu  Ala  Val  Gly  Gln  Gln  Gly  Pro  Ile  Ala  Arg
  1                  5                      10                      15

Ala  Glu  Thr  Arg  Glu  Gln  Val  Val  Arg  Leu  Leu  Asp  Met  Leu  Thr
             20                       25                      30

Lys  Ala  Ala  Ser  Arg  Gly  Ala  Asn  Phe  Ile  Val  Phe  Pro  Glu  Leu  Ala
              35                      40                      45

Leu  Thr  Thr  Phe  Phe  Pro  Arg  Trp  Leu  Phe  Thr  Asp  Glu  Ala  Glu  Leu
     50                       55                      60

Asp  Ser  Phe  Tyr  Glu  Thr  Glu  Met  Pro  Gly  Pro  Val  Val  Arg  Pro  Leu
 65                       70                      75                      80

Phe  Glu  Lys  Ala  Ala  Glu  Leu  Gly  Ile  Gly  Phe  Asn  Leu  Gly  Tyr  Ala
                   85                      90                      95

Glu  Leu  Val  Val  Glu  Gly  Val  Lys  Arg  Arg  Phe  Asn  Thr  Ser  Ile
                 100                     105                     110

Leu  Val  Asp  Lys  Ser  Gly  Lys  Ile  Val  Gly  Lys  Tyr  Arg  Lys  Ile  His
              115                     120                     125

Leu  Pro  Gly  His  Lys  Glu  Tyr  Glu  Ala  Tyr  Arg  Pro  Phe  Gln  His  Leu
     130                     135                     140

Glu  Lys  Arg  Tyr  Phe  Glu  Pro  Gly  Asp  Leu  Gly  Phe  Pro  Val  Tyr  Asp
145                      150                     155                     160

Val  Asp  Ala  Ala  Lys  Met  Gly  Met  Phe  Ile  Cys  Asn  Asp  Arg  Arg  Trp
                   165                     170                     175

Pro  Glu  Ala  Trp  Arg  Val  Met  Gly  Leu  Arg  Gly  Ala  Glu  Ile  Ile  Cys
              180                     185                     190

Gly  Gly  Tyr  Asn  Thr  Pro  Thr  His  Asn  Pro  Pro  Val  Pro  Gln  His  Asp
          195                     200                     205

His  Leu  Thr  Ser  Phe  His  His  Leu  Leu  Ser  Met  Gln  Ala  Gly  Ser  Tyr
     210                     215                     220

Gln  Asn  Gly  Ala  Trp  Ser  Ala  Ala  Ala  Gly  Lys  Val  Gly  Met  Glu  Glu
225                      230                     235                     240

Asn  Cys  Met  Leu  Leu  Gly  His  Ser  Cys  Ile  Val  Ala  Pro  Thr  Gly  Glu
                   245                     250                     255

Ile  Val  Ala  Leu  Thr  Thr  Thr  Leu  Glu  Asp  Glu  Val  Ile  Thr  Ala  Ala
              260                     265                     270

Val  Asp  Leu  Asp  Arg  Cys  Arg  Glu  Leu  Arg  Glu  His  Ile  Phe  Asn  Phe
          275                     280                     285

Lys  Gln  His  Arg  Gln  Pro  Gln  His  Tyr  Gly  Leu  Ile  Ala  Glu  Leu
     290                     295                     300
```

( 2 ) INFORMATION FOR SEQ ID NO:21:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD439

( i x ) FEATURE:
        ( A ) NAME/KEY: CDS
        ( B ) LOCATION: 233..1144

( x i ) SEQUENCE DESCRIPTION: SEQ ID NO:21:

```
GTCGACGGCG  GGCTCGCGCG  AGAGCTTGTC  AAGCAGCGCA  AATTCCGGTT  CCGCTCCGGT        60

TGACAGATCA  AAAATTTTAC  GCCTGTTATT  GTCGTGCTGC  ATGTAATATT  TCGTACTTTA       120

TGTAGAATTT  GCATTGCGCC  GCGAGTCACA  AAGCCGGTTT  TCGGCGATGT  GTTTCACAAC       180

GTTTTCCCGG  CCGCTGGGCC  GGACATCACC  TAGGAAGGAG  CAGAGGTTCA  TG ACA           235
                                                             Thr
                                                              1

CGT CAG ATG ATA CTT GCA GTG GGA CAA CAA GGT CCG ATC GCG CGC GCG              283
Arg Gln Met Ile Leu Ala Val Gly Gln Gln Gly Pro Ile Ala Arg Ala
            5                   10                  15

GAG ACA CGC GAA CAG GTC GTC GTT CGT CTT CTC GAC ATG CTG ACG AAA              331
Glu Thr Arg Glu Gln Val Val Val Arg Leu Leu Asp Met Leu Thr Lys
        20                  25                  30

GCC GCG AGC CGG GGC GCG AAT TTC ATT GTC TTC CCC GAA CTC GCG CTT              379
Ala Ala Ser Arg Gly Ala Asn Phe Ile Val Phe Pro Glu Leu Ala Leu
    35                  40                  45

ACG ACC TTC TTC CCG CGC TGG CAT TTC ACC GAC GAG GCC GAG CTC GAT              427
Thr Thr Phe Phe Pro Arg Trp His Phe Thr Asp Glu Ala Glu Leu Asp
50                  55                  60                  65

AGC TTC TAT GAG ACC GAA ATG CCC GGC CCG GTG GTC CGT CCA CTC TTT              475
Ser Phe Tyr Glu Thr Glu Met Pro Gly Pro Val Val Arg Pro Leu Phe
                70                  75                  80

GAG AAG GCC GCG GAA CTC GGG ATC GGC TTC AAT CTG GGC TAC GCT GAA              523
Glu Lys Ala Ala Glu Leu Gly Ile Gly Phe Asn Leu Gly Tyr Ala Glu
            85                  90                  95

CTC GTC GTC GAA GGC GGC GTC AAG CGT CGC TTC AAC ACG TCC ATT TTG              571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG              619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA              667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC              715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT              763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC              811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC              859
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG              907
```

```
Leu  Thr  Ser  Phe  His  His  Leu  Leu  Ser  Met  Gln  Ala  Gly  Ser  Tyr  Gln
210                 215                 220                 225

AAC  GGG  GCC  TGG  TCC  GCG  GCC  GCG  GGC  AAG  GCT  GGC  ATG  GAG  GAG  AAC        955
Asn  Gly  Ala  Trp  Ser  Ala  Ala  Ala  Gly  Lys  Ala  Gly  Met  Glu  Glu  Asn
                    230                      235                      240

TGC  ATG  CTG  CTC  GGC  CAC  TCC  TGC  ATC  GTG  GCG  CCG  ACC  GGG  GAA  ATC       1003
Cys  Met  Leu  Leu  Gly  His  Ser  Cys  Ile  Val  Ala  Pro  Thr  Gly  Glu  Ile
               245                      250                      255

GTC  GCT  CTC  ACT  ACG  ACG  CTG  GAA  GAC  GAG  GTG  ATC  ACC  GCC  GCC  GTC       1051
Val  Ala  Leu  Thr  Thr  Thr  Leu  Glu  Asp  Glu  Val  Ile  Thr  Ala  Ala  Val
               260                      265                      270

GAT  CTC  GAT  CGC  TGC  CGG  GAA  CTG  CGT  GAA  CAC  ATC  TTC  AAC  TTC  AAG       1099
Asp  Leu  Asp  Arg  Cys  Arg  Glu  Leu  Arg  Glu  His  Ile  Phe  Asn  Phe  Lys
          275                      280                      285

CAG  CAT  CGT  CAG  CCC  CAG  CAC  TAT  GGT  CTG  ATC  GCG  GAA  CTC  TGAGGTTGCC     1151
Gln  His  Arg  Gln  Pro  Gln  His  Tyr  Gly  Leu  Ile  Ala  Glu  Leu
290                      295                      300

GAAAAGCATG  TGTGTCGTTG  TTCTCGGCGC  CTGGGTCACA  TCCAGGCGCG  CCAGGGTGAC              1211

GCTGGTGGAA  TAGTACCACG  ACCGCTTCAG  GGCGATCCGC  AAGGAGATGC  GGGTCGCCGG              1271

AGCGGCAAAG  CCCGACATTC  GTTTCGCACC  GACGGCCGTC  GTGAACTCGA  CAGTCCGCGA              1331

GAAGGGCGTA  TTGCGCGGCC  TGGACCTGTA  CGTGGAACTG  TAGCCCATAT  ATAGATTTCC              1391

AAAGAGTTTC  GGCGAGGCGC  GGCGCGCCTA  GCCCCATGTG  AGCGAGAACC  GTGCCCAGAT              1451

CAAAGAATGA  GACCGACGCG  CCGGCCGCGG  CAAAGGATGA  TCCTCAGGGT  CGGATCTATC              1511

GCTCCGCCCT  GAAGCAGGAG  GGCGCACGCT  GGCTGCTGAC  GGCGGAGGAA  GGGTTGCTGG              1571

CAAAGCCCAA  GCCGCCCGGC  CTTGTTCCGG  CACTTGAGAA  TGCGATCGCC  ATCGTCGATT              1631

ACATCAACGG  TACACCGCCC  CATATCGCGT  CCCTGGCGGA  GCTTTCAACG  ACGCTCGGGA              1691

TATCCAAGAG  CCACTGTCAC  TCCATCCTCA  AGACGCTGAC  GCATTTCGGC  TGGCTGAAAT              1751

TCGACAATCG  CTCAAAGAGC  TACGAGCTGA  ATTC                                            1785
```

(2) INFORMATION FOR SEQ ID NO:22:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:22:

```
Thr  Arg  Gln  Met  Ile  Leu  Ala  Val  Gly  Gln  Gln  Gly  Pro  Ile  Ala  Arg
1                   5                   10                  15

Ala  Glu  Thr  Arg  Glu  Gln  Val  Val  Val  Arg  Leu  Leu  Asp  Met  Leu  Thr
               20                  25                  30

Lys  Ala  Ala  Ser  Arg  Gly  Ala  Asn  Phe  Ile  Val  Phe  Pro  Glu  Leu  Ala
               35                  40                  45

Leu  Thr  Thr  Phe  Phe  Pro  Arg  Trp  His  Phe  Thr  Asp  Glu  Ala  Glu  Leu
     50                  55                  60

Asp  Ser  Phe  Tyr  Glu  Thr  Glu  Met  Pro  Gly  Pro  Val  Val  Arg  Pro  Leu
65                  70                  75                       80

Phe  Glu  Lys  Ala  Ala  Glu  Leu  Gly  Ile  Gly  Phe  Asn  Leu  Gly  Tyr  Ala
               85                  90                  95

Glu  Leu  Val  Val  Glu  Gly  Gly  Val  Lys  Arg  Arg  Phe  Asn  Thr  Ser  Ile
               100                 105                 110

Leu  Val  Asp  Lys  Ser  Gly  Lys  Ile  Val  Gly  Lys  Tyr  Arg  Lys  Ile  His
               115                 120                 125
```

```
Leu  Pro  Gly  His  Lys  Glu  Tyr  Glu  Ala  Tyr  Arg  Pro  Phe  Gln  His  Leu
     130                 135                      140

Glu  Lys  Arg  Tyr  Phe  Glu  Pro  Gly  Asp  Leu  Gly  Phe  Pro  Val  Tyr  Asp
145                      150                      155                      160

Val  Asp  Ala  Ala  Lys  Met  Gly  Met  Phe  Ile  Cys  Asn  Asp  Arg  Arg  Trp
                    165                 170                           175

Pro  Glu  Ala  Trp  Arg  Val  Met  Gly  Leu  Arg  Gly  Ala  Glu  Ile  Ile  Cys
               180                      185                      190

Gly  Gly  Tyr  Asn  Thr  Pro  Thr  His  Asn  Pro  Pro  Val  Pro  Gln  His  Asp
          195                      200                      205

His  Leu  Thr  Ser  Phe  His  His  Leu  Leu  Ser  Met  Gln  Ala  Gly  Ser  Tyr
     210                     215                      220

Gln  Asn  Gly  Ala  Trp  Ser  Ala  Ala  Ala  Gly  Lys  Ala  Gly  Met  Glu  Glu
225                      230                      235                      240

Asn  Cys  Met  Leu  Leu  Gly  His  Ser  Cys  Ile  Val  Ala  Pro  Thr  Gly  Glu
               245                      250                      255

Ile  Val  Ala  Leu  Thr  Thr  Thr  Leu  Glu  Asp  Glu  Val  Ile  Thr  Ala  Ala
               260                      265                      270

Val  Asp  Leu  Asp  Arg  Cys  Arg  Glu  Leu  Arg  Glu  His  Ile  Phe  Asn  Phe
          275                      280                      285

Lys  Gln  His  Arg  Gln  Pro  Gln  His  Tyr  Gly  Leu  Ile  Ala  Glu  Leu
     290                      295                      300
```

( 2 ) INFORMATION FOR SEQ ID NO:23:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD441

( i x ) FEATURE:
        ( A ) NAME/KEY: CDS
        ( B ) LOCATION: 233..1144

( x i ) SEQUENCE DESCRIPTION: SEQ ID NO:23:

```
GTCGACGGCG  GGCTCGCGCG  AGAGCTTGTC  AAGCAGCGCA  AATTCCGGTT  CCGCTCCGGT         60

TGACAGATCA  AAAATTTTAC  GCCTGTTATT  GTCGTGCTGC  ATGTAATATT  TCGTACTTTA        120

TGTAGAATTT  GCATTGCGCC  GCGAGTCACA  AAGCCGGTTT  TCGGCGATGT  GTTTCACAAC        180

GTTTTCCCGG  CCGCTGGGCC  GGACATCACC  TAGGAAGGAG  CAGAGGTTCA  TG ACA            235
                                                              Thr
                                                                1

CGT  CAG  ATG  ATA  CTT  GCA  GTG  GGA  CAA  CAA  GGT  CCG  ATC  GCG  CGC  GCG     283
Arg  Gln  Met  Ile  Leu  Ala  Val  Gly  Gln  Gln  Gly  Pro  Ile  Ala  Arg  Ala
               5                        10                       15

GAG  ACA  CGC  GAA  CAG  GTC  GTC  GTT  CGT  CTT  CTC  GAC  ATG  CTG  ACG  AAA     331
Glu  Thr  Arg  Glu  Gln  Val  Val  Val  Arg  Leu  Leu  Asp  Met  Leu  Thr  Lys
          20                       25                       30

GCC  GCG  AGC  CGG  GGC  GCG  AAT  TTC  ATT  GTC  TTC  CCC  GAA  CTC  GCG  CTT     379
Ala  Ala  Ser  Arg  Gly  Ala  Asn  Phe  Ile  Val  Phe  Pro  Glu  Leu  Ala  Leu
     35                       40                       45

ACG  ACC  TTC  TTC  CCG  CGC  TGG  CAT  TTC  ACC  GAC  GAG  GCC  GAG  CTC  GAT     427
Thr  Thr  Phe  Phe  Pro  Arg  Trp  His  Phe  Thr  Asp  Glu  Ala  Glu  Leu  Asp
50                       55                       60                       65

AGC  TTC  TAT  GAG  ACC  GAA  ATG  CCC  GGC  CCG  GTG  GTC  CGT  CCA  CTC  TTT     475
Ser  Phe  Tyr  Glu  Thr  Glu  Met  Pro  Gly  Pro  Val  Val  Arg  Pro  Leu  Phe
```

-continued

```
                       70                        75                         80
GAG  AAG  GCC  GCG  GAA  CTC  GGG  ATC  GGC  TTC  AAT  CTG  GGC  TAC  GCT  GAA      523
Glu  Lys  Ala  Ala  Glu  Leu  Gly  Ile  Gly  Phe  Asn  Leu  Gly  Tyr  Ala  Glu
               85                        90                        95

CTC  GTC  GTC  GAA  GGC  GGC  GTC  AAG  CGT  CGC  TTC  AAC  ACG  TCC  ATT  TTG      571
Leu  Val  Val  Glu  Gly  Gly  Val  Lys  Arg  Arg  Phe  Asn  Thr  Ser  Ile  Leu
              100                       105                       110

GTG  GAT  AAG  TCA  GGC  AAG  ATC  GTC  GGC  AAG  TAT  CGT  AAG  ATC  CAT  TTG      619
Val  Asp  Lys  Ser  Gly  Lys  Ile  Val  Gly  Lys  Tyr  Arg  Lys  Ile  His  Leu
              115                       120                       125

CCG  GGT  CAC  AAG  GAG  TAC  GAG  GCC  TAC  CGG  CCG  TTC  CAG  CAT  CTT  GAA      667
Pro  Gly  His  Lys  Glu  Tyr  Glu  Ala  Tyr  Arg  Pro  Phe  Gln  His  Leu  Glu
130                       135                       140                       145

AAG  CGT  TAT  TTC  GAG  CCG  GGC  GAT  CTC  GGC  TTC  CCG  GTC  TAT  GAC  GTC      715
Lys  Arg  Tyr  Phe  Glu  Pro  Gly  Asp  Leu  Gly  Phe  Pro  Val  Tyr  Asp  Val
                         150                       155                       160

GAC  GCC  GCG  AAA  ATG  GGG  ATG  TTC  ATC  TGC  AAC  GAT  CGC  CGC  TGG  CCT      763
Asp  Ala  Ala  Lys  Met  Gly  Met  Phe  Ile  Cys  Asn  Asp  Arg  Arg  Trp  Pro
               165                       170                       175

GAA  GCC  TGG  CGG  GTG  ATG  GGC  CTC  AGG  GGC  GCC  GAG  ATC  ATC  TGC  GGC      811
Glu  Ala  Trp  Arg  Val  Met  Gly  Leu  Arg  Gly  Ala  Glu  Ile  Ile  Cys  Gly
               180                       185                       190

GGC  TAC  AAC  ACG  CCG  ACC  CAC  AAT  CCC  CCT  GTT  CCC  CAG  CAC  GAC  CAC      859
Gly  Tyr  Asn  Thr  Pro  Thr  His  Asn  Pro  Pro  Val  Pro  Gln  His  Asp  His
195                       200                       205

CTG  ACG  TCC  TTC  CAC  CAT  CTC  CTA  TCG  ATG  CAG  GCC  GGG  TCT  TAT  CAG      907
Leu  Thr  Ser  Phe  His  His  Leu  Leu  Ser  Met  Gln  Ala  Gly  Ser  Tyr  Gln
210                       215                       220                       225

AAC  GGG  GCC  TGG  TCC  GCG  GCC  GCG  GGC  AAG  AGT  GGC  ATG  GAG  GAG  AAC      955
Asn  Gly  Ala  Trp  Ser  Ala  Ala  Ala  Gly  Lys  Ser  Gly  Met  Glu  Glu  Asn
                         230                       235                       240

TGC  ATG  CTG  CTC  GGC  CAC  TCC  TGC  ATC  GTG  GCG  CCG  ACC  GGG  GAA  ATC     1003
Cys  Met  Leu  Leu  Gly  His  Ser  Cys  Ile  Val  Ala  Pro  Thr  Gly  Glu  Ile
               245                       250                       255

GTC  GCT  CTC  ACT  ACG  ACG  CTG  GAA  GAC  GAG  GTG  ATC  ACC  GCC  GCC  GTC     1051
Val  Ala  Leu  Thr  Thr  Thr  Leu  Glu  Asp  Glu  Val  Ile  Thr  Ala  Ala  Val
               260                       265                       270

GAT  CTC  GAT  CGC  TGC  CGG  GAA  CTG  CGT  GAA  CAC  ATC  TTC  AAC  TTC  AAG     1099
Asp  Leu  Asp  Arg  Cys  Arg  Glu  Leu  Arg  Glu  His  Ile  Phe  Asn  Phe  Lys
275                       280                       285

CAG  CAT  CGT  CAG  CCC  CAG  CAC  TAT  GGT  CTG  ATC  GCG  GAA  CTC  TGAGGTTGCC   1151
Gln  His  Arg  Gln  Pro  Gln  His  Tyr  Gly  Leu  Ile  Ala  Glu  Leu
290                       295                       300

GAAAAGCATG  TGTGTCGTTG  TTCTCGGCGC  CTGGGTCACA  TCCAGGCGCG  CCAGGGTGAC            1211

GCTGGTGGAA  TAGTACCACG  ACCGCTTCAG  GGCGATCCGC  AAGGAGATGC  GGGTCGCCGG            1271

AGCGGCAAAG  CCCGACATTC  GTTTCGCACC  GACGGCCGTC  GTGAACTCGA  CAGTCCGCGA            1331

GAAGGGCGTA  TTGCGCGGCC  TGGACCTGTA  CGTGGAACTG  TAGCCCATAT  ATAGATTTCC            1391

AAAGAGTTTC  GGCGAGGCGC  GGCGCGCCTA  GCCCCATGTG  AGCGAGAACC  GTGCCCAGAT            1451

CAAAGAATGA  GACCGACGCG  CCGGCCGCGG  CAAAGGATGA  TCCTCAGGGT  CGGATCTATC            1511

GCTCCGCCCT  GAAGCAGGAG  GGCGCACGCT  GGCTGCTGAC  GGCGGAGGAA  GGGTTGCTGG            1571

CAAAGCCCAA  GCCGCCCGGC  CTTGTTCCGG  CACTTGAGAA  TGCGATCGCC  ATCGTCGATT            1631

ACATCAACGG  TACACCGCCC  CATATCGCGT  CCCTGGCGGA  GCTTTCAACG  ACGCTCGGGA            1691

TATCCAAGAG  CCACTGTCAC  TCCATCCTCA  AGACGCTGAC  GCATTTCGGC  TGGCTGAAAT            1751

TCGACAATCG  CTCAAAGAGC  TACGAGCTGA  ATTC                                          1785
```

( 2 ) INFORMATION FOR SEQ ID NO:24:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Thr Arg Gln Met Ile Leu Ala Val Gly Gln Gly Pro Ile Ala Arg
 1               5                  10                 15
Ala Glu Thr Arg Glu Gln Val Val Val Arg Leu Leu Asp Met Leu Thr
            20                  25                 30
Lys Ala Ala Ser Arg Gly Ala Asn Phe Ile Val Phe Pro Glu Leu Ala
        35                  40                  45
Leu Thr Thr Phe Phe Pro Arg Trp His Phe Thr Asp Glu Ala Glu Leu
    50                  55                  60
Asp Ser Phe Tyr Glu Thr Glu Met Pro Gly Pro Val Val Arg Pro Leu
65                  70                  75                  80
Phe Glu Lys Ala Ala Glu Leu Gly Ile Gly Phe Asn Leu Gly Tyr Ala
                85                  90                  95
Glu Leu Val Val Glu Gly Gly Val Lys Arg Arg Phe Asn Thr Ser Ile
               100                 105                 110
Leu Val Asp Lys Ser Gly Lys Ile Val Gly Lys Tyr Arg Lys Ile His
            115                 120                 125
Leu Pro Gly His Lys Glu Tyr Glu Ala Tyr Arg Pro Phe Gln His Leu
    130                 135                 140
Glu Lys Arg Tyr Phe Glu Pro Gly Asp Leu Gly Phe Pro Val Tyr Asp
145                 150                 155                 160
Val Asp Ala Ala Lys Met Gly Met Phe Ile Cys Asn Asp Arg Arg Trp
                165                 170                 175
Pro Glu Ala Trp Arg Val Met Gly Leu Arg Gly Ala Glu Ile Ile Cys
               180                 185                 190
Gly Gly Tyr Asn Thr Pro Thr His Asn Pro Pro Val Pro Gln His Asp
            195                 200                 205
His Leu Thr Ser Phe His His Leu Leu Ser Met Gln Ala Gly Ser Tyr
    210                 215                 220
Gln Asn Gly Ala Trp Ser Ala Ala Ala Gly Lys Ser Gly Met Glu Glu
225                 230                 235                 240
Asn Cys Met Leu Leu Gly His Ser Cys Ile Val Ala Pro Thr Gly Glu
                245                 250                 255
Ile Val Ala Leu Thr Thr Thr Leu Glu Asp Glu Val Ile Thr Ala Ala
            260                 265                 270
Val Asp Leu Asp Arg Cys Arg Glu Leu Arg Glu His Ile Phe Asn Phe
    275                 280                 285
Lys Gln His Arg Gln Pro Gln His Tyr Gly Leu Ile Ala Glu Leu
        290                 295                 300
```

( 2 ) INFORMATION FOR SEQ ID NO:25:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD445

( i x ) FEATURE:
    ( A ) NAME/KEY: CDS
    ( B ) LOCATION: 233..1144

( x i ) SEQUENCE DESCRIPTION: SEQ ID NO:25:

```
GTCGACGGCG GGCTCGCGCG AGAGCTTGTC AAGCAGCGCA AATTCCGGTT CCGCTCCGGT        60

TGACAGATCA AAAATTTTAC GCCTGTTATT GTCGTGCTGC ATGTAATATT TCGTACTTTA       120

TGTAGAATTT GCATTGCGCC GCGAGTCACA AAGCCGGTTT TCGGCGATGT GTTTCACAAC       180

GTTTTCCCGG CCGCTGGGCC GGACATCACC TAGGAAGGAG CAGAGGTTCA TG ACA           235
                                                         Thr
                                                          1

CGT CAG ATG ATA CTT GCA GTG GGA CAA CAA GGT CCG ATC GCG CGC GCG         283
Arg Gln Met Ile Leu Ala Val Gly Gln Gln Gly Pro Ile Ala Arg Ala
             5                  10                  15

GAG ACA CGC GAA CAG GTC GTC GTT CGT CTT CTC GAC ATG CTG ACG AAA         331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT         379
Ala Ala Ser Arg Gly Ala Asn Phe Ile Val Phe Pro Glu Leu Ala Leu
     35                  40                  45

ACG ACC TTC TTC CCG CGC TGG CAT TTC ACC GAC GAG GCC GAG CTC GAT         427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT         475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA         523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG         571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG         619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA         667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC         715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT         763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC         811
Glu Ala Trp Arg Val Met Gly Leu Arg Gly Ala Glu Ile Ile Cys Gly
        180                 185                 190

GGC TAC AAC ACG CCG ACC CAC AAT CCC ACC GTT CCC CAG CAC GAC CAC         859
Gly Tyr Asn Thr Pro Thr His Asn Pro Thr Val Pro Gln His Asp His
    195                 200                 205

CTG ACG TCC TTC CAC CAT CTC CTA TCG ATG CAG GCC GGG TCT TAT CAG         907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC         955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC        1003
Cys Met Leu Leu Gly His Ser Cys Ile Val Ala Pro Thr Gly Glu Ile
            245                 250                 255
```

```
GTC GCT CTC ACT ACG ACG CTG GAA GAC GAG GTG ATC ACC GCC GCC GTC        1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG        1099
Asp Leu Asp Arg Cys Arg Glu Leu Arg Glu His Ile Phe Asn Phe Lys
        275                 280                 285

CAG CAT CGT CAG CCC CAG CAC TAT GGT CTG ATC GCG GAA CTC TGAGGTTGCC     1151
Gln His Arg Gln Pro Gln His Tyr Gly Leu Ile Ala Glu Leu
290                 295                 300

GAAAAGCATG TGTGTCGTTG TTCTCGGCGC CTGGGTCACA TCCAGGCGCG CCAGGGTGAC      1211
GCTGGTGGAA TAGTACCACG ACCGCTTCAG GGCGATCCGC AAGGAGATGC GGGTCGCCGG      1271
AGCGGCAAAG CCCGACATTC GTTTCGCACC GACGGCCGTC GTGAACTCGA CAGTCCGCGA      1331
GAAGGGCGTA TTGCGCGGCC TGGACCTGTA CGTGGAACTG TAGCCCATAT ATAGATTTCC      1391
AAAGAGTTTC GGCGAGGCGC GGCGCGCCTA GCCCCATGTG AGCGAGAACC GTGCCCAGAT      1451
CAAAGAATGA GACCGACGCG CCGGCCGCGG CAAAGGATGA TCCTCAGGGT CGGATCTATC      1511
GCTCCGCCCT GAAGCAGGAG GGCGCACGCT GGCTGCTGAC GGCGGAGGAA GGGTTGCTGG      1571
CAAAGCCCAA GCCGCCCGGC CTTGTTCCGG CACTTGAGAA TGCGATCGCC ATCGTCGATT      1631
ACATCAACGG TACACCGCCC CATATCGCGT CCCTGGCGGA GCTTTCAACG ACGCTCGGGA      1691
TATCCAAGAG CCACTGTCAC TCCATCCTCA AGACGCTGAC GCATTTCGGC TGGCTGAAAT      1751
TCGACAATCG CTCAAAGAGC TACGAGCTGA ATTC                                  1785
```

(2) INFORMATION FOR SEQ ID NO:26:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:26:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
                20                  25                  30

Lys Ala Ala Ser Arg Gly Ala Asn Phe Ile Val Phe Pro Glu Leu Ala
            35                  40                  45

Leu Thr Thr Phe Phe Pro Arg Trp His Phe Thr Asp Glu Ala Glu Leu
        50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175
```

-continued

| Pro | Glu | Ala | Trp | Arg | Val | Met | Gly | Leu | Arg | Gly | Ala | Glu | Ile | Ile | Cys |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Gly | Gly | Tyr | Asn | Thr | Pro | Thr | His | Asn | Pro | Thr | Val | Pro | Gln | His | Asp |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| His | Leu | Thr | Ser | Phe | His | His | Leu | Leu | Ser | Met | Gln | Ala | Gly | Ser | Tyr |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gln | Asn | Gly | Ala | Trp | Ser | Ala | Ala | Gly | Lys | Val | Gly | Met | Glu | Glu |
|-----|-----|-----|-----|-----|-----|-----|-----|-----|-----|-----|-----|-----|-----|-----|
| 225 |     |     |     |     | 230 |     |     |     | 235 |     |     |     |     | 240 |

| Asn | Cys | Met | Leu | Leu | Gly | His | Ser | Cys | Ile | Val | Ala | Pro | Thr | Gly | Glu |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ile | Val | Ala | Leu | Thr | Thr | Thr | Leu | Glu | Asp | Glu | Val | Ile | Thr | Ala | Ala |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Val | Asp | Leu | Asp | Arg | Cys | Arg | Glu | Leu | Arg | Glu | His | Ile | Phe | Asn | Phe |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Lys | Gln | His | Arg | Gln | Pro | Gln | His | Tyr | Gly | Leu | Ile | Ala | Glu | Leu |
|-----|-----|-----|-----|-----|-----|-----|-----|-----|-----|-----|-----|-----|-----|-----|
|     | 290 |     |     |     |     | 295 |     |     |     |     | 300 |     |     |     |

( 2 ) INFORMATION FOR SEQ ID NO:27:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD447

( i x ) FEATURE:
        ( A ) NAME/KEY: CDS
        ( B ) LOCATION: 233..1144

( x i ) SEQUENCE DESCRIPTION: SEQ ID NO:27:

```
GTCGACGGCG   GGCTCGCGCG   AGAGCTTGTC   AAGCAGCGCA   AATTCCGGTT   CCGCTCCGGT        60

TGACAGATCA   AAAATTTTAC   GCCTGTTATT   GTCGTGCTGC   ATGTAATATT   TCGTACTTTA       120

TGTAGAATTT   GCATTGCGCC   GCGAGTCACA   AAGCCGGTTT   TCGGCGATGT   GTTTCACAAC       180

GTTTTCCCGG   CCGCTGGGCC   GGACATCACC   TAGGAAGGAG   CAGAGGTTCA   TG  ACA          235
                                                                   Thr
                                                                    1
```

| CGT | CAG | ATG | ATA | CTT | GCA | GTG | GGA | CAA | CAA | GGT | CCG | ATC | GCG | CGC | GCG | 283 |
|-----|-----|-----|-----|-----|-----|-----|-----|-----|-----|-----|-----|-----|-----|-----|-----|-----|
| Arg | Gln | Met | Ile | Leu | Ala | Val | Gly | Gln | Gln | Gly | Pro | Ile | Ala | Arg | Ala |     |
|     |     |     | 5   |     |     |     |     |     | 10  |     |     |     |     | 15  |     |     |

| GAG | ACA | CGC | GAA | CAG | GTC | GTC | GTT | CGT | CTT | CTC | GAC | ATG | CTG | ACG | AAA | 331 |
|-----|-----|-----|-----|-----|-----|-----|-----|-----|-----|-----|-----|-----|-----|-----|-----|-----|
| Glu | Thr | Arg | Glu | Gln | Val | Val | Val | Arg | Leu | Leu | Asp | Met | Leu | Thr | Lys |     |
|     |     | 20  |     |     |     |     | 25  |     |     |     |     | 30  |     |     |     |     |

| GCC | GCG | AGC | CGG | GGC | GCG | AAT | TTC | ATT | GTC | TTC | CCC | GAA | CTC | GCG | CTT | 379 |
|-----|-----|-----|-----|-----|-----|-----|-----|-----|-----|-----|-----|-----|-----|-----|-----|-----|
| Ala | Ala | Ser | Arg | Gly | Ala | Asn | Phe | Ile | Val | Phe | Pro | Glu | Leu | Ala | Leu |     |
|     |     | 35  |     |     |     |     | 40  |     |     |     |     | 45  |     |     |     |     |

| ACG | ACC | TTC | TTC | CCG | CGC | TGG | CAT | TTC | ACC | GAC | GAG | GCC | GAG | CTC | GAT | 427 |
|-----|-----|-----|-----|-----|-----|-----|-----|-----|-----|-----|-----|-----|-----|-----|-----|-----|
| Thr | Thr | Phe | Phe | Pro | Arg | Trp | His | Phe | Thr | Asp | Glu | Ala | Glu | Leu | Asp |     |
| 50  |     |     |     |     | 55  |     |     |     |     | 60  |     |     |     |     | 65  |     |

| AGC | TTC | TAT | GAG | ACC | GAA | ATG | CCC | GGC | CCG | GTG | GTC | CGT | CCA | CTC | TTT | 475 |
|-----|-----|-----|-----|-----|-----|-----|-----|-----|-----|-----|-----|-----|-----|-----|-----|-----|
| Ser | Phe | Tyr | Glu | Thr | Glu | Met | Pro | Gly | Pro | Val | Val | Arg | Pro | Leu | Phe |     |
|     |     |     |     | 70  |     |     |     |     | 75  |     |     |     |     | 80  |     |     |

| GAG | AAG | GCC | GCG | GAA | CTC | GGG | ATC | GGC | TTC | AAT | CTG | GGC | TAC | GCT | GAA | 523 |
|-----|-----|-----|-----|-----|-----|-----|-----|-----|-----|-----|-----|-----|-----|-----|-----|-----|
| Glu | Lys | Ala | Ala | Glu | Leu | Gly | Ile | Gly | Phe | Asn | Leu | Gly | Tyr | Ala | Glu |     |
|     |     |     | 85  |     |     |     |     | 90  |     |     |     |     | 95  |     |     |     |

| CTC | GTC | GTC | GAA | GGC | GGC | GTC | AAG | CGT | CGC | TTC | AAC | ACG | TCC | ATT | TTG | 571 |
|-----|-----|-----|-----|-----|-----|-----|-----|-----|-----|-----|-----|-----|-----|-----|-----|-----|
| Leu | Val | Val | Glu | Gly | Gly | Val | Lys | Arg | Arg | Phe | Asn | Thr | Ser | Ile | Leu |     |
|     |     | 100 |     |     |     |     | 105 |     |     |     |     | 110 |     |     |     |     |

-continued

```
GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
    115             120             125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
130             135             140                     145

AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
                150             155             160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
            165             170             175

GAA GCC TGG CGG GTG ATG GGC CTC AGG GGC GCC GAG ATC ATC TGC GGC      811
Glu Ala Trp Arg Val Met Gly Leu Arg Gly Ala Glu Ile Ile Cys Gly
        180             185             190

GGC TAC AAC ACG CCG ACC CAC AAT CCC CCT GTT CCC CAG CAC GAC CAC      859
Gly Tyr Asn Thr Pro Thr His Asn Pro Pro Val Pro Gln His Asp His
    195             200             205

CTG ACG TCC TTC CAC CAT CTC CTA TCG ATG CAG GCC GGG TCT TAT CAG      907
Leu Thr Ser Phe His His Leu Leu Ser Met Gln Ala Gly Ser Tyr Gln
210             215             220             225

AAC GGG GCC TGG TCC GCG GCC GCG GGC AAG TCA GGC ATG GAG GAG AAC      955
Asn Gly Ala Trp Ser Ala Ala Ala Gly Lys Ser Gly Met Glu Glu Asn
                230             235             240

TGC ATG CTG CTC GGC CAC TCC TGC ATC GTG GCG CCG ACC GGG GAA ATC     1003
Cys Met Leu Leu Gly His Ser Cys Ile Val Ala Pro Thr Gly Glu Ile
            245             250             255

GTC GCT CTC ACT ACG ACG CTG GAA GAC GAG GTG ATC ACC GCC GCC GTC     1051
Val Ala Leu Thr Thr Thr Leu Glu Asp Glu Val Ile Thr Ala Ala Val
        260             265             270

GAT CTC GAT CGC TGC CGG GAA CTG CGT GAA CAC ATC TTC AAC TTC AAG     1099
Asp Leu Asp Arg Cys Arg Glu Leu Arg Glu His Ile Phe Asn Phe Lys
    275             280             285

CAG CAT CGT CAG CCC CAG CAC TAT GGT CTG ATC GCG GAA CTC TGAGGTTGCC  1151
Gln His Arg Gln Pro Gln His Tyr Gly Leu Ile Ala Glu Leu
290             295             300

GAAAAGCATG TGTGTCGTTG TTCTCGGCGC CTGGGTCACA TCCAGGCGCG CCAGGGTGAC   1211
GCTGGTGGAA TAGTACCACG ACCGCTTCAG GGCGATCCGC AAGGAGATGC GGGTCGCCGG   1271
AGCGGCAAAG CCCGACATTC GTTTCGCACC GACGGCCGTC GTGAACTCGA CAGTCCGCGA   1331
GAAGGGCGTA TTGCGCGGCC TGGACCTGTA CGTGGAACTG TAGCCCATAT ATAGATTTCC   1391
AAAGAGTTTC GGCGAGGCGC GGCGCGCCTA GCCCCATGTG AGCGAGAACC GTGCCCAGAT   1451
CAAAGAATGA GACCGACGCG CCGGCCGCGG CAAAGGATGA TCCTCAGGGT CGGATCTATC   1511
GCTCCGCCCT GAAGCAGGAG GGCGCACGCT GGCTGCTGAC GGCGGAGGAA GGGTTGCTGG   1571
CAAAGCCCAA GCCGCCCGGC CTTGTTCCGG CACTTGAGAA TGCGATCGCC ATCGTCGATT   1631
ACATCAACGG TACACCGCCC CATATCGCGT CCCTGGCGGA GCTTTCAACG ACGCTCGGGA   1691
TATCCAAGAG CCACTGTCAC TCCATCCTCA AGACGCTGAC GCATTTCGGC TGGCTGAAAT   1751
TCGACAATCG CTCAAAGAGC TACGAGCTGA ATTC                              1785
```

(2) INFORMATION FOR SEQ ID NO:28:

(i) SEQUENCE CHARACTERISTICS:
(A) LENGTH: 303 amino acids
(B) TYPE: amino acid
(D) TOPOLOGY: linear (ii) MOLECULE TYPE: protein ( x i ) SEQUENCE DESCRIPTION: SEQ ID NO:28:

| Thr | Arg | Gln | Met | Ile | Leu | Ala | Val | Gly | Gln | Gln | Gly | Pro | Ile | Ala | Arg |
|---|---|---|---|---|---|---|---|---|---|---|---|---|---|---|---|
| 1 | | | | 5 | | | | | 10 | | | | | 15 | |
| Ala | Glu | Thr | Arg | Glu | Gln | Val | Val | Val | Arg | Leu | Leu | Asp | Met | Leu | Thr |
| | | | 20 | | | | | 25 | | | | | 30 | | |
| Lys | Ala | Ala | Ser | Arg | Gly | Ala | Asn | Phe | Ile | Val | Phe | Pro | Glu | Leu | Ala |
| | | | 35 | | | | 40 | | | | | 45 | | | |
| Leu | Thr | Thr | Phe | Phe | Pro | Arg | Trp | His | Phe | Thr | Asp | Glu | Ala | Glu | Leu |
| | 50 | | | | | 55 | | | | | 60 | | | | |
| Asp | Ser | Phe | Tyr | Glu | Thr | Glu | Met | Pro | Gly | Pro | Val | Val | Arg | Pro | Leu |
| 65 | | | | | 70 | | | | | 75 | | | | | 80 |
| Phe | Glu | Lys | Ala | Ala | Glu | Leu | Gly | Ile | Gly | Phe | Asn | Leu | Gly | Tyr | Ala |
| | | | | 85 | | | | | 90 | | | | | 95 | |
| Glu | Leu | Val | Val | Glu | Gly | Gly | Val | Lys | Arg | Arg | Phe | Asn | Thr | Ser | Ile |
| | | | | 100 | | | | | 105 | | | | | 110 | |
| Leu | Val | Asp | Lys | Ser | Gly | Lys | Ile | Val | Gly | Lys | Tyr | Arg | Lys | Ile | His |
| | | | 115 | | | | | 120 | | | | | 125 | | |
| Leu | Pro | Gly | His | Lys | Glu | Tyr | Glu | Ala | Tyr | Arg | Pro | Phe | Gln | His | Leu |
| | | 130 | | | | | 135 | | | | | 140 | | | |
| Glu | Lys | Arg | Tyr | Phe | Glu | Pro | Gly | Asp | Leu | Gly | Phe | Pro | Val | Tyr | Asp |
| 145 | | | | | 150 | | | | | 155 | | | | | 160 |
| Val | Asp | Ala | Ala | Lys | Met | Gly | Met | Phe | Ile | Cys | Asn | Asp | Arg | Arg | Trp |
| | | | | 165 | | | | | 170 | | | | | 175 | |
| Pro | Glu | Ala | Trp | Arg | Val | Met | Gly | Leu | Arg | Gly | Ala | Glu | Ile | Ile | Cys |
| | | | 180 | | | | | 185 | | | | | 190 | | |
| Gly | Gly | Tyr | Asn | Thr | Pro | Thr | His | Asn | Pro | Pro | Val | Pro | Gln | His | Asp |
| | | 195 | | | | | 200 | | | | | 205 | | | |
| His | Leu | Thr | Ser | Phe | His | His | Leu | Leu | Ser | Met | Gln | Ala | Gly | Ser | Tyr |
| | 210 | | | | | 215 | | | | | 220 | | | | |
| Gln | Asn | Gly | Ala | Trp | Ser | Ala | Ala | Ala | Gly | Lys | Ser | Gly | Met | Glu | Glu |
| 225 | | | | | 230 | | | | | 235 | | | | | 240 |
| Asn | Cys | Met | Leu | Leu | Gly | His | Ser | Cys | Ile | Val | Ala | Pro | Thr | Gly | Glu |
| | | | | 245 | | | | | 250 | | | | | 255 | |
| Ile | Val | Ala | Leu | Thr | Thr | Thr | Leu | Glu | Asp | Glu | Val | Ile | Thr | Ala | Ala |
| | | | | 260 | | | | | 265 | | | | | 270 | |
| Val | Asp | Leu | Asp | Arg | Cys | Arg | Glu | Leu | Arg | Glu | His | Ile | Phe | Asn | Phe |
| | | | 275 | | | | | 280 | | | | | 285 | | |
| Lys | Gln | His | Arg | Gln | Pro | Gln | His | Tyr | Gly | Leu | Ile | Ala | Glu | Leu | |
| | | 290 | | | | | 295 | | | | | 300 | | | |

( 2 ) INFORMATION FOR SEQ ID NO:29:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD448

( i x ) FEATURE:
        ( A ) NAME/KEY: CDS
        ( B ) LOCATION: 233..1144

( x i ) SEQUENCE DESCRIPTION: SEQ ID NO:29:

```
GTCGACGGCG GGCTCGCGCG AGAGCTTGTC AAGCAGCGCA AATTCCGGTT CCGCTCCGGT        60

TGACAGATCA AAAATTTTAC GCCTGTTATT GTCGTGCTGC ATGTAATATT TCGTACTTTA       120
```

| | | | | | |
|---|---|---|---|---|---|
| TGTAGAATTT | GCATTGCGCC | GCGAGTCACA | AAGCCGGTTT | TCGGCGATGT | GTTTCACAAC | 180 |
| GTTTTCCCGG | CCGCTGGGCC | GGACATCACC | TAGGAAGGAG | CAGAGGTTCA | TG ACA | 235 |
| | | | | | Thr |
| | | | | | 1 |

```
CGT CAG ATG ATA CTT GCA GTG GGA CAA CAA GGT CCG ATC GCG CGC GCG       283
Arg Gln Met Ile Leu Ala Val Gly Gln Gln Gly Pro Ile Ala Arg Ala
         5               10                  15

GAG ACA CGC GAA CAG GTC GTC GTT CGT CTT CTC GAC ATG CTG ACG AAA       331
Glu Thr Arg Glu Gln Val Val Val Arg Leu Leu Asp Met Leu Thr Lys
        20                  25                  30

GCC GCG AGC CGG GGC GCG AAT TTC ATT GTC TTC CCC GAA CTC GCG CTT       379
Ala Ala Ser Arg Gly Ala Asn Phe Ile Val Phe Pro Glu Leu Ala Leu
        35                  40                  45

ACG ACC TTC TTC CCG CGC TGG CAT TTC ACC GAC GAG GCC GAG CTC GAT       427
Thr Thr Phe Phe Pro Arg Trp His Phe Thr Asp Glu Ala Glu Leu Asp
50              55                  60                     65

AGC TTC TAT GAG ACC GAA ATG CCC GGC CCG GTG GTC CGT CCA CTC TTT       475
Ser Phe Tyr Glu Thr Glu Met Pro Gly Pro Val Val Arg Pro Leu Phe
                70                  75                     80

GAG AAG GCC GCG GAA CTC GGG ATC GGC TTC AAT CTG GGC TAC GCT GAA       523
Glu Lys Ala Ala Glu Leu Gly Ile Gly Phe Asn Leu Gly Tyr Ala Glu
                85                  90                  95

CTC GTC GTC GAA GGC GGC GTC AAG CGT CGC TTC AAC ACG TCC ATT TTG       571
Leu Val Val Glu Gly Gly Val Lys Arg Arg Phe Asn Thr Ser Ile Leu
            100                 105                 110

GTG GAT AAG TCA GGC AAG ATC GTC GGC AAG TAT CGT AAG ATC CAT TTG       619
Val Asp Lys Ser Gly Lys Ile Val Gly Lys Tyr Arg Lys Ile His Leu
        115                 120                 125

CCG GGT CAC AAG GAG TAC GAG GCC TAC CGG CCG TTC CAG CAT CTT GAA       667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC       715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT       763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC       811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC       859
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG       907
Leu Thr Ser Phe His His Leu Leu Ser Met Gln Ala Gly Ser Tyr Gln
210                 215                 220                 225

AAC GGG GCC TGG TCC GCG GCC GCG GGC AAG TCG GGC ATG GAG GAG AAC       955
Asn Gly Ala Trp Ser Ala Ala Ala Gly Lys Ser Gly Met Glu Glu Asn
                230                 235                 240

TGC ATG CTG CTC GGC CAC TCC TGC ATC GTG GCG CCG ACC GGG GAA ATC      1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC      1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG      1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC TGAGGTTGCC   1151
Gln His Arg Gln Pro Gln His Tyr Gly Leu Ile Ala Glu Leu
```

```
Gln  His  Arg  Gln  Pro  Gln  His  Tyr  Gly  Leu  Ile  Ala  Glu  Leu
290                 295                      300
```

| | | | | | |
|---|---|---|---|---|---|
| GAAAAGCATG | TGTGTCGTTG | TTCTCGGCGC | CTGGGTCACA | TCCAGGCGCG | CCAGGGTGAC | 1211 |
| GCTGGTGGAA | TAGTACCACG | ACCGCTTCAG | GGCGATCCGC | AAGGAGATGC | GGGTCGCCGG | 1271 |
| AGCGGCAAAG | CCCGACATTC | GTTTCGCACC | GACGGCCGTC | GTGAACTCGA | CAGTCCGCGA | 1331 |
| GAAGGGCGTA | TTGCGCGGCC | TGGACCTGTA | CGTGGAACTG | TAGCCCATAT | ATAGATTTCC | 1391 |
| AAAGAGTTTC | GGCGAGGCGC | GGCGCGCCTA | GCCCATGTG | AGCGAGAACC | GTGCCAGAT | 1451 |
| CAAAGAATGA | GACCGACGCG | CCGGCCGCGG | CAAAGGATGA | TCCTCAGGGT | CGGATCTATC | 1511 |
| GCTCCGCCCT | GAAGCAGGAG | GGCGCACGCT | GGCTGCTGAC | GGCGGAGGAA | GGGTTGCTGG | 1571 |
| CAAAGCCCAA | GCCGCCCGGC | CTTGTTCCGG | CACTTGAGAA | TGCGATCGCC | ATCGTCGATT | 1631 |
| ACATCAACGG | TACACCGCCC | CATATCGCGT | CCCTGGCGGA | GCTTTCAACG | ACGCTCGGGA | 1691 |
| TATCCAAGAG | CCACTGTCAC | TCCATCCTCA | AGACGCTGAC | GCATTTCGGC | TGGCTGAAAT | 1751 |
| TCGACAATCG | CTCAAAGAGC | TACGAGCTGA | ATTC | | | 1785 |

( 2 ) INFORMATION FOR SEQ ID NO:30:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Thr  Arg  Gln  Met  Ile  Leu  Ala  Val  Gly  Gln  Gln  Gly  Pro  Ile  Ala  Arg
 1                   5                        10                       15

Ala  Glu  Thr  Arg  Glu  Gln  Val  Val  Val  Arg  Leu  Leu  Asp  Met  Leu  Thr
               20                       25                       30

Lys  Ala  Ala  Ser  Arg  Gly  Ala  Asn  Phe  Ile  Val  Phe  Pro  Glu  Leu  Ala
          35                       40                       45

Leu  Thr  Thr  Phe  Phe  Pro  Arg  Trp  His  Phe  Thr  Asp  Glu  Ala  Glu  Leu
     50                       55                       60

Asp  Ser  Phe  Tyr  Glu  Thr  Glu  Met  Pro  Gly  Pro  Val  Val  Arg  Pro  Leu
65                        70                       75                        80

Phe  Glu  Lys  Ala  Ala  Glu  Leu  Gly  Ile  Gly  Phe  Asn  Leu  Gly  Tyr  Ala
                    85                       90                       95

Glu  Leu  Val  Val  Glu  Gly  Gly  Val  Lys  Arg  Arg  Phe  Asn  Thr  Ser  Ile
                    100                      105                      110

Leu  Val  Asp  Lys  Ser  Gly  Lys  Ile  Val  Gly  Lys  Tyr  Arg  Lys  Ile  His
               115                      120                      125

Leu  Pro  Gly  His  Lys  Glu  Tyr  Glu  Ala  Tyr  Arg  Pro  Phe  Gln  His  Leu
     130                      135                      140

Glu  Lys  Arg  Tyr  Phe  Glu  Pro  Gly  Asp  Leu  Gly  Phe  Pro  Val  Tyr  Asp
145                       150                      155                       160

Val  Asp  Ala  Ala  Lys  Met  Gly  Met  Phe  Ile  Cys  Asn  Asp  Arg  Arg  Trp
                    165                      170                      175

Pro  Glu  Ala  Trp  Arg  Val  Met  Gly  Leu  Arg  Gly  Ala  Glu  Ile  Ile  Cys
               180                      185                      190

Gly  Gly  Tyr  Asn  Thr  Pro  Thr  His  Asn  Pro  Pro  Val  Pro  Gln  His  Asp
               195                      200                      205

His  Leu  Thr  Ser  Phe  His  His  Leu  Leu  Ser  Met  Gln  Ala  Gly  Ser  Tyr
     210                      215                      220

Gln  Asn  Gly  Ala  Trp  Ser  Ala  Ala  Ala  Gly  Lys  Ser  Gly  Met  Glu  Glu
```

```
225                          230                         235                           240
Asn  Cys  Met  Leu  Leu  Gly  His  Ser  Cys  Ile  Val  Ala  Pro  Thr  Gly  Glu
                    245                      250                      255

Ile  Val  Ala  Leu  Thr  Thr  Thr  Leu  Glu  Asp  Glu  Val  Ile  Thr  Ala  Ala
                    260                      265                      270

Val  Asp  Leu  Asp  Arg  Cys  Arg  Glu  Leu  Arg  Glu  His  Ile  Phe  Asn  Phe
                    275                      280                      285

Lys  Gln  His  Arg  Gln  Pro  Gln  His  Tyr  Gly  Leu  Ile  Ala  Glu  Leu
                    290                      295                      300
```

( 2 ) INFORMATION FOR SEQ ID NO:31:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD450

( i x ) FEATURE:
        ( A ) NAME/KEY: CDS
        ( B ) LOCATION: 233..1144

( x i ) SEQUENCE DESCRIPTION: SEQ ID NO:31:

```
GTCGACGGCG  GGCTCGCGCG  AGAGCTTGTC  AAGCAGCGCA  AATTCCGGTT  CCGCTCCGGT      60

TGACAGATCA  AAAATTTTAC  GCCTGTTATT  GTCGTGCTGC  ATGTAATATT  TCGTACTTTA     120

TGTAGAATTT  GCATTGCGCC  GCGAGTCACA  AAGCCGGTTT  TCGGCGATGT  GTTTCACAAC     180

GTTTTCCCGG  CCGCTGGGCC  GGACATCACC  TAGGAAGGAG  CAGAGGTTCA  TG ACA        235
                                                             Thr
                                                             1

CGT  CAG  ATG  ATA  CTT  GCA  GTG  GGA  CAA  CAA  GGT  CCG  ATC  GCG  CGC  GCG    283
Arg  Gln  Met  Ile  Leu  Ala  Val  Gly  Gln  Gln  Gly  Pro  Ile  Ala  Arg  Ala
               5                        10                       15

GAG  ACA  CGC  GAA  CAG  GTC  GTC  GTT  CGT  CTT  CTC  GAC  ATG  CTG  ACG  AAA    331
Glu  Thr  Arg  Glu  Gln  Val  Val  Val  Arg  Leu  Leu  Asp  Met  Leu  Thr  Lys
          20                       25                       30

GCC  GCG  AGC  CGG  GGC  GCG  AAT  TTC  ATT  GTC  TTC  CCC  GAA  CTC  GCG  CTT    379
Ala  Ala  Ser  Arg  Gly  Ala  Asn  Phe  Ile  Val  Phe  Pro  Glu  Leu  Ala  Leu
     35                       40                       45

ACG  ACC  TTC  TTC  CCG  CGC  TGG  CAT  TTC  ACC  GAC  GAG  GCC  GAG  CTC  GAT    427
Thr  Thr  Phe  Phe  Pro  Arg  Trp  His  Phe  Thr  Asp  Glu  Ala  Glu  Leu  Asp
50                       55                       60                       65

AGC  TTC  TAT  GAG  ACC  GAA  ATG  CCC  GGC  CCG  GTG  GTC  CGT  CCA  CTC  TTT    475
Ser  Phe  Tyr  Glu  Thr  Glu  Met  Pro  Gly  Pro  Val  Val  Arg  Pro  Leu  Phe
               70                       75                       80

GAG  AAG  GCC  GCG  GAA  CTC  GGG  ATC  GGC  TTC  AAT  CTG  GGC  TAC  GCT  GAA    523
Glu  Lys  Ala  Ala  Glu  Leu  Gly  Ile  Gly  Phe  Asn  Leu  Gly  Tyr  Ala  Glu
               85                       90                       95

CTC  GTC  GTC  GAA  GGC  GGC  GTC  AAG  CGT  CGC  TTC  AAC  ACG  TCC  ATT  TTG    571
Leu  Val  Val  Glu  Gly  Gly  Val  Lys  Arg  Arg  Phe  Asn  Thr  Ser  Ile  Leu
               100                      105                      110

GTG  GAT  AAG  TCA  GGC  AAG  ATC  GTC  GGC  AAG  TAT  CGT  AAG  ATC  CAT  TTG    619
Val  Asp  Lys  Ser  Gly  Lys  Ile  Val  Gly  Lys  Tyr  Arg  Lys  Ile  His  Leu
     115                      120                      125

CCG  GGT  CAC  AAG  GAG  TAC  GAG  GCC  TAC  CGG  CCG  TTC  CAG  CAT  CTT  GAA    667
Pro  Gly  His  Lys  Glu  Tyr  Glu  Ala  Tyr  Arg  Pro  Phe  Gln  His  Leu  Glu
130                      135                      140                      145

AAG  CGT  TAT  TTC  GAG  CCG  GGC  GAT  CTC  GGC  TTC  CCG  GTC  TAT  GAC  GTC    715
Lys  Arg  Tyr  Phe  Glu  Pro  Gly  Asp  Leu  Gly  Phe  Pro  Val  Tyr  Asp  Val
```

```
                        150                           155                           160
GAC  GCC  GCG  AAA  ATG  GGG  ATG  TTC  ATC  TGC  AAC  GAT  CGC  CGC  TGG  CCT        763
Asp  Ala  Ala  Lys  Met  Gly  Met  Phe  Ile  Cys  Asn  Asp  Arg  Arg  Trp  Pro
               165                      170                 175

GAA  GCC  TGG  CGG  GTG  ATG  GGC  CTC  AGG  GGC  GCC  GAG  ATC  ATC  TGC  GGC        811
Glu  Ala  Trp  Arg  Val  Met  Gly  Leu  Arg  Gly  Ala  Glu  Ile  Ile  Cys  Gly
          180                      185                      190

GGC  TAC  AAC  ACG  CCG  ACC  CAC  AAT  CCC  CCT  GTT  CCC  CAG  CAC  GAC  CAC        859
Gly  Tyr  Asn  Thr  Pro  Thr  His  Asn  Pro  Pro  Val  Pro  Gln  His  Asp  His
     195                           200                      205

CTG  ACG  TCC  TTC  CAC  CAT  CTC  CTA  TCG  ATG  CAG  GCC  GGG  TCT  TAT  CAG        907
Leu  Thr  Ser  Phe  His  His  Leu  Leu  Ser  Met  Gln  Ala  Gly  Ser  Tyr  Gln
210                      215                      220                      225

AAC  GGG  GCC  TGG  TCC  GCG  GCC  GCG  GGC  AAG  ACG  GGC  ATG  GAG  GAG  AAC        955
Asn  Gly  Ala  Trp  Ser  Ala  Ala  Ala  Gly  Lys  Thr  Gly  Met  Glu  Glu  Asn
                    230                      235                      240

TGC  ATG  CTG  CTC  GGC  CAC  TCC  TGC  ATC  GTG  GCG  CCG  ACC  GGG  GAA  ATC       1003
Cys  Met  Leu  Leu  Gly  His  Ser  Cys  Ile  Val  Ala  Pro  Thr  Gly  Glu  Ile
               245                      250                      255

GTC  GCT  CTC  ACT  ACG  ACG  CTG  GAA  GAC  GAG  GTG  ATC  ACC  GCC  GCC  GTC       1051
Val  Ala  Leu  Thr  Thr  Thr  Leu  Glu  Asp  Glu  Val  Ile  Thr  Ala  Ala  Val
          260                      265                      270

GAT  CTC  GAT  CGC  TGC  CGG  GAA  CTG  CGT  GAA  CAC  ATC  TTC  AAC  TTC  AAG       1099
Asp  Leu  Asp  Arg  Cys  Arg  Glu  Leu  Arg  Glu  His  Ile  Phe  Asn  Phe  Lys
     275                           280                      285

CAG  CAT  CGT  CAG  CCC  CAG  CAC  TAT  GGT  CTG  ATC  GCG  GAA  CTC  TGAGGTTGCC       1151
Gln  His  Arg  Gln  Pro  Gln  His  Tyr  Gly  Leu  Ile  Ala  Glu  Leu
290                      295                      300

GAAAAGCATG  TGTGTCGTTG  TTCTCGGCGC  CTGGGTCACA  TCCAGGCGCG  CCAGGGTGAC             1211

GCTGGTGGAA  TAGTACCACG  ACCGCTTCAG  GGCGATCCGC  AAGGAGATGC  GGGTCGCCGG             1271

AGCGGCAAAG  CCCGACATTC  GTTTCGCACC  GACGGCCGTC  GTGAACTCGA  CAGTCCGCGA             1331

GAAGGGCGTA  TTGCGCGGCC  TGGACCTGTA  CGTGGAACTG  TAGCCCATAT  ATAGATTTCC             1391

AAAGAGTTTC  GGCGAGGCGC  GGCGCGCCTA  GCCCCATGTG  AGCGAGAACC  GTGCCCAGAT             1451

CAAAGAATGA  GACCGACGCG  CCGGCCGCGG  CAAAGGATGA  TCCTCAGGGT  CGGATCTATC             1511

GCTCCGCCCT  GAAGCAGGAG  GGCGCACGCT  GGCTGCTGAC  GGCGGAGGAA  GGGTTGCTGG             1571

CAAAGCCCAA  GCCGCCCGGC  CTTGTTCCGG  CACTTGAGAA  TGCGATCGCC  ATCGTCGATT             1631

ACATCAACGG  TACACCGCCC  CATATCGCGT  CCCTGGCGGA  GCTTTCAACG  ACGCTCGGGA             1691

TATCCAAGAG  CCACTGTCAC  TCCATCCTCA  AGACGCTGAC  GCATTTCGGC  TGGCTGAAAT             1751

TCGACAATCG  CTCAAAGAGC  TACGAGCTGA  ATTC                                          1785
```

( 2 ) INFORMATION FOR SEQ ID NO:32:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Thr  Arg  Gln  Met  Ile  Leu  Ala  Val  Gly  Gln  Gln  Gly  Pro  Ile  Ala  Arg
 1                  5                        10                          15

Ala  Glu  Thr  Arg  Glu  Gln  Val  Val  Arg  Leu  Leu  Asp  Met  Leu  Thr
               20                      25                      30

Lys  Ala  Ala  Ser  Arg  Gly  Ala  Asn  Phe  Ile  Val  Phe  Pro  Glu  Leu  Ala
               35                      40                      45
```

```
Leu  Thr  Thr  Phe  Phe  Pro  Arg  Trp  His  Phe  Thr  Asp  Glu  Ala  Glu  Leu
     50                       55                      60

Asp  Ser  Phe  Tyr  Glu  Thr  Glu  Met  Pro  Gly  Pro  Val  Val  Arg  Pro  Leu
65                       70                      75                           80

Phe  Glu  Lys  Ala  Ala  Glu  Leu  Gly  Ile  Gly  Phe  Asn  Leu  Gly  Tyr  Ala
               85                       90                           95

Glu  Leu  Val  Val  Glu  Gly  Gly  Val  Lys  Arg  Arg  Phe  Asn  Thr  Ser  Ile
               100                      105                     110

Leu  Val  Asp  Lys  Ser  Gly  Lys  Ile  Val  Gly  Lys  Tyr  Arg  Lys  Ile  His
          115                      120                     125

Leu  Pro  Gly  His  Lys  Glu  Tyr  Glu  Ala  Tyr  Arg  Pro  Phe  Gln  His  Leu
          130                      135                     140

Glu  Lys  Arg  Tyr  Phe  Glu  Pro  Gly  Asp  Leu  Gly  Phe  Pro  Val  Tyr  Asp
145                           150                      155                     160

Val  Asp  Ala  Ala  Lys  Met  Gly  Met  Phe  Ile  Cys  Asn  Asp  Arg  Arg  Trp
                    165                      170                     175

Pro  Glu  Ala  Trp  Arg  Val  Met  Gly  Leu  Arg  Gly  Ala  Glu  Ile  Ile  Cys
                180                      185                     190

Gly  Gly  Tyr  Asn  Thr  Pro  Thr  His  Asn  Pro  Pro  Val  Pro  Gln  His  Asp
               195                      200                     205

His  Leu  Thr  Ser  Phe  His  His  Leu  Leu  Ser  Met  Gln  Ala  Gly  Ser  Tyr
     210                      215                      220

Gln  Asn  Gly  Ala  Trp  Ser  Ala  Ala  Gly  Lys  Thr  Gly  Met  Glu  Glu
225                      230                      235                          240

Asn  Cys  Met  Leu  Leu  Gly  His  Ser  Cys  Ile  Val  Ala  Pro  Thr  Gly  Glu
               245                      250                      255

Ile  Val  Ala  Leu  Thr  Thr  Thr  Leu  Glu  Asp  Glu  Val  Ile  Thr  Ala  Ala
               260                      265                      270

Val  Asp  Leu  Asp  Arg  Cys  Arg  Glu  Leu  Arg  Glu  His  Ile  Phe  Asn  Phe
          275                      280                      285

Lys  Gln  His  Arg  Gln  Pro  Gln  His  Tyr  Gly  Leu  Ile  Ala  Glu  Leu
     290                      295                      300
```

( 2 ) INFORMATION FOR SEQ ID NO:33:

( i ) SEQUENCE CHARACTERISTICS:
        ( A ) LENGTH: 1559 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD421

( i x ) FEATURE:
        ( A ) NAME/KEY: CDS
        ( B ) LOCATION: 7..918

( x i ) SEQUENCE DESCRIPTION: SEQ ID NO:33:

```
CATATG  ACA  CGT  CAG  ATG  ATA  CTT  GCA  GTG  GGA  CAA  CAA  GGT  CCG  ATC         48
        Thr  Arg  Gln  Met  Ile  Leu  Ala  Val  Gly  Gln  Gln  Gly  Pro  Ile
         1                   5                        10

GCG  CGC  GCG  GAG  ACA  CGC  GAA  CAG  GTC  GTC  GTT  CGT  CTT  CTC  GAC  ATG       96
Ala  Arg  Ala  Glu  Thr  Arg  Glu  Gln  Val  Val  Val  Arg  Leu  Leu  Asp  Met
15                        20                       25                        30

CTG  ACG  AAA  GCC  GCG  AGC  CGG  GGC  GCG  AAT  TTC  ATT  GTC  TTC  CCC  GAA      144
Leu  Thr  Lys  Ala  Ala  Ser  Arg  Gly  Ala  Asn  Phe  Ile  Val  Phe  Pro  Glu
                    35                        40                       45

CTC  GCG  CTT  ACG  ACC  TTC  TTC  CCG  CGC  TGG  TAT  TTC  ACC  GAC  GAG  GCC      192
```

```
Leu Ala Leu Thr Thr Phe Phe Pro Arg Trp Tyr Phe Thr Asp Glu Ala
            50              55                  60

GAG CTC GAT AGC TTC TAT GAG ACC GAA ATG CCC GGC CCG GTG GTC CGT    240
Glu Leu Asp Ser Phe Tyr Glu Thr Glu Met Pro Gly Pro Val Val Arg
            65              70                  75

CCA CTC TTT GAG AAG GCC GCG GAA CTC GGG ATC GGC TTC AAT CTG GGC    288
Pro Leu Phe Glu Lys Ala Ala Glu Leu Gly Ile Gly Phe Asn Leu Gly
        80              85                  90

TAC GCT GAA CTC GTC GTC GAA GGC GGC GTC AAG CGT CGC TTC AAC ACG    336
Tyr Ala Glu Leu Val Val Glu Gly Gly Val Lys Arg Arg Phe Asn Thr
95              100                 105                 110

TCC ATT TTG GTG GAT AAG TCA GGC AAG ATC GTC GGC AAG TAT CGT AAG    384
Ser Ile Leu Val Asp Lys Ser Gly Lys Ile Val Gly Lys Tyr Arg Lys
                115                 120                 125

ATC CAT TTG CCG GGT CAC AAG GAG TAC GAG GCC TAC CGG CCG TTC CAG    432
Ile His Leu Pro Gly His Lys Glu Tyr Glu Ala Tyr Arg Pro Phe Gln
            130                 135                 140

CAT CTT GAA AAG CGT TAT TTC GAG CCG GGC GAT CTC GGC TTC CCG GTC    480
His Leu Glu Lys Arg Tyr Phe Glu Pro Gly Asp Leu Gly Phe Pro Val
        145                 150                 155

TAT GAC GTC GAC GCC GCG AAA ATG GGG ATG TTC ATC TGC AAC GAT CGC    528
Tyr Asp Val Asp Ala Ala Lys Met Gly Met Phe Ile Cys Asn Asp Arg
    160                 165                 170

CGC TGG CCT GAA GCC TGG CGG GTG ATG GGC CTC AGG GGC GCC GAG ATC    576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC CTT GTT CCC CAG    624
Ile Cys Gly Gly Tyr Asn Thr Pro Thr His Asn Pro Leu Val Pro Gln
                195                 200                 205

CAC GAC CAC CTG ACG TCC TTC CAC CAT CTC CTA TCG ATG CAG GCC GGG    672
His Asp His Leu Thr Ser Phe His His Leu Leu Ser Met Gln Ala Gly
            210                 215                 220

TCT TAT CAG AAC GGG GCC TGG TCC GCG GCC GCG GGC AAG GTG GGC ATG    720
Ser Tyr Gln Asn Gly Ala Trp Ser Ala Ala Ala Gly Lys Val Gly Met
        225                 230                 235

GAG GAG AAC TGC ATG CTG CTC GGC CAC TCC TGC ATC GTG GCG CCG ACC    768
Glu Glu Asn Cys Met Leu Leu Gly His Ser Cys Ile Val Ala Pro Thr
    240                 245                 250

GGG GAA ATC GTC GCT CTC ACT ACG ACG CTG GAA GAC GAG GTG ATC ACC    816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC    864
Ala Ala Val Asp Leu Asp Arg Cys Arg Glu Leu Arg Glu His Ile Phe
                275                 280                 285

AAC TTC AAG CAG CAT CGT CAG CCC CAG CAC TAT GGT CTG ATC GCG GAA    912
Asn Phe Lys Gln His Arg Gln Pro Gln His Tyr Gly Leu Ile Ala Glu
            290                 295                 300

CTC TGAGGTTGCC GAAAAGCATG TGTGTCGTTG TTCTCGGCGC CTGGGTCACA         965
Leu

TCCAGGCGCG CCAGGGTGAC GCTGGTGGAA TAGTACCACG ACCGCTTCAG GGCGATCCGC  1025

AAGGAGATGC GGGTCGCCGG AGCGGCAAAG CCCGACATTC GTTTCGCACC GACGGCCGTC  1085

GTGAACTCGA CAGTCCGCGA GAAGGGCGTA TTGCGCGGCC TGGACCTGTA CGTGGAACTG  1145

TAGCCCATAT ATAGATTTCC AAAGAGTTTC GGCGAGGCGC GGCGCGCCTA GCCCATGTG   1205

AGCGAGAACC GTGCCCAGAT CAAAGAATGA GACCGACGCG CCGGCCGCGG CAAAGGATGA  1265

TCCTCAGGGT CGGATCTATC GCTCCGCCCT GAAGCAGGAG GGCGCACGCT GGCTGCTGAC  1325

GGCGGAGGAA GGGTTGCTGG CAAAGCCCAA GCCGCCCGGC CTTGTTCCGG CACTTGAGAA  1385
```

| | | | | |
|---|---|---|---|---|
| TGCGATCGCC | ATCGTCGATT | ACATCAACGG | TACACCGCCC | CATATCGCGT | CCCTGGCGGA | 1445 |
| GCTTTCAACG | ACGCTCGGGA | TATCCAAGAG | CCACTGTCAC | TCCATCCTCA | AGACGCTGAC | 1505 |
| GCATTTCGGC | TGGCTGAAAT | TCGACAATCG | CTCAAAGAGC | TACGAGCTGA | ATTC | 1559 |

( 2 ) INFORMATION FOR SEQ ID NO:34:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

```
Thr Arg Gln Met Ile Leu Ala Val Gly Gln Gly Pro Ile Ala Arg
 1               5                  10                  15
Ala Glu Thr Arg Glu Gln Val Val Arg Leu Leu Asp Met Leu Thr
                20                  25                  30
Lys Ala Ala Ser Arg Gly Ala Asn Phe Ile Val Phe Pro Glu Leu Ala
                35                  40                  45
Leu Thr Thr Phe Phe Pro Arg Trp Tyr Phe Thr Asp Glu Ala Glu Leu
        50                  55                  60
Asp Ser Phe Tyr Glu Thr Glu Met Pro Gly Pro Val Val Arg Pro Leu
 65                 70                  75                  80
Phe Glu Lys Ala Ala Glu Leu Gly Ile Gly Phe Asn Leu Gly Tyr Ala
                    85                  90                  95
Glu Leu Val Val Glu Gly Gly Val Lys Arg Arg Phe Asn Thr Ser Ile
                100                 105                 110
Leu Val Asp Lys Ser Gly Lys Ile Val Gly Lys Tyr Arg Lys Ile His
                115                 120                 125
Leu Pro Gly His Lys Glu Tyr Glu Ala Tyr Arg Pro Phe Gln His Leu
        130                 135                 140
Glu Lys Arg Tyr Phe Glu Pro Gly Asp Leu Gly Phe Pro Val Tyr Asp
145                 150                 155                 160
Val Asp Ala Ala Lys Met Gly Met Phe Ile Cys Asn Asp Arg Arg Trp
                    165                 170                 175
Pro Glu Ala Trp Arg Val Met Gly Leu Arg Gly Ala Glu Ile Ile Cys
                180                 185                 190
Gly Gly Tyr Asn Thr Pro Thr His Asn Pro Leu Val Pro Gln His Asp
                195                 200                 205
His Leu Thr Ser Phe His His Leu Leu Ser Met Gln Ala Gly Ser Tyr
        210                 215                 220
Gln Asn Gly Ala Trp Ser Ala Ala Ala Gly Lys Val Gly Met Glu Glu
225                 230                 235                 240
Asn Cys Met Leu Leu Gly His Ser Cys Ile Val Ala Pro Thr Gly Glu
                    245                 250                 255
Ile Val Ala Leu Thr Thr Thr Leu Glu Asp Glu Val Ile Thr Ala Ala
                260                 265                 270
Val Asp Leu Asp Arg Cys Arg Glu Leu Arg Glu His Ile Phe Asn Phe
                275                 280                 285
Lys Gln His Arg Gln Pro Gln His Tyr Gly Leu Ile Ala Glu Leu
290                 295                 300
```

( 2 ) INFORMATION FOR SEQ ID NO:35:

( i ) SEQUENCE CHARACTERISTICS:
        ( A ) LENGTH: 1559 base pairs (B) TYPE: nucleic acid
(C) STRANDEDNESS: double
(D) TOPOLOGY: linear (vi) ORIGINAL SOURCE:
(B) STRAIN: JM109 pAD422

(ix) FEATURE:
(A) NAME/KEY: CDS
(B) LOCATION: 7..918

(xi) SEQUENCE DESCRIPTION: SEQ ID NO:35:

| | | | | | | | | | | | | | | | | |
|---|---|---|---|---|---|---|---|---|---|---|---|---|---|---|---|---|
| CATATG | ACA | CGT | CAG | ATG | ATA | CTT | GCA | GTG | GGA | CAA | CAA | GGT | CCG | ATC | | 48 |
| | Thr | Arg | Gln | Met | Ile | Leu | Ala | Val | Gly | Gln | Gln | Gly | Pro | Ile | | |
| | 1 | | | | 5 | | | | | 10 | | | | | | |
| GCG | CGC | GCG | GAG | ACA | CGC | GAA | CAG | GTC | GTC | GTT | CGT | CTT | CTC | GAC | ATG | 96 |
| Ala | Arg | Ala | Glu | Thr | Arg | Glu | Gln | Val | Val | Val | Arg | Leu | Leu | Asp | Met | |
| 15 | | | | | 20 | | | | | 25 | | | | | 30 | |
| CTG | ACG | AAA | GCC | GCG | AGC | CGG | GGC | GCG | AAT | TTC | ATT | GTC | TTC | CCC | GAA | 144 |
| Leu | Thr | Lys | Ala | Ala | Ser | Arg | Gly | Ala | Asn | Phe | Ile | Val | Phe | Pro | Glu | |
| | | | | 35 | | | | | 40 | | | | | 45 | | |
| CTC | GCG | CTT | ACG | ACC | TTC | TTC | CCG | CGC | TGG | TAT | TTC | ACC | GAC | GAG | GCC | 192 |
| Leu | Ala | Leu | Thr | Thr | Phe | Phe | Pro | Arg | Trp | Tyr | Phe | Thr | Asp | Glu | Ala | |
| | | | 50 | | | | | 55 | | | | | 60 | | | |
| GAG | CTC | GAT | AGC | TTC | TAT | GAG | ACC | GAA | ATG | CCC | GGC | CCG | GTG | GTC | CGT | 240 |
| Glu | Leu | Asp | Ser | Phe | Tyr | Glu | Thr | Glu | Met | Pro | Gly | Pro | Val | Val | Arg | |
| | | 65 | | | | | 70 | | | | | 75 | | | | |
| CCA | CTC | TTT | GAG | AAG | GCC | GCG | GAA | CTC | GGG | ATC | GGC | TTC | AAT | CTG | GGC | 288 |
| Pro | Leu | Phe | Glu | Lys | Ala | Ala | Glu | Leu | Gly | Ile | Gly | Phe | Asn | Leu | Gly | |
| | 80 | | | | | 85 | | | | | 90 | | | | | |
| TAC | GCT | GAA | CTC | GTC | GTC | GAA | GGC | GGC | GTC | AAG | CGT | CGC | TTC | AAC | ACG | 336 |
| Tyr | Ala | Glu | Leu | Val | Val | Glu | Gly | Gly | Val | Lys | Arg | Arg | Phe | Asn | Thr | |
| 95 | | | | | 100 | | | | | 105 | | | | | 110 | |
| TCC | ATT | TTG | GTG | GAT | AAG | TCA | GGC | AAG | ATC | GTC | GGC | AAG | TAT | CGT | AAG | 384 |
| Ser | Ile | Leu | Val | Asp | Lys | Ser | Gly | Lys | Ile | Val | Gly | Lys | Tyr | Arg | Lys | |
| | | | | 115 | | | | | 120 | | | | | 125 | | |
| ATC | CAT | TTG | CCG | GGT | CAC | AAG | GAG | TAC | GAG | GCC | TAC | CGG | CCG | TTC | CAG | 432 |
| Ile | His | Leu | Pro | Gly | His | Lys | Glu | Tyr | Glu | Ala | Tyr | Arg | Pro | Phe | Gln | |
| | | | 130 | | | | | 135 | | | | | 140 | | | |
| CAT | CTT | GAA | AAG | CGT | TAT | TTC | GAG | CCG | GGC | GAT | CTC | GGC | TTC | CCG | GTC | 480 |
| His | Leu | Glu | Lys | Arg | Tyr | Phe | Glu | Pro | Gly | Asp | Leu | Gly | Phe | Pro | Val | |
| | | 145 | | | | | 150 | | | | | 155 | | | | |
| TAT | GAC | GTC | GAC | GCC | GCG | AAA | ATG | GGG | ATG | TTC | ATC | TGC | AAC | GAT | CGC | 528 |
| Tyr | Asp | Val | Asp | Ala | Ala | Lys | Met | Gly | Met | Phe | Ile | Cys | Asn | Asp | Arg | |
| | 160 | | | | | 165 | | | | | 170 | | | | | |
| CGC | TGG | CCT | GAA | GCC | TGG | CGG | GTG | ATG | GGC | CTC | AGG | GGC | GCC | GAG | ATC | 576 |
| Arg | Trp | Pro | Glu | Ala | Trp | Arg | Val | Met | Gly | Leu | Arg | Gly | Ala | Glu | Ile | |
| 175 | | | | | 180 | | | | | 185 | | | | | 190 | |
| ATC | TGC | GGC | GGC | TAC | AAC | ACG | CCG | ACC | CAC | AAT | CCC | TCT | GTT | CCC | CAG | 624 |
| Ile | Cys | Gly | Gly | Tyr | Asn | Thr | Pro | Thr | His | Asn | Pro | Ser | Val | Pro | Gln | |
| | | | | 195 | | | | | 200 | | | | | 205 | | |
| CAC | GAC | CAC | CTG | ACG | TCC | TTC | CAC | CAT | CTC | CTA | TCG | ATG | CAG | GCC | GGG | 672 |
| His | Asp | His | Leu | Thr | Ser | Phe | His | His | Leu | Leu | Ser | Met | Gln | Ala | Gly | |
| | | | 210 | | | | | 215 | | | | | 220 | | | |
| TCT | TAT | CAG | AAC | GGG | GCC | TGG | TCC | GCG | GCC | GCG | GGC | AAG | GTG | GGC | ATG | 720 |
| Ser | Tyr | Gln | Asn | Gly | Ala | Trp | Ser | Ala | Ala | Ala | Gly | Lys | Val | Gly | Met | |
| | | 225 | | | | | 230 | | | | | 235 | | | | |
| GAG | GAG | AAC | TGC | ATG | CTG | CTC | GGC | CAC | TCC | TGC | ATC | GTG | GCG | CCG | ACC | 768 |
| Glu | Glu | Asn | Cys | Met | Leu | Leu | Gly | His | Ser | Cys | Ile | Val | Ala | Pro | Thr | |
| | 240 | | | | | 245 | | | | | 250 | | | | | |
| GGG | GAA | ATC | GTC | GCT | CTC | ACT | ACG | ACG | CTG | GAA | GAC | GAG | GTG | ATC | ACC | 816 |
| Gly | Glu | Ile | Val | Ala | Leu | Thr | Thr | Thr | Leu | Glu | Asp | Glu | Val | Ile | Thr | |
| 255 | | | | | 260 | | | | | 265 | | | | | 270 | |

| | | | | | | | | | | | | | | | | |
|---|---|---|---|---|---|---|---|---|---|---|---|---|---|---|---|---|
| GCC | GCC | GTC | GAT | CTC | GAT | CGC | TGC | CGG | GAA | CTG | CGT | GAA | CAC | ATC | TTC | 864 |
| Ala | Ala | Val | Asp<br>275 | Leu | Asp | Arg | Cys | Arg<br>280 | Glu | Leu | Arg | Glu | His<br>285 | Ile | Phe | |
| AAC | TTC | AAG | CAG | CAT | CGT | CAG | CCC | CAG | CAC | TAT | GGT | CTG | ATC | GCG | GAA | 912 |
| Asn | Phe | Lys | Gln<br>290 | His | Arg | Gln | Pro | Gln<br>295 | His | Tyr | Gly | Leu | Ile<br>300 | Ala | Glu | |
| CTC<br>Leu | TGAGGTTGCC | GAAAAGCATG | TGTGTCGTTG | TTCTCGGCGC | CTGGGTCACA | | | | | | | | | | | 965 |

```
TCCAGGCGCG  CCAGGGTGAC  GCTGGTGGAA  TAGTACCACG  ACCGCTTCAG  GGCGATCCGC      1025

AAGGAGATGC  GGGTCGCCGG  AGCGGCAAAG  CCCGACATTC  GTTTCGCACC  GACGGCCGTC      1085

GTGAACTCGA  CAGTCCGCGA  GAAGGGCGTA  TTGCGCGGCC  TGGACCTGTA  CGTGGAACTG      1145

TAGCCCATAT  ATAGATTTCC  AAAGAGTTTC  GGCGAGGCGC  GGCGCGCCTA  GCCCCATGTG      1205

AGCGAGAACC  GTGCCCAGAT  CAAAGAATGA  GACCGACGCG  CCGGCCGCGG  CAAAGGATGA      1265

TCCTCAGGGT  CGGATCTATC  GCTCCGCCCT  GAAGCAGGAG  GGCGCACGCT  GGCTGCTGAC      1325

GGCGGAGGAA  GGGTTGCTGG  CAAAGCCCAA  GCCGCCCGGC  CTTGTTCCGG  CACTTGAGAA      1385

TGCGATCGCC  ATCGTCGATT  ACATCAACGG  TACACCGCCC  CATATCGCGT  CCCTGGCGGA      1445

GCTTTCAACG  ACGCTCGGGA  TATCCAAGAG  CCACTGTCAC  TCCATCCTCA  AGACGCTGAC      1505

GCATTTCGGC  TGGCTGAAAT  TCGACAATCG  CTCAAGAGC   TACGAGCTGA  ATTC           1559
```

( 2 ) INFORMATION FOR SEQ ID NO:36:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

| | | | | | | | | | | | | | | |
|---|---|---|---|---|---|---|---|---|---|---|---|---|---|---|
| Thr<br>1 | Arg | Gln | Met | Ile<br>5 | Leu | Ala | Val | Gly | Gln<br>10 | Gln | Gly | Pro | Ile | Ala<br>15 | Arg |
| Ala | Glu | Thr | Arg<br>20 | Glu | Gln | Val | Val | Arg<br>25 | Leu | Leu | Asp | Met | Leu<br>30 | Thr |
| Lys | Ala | Ala<br>35 | Ser | Arg | Gly | Ala | Asn<br>40 | Phe | Ile | Val | Phe | Pro<br>45 | Glu | Leu | Ala |
| Leu | Thr<br>50 | Thr | Phe | Phe | Pro | Arg<br>55 | Trp | Tyr | Phe | Thr | Asp<br>60 | Glu | Ala | Glu | Leu |
| Asp<br>65 | Ser | Phe | Tyr | Glu | Thr<br>70 | Glu | Met | Pro | Gly | Pro<br>75 | Val | Val | Arg | Pro | Leu<br>80 |
| Phe | Glu | Lys | Ala | Ala<br>85 | Glu | Leu | Gly | Ile | Gly<br>90 | Phe | Asn | Leu | Gly | Tyr<br>95 | Ala |
| Glu | Leu | Val | Val<br>100 | Glu | Gly | Gly | Val | Lys<br>105 | Arg | Arg | Phe | Asn | Thr<br>110 | Ser | Ile |
| Leu | Val | Asp<br>115 | Lys | Ser | Gly | Lys | Ile<br>120 | Val | Gly | Lys | Tyr | Arg<br>125 | Lys | Ile | His |
| Leu | Pro<br>130 | Gly | His | Lys | Glu | Tyr<br>135 | Glu | Ala | Tyr | Arg | Pro<br>140 | Phe | Gln | His | Leu |
| Glu<br>145 | Lys | Arg | Tyr | Phe | Glu<br>150 | Pro | Gly | Asp | Leu | Gly<br>155 | Phe | Pro | Val | Tyr | Asp<br>160 |
| Val | Asp | Ala | Ala | Lys<br>165 | Met | Gly | Met | Phe | Ile<br>170 | Cys | Asn | Asp | Arg | Arg<br>175 | Trp |
| Pro | Glu | Ala | Trp<br>180 | Arg | Val | Met | Gly | Leu<br>185 | Arg | Gly | Ala | Glu | Ile<br>190 | Ile | Cys |

| | | | | | | | | | | | | | | |
|---|---|---|---|---|---|---|---|---|---|---|---|---|---|---|
| Gly | Gly | Tyr<br>195 | Asn | Thr | Pro | Thr | His<br>200 | Asn | Pro | Ser | Val | Pro<br>205 | Gln | His | Asp |
| His | Leu<br>210 | Thr | Ser | Phe | His | His<br>215 | Leu | Leu | Ser | Met | Gln<br>220 | Ala | Gly | Ser | Tyr |
| Gln<br>225 | Asn | Gly | Ala | Trp | Ser<br>230 | Ala | Ala | Ala | Gly | Lys<br>235 | Val | Gly | Met | Glu | Glu<br>240 |
| Asn | Cys | Met | Leu | Leu<br>245 | Gly | His | Ser | Cys | Ile<br>250 | Val | Ala | Pro | Thr | Gly<br>255 | Glu |
| Ile | Val | Ala | Leu<br>260 | Thr | Thr | Thr | Leu | Glu<br>265 | Asp | Glu | Val | Ile | Thr<br>270 | Ala | Ala |
| Val | Asp | Leu<br>275 | Asp | Arg | Cys | Arg | Glu<br>280 | Leu | Arg | Glu | His | Ile<br>285 | Phe | Asn | Phe |
| Lys | Gln<br>290 | His | Arg | Gln | Pro | Gln<br>295 | His | Tyr | Gly | Leu | Ile<br>300 | Ala | Glu | Leu | |

(2) INFORMATION FOR SEQ ID NO:37:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (vi) ORIGINAL SOURCE:
        (B) STRAIN: JM109 pAD423

(ix) FEATURE:
        (A) NAME/KEY: CDS
        (B) LOCATION: 7..918

(xi) SEQUENCE DESCRIPTION: SEQ ID NO:37:

| | | | | | | | | | | | | | | | |
|---|---|---|---|---|---|---|---|---|---|---|---|---|---|---|---|
| CATATG | ACA | CGT | CAG | ATG | ATA | CTT | GCA | GTG | GGA | CAA | CAA | GGT | CCG | ATC | 48 |
| | Thr<br>1 | Arg | Gln | Met | Ile<br>5 | Leu | Ala | Val | Gly | Gln<br>10 | Gln | Gly | Pro | Ile | |
| GCG | CGC | GCG | GAG | ACA | CGC | GAA | CAG | GTC | GTC | GTT | CGT | CTT | CTC | GAC | ATG | 96 |
| Ala | Arg<br>15 | Ala | Glu | Thr | Arg<br>20 | Glu | Gln | Val | Val | Val<br>25 | Arg | Leu | Leu | Asp | Met<br>30 |
| CTG | ACG | AAA | GCC | GCG | AGC | CGG | GGC | GCG | AAT | TTC | ATT | GTC | TTC | CCC | GAA | 144 |
| Leu | Thr | Lys | Ala | Ala<br>35 | Ser | Arg | Gly | Ala | Asn<br>40 | Phe | Ile | Val | Phe | Pro<br>45 | Glu |
| CTC | GCG | CTT | ACG | ACC | TTC | TTC | CCG | CGC | TGG | TAT | TTC | ACC | GAC | GAG | GCC | 192 |
| Leu | Ala | Leu | Thr<br>50 | Thr | Phe | Phe | Pro | Arg<br>55 | Trp | Tyr | Phe | Thr | Asp<br>60 | Glu | Ala |
| GAG | CTC | GAT | AGC | TTC | TAT | GAG | ACC | GAA | ATG | CCC | GGC | CCG | GTG | GTC | CGT | 240 |
| Glu | Leu | Asp<br>65 | Ser | Phe | Tyr | Glu | Thr<br>70 | Glu | Met | Pro | Gly | Pro<br>75 | Val | Val | Arg |
| CCA | CTC | TTT | GAG | AAG | GCC | GCG | GAA | CTC | GGG | ATC | GGC | TTC | AAT | CTG | GGC | 288 |
| Pro | Leu | Phe | Glu<br>80 | Lys | Ala | Ala | Glu<br>85 | Leu | Gly | Ile | Gly | Phe<br>90 | Asn | Leu | Gly |
| TAC | GCT | GAA | CTC | GTC | GTC | GAA | GGC | GGC | GTC | AAG | CGT | CGC | TTC | AAC | ACG | 336 |
| Tyr | Ala<br>95 | Glu | Leu | Val | Val<br>100 | Glu | Gly | Gly | Val | Lys<br>105 | Arg | Arg | Phe | Asn | Thr<br>110 |
| TCC | ATT | TTG | GTG | GAT | AAG | TCA | GGC | AAG | ATC | GTC | GGC | AAG | TAT | CGT | AAG | 384 |
| Ser | Ile | Leu | Val | Asp<br>115 | Lys | Ser | Gly | Lys | Ile<br>120 | Val | Gly | Lys | Tyr | Arg<br>125 | Lys |
| ATC | CAT | TTG | CCG | GGT | CAC | AAG | GAG | TAC | GAG | GCC | TAC | CGG | CCG | TTC | CAG | 432 |
| Ile | His | Leu | Pro<br>130 | Gly | His | Lys | Glu | Tyr<br>135 | Glu | Ala | Tyr | Arg | Pro<br>140 | Phe | Gln |
| CAT | CTT | GAA | AAG | CGT | TAT | TTC | GAG | CCG | GGC | GAT | CTC | GGC | TTC | CCG | GTC | 480 |
| His | Leu | Glu | Lys<br>145 | Arg | Tyr | Phe | Glu | Pro<br>150 | Gly | Asp | Leu | Gly | Phe<br>155 | Pro | Val |
| TAT | GAC | GTC | GAC | GCC | GCG | AAA | ATG | GGG | ATG | TTC | ATC | TGC | AAC | GAT | CGC | 528 |

```
        Tyr  Asp  Val  Asp  Ala  Ala  Lys  Met  Gly  Met  Phe  Ile  Cys  Asn  Asp  Arg
             160                 165                      170

CGC  TGG  CCT  GAA  GCC  TGG  CGG  GTG  ATG  GGC  CTC  AGG  GGC  GCC  GAG  ATC          576
Arg  Trp  Pro  Glu  Ala  Trp  Arg  Val  Met  Gly  Leu  Arg  Gly  Ala  Glu  Ile
175                 180                      185                      190

ATC  TGC  GGC  GGC  TAC  AAC  ACG  CCG  ACC  CAC  AAT  CCC  CCT  GTT  CCC  CAG          624
Ile  Cys  Gly  Gly  Tyr  Asn  Thr  Pro  Thr  His  Asn  Pro  Pro  Val  Pro  Gln
                    195                      200                      205

CAC  GAC  CAC  CTG  ACG  TCC  TTC  CAC  CAT  CTC  CTA  TCG  ATG  CAG  GCC  GGG          672
His  Asp  His  Leu  Thr  Ser  Phe  His  His  Leu  Leu  Ser  Met  Gln  Ala  Gly
               210                      215                      220

TCT  TAT  CAG  AAC  GGG  GCC  TGG  TCC  GCG  GCC  GCG  GGC  AAG  GCG  GGC  ATG          720
Ser  Tyr  Gln  Asn  Gly  Ala  Trp  Ser  Ala  Ala  Ala  Gly  Lys  Ala  Gly  Met
          225                      230                      235

GAG  GAG  AAC  TGC  ATG  CTG  CTC  GGC  CAC  TCC  TGC  ATC  GTG  GCG  CCG  ACC          768
Glu  Glu  Asn  Cys  Met  Leu  Leu  Gly  His  Ser  Cys  Ile  Val  Ala  Pro  Thr
     240                      245                      250

GGG  GAA  ATC  GTC  GCT  CTC  ACT  ACG  ACG  CTG  GAA  GAC  GAG  GTG  ATC  ACC          816
Gly  Glu  Ile  Val  Ala  Leu  Thr  Thr  Thr  Leu  Glu  Asp  Glu  Val  Ile  Thr
255                      260                      265                      270

GCC  GCC  GTC  GAT  CTC  GAT  CGC  TGC  CGG  GAA  CTG  CGT  GAA  CAC  ATC  TTC          864
Ala  Ala  Val  Asp  Leu  Asp  Arg  Cys  Arg  Glu  Leu  Arg  Glu  His  Ile  Phe
                    275                      280                      285

AAC  TTC  AAG  CAG  CAT  CGT  CAG  CCC  CAG  CAC  TAT  GGT  CTG  ATC  GCG  GAA          912
Asn  Phe  Lys  Gln  His  Arg  Gln  Pro  Gln  His  Tyr  Gly  Leu  Ile  Ala  Glu
               290                      295                      300

CTC  TGAGGTTGCC  GAAAAGCATG  TGTGTCGTTG  TTCTCGGCGC  CTGGGTCACA                         965
Leu

TCCAGGCGCG  CCAGGGTGAC  GCTGGTGGAA  TAGTACCACG  ACCGCTTCAG  GGCGATCCGC                 1025

AAGGAGATGC  GGGTCGCCGG  AGCGGCAAAG  CCCGACATTC  GTTTCGCACC  GACGGCCGTC                 1085

GTGAACTCGA  CAGTCCGCGA  GAAGGGCGTA  TTGCGCGGCC  TGGACCTGTA  CGTGGAACTG                 1145

TAGCCCATAT  ATAGATTTCC  AAAGAGTTTC  GGCGAGGCGC  GGCGCGCCTA  GCCCCATGTG                 1205

AGCGAGAACC  GTGCCCAGAT  CAAAGAATGA  GACCGACGCG  CCGGCCGCGG  CAAAGGATGA                 1265

TCCTCAGGGT  CGGATCTATC  GCTCCGCCCT  GAAGCAGGAG  GGCGCACGCT  GGCTGCTGAC                 1325

GGCGGAGGAA  GGGTTGCTGG  CAAAGCCCAA  GCCGCCCGGC  CTTGTTCCGG  CACTTGAGAA                 1385

TGCGATCGCC  ATCGTCGATT  ACATCAACGG  TACACCGCCC  CATATCGCGT  CCCTGGCGGA                 1445

GCTTTCAACG  ACGCTCGGGA  TATCCAAGAG  CCACTGTCAC  TCCATCCTCA  AGACGCTGAC                 1505

GCATTTCGGC  TGGCTGAAAT  TCGACAATCG  CTCAAAGAGC  TACGAGCTGA  ATTC                       1559
```

( 2 ) INFORMATION FOR SEQ ID NO:38:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Thr  Arg  Gln  Met  Ile  Leu  Ala  Val  Gly  Gln  Gln  Gly  Pro  Ile  Ala  Arg
1                   5                        10                       15

Ala  Glu  Thr  Arg  Glu  Gln  Val  Val  Arg  Leu  Leu  Asp  Met  Leu  Thr
               20                       25                       30

Lys  Ala  Ala  Ser  Arg  Gly  Ala  Asn  Phe  Ile  Val  Phe  Pro  Glu  Leu  Ala
               35                       40                       45

Leu  Thr  Thr  Phe  Phe  Pro  Arg  Trp  Tyr  Phe  Thr  Asp  Glu  Ala  Glu  Leu
```

| | | | | | | 50 | | | | | 55 | | | | | 60 | | |
|---|---|---|---|---|---|---|---|---|---|---|---|---|---|---|---|---|---|---|

Asp Ser Phe Tyr Glu Thr Glu Met Pro Gly Pro Val Val Arg Pro Leu
65                      70                     75                          80

Phe Glu Lys Ala Ala Glu Leu Gly Ile Gly Phe Asn Leu Gly Tyr Ala
              85                     90                       95

Glu Leu Val Val Glu Gly Gly Val Lys Arg Arg Phe Asn Thr Ser Ile
              100                    105                      110

Leu Val Asp Lys Ser Gly Lys Ile Val Gly Lys Tyr Arg Lys Ile His
              115                    120                      125

Leu Pro Gly His Lys Glu Tyr Glu Ala Tyr Arg Pro Phe Gln His Leu
         130                     135                      140

Glu Lys Arg Tyr Phe Glu Pro Gly Asp Leu Gly Phe Pro Val Tyr Asp
145                     150                     155                         160

Val Asp Ala Ala Lys Met Gly Met Phe Ile Cys Asn Asp Arg Arg Trp
              165                    170                      175

Pro Glu Ala Trp Arg Val Met Gly Leu Arg Gly Ala Glu Ile Ile Cys
         180                     185                      190

Gly Gly Tyr Asn Thr Pro Thr His Asn Pro Pro Val Pro Gln His Asp
              195                    200                      205

His Leu Thr Ser Phe His His Leu Leu Ser Met Gln Ala Gly Ser Tyr
         210                     215                      220

Gln Asn Gly Ala Trp Ser Ala Ala Ala Gly Lys Ala Gly Met Glu Glu
225                     230                     235                         240

Asn Cys Met Leu Leu Gly His Ser Cys Ile Val Ala Pro Thr Gly Glu
              245                    250                      255

Ile Val Ala Leu Thr Thr Thr Leu Glu Asp Glu Val Ile Thr Ala Ala
              260                    265                      270

Val Asp Leu Asp Arg Cys Arg Glu Leu Arg Glu His Ile Phe Asn Phe
              275                    280                      285

Lys Gln His Arg Gln Pro Gln His Tyr Gly Leu Ile Ala Glu Leu
         290                     295                      300

( 2 ) INFORMATION FOR SEQ ID NO:39:

( i ) SEQUENCE CHARACTERISTICS:
        ( A ) LENGTH: 1559 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD424 (FERM BP- 4034)

( i x ) FEATURE:
        ( A ) NAME/KEY: CDS
        ( B ) LOCATION: 7..918

( x i ) SEQUENCE DESCRIPTION: SEQ ID NO:39:

CATATG ACA CGT CAG ATG ATA CTT GCA GTG GGA CAA CAA GGT CCG ATC    48
       Thr Arg Gln Met Ile Leu Ala Val Gly Gln Gln Gly Pro Ile
        1                5                 10

GCG CGC GCG GAG ACA CGC GAA CAG GTC GTC GTT CGT CTT CTC GAC ATG    96
Ala Arg Ala Glu Thr Arg Glu Gln Val Val Val Arg Leu Leu Asp Met
15               20                    25                   30

CTG ACG AAA GCC GCG AGC CGG GGC GCG AAT TTC ATT GTC TTC CCC GAA    144
Leu Thr Lys Ala Ala Ser Arg Gly Ala Asn Phe Ile Val Phe Pro Glu
                 35                   40                   45

CTC GCG CTT ACG ACC TTC TTC CCG CGC TGG CAT TTC ACC GAC GAG GCC    192
Leu Ala Leu Thr Thr Phe Phe Pro Arg Trp His Phe Thr Asp Glu Ala
                 50                   55                   60

```
GAG CTC GAT AGC TTC TAT GAG ACC GAA ATG CCC GGC CCG GTG GTC CGT      240
Glu Leu Asp Ser Phe Tyr Glu Thr Glu Met Pro Gly Pro Val Val Arg
         65                      70                  75

CCA CTC TTT GAG AAG GCC GCG GAA CTC GGG ATC GGC TTC AAT CTG GGC      288
Pro Leu Phe Glu Lys Ala Ala Glu Leu Gly Ile Gly Phe Asn Leu Gly
         80                      85                  90

TAC GCT GAA CTC GTC GTC GAA GGC GGC GTC AAG CGT CGC TTC AAC ACG      336
Tyr Ala Glu Leu Val Val Glu Gly Gly Val Lys Arg Arg Phe Asn Thr
 95                     100                     105             110

TCC ATT TTG GTG GAT AAG TCA GGC AAG ATC GTC GGC AAG TAT CGT AAG      384
Ser Ile Leu Val Asp Lys Ser Gly Lys Ile Val Gly Lys Tyr Arg Lys
                    115                     120                 125

ATC CAT TTG CCG GGT CAC AAG GAG TAC GAG GCC TAC CGG CCG TTC CAG      432
Ile His Leu Pro Gly His Lys Glu Tyr Glu Ala Tyr Arg Pro Phe Gln
                130                     135                 140

CAT CTT GAA AAG CGT TAT TTC GAG CCG GGC GAT CTC GGC TTC CCG GTC      480
His Leu Glu Lys Arg Tyr Phe Glu Pro Gly Asp Leu Gly Phe Pro Val
            145                     150                 155

TAT GAC GTC GAC GCC GCG AAA ATG GGG ATG TTC ATC TGC AAC GAT CGC      528
Tyr Asp Val Asp Ala Ala Lys Met Gly Met Phe Ile Cys Asn Asp Arg
160                     165                     170

CGC TGG CCT GAA GCC TGG CGG GTG ATG GGC CTC AGG GGC GCC GAG ATC      576
Arg Trp Pro Glu Ala Trp Arg Val Met Gly Leu Arg Gly Ala Glu Ile
175                     180                     185             190

ATC TGC GGC GGC TAC AAC ACG CCG ACC CAC AAT CCC CTT GTT CCC CAG      624
Ile Cys Gly Gly Tyr Asn Thr Pro Thr His Asn Pro Leu Val Pro Gln
                195                     200                 205

CAC GAC CAC CTG ACG TCC TTC CAC CAT CTC CTA TCG ATG CAG GCC GGG      672
His Asp His Leu Thr Ser Phe His His Leu Leu Ser Met Gln Ala Gly
            210                     215                 220

TCT TAT CAG AAC GGG GCC TGG TCC GCG GCC GCG GGC AAG GCG GGC ATG      720
Ser Tyr Gln Asn Gly Ala Trp Ser Ala Ala Ala Gly Lys Ala Gly Met
        225                     230                 235

GAG GAG AAC TGC ATG CTC CTC GGC CAC TCC TGC ATC GTG GCG CCG ACC      768
Glu Glu Asn Cys Met Leu Leu Gly His Ser Cys Ile Val Ala Pro Thr
240                     245                     250

GGG GAA ATC GTC GCT CTC ACT ACG ACG CTG GAA GAC GAG GTG ATC ACC      816
Gly Glu Ile Val Ala Leu Thr Thr Thr Leu Glu Asp Glu Val Ile Thr
255                     260                     265             270

GCC GCC GTC GAT CTC GAT CGC TGC CGG GAA CTG CGT GAA CAC ATC TTC      864
Ala Ala Val Asp Leu Asp Arg Cys Arg Glu Leu Arg Glu His Ile Phe
                    275                     280             285

AAC TTC AAG CAG CAT CGT CAG CCC CAG CAC TAT GGT CTG ATC GCG GAA      912
Asn Phe Lys Gln His Arg Gln Pro Gln His Tyr Gly Leu Ile Ala Glu
            290                     295                 300

CTC TGAGGTTGCC GAAAAGCATG TGTGTCGTTG TTCTCGGCGC CTGGGTCACA           965
Leu

TCCAGGCGCG CCAGGGTGAC GCTGGTGGAA TAGTACCACG ACCGCTTCAG GGCGATCCGC   1025

AAGGAGATGC GGGTCGCCGG AGCGGCAAAG CCCGACATTC GTTTCGCACC GACGGCCGTC   1085

GTGAACTCGA CAGTCCGCGA GAAGGGCGTA TTGCGCGGCC TGGACCTGTA CGTGGAACTG   1145

TAGCCCATAT ATAGATTTCC AAAGAGTTTC GGCGAGGCGC GGCGCGCCTA GCCCATGTG    1205

AGCGAGAACC GTGCCCAGAT CAAAGAATGA GACCGACGCG CCGGCCGCGG CAAAGGATGA   1265

TCCTCAGGGT CGGATCTATC GCTCCGCCCT GAAGCAGGAG GGCGCACGCT GGCTGCTGAC   1325

GGCGGAGGAA GGGTTGCTGG CAAAGCCCAA GCCGCCCGGC CTTGTTCCGG CACTTGAGAA   1385

TGCGATCGCC ATCGTCGATT ACATCAACGG TACACCGCCC CATATCGCGT CCCTGGCGGA   1445
```

GCTTTCAACG ACGCTCGGGA TATCCAAGAG CCACTGTCAC TCCATCCTCA AGACGCTGAC    1505

GCATTTCGGC TGGCTGAAAT TCGACAATCG CTCAAAGAGC TACGAGCTGA ATTC    1559

( 2 ) INFORMATION FOR SEQ ID NO:40:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Thr Arg Gln Met Ile Leu Ala Val Gly Gln Gln Gly Pro Ile Ala Arg
 1               5                  10                  15
Ala Glu Thr Arg Glu Gln Val Val Val Arg Leu Leu Asp Met Leu Thr
             20                  25                  30
Lys Ala Ala Ser Arg Gly Ala Asn Phe Ile Val Phe Pro Glu Leu Ala
         35                  40                  45
Leu Thr Thr Phe Phe Pro Arg Trp His Phe Thr Asp Glu Ala Glu Leu
     50                  55                  60
Asp Ser Phe Tyr Glu Thr Glu Met Pro Gly Pro Val Val Arg Pro Leu
 65                  70                  75                  80
Phe Glu Lys Ala Ala Glu Leu Gly Ile Gly Phe Asn Leu Gly Tyr Ala
                 85                  90                  95
Glu Leu Val Val Glu Gly Gly Val Lys Arg Arg Phe Asn Thr Ser Ile
            100                 105                 110
Leu Val Asp Lys Ser Gly Lys Ile Val Gly Lys Tyr Arg Lys Ile His
        115                 120                 125
Leu Pro Gly His Lys Glu Tyr Glu Ala Tyr Arg Pro Phe Gln His Leu
    130                 135                 140
Glu Lys Arg Tyr Phe Glu Pro Gly Asp Leu Gly Phe Pro Val Tyr Asp
145                 150                 155                 160
Val Asp Ala Ala Lys Met Gly Met Phe Ile Cys Asn Asp Arg Arg Trp
                165                 170                 175
Pro Glu Ala Trp Arg Val Met Gly Leu Arg Gly Ala Glu Ile Ile Cys
            180                 185                 190
Gly Gly Tyr Asn Thr Pro Thr His Asn Pro Leu Val Pro Gln His Asp
        195                 200                 205
His Leu Thr Ser Phe His His Leu Leu Ser Met Gln Ala Gly Ser Tyr
    210                 215                 220
Gln Asn Gly Ala Trp Ser Ala Ala Ala Gly Lys Ala Gly Met Glu Glu
225                 230                 235                 240
Asn Cys Met Leu Leu Gly His Ser Cys Ile Val Ala Pro Thr Gly Glu
                245                 250                 255
Ile Val Ala Leu Thr Thr Thr Leu Glu Asp Glu Val Ile Thr Ala Ala
            260                 265                 270
Val Asp Leu Asp Arg Cys Arg Glu Leu Arg Glu His Ile Phe Asn Phe
        275                 280                 285
Lys Gln His Arg Gln Pro Gln His Tyr Gly Leu Ile Ala Glu Leu
    290                 295                 300
```

( 2 ) INFORMATION FOR SEQ ID NO:41:

( i ) SEQUENCE CHARACTERISTICS:
        ( A ) LENGTH: 1559 base pairs
        ( B ) TYPE: nucleic acid
        ( C ) STRANDEDNESS: double ( D ) TOPOLOGY: linear ( v i ) ORIGINAL SOURCE:
   ( B ) STRAIN: JM109 pAD425

( i x ) FEATURE:
   ( A ) NAME/KEY: CDS
   ( B ) LOCATION: 7..918

( x i ) SEQUENCE DESCRIPTION: SEQ ID NO:41:

```
CATATG ACA CGT CAG ATG ATA CTT GCA GTG GGA CAA CAA GGT CCG ATC          48
       Thr Arg Gln Met Ile Leu Ala Val Gly Gln Gln Gly Pro Ile
        1               5                      10

GCG CGC GCG GAG ACA CGC GAA CAG GTC GTC GTT CGT CTT CTC GAC ATG          96
Ala Arg Ala Glu Thr Arg Glu Gln Val Val Val Arg Leu Leu Asp Met
 15              20                  25                      30

CTG ACG AAA GCC GCG AGC CGG GGC GCG AAT TTC ATT GTC TTC CCC GAA         144
Leu Thr Lys Ala Ala Ser Arg Gly Ala Asn Phe Ile Val Phe Pro Glu
                 35                  40                  45

CTC GCG CTT ACG ACC TTC TTC CCG CGC TGG CAT TTC ACC GAC GAG GCC         192
Leu Ala Leu Thr Thr Phe Phe Pro Arg Trp His Phe Thr Asp Glu Ala
             50                  55                  60

GAG CTC GAT AGC TTC TAT GAG ACC GAA ATG CCC GGC CCG GTG GTC CGT         240
Glu Leu Asp Ser Phe Tyr Glu Thr Glu Met Pro Gly Pro Val Val Arg
         65                  70                  75

CCA CTC TTT GAG AAG GCC GCG GAA CTC GGG ATC GGC TTC AAT CTG GGC         288
Pro Leu Phe Glu Lys Ala Ala Glu Leu Gly Ile Gly Phe Asn Leu Gly
     80                  85                  90

TAC GCT GAA CTC GTC GTC GAA GGC GGC GTC AAG CGT CGC TTC AAC ACG         336
Tyr Ala Glu Leu Val Val Glu Gly Gly Val Lys Arg Arg Phe Asn Thr
 95                 100                 105                 110

TCC ATT TTG GTG GAT AAG TCA GGC AAG ATC GTC GGC AAG TAT CGT AAG         384
Ser Ile Leu Val Asp Lys Ser Gly Lys Ile Val Gly Lys Tyr Arg Lys
                115                 120                 125

ATC CAT TTG CCG GGT CAC AAG GAG TAC GAG GCC TAC CGG CCG TTC CAG         432
Ile His Leu Pro Gly His Lys Glu Tyr Glu Ala Tyr Arg Pro Phe Gln
            130                 135                 140

CAT CTT GAA AAG CGT TAT TTC GAG CCG GGC GAT CTC GGC TTC CCG GTC         480
His Leu Glu Lys Arg Tyr Phe Glu Pro Gly Asp Leu Gly Phe Pro Val
        145                 150                 155

TAT GAC GTC GAC GCC GCG AAA ATG GGG ATG TTC ATC TGC AAC GAT CGC         528
Tyr Asp Val Asp Ala Ala Lys Met Gly Met Phe Ile Cys Asn Asp Arg
    160                 165                 170

CGC TGG CCT GAA GCC TGG CGG GTG ATG GGC CTC AGG GGC GCC GAG ATC         576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC TCT GTT CCC CAG         624
Ile Cys Gly Gly Tyr Asn Thr Pro Thr His Asn Pro Ser Val Pro Gln
                195                 200                 205

CAC GAC CAC CTG ACG TCC TTC CAC CAT CTC CTA TCG ATG CAG GCC GGG         672
His Asp His Leu Thr Ser Phe His His Leu Leu Ser Met Gln Ala Gly
            210                 215                 220

TCT TAT CAG AAC GGG GCC TGG TCC GCG GCC GCG GGC AAG GCG GGC ATG         720
Ser Tyr Gln Asn Gly Ala Trp Ser Ala Ala Ala Gly Lys Ala Gly Met
        225                 230                 235

GAG GAG AAC TGC ATG CTG CTC GGC CAC TCC TGC ATC GTG GCG CCG ACC         768
Glu Glu Asn Cys Met Leu Leu Gly His Ser Cys Ile Val Ala Pro Thr
    240                 245                 250

GGG GAA ATC GTC GCT CTC ACT ACG ACG CTG GAA GAC GAG GTG ATC ACC         816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC         864
```

```
    Ala   Ala   Val   Asp   Leu   Asp   Arg   Cys   Arg   Glu   Leu   Arg   Glu   His   Ile   Phe
                      275                     280                           285
```

```
AAC   TTC   AAG   CAG   CAT   CGT   CAG   CCC   CAG   CAC   TAT   GGT   CTG   ATC   GCG   GAA              912
Asn   Phe   Lys   Gln   His   Arg   Gln   Pro   Gln   His   Tyr   Gly   Leu   Ile   Ala   Glu
                  290                           295                           300
```

```
CTC   TGAGGTTGCC   GAAAAGCATG   TGTGTCGTTG   TTCTCGGCGC   CTGGGTCACA                                       965
Leu

TCCAGGCGCG   CCAGGGTGAC   GCTGGTGGAA   TAGTACCACG   ACCGCTTCAG   GGCGATCCGC                                1025

AAGGAGATGC   GGGTCGCCGG   AGCGGCAAAG   CCCGACATTC   GTTTCGCACC   GACGGCCGTC                                1085

GTGAACTCGA   CAGTCCGCGA   GAAGGGCGTA   TTGCGCGGCC   TGGACCTGTA   CGTGGAACTG                                1145

TAGCCCATAT   ATAGATTTCC   AAAGAGTTTC   GGCGAGGCGC   GGCGCGCCTA   GCCCCATGTG                                1205

AGCGAGAACC   GTGCCCAGAT   CAAAGAATGA   GACCGACGCG   CCGGCCGCGG   CAAAGGATGA                                1265

TCCTCAGGGT   CGGATCTATC   GCTCCGCCCT   GAAGCAGGAG   GGCGCACGCT   GGCTGCTGAC                                1325

GGCGGAGGAA   GGGTTGCTGG   CAAAGCCCAA   GCCGCCCGGC   CTTGTTCCGG   CACTTGAGAA                                1385

TGCGATCGCC   ATCGTCGATT   ACATCAACGG   TACACCGCCC   CATATCGCGT   CCCTGGCGGA                                1445

GCTTTCAACG   ACGCTCGGGA   TATCCAAGAG   CCACTGTCAC   TCCATCCTCA   AGACGCTGAC                                1505

GCATTTCGGC   TGGCTGAAAT   TCGACAATCG   CTCAAAGAGC   TACGAGCTGA   ATTC                                      1559
```

( 2 ) INFORMATION FOR SEQ ID NO:42:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Thr   Arg   Gln   Met   Ile   Leu   Ala   Val   Gly   Gln   Gln   Gly   Pro   Ile   Ala   Arg
 1                      5                           10                          15

Ala   Glu   Thr   Arg   Glu   Gln   Val   Val   Arg   Leu   Leu   Asp   Met   Leu   Thr
                  20                      25                          30

Lys   Ala   Ala   Ser   Arg   Gly   Ala   Asn   Phe   Ile   Val   Phe   Pro   Glu   Leu   Ala
                  35                      40                          45

Leu   Thr   Thr   Phe   Phe   Pro   Arg   Trp   His   Phe   Thr   Asp   Glu   Ala   Glu   Leu
      50                            55                                60

Asp   Ser   Phe   Tyr   Glu   Thr   Glu   Met   Pro   Gly   Pro   Val   Val   Arg   Pro   Leu
65                            70                          75                            80

Phe   Glu   Lys   Ala   Ala   Glu   Leu   Gly   Ile   Gly   Phe   Asn   Leu   Gly   Tyr   Ala
                        85                      90                            95

Glu   Leu   Val   Val   Glu   Gly   Gly   Val   Lys   Arg   Arg   Phe   Asn   Thr   Ser   Ile
                  100                           105                           110

Leu   Val   Asp   Lys   Ser   Gly   Lys   Ile   Val   Gly   Lys   Tyr   Arg   Lys   Ile   His
            115                           120                           125

Leu   Pro   Gly   His   Lys   Glu   Tyr   Glu   Ala   Tyr   Arg   Pro   Phe   Gln   His   Leu
      130                           135                     140

Glu   Lys   Arg   Tyr   Phe   Glu   Pro   Gly   Asp   Leu   Gly   Phe   Pro   Val   Tyr   Asp
145                           150                           155                           160

Val   Asp   Ala   Ala   Lys   Met   Gly   Met   Phe   Ile   Cys   Asn   Asp   Arg   Arg   Trp
                        165                           170                           175

Pro   Glu   Ala   Trp   Arg   Val   Met   Gly   Leu   Arg   Gly   Ala   Glu   Ile   Ile   Cys
                  180                           185                           190

Gly   Gly   Tyr   Asn   Thr   Pro   Thr   His   Asn   Pro   Ser   Val   Pro   Gln   His   Asp
                  195                           200                           205
```

| | | | | | | | | | | | | | | |
|---|---|---|---|---|---|---|---|---|---|---|---|---|---|---|
| His | Leu | Thr | Ser | Phe | His | His | Leu | Leu | Ser | Met | Gln | Ala | Gly | Ser | Tyr |
| | 210 | | | | | 215 | | | | | 220 | | | | |
| Gln | Asn | Gly | Ala | Trp | Ser | Ala | Ala | Ala | Gly | Lys | Ala | Gly | Met | Glu | Glu |
| 225 | | | | | 230 | | | | | 235 | | | | | 240 |
| Asn | Cys | Met | Leu | Leu | Gly | His | Ser | Cys | Ile | Val | Ala | Pro | Thr | Gly | Glu |
| | | | | 245 | | | | | 250 | | | | | 255 | |
| Ile | Val | Ala | Leu | Thr | Thr | Thr | Leu | Glu | Asp | Glu | Val | Ile | Thr | Ala | Ala |
| | | | 260 | | | | | 265 | | | | | 270 | | |
| Val | Asp | Leu | Asp | Arg | Cys | Arg | Glu | Leu | Arg | Glu | His | Ile | Phe | Asn | Phe |
| | | 275 | | | | | 280 | | | | | 285 | | | |
| Lys | Gln | His | Arg | Gln | Pro | Gln | His | Tyr | Gly | Leu | Ile | Ala | Glu | Leu | |
| | 290 | | | | | 295 | | | | | 300 | | | | |

( 2 ) INFORMATION FOR SEQ ID NO:43:

( i ) SEQUENCE CHARACTERISTICS:
        ( A ) LENGTH: 1559 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD426

( i x ) FEATURE:
        ( A ) NAME/KEY: CDS
        ( B ) LOCATION: 7..918

( x i ) SEQUENCE DESCRIPTION: SEQ ID NO:43:

| | | | | | | | | | | | | | | | | |
|---|---|---|---|---|---|---|---|---|---|---|---|---|---|---|---|---|
| CATATG | ACA | CGT | CAG | ATG | ATA | CTT | GCA | GTG | GGA | CAA | CAA | GGT | CCG | ATC | | 48 |
| | Thr | Arg | Gln | Met | Ile | Leu | Ala | Val | Gly | Gln | Gln | Gly | Pro | Ile | | |
| | 1 | | | | 5 | | | | | 10 | | | | | | |
| GCG | CGC | GCG | GAG | ACA | CGC | GAA | CAG | GTC | GTC | GTT | CGT | CTT | CTC | GAC | ATG | 96 |
| Ala | Arg | Ala | Glu | Thr | Arg | Glu | Gln | Val | Val | Val | Arg | Leu | Leu | Asp | Met | |
| 15 | | | | | 20 | | | | | 25 | | | | | 30 | |
| CTG | ACG | AAA | GCC | GCG | AGC | CGG | GGC | GCG | AAT | TTC | ATT | GTC | TTC | CCC | GAA | 144 |
| Leu | Thr | Lys | Ala | Ala | Ser | Arg | Gly | Ala | Asn | Phe | Ile | Val | Phe | Pro | Glu | |
| | | | | 35 | | | | | 40 | | | | | 45 | | |
| CTC | GCG | CTT | ACG | ACC | TTC | TTC | CCG | CGC | TGG | TAT | TTC | ACC | GAC | GAG | GCC | 192 |
| Leu | Ala | Leu | Thr | Thr | Phe | Phe | Pro | Arg | Trp | Tyr | Phe | Thr | Asp | Glu | Ala | |
| | | | 50 | | | | | 55 | | | | | 60 | | | |
| GAG | CTC | GAT | AGC | TTC | TAT | GAG | ACC | GAA | ATG | CCC | GGC | CCG | GTG | GTC | CGT | 240 |
| Glu | Leu | Asp | Ser | Phe | Tyr | Glu | Thr | Glu | Met | Pro | Gly | Pro | Val | Val | Arg | |
| | | | 65 | | | | | 70 | | | | | 75 | | | |
| CCA | CTC | TTT | GAG | AAG | GCC | GCG | GAA | CTC | GGG | ATC | GGC | TTC | AAT | CTG | GGC | 288 |
| Pro | Leu | Phe | Glu | Lys | Ala | Ala | Glu | Leu | Gly | Ile | Gly | Phe | Asn | Leu | Gly | |
| | 80 | | | | | 85 | | | | | 90 | | | | | |
| TAC | GCT | GAA | CTC | GTC | GTC | GAA | GGC | GGC | GTC | AAG | CGT | CGC | TTC | AAC | ACG | 336 |
| Tyr | Ala | Glu | Leu | Val | Val | Glu | Gly | Gly | Val | Lys | Arg | Arg | Phe | Asn | Thr | |
| 95 | | | | | 100 | | | | | 105 | | | | | 110 | |
| TCC | ATT | TTG | GTG | GAT | AAG | TCA | GGC | AAG | ATC | GTC | GGC | AAG | TAT | CGT | AAG | 384 |
| Ser | Ile | Leu | Val | Asp | Lys | Ser | Gly | Lys | Ile | Val | Gly | Lys | Tyr | Arg | Lys | |
| | | | | 115 | | | | | 120 | | | | | 125 | | |
| ATC | CAT | TTG | CCG | GGT | CAC | AAG | GAG | TAC | GAG | GCC | TAC | CGG | CCG | TTC | CAG | 432 |
| Ile | His | Leu | Pro | Gly | His | Lys | Glu | Tyr | Glu | Ala | Tyr | Arg | Pro | Phe | Gln | |
| | | | 130 | | | | | 135 | | | | | 140 | | | |
| CAT | CTT | GAA | AAG | CGT | TAT | TTC | GAG | CCG | GGC | GAT | CTC | GGC | TTC | CCG | GTC | 480 |
| His | Leu | Glu | Lys | Arg | Tyr | Phe | Glu | Pro | Gly | Asp | Leu | Gly | Phe | Pro | Val | |
| | | 145 | | | | | 150 | | | | | 155 | | | | |
| TAT | GAC | GTC | GAC | GCC | GCG | AAA | ATG | GGG | ATG | TTC | ATC | TGC | AAC | GAT | CGC | 528 |
| Tyr | Asp | Val | Asp | Ala | Ala | Lys | Met | Gly | Met | Phe | Ile | Cys | Asn | Asp | Arg | |
| | 160 | | | | | 165 | | | | | 170 | | | | | |

```
CGC TGG CCT GAA GCC TGG CGG GTG ATG GGC CTC AGG GGC GCC GAG ATC      576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC CTT GTT CCC CAG      624
Ile Cys Gly Gly Tyr Asn Thr Pro Thr His Asn Pro Leu Val Pro Gln
            195                 200                 205

CAC GAC CAC CTG ACG TCC TTC CAC CAT CTC CTA TCG ATG CAG GCC GGG      672
His Asp His Leu Thr Ser Phe His His Leu Leu Ser Met Gln Ala Gly
        210                 215                 220

TCT TAT CAG AAC GGG GCC TGG TCC GCG GCC GCG GGC AAG GCG GGC ATG      720
Ser Tyr Gln Asn Gly Ala Trp Ser Ala Ala Ala Gly Lys Ala Gly Met
    225                 230                 235

GAG GAG AAC TGC ATG CTG CTC GGC CAC TCC TGC ATC GTG GCG CCG ACC      768
Glu Glu Asn Cys Met Leu Leu Gly His Ser Cys Ile Val Ala Pro Thr
240                 245                 250

GGG GAA ATC GTC GCT CTC ACT ACG ACG CTG GAA GAC GAG GTG ATC ACC      816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC      864
Ala Ala Val Asp Leu Asp Arg Cys Arg Glu Leu Arg Glu His Ile Phe
                275                 280                 285

AAC TTC AAG CAG CAT CGT CAG CCC CAG CAC TAT GGT CTG ATC GCG GAA      912
Asn Phe Lys Gln His Arg Gln Pro Gln His Tyr Gly Leu Ile Ala Glu
            290                 295                 300

CTC TGAGGTTGCC GAAAAGCATG TGTGTCGTTG TTCTCGGCGC CTGGGTCACA           965
Leu

TCCAGGCGCG CCAGGGTGAC GCTGGTGGAA TAGTACCACG ACCGCTTCAG GGCGATCCGC   1025

AAGGAGATGC GGGTCGCCGG AGCGGCAAAG CCCGACATTC GTTTCGCACC GACGGCCGTC   1085

GTGAACTCGA CAGTCCGCGA GAAGGGCGTA TTGCGCGGCC TGGACCTGTA CGTGGAACTG   1145

TAGCCCATAT ATAGATTTCC AAAGAGTTTC GGCGAGGCGC GGCGCGCCTA GCCCATGTG    1205

AGCGAGAACC GTGCCCAGAT CAAAGAATGA GACCGACGCG CCGGCCGCGG CAAAGGATGA   1265

TCCTCAGGGT CGGATCTATC GCTCCGCCCT GAAGCAGGAG GGCGCACGCT GGCTGCTGAC   1325

GGCGGAGGAA GGGTTGCTGG CAAAGCCCAA GCCGCCCGGC CTTGTTCCGG CACTTGAGAA   1385

TGCGATCGCC ATCGTCGATT ACATCAACGG TACACCGCCC CATATCGCGT CCCTGGCGGA   1445

GCTTTCAACG ACGCTCGGGA TATCCAAGAG CCACTGTCAC TCCATCCTCA AGACGCTGAC   1505

GCATTTCGGC TGGCTGAAAT TCGACAATCG CTCAAAGAGC TACGAGCTGA ATTC         1559
```

( 2 ) INFORMATION FOR SEQ ID NO:44:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

```
Thr Arg Gln Met Ile Leu Ala Val Gly Gln Gln Gly Pro Ile Ala Arg
1               5                   10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
            35                  40                  45

Leu Thr Thr Phe Phe Pro Arg Trp Tyr Phe Thr Asp Glu Ala Glu Leu
    50                  55                  60
```

| | | | | | | | | | | | | | | | |
|---|---|---|---|---|---|---|---|---|---|---|---|---|---|---|---|
|Asp|Ser|Phe|Tyr|Glu|Thr|Glu|Met|Pro|Gly|Pro|Val|Val|Arg|Pro|Leu|
|65| | | |70| | | |75| | | | |  |  |80|
|Phe|Glu|Lys|Ala|Ala|Glu|Leu|Gly|Ile|Gly|Phe|Asn|Leu|Gly|Tyr|Ala|
| | | | |85| | | |90| | | | |  |95|  |
|Glu|Leu|Val|Val|Glu|Gly|Gly|Val|Lys|Arg|Arg|Phe|Asn|Thr|Ser|Ile|
| | | |100| | | | |105| | | | |110|  |  |
|Leu|Val|Asp|Lys|Ser|Gly|Lys|Ile|Val|Gly|Lys|Tyr|Arg|Lys|Ile|His|
| | |115| | | | |120| | | | |125|  |  |  |
|Leu|Pro|Gly|His|Lys|Glu|Tyr|Glu|Ala|Tyr|Arg|Pro|Phe|Gln|His|Leu|
| |130| | | | |135| | | |140| | |  |  |  |
|Glu|Lys|Arg|Tyr|Phe|Glu|Pro|Gly|Asp|Leu|Gly|Phe|Pro|Val|Tyr|Asp|
|145| | | | |150| | | |155| | | |  |  |160|
|Val|Asp|Ala|Ala|Lys|Met|Gly|Met|Phe|Ile|Cys|Asn|Asp|Arg|Arg|Trp|
| | | | |165| | | |170| | | | |175|  |  |
|Pro|Glu|Ala|Trp|Arg|Val|Met|Gly|Leu|Arg|Gly|Ala|Glu|Ile|Ile|Cys|
| | | |180| | | | |185| | | | |190|  |  |
|Gly|Gly|Tyr|Asn|Thr|Pro|Thr|His|Asn|Pro|Leu|Val|Pro|Gln|His|Asp|
| | |195| | | | |200| | | | |205|  |  |  |
|His|Leu|Thr|Ser|Phe|His|His|Leu|Leu|Ser|Met|Gln|Ala|Gly|Ser|Tyr|
|210| | | | |215| | | | |220| | |  |  |  |
|Gln|Asn|Gly|Ala|Trp|Ser|Ala|Ala|Gly|Lys|Ala|Gly|Met|Glu|Glu|
|225| | | |230| | | | |235| | | |  |240|  |
|Asn|Cys|Met|Leu|Leu|Gly|His|Ser|Cys|Ile|Val|Ala|Pro|Thr|Gly|Glu|
| | | |245| | | | |250| | | | |255|  |  |
|Ile|Val|Ala|Leu|Thr|Thr|Thr|Leu|Glu|Asp|Glu|Val|Ile|Thr|Ala|Ala|
| | |260| | | | |265| | | | |270|  |  |  |
|Val|Asp|Leu|Asp|Arg|Cys|Arg|Glu|Leu|Arg|Glu|His|Ile|Phe|Asn|Phe|
| |275| | | | |280| | | |285| | |  |  |  |
|Lys|Gln|His|Arg|Gln|Pro|Gln|His|Tyr|Gly|Leu|Ile|Ala|Glu|Leu|
|290| | | | |295| | | |300| | | |  |  |  |

(2) INFORMATION FOR SEQ ID NO:45:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (vi) ORIGINAL SOURCE:
        (B) STRAIN: JM109 pAD427

(ix) FEATURE:
        (A) NAME/KEY: CDS
        (B) LOCATION: 7..918

(xi) SEQUENCE DESCRIPTION: SEQ ID NO:45:

```
CATATG ACA CGT CAG ATG ATA CTT GCA GTG GGA CAA CAA GGT CCG ATC         48
       Thr Arg Gln Met Ile Leu Ala Val Gly Gln Gln Gly Pro Ile
        1               5                  10

GCG CGC GCG GAG ACA CGC GAA CAG GTC GTC GTT CGT CTT CTC GAC ATG         96
Ala Arg Ala Glu Thr Arg Glu Gln Val Val Val Arg Leu Leu Asp Met
 15              20                  25                  30

CTG ACG AAA GCC GCG AGC CGG GGC GCG AAT TTC ATT GTC TTC CCC GAA        144
Leu Thr Lys Ala Ala Ser Arg Gly Ala Asn Phe Ile Val Phe Pro Glu
             35                  40                  45

CTC GCG CTT ACG ACC TTC TTC CCG CGC TGG TAT TTC ACC GAC GAG GCC        192
Leu Ala Leu Thr Thr Phe Phe Pro Arg Trp Tyr Phe Thr Asp Glu Ala
                 50                  55                  60

GAG CTC GAT AGC TTC TAT GAG ACC GAA ATG CCC GGC CCG GTG GTC CGT        240
```

-continued

```
                Glu  Leu  Asp  Ser  Phe  Tyr  Glu  Thr  Glu  Met  Pro  Gly  Pro  Val  Val  Arg
                 65                      70                       75

CCA  CTC  TTT  GAG  AAG  GCC  GCG  GAA  CTC  GGG  ATC  GGC  TTC  AAT  CTG  GGC                  288
Pro  Leu  Phe  Glu  Lys  Ala  Ala  Glu  Leu  Gly  Ile  Gly  Phe  Asn  Leu  Gly
      80                      85                       90

TAC  GCT  GAA  CTC  GTC  GTC  GAA  GGC  GGC  GTC  AAG  CGT  CGC  TTC  AAC  ACG                  336
Tyr  Ala  Glu  Leu  Val  Val  Glu  Gly  Gly  Val  Lys  Arg  Arg  Phe  Asn  Thr
 95                     100                      105                     110

TCC  ATT  TTG  GTG  GAT  AAG  TCA  GGC  AAG  ATC  GTC  GGC  AAG  TAT  CGT  AAG                  384
Ser  Ile  Leu  Val  Asp  Lys  Ser  Gly  Lys  Ile  Val  Gly  Lys  Tyr  Arg  Lys
                115                      120                      125

ATC  CAT  TTG  CCG  GGT  CAC  AAG  GAG  TAC  GAG  GCC  TAC  CGG  CCG  TTC  CAG                  432
Ile  His  Leu  Pro  Gly  His  Lys  Glu  Tyr  Glu  Ala  Tyr  Arg  Pro  Phe  Gln
                130                      135                      140

CAT  CTT  GAA  AAG  CGT  TAT  TTC  GAG  CCG  GGC  GAT  CTC  GGC  TTC  CCG  GTC                  480
His  Leu  Glu  Lys  Arg  Tyr  Phe  Glu  Pro  Gly  Asp  Leu  Gly  Phe  Pro  Val
           145                      150                      155

TAT  GAC  GTC  GAC  GCC  GCG  AAA  ATG  GGG  ATG  TTC  ATC  TGC  AAC  GAT  CGC                  528
Tyr  Asp  Val  Asp  Ala  Ala  Lys  Met  Gly  Met  Phe  Ile  Cys  Asn  Asp  Arg
      160                     165                      170

CGC  TGG  CCT  GAA  GCC  TGG  CGG  GTG  ATG  GGC  CTC  AGG  GGC  GCC  GAG  ATC                  576
Arg  Trp  Pro  Glu  Ala  Trp  Arg  Val  Met  Gly  Leu  Arg  Gly  Ala  Glu  Ile
175                     180                      185                     190

ATC  TGC  GGC  GGC  TAC  AAC  ACG  CCG  ACC  CAC  AAT  CCC  TCT  GTT  CCC  CAG                  624
Ile  Cys  Gly  Gly  Tyr  Asn  Thr  Pro  Thr  His  Asn  Pro  Ser  Val  Pro  Gln
                195                      200                      205

CAC  GAC  CAC  CTG  ACG  TCC  TTC  CAC  CAT  CTC  CTA  TCG  ATG  CAG  GCC  GGG                  672
His  Asp  His  Leu  Thr  Ser  Phe  His  His  Leu  Leu  Ser  Met  Gln  Ala  Gly
                210                      215                      220

TCT  TAT  CAG  AAC  GGG  GCC  TGG  TCC  GCG  GCC  GCG  GGC  AAG  GCG  GGC  ATG                  720
Ser  Tyr  Gln  Asn  Gly  Ala  Trp  Ser  Ala  Ala  Ala  Gly  Lys  Ala  Gly  Met
           225                      230                      235

GAG  GAG  AAC  TGC  ATG  CTG  CTC  GGC  CAC  TCC  TGC  ATC  GTG  GCG  CCG  ACC                  768
Glu  Glu  Asn  Cys  Met  Leu  Leu  Gly  His  Ser  Cys  Ile  Val  Ala  Pro  Thr
      240                     245                      250

GGG  GAA  ATC  GTC  GCT  CTC  ACT  ACG  ACG  CTG  GAA  GAC  GAG  GTG  ATC  ACC                  816
Gly  Glu  Ile  Val  Ala  Leu  Thr  Thr  Thr  Leu  Glu  Asp  Glu  Val  Ile  Thr
255                     260                      265                     270

GCC  GCC  GTC  GAT  CTC  GAT  CGC  TGC  CGG  GAA  CTG  CGT  GAA  CAC  ATC  TTC                  864
Ala  Ala  Val  Asp  Leu  Asp  Arg  Cys  Arg  Glu  Leu  Arg  Glu  His  Ile  Phe
                275                      280                      285

AAC  TTC  AAG  CAG  CAT  CGT  CAG  CCC  CAG  CAC  TAT  GGT  CTG  ATC  GCG  GAA                  912
Asn  Phe  Lys  Gln  His  Arg  Gln  Pro  Gln  His  Tyr  Gly  Leu  Ile  Ala  Glu
                290                      295                      300

CTC  TGAGGTTGCC  GAAAAGCATG  TGTGTCGTTG  TTCTCGGCGC  CTGGGTCACA                                  965
Leu

TCCAGGCGCG  CCAGGGTGAC  GCTGGTGGAA  TAGTACCACG  ACCGCTTCAG  GGCGATCCGC                          1025

AAGGAGATGC  GGGTCGCCGG  AGCGGCAAAG  CCCGACATTC  GTTTCGCACC  GACGGCCGTC                          1085

GTGAACTCGA  CAGTCCGCGA  GAAGGGCGTA  TTGCGCGGCC  TGGACCTGTA  CGTGGAACTG                          1145

TAGCCCATAT  ATAGATTTCC  AAAGAGTTTC  GGCGAGGCGC  GGCGCGCCTA  GCCCCATGTG                          1205

AGCGAGAACC  GTGCCCAGAT  CAAAGAATGA  GACCGACGCG  CCGGCCGCGG  CAAAGGATGA                          1265

TCCTCAGGGT  CGGATCTATC  GCTCCGCCCT  GAAGCAGGAG  GGCGCACGCT  GGCTGCTGAC                          1325

GGCGGAGGAA  GGGTTGCTGG  CAAAGCCCAA  GCCGCCCGGC  CTTGTTCCGG  CACTTGAGAA                          1385

TGCGATCGCC  ATCGTCGATT  ACATCAACGG  TACACCGCCC  CATATCGCGT  CCCTGGCGGA                          1445

GCTTTCAACG  ACGCTCGGGA  TATCCAAGAG  CCACTGTCAC  TCCATCCTCA  AGACGCTGAC                          1505
```

GCATTTCGGC TGGCTGAAAT TCGACAATCG CTCAAAGAGC TACGAGCTGA ATTC  1559

( 2 ) INFORMATION FOR SEQ ID NO:46:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Thr Arg Gln Met Ile Leu Ala Val Gly Gln Gly Pro Ile Ala Arg
 1               5                  10                 15
Ala Glu Thr Arg Glu Gln Val Val Arg Leu Leu Asp Met Leu Thr
            20                  25                  30
Lys Ala Ala Ser Arg Gly Ala Asn Phe Ile Val Phe Pro Glu Leu Ala
        35                  40                  45
Leu Thr Thr Phe Phe Pro Arg Trp Tyr Phe Thr Asp Glu Ala Glu Leu
     50                  55                  60
Asp Ser Phe Tyr Glu Thr Glu Met Pro Gly Pro Val Val Arg Pro Leu
 65                  70                  75                  80
Phe Glu Lys Ala Ala Glu Leu Gly Ile Gly Phe Asn Leu Gly Tyr Ala
                 85                  90                  95
Glu Leu Val Val Glu Gly Gly Val Lys Arg Arg Phe Asn Thr Ser Ile
            100                 105                 110
Leu Val Asp Lys Ser Gly Lys Ile Val Gly Lys Tyr Arg Lys Ile His
        115                 120                 125
Leu Pro Gly His Lys Glu Tyr Glu Ala Tyr Arg Pro Phe Gln His Leu
    130                 135                 140
Glu Lys Arg Tyr Phe Glu Pro Gly Asp Leu Gly Phe Pro Val Tyr Asp
145                 150                 155                 160
Val Asp Ala Ala Lys Met Gly Met Phe Ile Cys Asn Asp Arg Arg Trp
                165                 170                 175
Pro Glu Ala Trp Arg Val Met Gly Leu Arg Gly Ala Glu Ile Ile Cys
            180                 185                 190
Gly Gly Tyr Asn Thr Pro Thr His Asn Pro Ser Val Pro Gln His Asp
        195                 200                 205
His Leu Thr Ser Phe His His Leu Leu Ser Met Gln Ala Gly Ser Tyr
    210                 215                 220
Gln Asn Gly Ala Trp Ser Ala Ala Ala Gly Lys Ala Gly Met Glu Glu
225                 230                 235                 240
Asn Cys Met Leu Leu Gly His Ser Cys Ile Val Ala Pro Thr Gly Glu
                245                 250                 255
Ile Val Ala Leu Thr Thr Thr Leu Glu Asp Glu Val Ile Thr Ala Ala
            260                 265                 270
Val Asp Leu Asp Arg Cys Arg Glu Leu Arg Glu His Ile Phe Asn Phe
        275                 280                 285
Lys Gln His Arg Gln Pro Gln His Tyr Gly Leu Ile Ala Glu Leu
    290                 295                 300
```

( 2 ) INFORMATION FOR SEQ ID NO:47:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
    ( B ) STRAIN: JM109 pAD451

( i x ) FEATURE:
    ( A ) NAME/KEY: CDS
    ( B ) LOCATION: 233..1144

( x i ) SEQUENCE DESCRIPTION: SEQ ID NO:47:

```
GTCGACGGCG  GGCTCGCGCG  AGAGCTTGTC  AAGCAGCGCA  AATTCCGGTT  CCGCTCCGGT           60

TGACAGATCA  AAAATTTTAC  GCCTGTTATT  GTCGTGCTGC  ATGTAATATT  TCGTACTTTA          120

TGTAGAATTT  GCATTGCGCC  GCGAGTCACA  AAGCCGGTTT  TCGGCGATGT  GTTTCACAAC          180

GTTTTCCCGG  CCGCTGGGCC  GGACATCACC  TAGGAAGGAG  CAGAGGTTCA  TG ACA              235
                                                              Thr
                                                               1

CGT  CAG  ATG  ATA  CTT  GCA  GTG  GGA  CAA  CAA  GGT  CCG  ATC  GCG  CGC  GCG  283
Arg  Gln  Met  Ile  Leu  Ala  Val  Gly  Gln  Gln  Gly  Pro  Ile  Ala  Arg  Ala
               5                        10                      15

GAG  ACA  CGC  GAA  CAG  GTC  GTC  GTT  CGT  CTT  CTC  GAC  ATG  CTG  ACG  AAA  331
Glu  Thr  Arg  Glu  Gln  Val  Val  Val  Arg  Leu  Leu  Asp  Met  Leu  Thr  Lys
          20                        25                      30

GCC  GCG  AGC  CGG  GGC  GCG  AAT  TTC  ATT  GTC  TTC  CCC  GAA  CTC  GCG  CTT  379
Ala  Ala  Ser  Arg  Gly  Ala  Asn  Phe  Ile  Val  Phe  Pro  Glu  Leu  Ala  Leu
     35                        40                      45

ACG  ACC  TTC  TTC  CCG  CGC  TGG  TAT  TTC  ACC  GAC  GAG  GCC  GAG  CTC  GAT  427
Thr  Thr  Phe  Phe  Pro  Arg  Trp  Tyr  Phe  Thr  Asp  Glu  Ala  Glu  Leu  Asp
50                        55                      60                         65

AGC  TTC  TAT  GAG  ACC  GAA  ATG  CCC  GGC  CCG  GTG  GTC  CGT  CCA  CTC  TTT  475
Ser  Phe  Tyr  Glu  Thr  Glu  Met  Pro  Gly  Pro  Val  Val  Arg  Pro  Leu  Phe
               70                       75                       80

GAG  AAG  GCC  GCG  GAA  CTC  GGG  ATC  GGC  TTC  AAT  CTG  GGC  TAC  GCT  GAA  523
Glu  Lys  Ala  Ala  Glu  Leu  Gly  Ile  Gly  Phe  Asn  Leu  Gly  Tyr  Ala  Glu
          85                        90                      95

CTC  GTC  GTC  GAA  GGC  GGC  GTC  AAG  CGT  CGC  TTC  AAC  ACG  TCC  ATT  TTG  571
Leu  Val  Val  Glu  Gly  Gly  Val  Lys  Arg  Arg  Phe  Asn  Thr  Ser  Ile  Leu
     100                       105                      110

GTG  GAT  AAG  TCA  GGC  AAG  ATC  GTC  GGC  AAG  TAT  CGT  AAG  ATC  CAT  TTG  619
Val  Asp  Lys  Ser  Gly  Lys  Ile  Val  Gly  Lys  Tyr  Arg  Lys  Ile  His  Leu
115                       120                      125

CCG  GGT  CAC  AAG  GAG  TAC  GAG  GCC  TAC  CGG  CCG  TTC  CAG  CAT  CTT  GAA  667
Pro  Gly  His  Lys  Glu  Tyr  Glu  Ala  Tyr  Arg  Pro  Phe  Gln  His  Leu  Glu
130                       135                      140                     145

AAG  CGT  TAT  TTC  GAG  CCG  GGC  GAT  CTC  GGC  TTC  CCG  GTC  TAT  GAC  GTC  715
Lys  Arg  Tyr  Phe  Glu  Pro  Gly  Asp  Leu  Gly  Phe  Pro  Val  Tyr  Asp  Val
               150                      155                     160

GAC  GCC  GCG  AAA  ATG  GGG  ATG  TTC  ATC  TGC  AAC  GAT  CGC  CGC  TGG  CCT  763
Asp  Ala  Ala  Lys  Met  Gly  Met  Phe  Ile  Cys  Asn  Asp  Arg  Arg  Trp  Pro
          165                      170                     175

GAA  GCC  TGG  CGG  GTG  ATG  GGC  CTC  AGG  GGC  GCC  GAG  ATC  ATC  TGC  GGC  811
Glu  Ala  Trp  Arg  Val  Met  Gly  Leu  Arg  Gly  Ala  Glu  Ile  Ile  Cys  Gly
     180                      185                     190

GGC  TAC  AAC  ACG  CCG  ACC  CAC  AAT  CCC  GAA  GTT  CCC  CAG  CAC  GAC  CAC  859
Gly  Tyr  Asn  Thr  Pro  Thr  His  Asn  Pro  Glu  Val  Pro  Gln  His  Asp  His
     195                      200                     205

CTG  ACG  TCC  TTC  CAC  CAT  CTC  CTA  TCG  ATG  CAG  GCC  GGG  TCT  TAT  CAG  907
Leu  Thr  Ser  Phe  His  His  Leu  Leu  Ser  Met  Gln  Ala  Gly  Ser  Tyr  Gln
210                      215                     220                      225

AAC  GGG  GCC  TGG  TCC  GCG  GCC  GCG  GGC  AAG  GTG  GGC  ATG  GAG  GAG  AAC  955
Asn  Gly  Ala  Trp  Ser  Ala  Ala  Ala  Gly  Lys  Val  Gly  Met  Glu  Glu  Asn
               230                      235                     240

TGC  ATG  CTG  CTC  GGC  CAC  TCC  TGC  ATC  GTG  GCG  CCG  ACC  GGG  GAA  ATC  1003
```

```
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC    1051
Val Ala Leu Thr Thr Thr Leu Glu Asp Glu Val Ile Thr Ala Ala Val
            260                 265                 270

GAT CTC GAT CGC TGC CGG GAA CTG CGT GAA CAC ATC TTC AAC TTC AAG    1099
Asp Leu Asp Arg Cys Arg Glu Leu Arg Glu His Ile Phe Asn Phe Lys
            275                 280                 285

CAG CAT CGT CAG CCC CAG CAC TAT GGT CTG ATC GCG GAA CTC TGAGGTTGCC 1151
Gln His Arg Gln Pro Gln His Tyr Gly Leu Ile Ala Glu Leu
290                 295                 300

GAAAAGCATG TGTGTCGTTG TTCTCGGCGC CTGGGTCACA TCCAGGCGCG CCAGGGTGAC   1211

GCTGGTGGAA TAGTACCACG ACCGCTTCAG GGCGATCCGC AAGGAGATGC GGGTCGCCGG   1271

AGCGGCAAAG CCCGACATTC GTTTCGCACC GACGGCCGTC GTGAACTCGA CAGTCCGCGA   1331

GAAGGGCGTA TTGCGCGGCC TGGACCTGTA CGTGGAACTG TAGCCCATAT ATAGATTTCC   1391

AAAGAGTTTC GGCGAGGCGC GGCGCGCCTA GCCCCATGTG AGCGAGAACC GTGCCCAGAT   1451

CAAAGAATGA GACCGACGCG CCGGCCGCGG CAAAGGATGA TCCTCAGGGT CGGATCTATC   1511

GCTCCGCCCT GAAGCAGGAG GGCGCACGCT GGCTGCTGAC GGCGGAGGAA GGGTTGCTGG   1571

CAAAGCCCAA GCCGCCCGGC CTTGTTCCGG CACTTGAGAA TGCGATCGCC ATCGTCGATT   1631

ACATCAACGG TACACCGCCC CATATCGCGT CCCTGGCGGA GCTTTCAACG ACGCTCGGGA   1691

TATCCAAGAG CCACTGTCAC TCCATCCTCA AGACGCTGAC GCATTCGGC TGGCTGAAAT    1751

TCGACAATCG CTCAAAGAGC TACGAGCTGA ATTC                               1785
```

( 2 ) INFORMATION FOR SEQ ID NO:48:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
            35                  40                  45

Leu Thr Thr Phe Phe Pro Arg Trp Tyr Phe Thr Asp Glu Ala Glu Leu
        50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
```

|     |     |     |     |     | 165 |     |     |     |     | 170 |     |     |     |     | 175 |     |
| --- | --- | --- | --- | --- | --- | --- | --- | --- | --- | --- | --- | --- | --- | --- | --- | --- |
| Pro | Glu | Ala | Trp<br>180 | Arg | Val | Met | Gly | Leu<br>185 | Arg | Gly | Ala | Glu | Ile<br>190 | Ile | Cys |
| Gly | Gly | Tyr<br>195 | Asn | Thr | Pro | Thr | His<br>200 | Asn | Pro | Glu | Val | Pro<br>205 | Gln | His | Asp |
| His | Leu | Thr<br>210 | Ser | Phe | His | His<br>215 | Leu | Leu | Ser | Met | Gln<br>220 | Ala | Gly | Ser | Tyr |
| Gln<br>225 | Asn | Gly | Ala | Trp | Ser<br>230 | Ala | Ala | Ala | Gly | Lys<br>235 | Val | Gly | Met | Glu | Glu<br>240 |
| Asn | Cys | Met | Leu | Leu<br>245 | Gly | His | Ser | Cys | Ile<br>250 | Val | Ala | Pro | Thr | Gly<br>255 | Glu |
| Ile | Val | Ala | Leu<br>260 | Thr | Thr | Thr | Leu | Glu<br>265 | Asp | Glu | Val | Ile | Thr<br>270 | Ala | Ala |
| Val | Asp | Leu<br>275 | Asp | Arg | Cys | Arg | Glu<br>280 | Leu | Arg | Glu | His | Ile<br>285 | Phe | Asn | Phe |
| Lys | Gln<br>290 | His | Arg | Gln | Pro | Gln<br>295 | His | Tyr | Gly | Leu | Ile<br>300 | Ala | Glu | Leu |     |

( 2 ) INFORMATION FOR SEQ ID NO:49:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD452

( i x ) FEATURE:
        ( A ) NAME/KEY: CDS
        ( B ) LOCATION: 233..1144

( x i ) SEQUENCE DESCRIPTION: SEQ ID NO:49:

```
GTCGACGGCG  GGCTCGCGCG  AGAGCTTGTC  AAGCAGCGCA  AATTCCGGTT  CCGCTCCGGT         60

TGACAGATCA  AAAATTTTAC  GCCTGTTATT  GTCGTGCTGC  ATGTAATATT  TCGTACTTTA        120

TGTAGAATTT  GCATTGCGCC  GCGAGTCACA  AAGCCGGTTT  TCGGCGATGT  GTTTCACAAC        180

GTTTTCCCGG  CCGCTGGGCC  GGACATCACC  TAGGAAGGAG  CAGAGGTTCA TG ACA             235
                                                           Thr
                                                            1
```

| CGT | CAG | ATG | ATA | CTT | GCA | GTG | GGA | CAA | CAA | GGT | CCG | ATC | GCG | CGC | GCG | 283 |
| --- | --- | --- | --- | --- | --- | --- | --- | --- | --- | --- | --- | --- | --- | --- | --- | --- |
| Arg | Gln | Met | Ile<br>5 | Leu | Ala | Val | Gly | Gln<br>10 | Gln | Gly | Pro | Ile | Ala<br>15 | Arg | Ala |     |
| GAG | ACA | CGC | GAA | CAG | GTC | GTC | GTT | CGT | CTT | CTC | GAC | ATG | CTG | ACG | AAA | 331 |
| Glu | Thr | Arg<br>20 | Glu | Gln | Val | Val | Val<br>25 | Arg | Leu | Leu | Asp | Met<br>30 | Leu | Thr | Lys |     |
| GCC | GCG | AGC | CGG | GGC | GCG | AAT | TTC | ATT | GTC | TTC | CCC | GAA | CTC | GCG | CTT | 379 |
| Ala | Ala | Ser<br>35 | Arg | Gly | Ala | Asn | Phe<br>40 | Ile | Val | Phe | Pro<br>45 | Glu | Leu | Ala | Leu |     |
| ACG | ACC | TTC | TTC | CCG | CGC | TGG | TAT | TTC | ACC | GAC | GAG | GCC | GAG | CTC | GAT | 427 |
| Thr<br>50 | Thr | Phe | Phe | Pro | Arg<br>55 | Trp | Tyr | Phe | Thr | Asp<br>60 | Glu | Ala | Glu | Leu | Asp<br>65 |     |
| AGC | TTC | TAT | GAG | ACC | GAA | ATG | CCC | GGC | CCG | GTG | GTC | CGT | CCA | CTC | TTT | 475 |
| Ser | Phe | Tyr | Glu | Thr<br>70 | Glu | Met | Pro | Gly | Pro<br>75 | Val | Val | Arg | Pro | Leu<br>80 | Phe |     |
| GAG | AAG | GCC | GCG | GAA | CTC | GGG | ATC | GGC | TTC | AAT | CTG | GGC | TAC | GCT | GAA | 523 |
| Glu | Lys | Ala | Ala<br>85 | Glu | Leu | Gly | Ile | Gly<br>90 | Phe | Asn | Leu | Gly | Tyr<br>95 | Ala | Glu |     |
| CTC | GTC | GTC | GAA | GGC | GGC | GTC | AAG | CGT | CGC | TTC | AAC | ACG | TCC | ATT | TTG | 571 |
| Leu | Val | Val | Glu | Gly | Gly | Val | Lys | Arg | Arg | Phe | Asn | Thr | Ser | Ile | Leu |     |

|     |     |     |     |     | 100 |     |     |     |     | 105 |     |     |     |     | 110 |     |     |      |
|-----|-----|-----|-----|-----|-----|-----|-----|-----|-----|-----|-----|-----|-----|-----|-----|-----|-----|------|
| GTG | GAT | AAG | TCA | GGC | AAG | ATC | GTC | GGC | AAG | TAT | CGT | AAG | ATC | CAT | TTG |     |     | 619  |
| Val | Asp | Lys | Ser | Gly | Lys | Ile | Val | Gly | Lys | Tyr | Arg | Lys | Ile | His | Leu |     |     |      |
|     | 115 |     |     |     | 120 |     |     |     |     | 125 |     |     |     |     |     |     |     |      |

```
GTG GAT AAG TCA GGC AAG ATC GTC GGC AAG TAT CGT AAG ATC CAT TTG              619
Val Asp Lys Ser Gly Lys Ile Val Gly Lys Tyr Arg Lys Ile His Leu
    115             120                 125

CCG GGT CAC AAG GAG TAC GAG GCC TAC CGG CCG TTC CAG CAT CTT GAA              667
Pro Gly His Lys Glu Tyr Glu Ala Tyr Arg Pro Phe Gln His Leu Glu
130             135                 140                         145

AAG CGT TAT TTC GAG CCG GGC GAT CTC GGC TTC CCG GTC TAT GAC GTC              715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT              763
Asp Ala Ala Lys Met Gly Met Phe Ile Cys Asn Asp Arg Arg Trp Pro
                165                 170                 175

GAA GCC TGG CGG GTG ATG GGC CTC AGG GGC GCC GAG ATC ATC TGC GGC              811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC              859
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG              907
Leu Thr Ser Phe His His Leu Leu Ser Met Gln Ala Gly Ser Tyr Gln
210                 215                 220                 225

AAC GGG GCC TGG TCC GCG GCC GCG GGC AAG TCA GGC ATG GAG GAG AAC              955
Asn Gly Ala Trp Ser Ala Ala Ala Gly Lys Ser Gly Met Glu Glu Asn
                230                 235                 240

TGC ATG CTG CTC GGC CAC TCC TGC ATC GTG GCG CCG ACC GGG GAA ATC              1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC              1051
Val Ala Leu Thr Thr Thr Leu Glu Asp Glu Val Ile Thr Ala Ala Val
            260                 265                 270

GAT CTC GAT CGC TGC CGG GAA CTG CGT GAA CAC ATC TTC AAC TTC AAG              1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC TGAGGTTGCC           1151
Gln His Arg Gln Pro Gln His Tyr Gly Leu Ile Ala Glu Leu
290                 295                 300

GAAAAGCATG TGTGTCGTTG TTCTCGGCGC CTGGGTCACA TCCAGGCGCG CCAGGGTGAC            1211

GCTGGTGGAA TAGTACCACG ACCGCTTCAG GGCGATCCGC AAGGAGATGC GGGTCGCCGG            1271

AGCGGCAAAG CCCGACATTC GTTTCGCACC GACGGCCGTC GTGAACTCGA CAGTCCGCGA            1331

GAAGGGCGTA TTGCGCGGCC TGGACCTGTA CGTGGAACTG TAGCCCATAT ATAGATTTCC            1391

AAAGAGTTTC GGCGAGGCGC GGCGCGCCTA GCCCCATGTG AGCGAGAACC GTGCCCAGAT            1451

CAAAGAATGA GACCGACGCG CCGGCCGCGG CAAAGGATGA TCCTCAGGGT CGGATCTATC            1511

GCTCCGCCCT GAAGCAGGAG GGCGCACGCT GGCTGCTGAC GGCGGAGGAA GGGTTGCTGG            1571

CAAAGCCCAA GCCGCCCGGC CTTGTTCCGG CACTTGAGAA TGCGATCGCC ATCGTCGATT            1631

ACATCAACGG TACACCGCCC CATATCGCGT CCCTGGCGGA GCTTTCAACG ACGCTCGGGA            1691

TATCCAAGAG CCACTGTCAC TCCATCCTCA AGACGCTGAC GCATTTCGGC TGGCTGAAAT            1751

TCGACAATCG CTCAAAGAGC TACGAGCTGA ATTC                                        1785
```

( 2 ) INFORMATION FOR SEQ ID NO:50:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

| Thr | Arg | Gln | Met | Ile | Leu | Ala | Val | Gly | Gln | Gln | Gly | Pro | Ile | Ala | Arg |
|---|---|---|---|---|---|---|---|---|---|---|---|---|---|---|---|
| 1 | | | | 5 | | | | | 10 | | | | | 15 | |
| Ala | Glu | Thr | Arg | Glu | Gln | Val | Val | Val | Arg | Leu | Leu | Asp | Met | Leu | Thr |
| | | | 20 | | | | | 25 | | | | | 30 | | |
| Lys | Ala | Ala | Ser | Arg | Gly | Ala | Asn | Phe | Ile | Val | Phe | Pro | Glu | Leu | Ala |
| | | | 35 | | | | 40 | | | | | 45 | | | |
| Leu | Thr | Thr | Phe | Phe | Pro | Arg | Trp | Tyr | Phe | Thr | Asp | Glu | Ala | Glu | Leu |
| | 50 | | | | | 55 | | | | | 60 | | | | |
| Asp | Ser | Phe | Tyr | Glu | Thr | Glu | Met | Pro | Gly | Pro | Val | Val | Arg | Pro | Leu |
| 65 | | | | | 70 | | | | | 75 | | | | | 80 |
| Phe | Glu | Lys | Ala | Ala | Glu | Leu | Gly | Ile | Gly | Phe | Asn | Leu | Gly | Tyr | Ala |
| | | | | 85 | | | | | 90 | | | | | 95 | |
| Glu | Leu | Val | Val | Glu | Gly | Gly | Val | Lys | Arg | Arg | Phe | Asn | Thr | Ser | Ile |
| | | | | 100 | | | | | 105 | | | | | 110 | |
| Leu | Val | Asp | Lys | Ser | Gly | Lys | Ile | Val | Gly | Lys | Tyr | Arg | Lys | Ile | His |
| | | | 115 | | | | | 120 | | | | | 125 | | |
| Leu | Pro | Gly | His | Lys | Glu | Tyr | Glu | Ala | Tyr | Arg | Pro | Phe | Gln | His | Leu |
| | | 130 | | | | | 135 | | | | | 140 | | | |
| Glu | Lys | Arg | Tyr | Phe | Glu | Pro | Gly | Asp | Leu | Gly | Phe | Pro | Val | Tyr | Asp |
| 145 | | | | | | 150 | | | | | 155 | | | | 160 |
| Val | Asp | Ala | Ala | Lys | Met | Gly | Met | Phe | Ile | Cys | Asn | Asp | Arg | Arg | Trp |
| | | | | 165 | | | | | 170 | | | | | 175 | |
| Pro | Glu | Ala | Trp | Arg | Val | Met | Gly | Leu | Arg | Gly | Ala | Glu | Ile | Ile | Cys |
| | | | | 180 | | | | | 185 | | | | | 190 | |
| Gly | Gly | Tyr | Asn | Thr | Pro | Thr | His | Asn | Pro | Pro | Val | Pro | Gln | His | Asp |
| | | | | 195 | | | | | 200 | | | | | 205 | |
| His | Leu | Thr | Ser | Phe | His | His | Leu | Leu | Ser | Met | Gln | Ala | Gly | Ser | Tyr |
| | | 210 | | | | | 215 | | | | | 220 | | | |
| Gln | Asn | Gly | Ala | Trp | Ser | Ala | Ala | Ala | Gly | Lys | Ser | Gly | Met | Glu | Glu |
| 225 | | | | | 230 | | | | | 235 | | | | | 240 |
| Asn | Cys | Met | Leu | Leu | Gly | His | Ser | Cys | Ile | Val | Ala | Pro | Thr | Gly | Glu |
| | | | | 245 | | | | | 250 | | | | | 255 | |
| Ile | Val | Ala | Leu | Thr | Thr | Thr | Leu | Glu | Asp | Glu | Val | Ile | Thr | Ala | Ala |
| | | | | 260 | | | | | 265 | | | | | 270 | |
| Val | Asp | Leu | Asp | Arg | Cys | Arg | Glu | Leu | Arg | Glu | His | Ile | Phe | Asn | Phe |
| | | | 275 | | | | | 280 | | | | | 285 | | |
| Lys | Gln | His | Arg | Gln | Pro | Gln | His | Tyr | Gly | Leu | Ile | Ala | Glu | Leu | |
| | | 290 | | | | | 295 | | | | | 300 | | | |

( 2 ) INFORMATION FOR SEQ ID NO:51:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD453

( i x ) FEATURE:
        ( A ) NAME/KEY: CDS
        ( B ) LOCATION: 233..1144

( x i ) SEQUENCE DESCRIPTION: SEQ ID NO:51:

GTCGACGGCG    GGCTCGCGCG    AGAGCTTGTC    AAGCAGCGCA    AATTCCGGTT    CCGCTCCGGT    60

| | |
|---|---|
| TGACAGATCA AAAATTTTAC GCCTGTTATT GTCGTGCTGC ATGTAATATT TCGTACTTTA | 120 |
| TGTAGAATTT GCATTGCGCC GCGAGTCACA AAGCCGGTTT TCGGCGATGT GTTTCACAAC | 180 |
| GTTTTCCCGG CCGCTGGGCC GGACATCACC TAGGAAGGAG CAGAGGTTCA TG ACA<br>                                                                                                                                                         Thr<br>                                                                                                                                                        1 | 235 |

| | | | | | | | | | | | | | | | | |
|---|---|---|---|---|---|---|---|---|---|---|---|---|---|---|---|---|
| CGT | CAG | ATG | ATA | CTT | GCA | GTG | GGA | CAA | CAA | GGT | CCG | ATC | GCG | CGC | GCG | 283 |
| Arg | Gln | Met | Ile | Leu | Ala | Val | Gly | Gln | Gln | Gly | Pro | Ile | Ala | Arg | Ala | |
| | | | 5 | | | | | 10 | | | | | 15 | | | |
| GAG | ACA | CGC | GAA | CAG | GTC | GTC | GTT | CGT | CTT | CTC | GAC | ATG | CTG | ACG | AAA | 331 |
| Glu | Thr | Arg | Glu | Gln | Val | Val | Val | Arg | Leu | Leu | Asp | Met | Leu | Thr | Lys | |
| | | 20 | | | | | 25 | | | | | 30 | | | | |
| GCC | GCG | AGC | CGG | GGC | GCG | AAT | TTC | ATT | GTC | TTC | CCC | GAA | CTC | GCG | CTT | 379 |
| Ala | Ala | Ser | Arg | Gly | Ala | Asn | Phe | Ile | Val | Phe | Pro | Glu | Leu | Ala | Leu | |
| | 35 | | | | | 40 | | | | | 45 | | | | | |
| ACG | ACC | TTC | TTC | CCG | CGC | TGG | CAT | TTC | ACC | GAC | GAG | GCC | GAG | CTC | GAT | 427 |
| Thr | Thr | Phe | Phe | Pro | Arg | Trp | His | Phe | Thr | Asp | Glu | Ala | Glu | Leu | Asp | |
| 50 | | | | | 55 | | | | | 60 | | | | | 65 | |
| AGC | TTC | TAT | GAG | ACC | GAA | ATG | CCC | GGC | CCG | GTG | GTC | CGT | CCA | CTC | TTT | 475 |
| Ser | Phe | Tyr | Glu | Thr | Glu | Met | Pro | Gly | Pro | Val | Val | Arg | Pro | Leu | Phe | |
| | | | | 70 | | | | | 75 | | | | | 80 | | |
| GAG | AAG | GCC | GCG | GAA | CTC | GGG | ATC | GGC | TTC | AAT | CTG | GGC | TAC | GCT | GAA | 523 |
| Glu | Lys | Ala | Ala | Glu | Leu | Gly | Ile | Gly | Phe | Asn | Leu | Gly | Tyr | Ala | Glu | |
| | | | 85 | | | | | 90 | | | | | 95 | | | |
| CTC | GTC | GTC | GAA | GGC | GGC | GTC | AAG | CGT | CGC | TTC | AAC | ACG | TCC | ATT | TTG | 571 |
| Leu | Val | Val | Glu | Gly | Gly | Val | Lys | Arg | Arg | Phe | Asn | Thr | Ser | Ile | Leu | |
| | | 100 | | | | | 105 | | | | | 110 | | | | |
| GTG | GAT | AAG | TCA | GGC | AAG | ATC | GTC | GGC | AAG | TAT | CGT | AAG | ATC | CAT | TTG | 619 |
| Val | Asp | Lys | Ser | Gly | Lys | Ile | Val | Gly | Lys | Tyr | Arg | Lys | Ile | His | Leu | |
| | 115 | | | | | 120 | | | | | 125 | | | | | |
| CCG | GGT | CAC | AAG | GAG | TAC | GAG | GCC | TAC | CGG | CCG | TTC | CAG | CAT | CTT | GAA | 667 |
| Pro | Gly | His | Lys | Glu | Tyr | Glu | Ala | Tyr | Arg | Pro | Phe | Gln | His | Leu | Glu | |
| 130 | | | | | 135 | | | | | 140 | | | | | 145 | |
| AAG | CGT | TAT | TTC | GAG | CCG | GGC | GAT | CTC | GGC | TTC | CCG | GTC | TAT | GAC | GTC | 715 |
| Lys | Arg | Tyr | Phe | Glu | Pro | Gly | Asp | Leu | Gly | Phe | Pro | Val | Tyr | Asp | Val | |
| | | | | 150 | | | | | 155 | | | | | 160 | | |
| GAC | GCC | GCG | AAA | ATG | GGG | ATG | TTC | ATC | TGC | AAC | GAT | CGC | CGC | TGG | CCT | 763 |
| Asp | Ala | Ala | Lys | Met | Gly | Met | Phe | Ile | Cys | Asn | Asp | Arg | Arg | Trp | Pro | |
| | | | 165 | | | | | 170 | | | | | 175 | | | |
| GAA | GCC | TGG | CGG | GTG | ATG | GGC | CTC | AGG | GGC | GCC | GAG | ATC | ATC | TGC | GGC | 811 |
| Glu | Ala | Trp | Arg | Val | Met | Gly | Leu | Arg | Gly | Ala | Glu | Ile | Ile | Cys | Gly | |
| | | 180 | | | | | 185 | | | | | 190 | | | | |
| GGC | TAC | AAC | ACG | CCG | ACC | CAC | AAT | CCC | GAA | GTT | CCC | CAG | CAC | GAC | CAC | 859 |
| Gly | Tyr | Asn | Thr | Pro | Thr | His | Asn | Pro | Glu | Val | Pro | Gln | His | Asp | His | |
| | 195 | | | | | 200 | | | | | 205 | | | | | |
| CTG | ACG | TCC | TTC | CAC | CAT | CTC | CTA | TCG | ATG | CAG | GCC | GGG | TCT | TAT | CAG | 907 |
| Leu | Thr | Ser | Phe | His | His | Leu | Leu | Ser | Met | Gln | Ala | Gly | Ser | Tyr | Gln | |
| 210 | | | | | 215 | | | | | 220 | | | | | 225 | |
| AAC | GGG | GCC | TGG | TCC | GCG | GCC | GCG | GGC | AAG | TCA | GGC | ATG | GAG | GAG | AAC | 955 |
| Asn | Gly | Ala | Trp | Ser | Ala | Ala | Ala | Gly | Lys | Ser | Gly | Met | Glu | Glu | Asn | |
| | | | | 230 | | | | | 235 | | | | | 240 | | |
| TGC | ATG | CTG | CTC | GGC | CAC | TCC | TGC | ATC | GTG | GCG | CCG | ACC | GGG | GAA | ATC | 1003 |
| Cys | Met | Leu | Leu | Gly | His | Ser | Cys | Ile | Val | Ala | Pro | Thr | Gly | Glu | Ile | |
| | | | 245 | | | | | 250 | | | | | 255 | | | |
| GTC | GCT | CTC | ACT | ACG | ACG | CTG | GAA | GAC | GAG | GTG | ATC | ACC | GCC | GCC | GTC | 1051 |
| Val | Ala | Leu | Thr | Thr | Thr | Leu | Glu | Asp | Glu | Val | Ile | Thr | Ala | Ala | Val | |
| | | 260 | | | | | 265 | | | | | 270 | | | | |
| GAT | CTC | GAT | CGC | TGC | CGG | GAA | CTG | CGT | GAA | CAC | ATC | TTC | AAC | TTC | AAG | 1099 |
| Asp | Leu | Asp | Arg | Cys | Arg | Glu | Leu | Arg | Glu | His | Ile | Phe | Asn | Phe | Lys | |
| | 275 | | | | | 280 | | | | | 285 | | | | | |

```
CAG CAT CGT CAG CCC CAG CAC TAT GGT CTG ATC GCG GAA CTC TGAGGTTGCC     1151
Gln His Arg Gln Pro Gln His Tyr Gly Leu Ile Ala Glu Leu
290                 295                 300

GAAAAGCATG TGTGTCGTTG TTCTCGGCGC CTGGGTCACA TCCAGGCGCG CCAGGGTGAC       1211

GCTGGTGGAA TAGTACCACG ACCGCTTCAG GGCGATCCGC AAGGAGATGC GGGTCGCCGG       1271

AGCGGCAAAG CCCGACATTC GTTTCGCACC GACGGCCGTC GTGAACTCGA CAGTCCGCGA       1331

GAAGGGCGTA TTGCGCGGCC TGGACCTGTA CGTGGAACTG TAGCCCATAT ATAGATTTCC      1391

AAAGAGTTTC GGCGAGGCGC GGCGCGCCTA GCCCATGTG AGCGAGAACC GTGCCCAGAT       1451

CAAAGAATGA GACCGACGCG CCGGCCGCGG CAAAGGATGA TCCTCAGGGT CGGATCTATC      1511

GCTCCGCCCT GAAGCAGGAG GGCGCACGCT GGCTGCTGAC GGCGGAGGAA GGGTTGCTGG      1571

CAAAGCCCAA GCCGCCCGGC CTTGTTCCGG CACTTGAGAA TGCGATCGCC ATCGTCGATT      1631

ACATCAACGG TACACCGCCC CATATCGCGT CCCTGGCGGA GCTTTCAACG ACGCTCGGGA     1691

TATCCAAGAG CCACTGTCAC TCCATCCTCA AGACGCTGAC GCATTTCGGC TGGCTGAAAT     1751

TCGACAATCG CTCAAAGAGC TACGAGCTGA ATTC                                  1785
```

(2) INFORMATION FOR SEQ ID NO:52:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:52:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
                20                  25                  30

Lys Ala Ala Ser Arg Gly Ala Asn Phe Ile Val Phe Pro Glu Leu Ala
                35                  40                  45

Leu Thr Thr Phe Phe Pro Arg Trp His Phe Thr Asp Glu Ala Glu Leu
        50                  55                  60

Asp Ser Phe Tyr Glu Thr Glu Met Pro Gly Pro Val Val Arg Pro Leu
 65                 70                  75                  80

Phe Glu Lys Ala Ala Glu Leu Gly Ile Gly Phe Asn Leu Gly Tyr Ala
                    85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                    165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Glu Val Pro Gln His Asp
            195                 200                 205

His Leu Thr Ser Phe His His Leu Leu Ser Met Gln Ala Gly Ser Tyr
        210                 215                 220
```

```
Gln  Asn  Gly  Ala  Trp  Ser  Ala  Ala  Ala  Gly  Lys  Ser  Gly  Met  Glu  Glu
225                      230                 235                      240

Asn  Cys  Met  Leu  Leu  Gly  His  Ser  Cys  Ile  Val  Ala  Pro  Thr  Gly  Glu
               245                      250                      255

Ile  Val  Ala  Leu  Thr  Thr  Thr  Leu  Glu  Asp  Glu  Val  Ile  Thr  Ala  Ala
               260                      265                      270

Val  Asp  Leu  Asp  Arg  Cys  Arg  Glu  Leu  Arg  Glu  His  Ile  Phe  Asn  Phe
          275                      280                      285

Lys  Gln  His  Arg  Gln  Pro  Gln  His  Tyr  Gly  Leu  Ile  Ala  Glu  Leu
          290                      295                 300
```

( 2 ) INFORMATION FOR SEQ ID NO:53:

( i ) SEQUENCE CHARACTERISTICS:
        ( A ) LENGTH: 1559 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD461

( i x ) FEATURE:
        ( A ) NAME/KEY: CDS
        ( B ) LOCATION: 7..918

( x i ) SEQUENCE DESCRIPTION: SEQ ID NO:53:

```
CATATG ACA  CGT  CAG  ATG  ATA  CTT  GCA  GTG  GGA  CAA  CAA  GGT  CCG  ATC        48
       Thr  Arg  Gln  Met  Ile  Leu  Ala  Val  Gly  Gln  Gln  Gly  Pro  Ile
        1                 5                           10

GCG  CGC  GCG  GAG  ACA  CGC  GAA  CAG  GTC  GTC  GTT  CGT  CTT  CTC  GAC  ATG     96
Ala  Arg  Ala  Glu  Thr  Arg  Glu  Gln  Val  Val  Val  Arg  Leu  Leu  Asp  Met
15                      20                      25                      30

CTG  ACG  AAA  GCC  GCG  AGC  CGG  GGC  GCG  AAT  TTC  ATT  GTC  TTC  CCC  GAA    144
Leu  Thr  Lys  Ala  Ala  Ser  Arg  Gly  Ala  Asn  Phe  Ile  Val  Phe  Pro  Glu
                    35                      40                      45

CTC  GCG  CTT  ACG  ACC  TTC  TTC  CCG  CGC  TGG  CAT  TTC  ACC  GAC  GAG  GCC    192
Leu  Ala  Leu  Thr  Thr  Phe  Phe  Pro  Arg  Trp  His  Phe  Thr  Asp  Glu  Ala
               50                      55                      60

GAG  CTC  GAT  AGC  TTC  TAT  GAG  ACC  GAA  ATG  CCC  GGC  CCG  GTG  GTC  CGT    240
Glu  Leu  Asp  Ser  Phe  Tyr  Glu  Thr  Glu  Met  Pro  Gly  Pro  Val  Val  Arg
          65                      70                      75

CCA  CTC  TTT  GAG  AAG  GCC  GCG  GAA  CTC  GGG  ATC  GGC  TTC  AAT  CTG  GGC    288
Pro  Leu  Phe  Glu  Lys  Ala  Ala  Glu  Leu  Gly  Ile  Gly  Phe  Asn  Leu  Gly
     80                      85                      90

TAC  GCT  GAA  CTC  GTC  GTC  GAA  GGC  GGC  GTC  AAG  CGT  CGC  TTC  AAC  ACG    336
Tyr  Ala  Glu  Leu  Val  Val  Glu  Gly  Gly  Val  Lys  Arg  Arg  Phe  Asn  Thr
95                      100                     105                     110

TCC  ATT  TTG  GTG  GAT  AAG  TCA  GGC  AAG  ATC  GTC  GGC  AAG  TAT  CGT  AAG    384
Ser  Ile  Leu  Val  Asp  Lys  Ser  Gly  Lys  Ile  Val  Gly  Lys  Tyr  Arg  Lys
                    115                     120                     125

ATC  CAT  TTG  CCG  GGT  CAC  AAG  GAG  TAC  GAG  GCC  TAC  CGG  CCG  TTC  CAG    432
Ile  His  Leu  Pro  Gly  His  Lys  Glu  Tyr  Glu  Ala  Tyr  Arg  Pro  Phe  Gln
               130                     135                     140

CAT  CTT  GAA  AAG  CGT  TAT  TTC  GAG  CCG  GGC  GAT  CTC  GGC  TTC  CCG  GTC    480
His  Leu  Glu  Lys  Arg  Tyr  Phe  Glu  Pro  Gly  Asp  Leu  Gly  Phe  Pro  Val
          145                     150                     155

TAT  GAC  GTC  GAC  GCC  GCG  AAA  ATG  GGG  ATG  TTC  ATC  TGC  AAC  GAT  CGC    528
Tyr  Asp  Val  Asp  Ala  Ala  Lys  Met  Gly  Met  Phe  Ile  Cys  Asn  Asp  Arg
     160                     165                     170

CGC  TGG  CCT  GAA  GCC  TGG  CGG  GTG  ATG  GGC  CTC  AGG  GGC  GCC  GAG  ATC    576
Arg  Trp  Pro  Glu  Ala  Trp  Arg  Val  Met  Gly  Leu  Arg  Gly  Ala  Glu  Ile
```

| | | | | | | | | | | | | | | | | |
|---|---|---|---|---|---|---|---|---|---|---|---|---|---|---|---|---|
| 175 | | | | | 180 | | | | | 185 | | | | | 190 | |
| ATC | TGC | GGC | GGC | TAC | AAC | ACG | CCG | ACC | CAC | AAT | CCC | GAA | GTT | CCC | CAG | 624 |
| Ile | Cys | Gly | Gly | Tyr | Asn | Thr | Pro | Thr | His | Asn | Pro | Glu | Val | Pro | Gln | |
| | | | | 195 | | | | | 200 | | | | | 205 | | |
| CAC | GAC | CAC | CTG | ACG | TCC | TTC | CAC | CAT | CTC | CTA | TCG | ATG | CAG | GCC | GGG | 672 |
| His | Asp | His | Leu | Thr | Ser | Phe | His | His | Leu | Leu | Ser | Met | Gln | Ala | Gly | |
| | | | 210 | | | | | 215 | | | | | 220 | | | |
| TCT | TAT | CAG | AAC | GGG | GCC | TGG | TCC | GCG | GCC | GCG | GGC | AAG | GCG | GGC | ATG | 720 |
| Ser | Tyr | Gln | Asn | Gly | Ala | Trp | Ser | Ala | Ala | Ala | Gly | Lys | Ala | Gly | Met | |
| | | 225 | | | | | 230 | | | | | 235 | | | | |
| GAG | GAG | AAC | TGC | ATG | CTG | CTC | GGC | CAC | TCC | TGC | ATC | GTG | GCG | CCG | ACC | 768 |
| Glu | Glu | Asn | Cys | Met | Leu | Leu | Gly | His | Ser | Cys | Ile | Val | Ala | Pro | Thr | |
| | | 240 | | | | 245 | | | | | 250 | | | | | |
| GGG | GAA | ATC | GTC | GCT | CTC | ACT | ACG | ACG | CTG | GAA | GAC | GAG | GTG | ATC | ACC | 816 |
| Gly | Glu | Ile | Val | Ala | Leu | Thr | Thr | Thr | Leu | Glu | Asp | Glu | Val | Ile | Thr | |
| 255 | | | | | 260 | | | | | 265 | | | | | 270 | |
| GCC | GCC | GTC | GAT | CTC | GAT | CGC | TGC | CGG | GAA | CTG | CGT | GAA | CAC | ATC | TTC | 864 |
| Ala | Ala | Val | Asp | Leu | Asp | Arg | Cys | Arg | Glu | Leu | Arg | Glu | His | Ile | Phe | |
| | | | | 275 | | | | | 280 | | | | | 285 | | |
| AAC | TTC | AAG | CAG | CAT | CGT | CAG | CCC | CAG | CAC | TAT | GGT | CTG | ATC | GCG | GAA | 912 |
| Asn | Phe | Lys | Gln | His | Arg | Gln | Pro | Gln | His | Tyr | Gly | Leu | Ile | Ala | Glu | |
| | | | 290 | | | | | 295 | | | | | 300 | | | |

```
CTC   TGAGGTTGCC  GAAAAGCATG  TGTGTCGTTG  TTCTCGGCGC  CTGGGTCACA           965
Leu

TCCAGGCGCG  CCAGGGTGAC  GCTGGTGGAA  TAGTACCACG  ACCGCTTCAG  GGCGATCCGC    1025

AAGGAGATGC  GGGTCGCCGG  AGCGGCAAAG  CCCGACATTC  GTTTCGCACC  GACGGCCGTC    1085

GTGAACTCGA  CAGTCCGCGA  GAAGGGCGTA  TTGCGCGGCC  TGGACCTGTA  CGTGGAACTG    1145

TAGCCCATAT  ATAGATTTCC  AAAGAGTTTC  GGCGAGGCGC  GGCGCGCCTA  GCCCCATGTG    1205

AGCGAGAACC  GTGCCCAGAT  CAAAGAATGA  GACCGACGCG  CCGGCCGCGG  CAAAGGATGA    1265

TCCTCAGGGT  CGGATCTATC  GCTCCGCCCT  GAAGCAGGAG  GGCGCACGCT  GGCTGCTGAC    1325

GGCGGAGGAA  GGGTTGCTGG  CAAAGCCCAA  GCCGCCCGGC  CTTGTTCCGG  CACTTGAGAA    1385

TGCGATCGCC  ATCGTCGATT  ACATCAACGG  TACACCGCCC  CATATCGCGT  CCCTGGCGGA    1445

GCTTTCAACG  ACGCTCGGGA  TATCCAAGAG  CCACTGTCAC  TCCATCCTCA  AGACGCTGAC    1505

GCATTTCGGC  TGGCTGAAAT  TCGACAATCG  CTCAAAGAGC  TACGAGCTGA  ATTC          1559
```

( 2 ) INFORMATION FOR SEQ ID NO:54:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:54:

| | | | | | | | | | | | | | | | |
|---|---|---|---|---|---|---|---|---|---|---|---|---|---|---|---|
| Thr | Arg | Gln | Met | Ile | Leu | Ala | Val | Gly | Gln | Gln | Gly | Pro | Ile | Ala | Arg |
| 1 | | | | 5 | | | | | 10 | | | | | 15 | |
| Ala | Glu | Thr | Arg | Glu | Gln | Val | Val | Arg | Leu | Leu | Asp | Met | Leu | Thr | |
| | | | 20 | | | | | 25 | | | | | 30 | | |
| Lys | Ala | Ala | Ser | Arg | Gly | Ala | Asn | Phe | Ile | Val | Phe | Pro | Glu | Leu | Ala |
| | | | 35 | | | | | 40 | | | | | 45 | | |
| Leu | Thr | Thr | Phe | Phe | Pro | Arg | Trp | His | Phe | Thr | Asp | Glu | Ala | Glu | Leu |
| | | 50 | | | | | 55 | | | | | 60 | | | |
| Asp | Ser | Phe | Tyr | Glu | Thr | Glu | Met | Pro | Gly | Pro | Val | Val | Arg | Pro | Leu |
| 65 | | | | | 70 | | | | | 75 | | | | | 80 |

```
Phe  Glu  Lys  Ala  Ala  Glu  Leu  Gly  Ile  Gly  Phe  Asn  Leu  Gly  Tyr  Ala
                    85                       90                      95

Glu  Leu  Val  Val  Glu  Gly  Gly  Val  Lys  Arg  Arg  Phe  Asn  Thr  Ser  Ile
               100                      105                     110

Leu  Val  Asp  Lys  Ser  Gly  Lys  Ile  Val  Gly  Lys  Tyr  Arg  Lys  Ile  His
               115                      120                     125

Leu  Pro  Gly  His  Lys  Glu  Tyr  Glu  Ala  Tyr  Arg  Pro  Phe  Gln  His  Leu
          130                      135                     140

Glu  Lys  Arg  Tyr  Phe  Glu  Pro  Gly  Asp  Leu  Gly  Phe  Pro  Val  Tyr  Asp
145                           150                     155                     160

Val  Asp  Ala  Ala  Lys  Met  Gly  Met  Phe  Ile  Cys  Asn  Asp  Arg  Arg  Trp
               165                      170                     175

Pro  Glu  Ala  Trp  Arg  Val  Met  Gly  Leu  Arg  Gly  Ala  Glu  Ile  Ile  Cys
               180                      185                     190

Gly  Gly  Tyr  Asn  Thr  Pro  Thr  His  Asn  Pro  Glu  Val  Pro  Gln  His  Asp
          195                      200                     205

His  Leu  Thr  Ser  Phe  His  His  Leu  Leu  Ser  Met  Gln  Ala  Gly  Ser  Tyr
     210                      215                     220

Gln  Asn  Gly  Ala  Trp  Ser  Ala  Ala  Ala  Gly  Lys  Ala  Gly  Met  Glu  Glu
225                      230                     235                          240

Asn  Cys  Met  Leu  Leu  Gly  His  Ser  Cys  Ile  Val  Ala  Pro  Thr  Gly  Glu
                    245                      250                     255

Ile  Val  Ala  Leu  Thr  Thr  Thr  Leu  Glu  Asp  Glu  Val  Ile  Thr  Ala  Ala
               260                      265                     270

Val  Asp  Leu  Asp  Arg  Cys  Arg  Glu  Leu  Arg  Glu  His  Ile  Phe  Asn  Phe
          275                      280                     285

Lys  Gln  His  Arg  Gln  Pro  Gln  His  Tyr  Gly  Leu  Ile  Ala  Glu  Leu
290                      295                     300
```

( 2 ) INFORMATION FOR SEQ ID NO:55:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD454

( i x ) FEATURE:
        ( A ) NAME/KEY: CDS
        ( B ) LOCATION: 233..1144

( x i ) SEQUENCE DESCRIPTION: SEQ ID NO:55:

```
GTCGACGGCG  GGCTCGCGCG  AGAGCTTGTC  AAGCAGCGCA  AATTCCGGTT  CCGCTCCGGT      60

TGACAGATCA  AAAATTTTAC  GCCTGTTATT  GTCGTGCTGC  ATGTAATATT  TCGTACTTTA     120

TGTAGAATTT  GCATTGCGCC  GCGAGTCACA  AAGCCGGTTT  TCGGCGATGT  GTTTCACAAC     180

GTTTTCCCGG  CCGCTGGGCC  GGACATCACC  TAGGAAGGAG  CAGAGGTTCA  TG  ACA         235
                                                                Thr
                                                                 1

CGT  CAG  ATG  ATA  CTT  GCA  GTG  GGA  CAA  CAA  GGT  CCG  ATC  GCG  CGC  GCG   283
Arg  Gln  Met  Ile  Leu  Ala  Val  Gly  Gln  Gln  Gly  Pro  Ile  Ala  Arg  Ala
               5                        10                      15

GAG  ACA  CGC  GAA  CAG  GTC  GTC  GTT  CGT  CTT  CTC  GAC  ATG  CTG  ACG  AAA   331
Glu  Thr  Arg  Glu  Gln  Val  Val  Val  Arg  Leu  Leu  Asp  Met  Leu  Thr  Lys
          20                       25                      30

GCC  GCG  AGC  CGG  GGC  GCG  AAT  TTC  ATT  GTC  TTC  CCC  GAA  CTC  GCG  CTT   379
Ala  Ala  Ser  Arg  Gly  Ala  Asn  Phe  Ile  Val  Phe  Pro  Glu  Leu  Ala  Leu
```

-continued

```
              35                            40                              45
ACG  ACC  TTC  TTC  CCG  CGC  TGG  TAT  TTC  ACC  GAC  GAG  GCC  GAG  CTC  GAT      427
Thr  Thr  Phe  Phe  Pro  Arg  Trp  Tyr  Phe  Thr  Asp  Glu  Ala  Glu  Leu  Asp
50                  55                       60                            65

AGC  TTC  TAT  GAG  ACC  GAA  ATG  CCC  GGC  CCG  GTG  GTC  CGT  CCA  CTC  TTT      475
Ser  Phe  Tyr  Glu  Thr  Glu  Met  Pro  Gly  Pro  Val  Val  Arg  Pro  Leu  Phe
                    70                       75                       80

GAG  AAG  GCC  GCG  GAA  CTC  GGG  ATC  GGC  TTC  AAT  CTG  GGC  TAC  GCT  GAA      523
Glu  Lys  Ala  Ala  Glu  Leu  Gly  Ile  Gly  Phe  Asn  Leu  Gly  Tyr  Ala  Glu
               85                            90                       95

CTC  GTC  GTC  GAA  GGC  GGC  GTC  AAG  CGT  CGC  TTC  AAC  ACG  TCC  ATT  TTG      571
Leu  Val  Val  Glu  Gly  Gly  Val  Lys  Arg  Arg  Phe  Asn  Thr  Ser  Ile  Leu
               100                      105                      110

GTG  GAT  AAG  TCA  GGC  AAG  ATC  GTC  GGC  AAG  TAT  CGT  AAG  ATC  CAT  TTG      619
Val  Asp  Lys  Ser  Gly  Lys  Ile  Val  Gly  Lys  Tyr  Arg  Lys  Ile  His  Leu
115                      120                           125

CCG  GGT  CAC  AAG  GAG  TAC  GAG  GCC  TAC  CGG  CCG  TTC  CAG  CAT  CTT  GAA      667
Pro  Gly  His  Lys  Glu  Tyr  Glu  Ala  Tyr  Arg  Pro  Phe  Gln  His  Leu  Glu
130                      135                           140                      145

AAG  CGT  TAT  TTC  GAG  CCG  GGC  GAT  CTC  GGC  TTC  CCG  GTC  TAT  GAC  GTC      715
Lys  Arg  Tyr  Phe  Glu  Pro  Gly  Asp  Leu  Gly  Phe  Pro  Val  Tyr  Asp  Val
                    150                           155                      160

GAC  GCC  GCG  AAA  ATG  GGG  ATG  TTC  ATC  TGC  AAC  GAT  CGC  CGC  TGG  CCT      763
Asp  Ala  Ala  Lys  Met  Gly  Met  Phe  Ile  Cys  Asn  Asp  Arg  Arg  Trp  Pro
                    165                      170                      175

GAA  GCC  TGG  CGG  GTG  ATG  GGC  CTC  AGG  GGC  GCC  GAG  ATC  ATC  TGC  GGC      811
Glu  Ala  Trp  Arg  Val  Met  Gly  Leu  Arg  Gly  Ala  Glu  Ile  Ile  Cys  Gly
               180                      185                      190

GGC  TAC  AAC  ACG  CCG  ACC  CAC  AAT  CCC  GAA  GTT  CCC  CAG  CAC  GAC  CAC      859
Gly  Tyr  Asn  Thr  Pro  Thr  His  Asn  Pro  Glu  Val  Pro  Gln  His  Asp  His
          195                      200                      205

CTG  ACG  TCC  TTC  CAC  CAT  CTC  CTA  TCG  ATG  CAG  GCC  GGG  TCT  TAT  CAG      907
Leu  Thr  Ser  Phe  His  His  Leu  Leu  Ser  Met  Gln  Ala  Gly  Ser  Tyr  Gln
210                      215                      220                           225

AAC  GGG  GCC  TGG  TCC  GCG  GCC  GCG  GGC  AAG  TCA  GGC  ATG  GAG  GAG  AAC      955
Asn  Gly  Ala  Trp  Ser  Ala  Ala  Ala  Gly  Lys  Ser  Gly  Met  Glu  Glu  Asn
                    230                      235                           240

TGC  ATG  CTG  CTC  GGC  CAC  TCC  TGC  ATC  GTG  GCG  CCG  ACC  GGG  GAA  ATC     1003
Cys  Met  Leu  Leu  Gly  His  Ser  Cys  Ile  Val  Ala  Pro  Thr  Gly  Glu  Ile
               245                      250                      255

GTC  GCT  CTC  ACT  ACG  ACG  CTG  GAA  GAC  GAG  GTG  ATC  ACC  GCC  GCC  GTC     1051
Val  Ala  Leu  Thr  Thr  Thr  Leu  Glu  Asp  Glu  Val  Ile  Thr  Ala  Ala  Val
               260                      265                      270

GAT  CTC  GAT  CGC  TGC  CGG  GAA  CTG  CGT  GAA  CAC  ATC  TTC  AAC  TTC  AAG     1099
Asp  Leu  Asp  Arg  Cys  Arg  Glu  Leu  Arg  Glu  His  Ile  Phe  Asn  Phe  Lys
275                      280                           285

CAG  CAT  CGT  CAG  CCC  CAG  CAC  TAT  GGT  CTG  ATC  GCG  GAA  CTC  TGAGGTTGCC   1151
Gln  His  Arg  Gln  Pro  Gln  His  Tyr  Gly  Leu  Ile  Ala  Glu  Leu
290                      295                           300

GAAAAGCATG  TGTGTCGTTG  TTCTCGGCGC  CTGGGTCACA  TCCAGGCGCG  CCAGGGTGAC            1211

GCTGGTGGAA  TAGTACCACG  ACCGCTTCAG  GGCGATCCGC  AAGGAGATGC  GGGTCGCCGG            1271

AGCGGCAAAG  CCCGACATTC  GTTTCGCACC  GACGGCCGTC  GTGAACTCGA  CAGTCCGCGA            1331

GAAGGGCGTA  TTGCGCGGCC  TGGACCTGTA  CGTGGAACTG  TAGCCCATAT  ATAGATTTCC            1391

AAAGAGTTTC  GGCGAGGCGC  GGCGCGCCTA  GCCCATGTG   AGCGAGAACC  GTGCCCAGAT            1451

CAAAGAATGA  GACCGACGCG  CCGGCCGCGG  CAAAGGATGA  TCCTCAGGGT  CGGATCTATC            1511

GCTCCGCCCT  GAAGCAGGAG  GGCGCACGCT  GGCTGCTGAC  GGCGGAGGAA  GGGTTGCTGG            1571
```

```
CAAAGCCCAA   GCCGCCCGGC   CTTGTTCCGG   CACTTGAGAA   TGCGATCGCC   ATCGTCGATT       1631

ACATCAACGG   TACACCGCCC   CATATCGCGT   CCCTGGCGGA   GCTTTCAACG   ACGCTCGGGA       1691

TATCCAAGAG   CCACTGTCAC   TCCATCCTCA   AGACGCTGAC   GCATTTCGGC   TGGCTGAAAT       1751

TCGACAATCG   CTCAAAGAGC   TACGAGCTGA   ATTC                                       1785
```

( 2 ) INFORMATION FOR SEQ ID NO:56:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

```
Thr  Arg  Gln  Met  Ile  Leu  Ala  Val  Gly  Gln  Gln  Gly  Pro  Ile  Ala  Arg
 1                   5                        10                       15

Ala  Glu  Thr  Arg  Glu  Gln  Val  Val  Val  Arg  Leu  Leu  Asp  Met  Leu  Thr
              20                        25                       30

Lys  Ala  Ala  Ser  Arg  Gly  Ala  Asn  Phe  Ile  Val  Phe  Pro  Glu  Leu  Ala
         35                        40                       45

Leu  Thr  Thr  Phe  Phe  Pro  Arg  Trp  Tyr  Phe  Thr  Asp  Glu  Ala  Glu  Leu
     50                        55                       60

Asp  Ser  Phe  Tyr  Glu  Thr  Glu  Met  Pro  Gly  Pro  Val  Val  Arg  Pro  Leu
65                        70                       75                       80

Phe  Glu  Lys  Ala  Ala  Glu  Leu  Gly  Ile  Gly  Phe  Asn  Leu  Gly  Tyr  Ala
                    85                        90                       95

Glu  Leu  Val  Val  Glu  Gly  Gly  Val  Lys  Arg  Arg  Phe  Asn  Thr  Ser  Ile
               100                       105                      110

Leu  Val  Asp  Lys  Ser  Gly  Lys  Ile  Val  Gly  Lys  Tyr  Arg  Lys  Ile  His
          115                       120                      125

Leu  Pro  Gly  His  Lys  Glu  Tyr  Glu  Ala  Tyr  Arg  Pro  Phe  Gln  His  Leu
     130                       135                      140

Glu  Lys  Arg  Tyr  Phe  Glu  Pro  Gly  Asp  Leu  Gly  Phe  Pro  Val  Tyr  Asp
145                       150                      155                      160

Val  Asp  Ala  Ala  Lys  Met  Gly  Met  Phe  Ile  Cys  Asn  Asp  Arg  Arg  Trp
                    165                      170                      175

Pro  Glu  Ala  Trp  Arg  Val  Met  Gly  Leu  Arg  Gly  Ala  Glu  Ile  Ile  Cys
               180                      185                      190

Gly  Gly  Tyr  Asn  Thr  Pro  Thr  His  Asn  Pro  Glu  Val  Pro  Gln  His  Asp
          195                      200                      205

His  Leu  Thr  Ser  Phe  His  His  Leu  Leu  Ser  Met  Gln  Ala  Gly  Ser  Tyr
     210                      215                      220

Gln  Asn  Gly  Ala  Trp  Ser  Ala  Ala  Ala  Gly  Lys  Ser  Gly  Met  Glu  Glu
225                      230                      235                      240

Asn  Cys  Met  Leu  Leu  Gly  His  Ser  Cys  Ile  Val  Ala  Pro  Thr  Gly  Glu
                    245                      250                      255

Ile  Val  Ala  Leu  Thr  Thr  Thr  Leu  Glu  Asp  Glu  Val  Ile  Thr  Ala  Ala
               260                      265                      270

Val  Asp  Leu  Asp  Arg  Cys  Arg  Glu  Leu  Arg  Glu  His  Ile  Phe  Asn  Phe
          275                      280                      285

Lys  Gln  His  Arg  Gln  Pro  Gln  His  Tyr  Gly  Leu  Ile  Ala  Glu  Leu
     290                      295                      300
```

( 2 ) INFORMATION FOR SEQ ID NO:57:

( i ) SEQUENCE CHARACTERISTICS:
  ( A ) LENGTH: 1559 base pairs
  ( B ) TYPE: nucleic acid
  ( C ) STRANDEDNESS: double
  ( D ) TOPOLOGY: linear ( v i ) ORIGINAL SOURCE:
  ( A ) ORGANISM: JM109 pAD455 (FERM BP- 4036)

( i x ) FEATURE:
  ( A ) NAME/KEY: CDS
  ( B ) LOCATION: 7..918

( x i ) SEQUENCE DESCRIPTION: SEQ ID NO:57:

| | | | | | | | | | | | | | | | | |
|---|---|---|---|---|---|---|---|---|---|---|---|---|---|---|---|---|
| CATATG | ACA | CGT | CAG | ATG | ATA | CTT | GCA | GTG | GGA | CAA | CAA | GGT | CCG | ATC | | 48 |
| | Thr | Arg | Gln | Met | Ile | Leu | Ala | Val | Gly | Gln | Gln | Gly | Pro | Ile | | |
| | 1 | | | | 5 | | | | | 10 | | | | | | |
| GCG | CGC | GCG | GAG | ACA | CGC | GAA | CAG | GTC | GTC | GTT | CGT | CTT | CTC | GAC | ATG | 96 |
| Ala | Arg | Ala | Glu | Thr | Arg | Glu | Gln | Val | Val | Val | Arg | Leu | Leu | Asp | Met | |
| 15 | | | | 20 | | | | | 25 | | | | | | 30 | |
| CTG | ACG | AAA | GCC | GCG | AGC | CGG | GGC | GCG | AAT | TTC | ATT | GTC | TTC | CCC | GAA | 144 |
| Leu | Thr | Lys | Ala | Ala | Ser | Arg | Gly | Ala | Asn | Phe | Ile | Val | Phe | Pro | Glu | |
| | | | | 35 | | | | 40 | | | | | 45 | | | |
| CTC | GCG | CTT | ACG | ACC | TTC | TTC | CCG | CGC | TGG | TAT | TTC | ACC | GAC | GAG | GCC | 192 |
| Leu | Ala | Leu | Thr | Thr | Phe | Phe | Pro | Arg | Trp | Tyr | Phe | Thr | Asp | Glu | Ala | |
| | | | 50 | | | | 55 | | | | | 60 | | | | |
| GAG | CTC | GAT | AGC | TTC | TAT | GAG | ACC | GAA | ATG | CCC | GGC | CCG | GTG | GTC | CGT | 240 |
| Glu | Leu | Asp | Ser | Phe | Tyr | Glu | Thr | Glu | Met | Pro | Gly | Pro | Val | Val | Arg | |
| | | 65 | | | | 70 | | | | | 75 | | | | | |
| CCA | CTC | TTT | GAG | AAG | GCC | GCG | GAA | CTC | GGG | ATC | GGC | TTC | AAT | CTG | GGC | 288 |
| Pro | Leu | Phe | Glu | Lys | Ala | Ala | Glu | Leu | Gly | Ile | Gly | Phe | Asn | Leu | Gly | |
| 80 | | | | | 85 | | | | 90 | | | | | | | |
| TAC | GCT | GAA | CTC | GTC | GTC | GAA | GGC | GGC | GTC | AAG | CGT | CGC | TTC | AAC | ACG | 336 |
| Tyr | Ala | Glu | Leu | Val | Val | Glu | Gly | Gly | Val | Lys | Arg | Arg | Phe | Asn | Thr | |
| 95 | | | | 100 | | | | | 105 | | | | | | 110 | |
| TCC | ATT | TTG | GTG | GAT | AAG | TCA | GGC | AAG | ATC | GTC | GGC | AAG | TAT | CGT | AAG | 384 |
| Ser | Ile | Leu | Val | Asp | Lys | Ser | Gly | Lys | Ile | Val | Gly | Lys | Tyr | Arg | Lys | |
| | | | | 115 | | | | 120 | | | | | 125 | | | |
| ATC | CAT | TTG | CCG | GGT | CAC | AAG | GAG | TAC | GAG | GCC | TAC | CGG | CCG | TTC | CAG | 432 |
| Ile | His | Leu | Pro | Gly | His | Lys | Glu | Tyr | Glu | Ala | Tyr | Arg | Pro | Phe | Gln | |
| | | | 130 | | | | 135 | | | | | 140 | | | | |
| CAT | CTT | GAA | AAG | CGT | TAT | TTC | GAG | CCG | GGC | GAT | CTC | GGC | TTC | CCG | GTC | 480 |
| His | Leu | Glu | Lys | Arg | Tyr | Phe | Glu | Pro | Gly | Asp | Leu | Gly | Phe | Pro | Val | |
| | | 145 | | | | 150 | | | | | 155 | | | | | |
| TAT | GAC | GTC | GAC | GCC | GCG | AAA | ATG | GGG | ATG | TTC | ATC | TGC | AAC | GAT | CGC | 528 |
| Tyr | Asp | Val | Asp | Ala | Ala | Lys | Met | Gly | Met | Phe | Ile | Cys | Asn | Asp | Arg | |
| | 160 | | | | 165 | | | | | 170 | | | | | | |
| CGC | TGG | CCT | GAA | GCC | TGG | CGG | GTG | ATG | GGC | CTC | AGG | GGC | GCC | GAG | ATC | 576 |
| Arg | Trp | Pro | Glu | Ala | Trp | Arg | Val | Met | Gly | Leu | Arg | Gly | Ala | Glu | Ile | |
| 175 | | | | 180 | | | | | 185 | | | | | | 190 | |
| ATC | TGC | GGC | GGC | TAC | AAC | ACG | CCG | ACC | CAC | AAT | CCC | GAA | GTT | CCC | CAG | 624 |
| Ile | Cys | Gly | Gly | Tyr | Asn | Thr | Pro | Thr | His | Asn | Pro | Glu | Val | Pro | Gln | |
| | | | | 195 | | | | 200 | | | | | 205 | | | |
| CAC | GAC | CAC | CTG | ACG | TCC | TTC | CAC | CAT | CTC | CTA | TCG | ATG | CAG | GCC | GGG | 672 |
| His | Asp | His | Leu | Thr | Ser | Phe | His | His | Leu | Leu | Ser | Met | Gln | Ala | Gly | |
| | | | 210 | | | | 215 | | | | | 220 | | | | |
| TCT | TAT | CAG | AAC | GGG | GCC | TGG | TCC | GCG | GCC | GCG | GGC | AAG | GCG | GGC | ATG | 720 |
| Ser | Tyr | Gln | Asn | Gly | Ala | Trp | Ser | Ala | Ala | Ala | Gly | Lys | Ala | Gly | Met | |
| | | 225 | | | | 230 | | | | | 235 | | | | | |
| GAG | GAG | AAC | TGC | ATG | CTG | CTC | GGC | CAC | TCC | TGC | ATC | GTG | GCG | CCG | ACC | 768 |
| Glu | Glu | Asn | Cys | Met | Leu | Leu | Gly | His | Ser | Cys | Ile | Val | Ala | Pro | Thr | |
| | 240 | | | | 245 | | | | | 250 | | | | | | |
| GGG | GAA | ATC | GTC | GCT | CTC | ACT | ACG | ACG | CTG | GAA | GAC | GAG | GTG | ATC | ACC | 816 |

```
Gly  Glu  Ile  Val  Ala  Leu  Thr  Thr  Thr  Leu  Glu  Asp  Glu  Val  Ile  Thr
255                 260                      265                      270

GCC  GCC  GTC  GAT  CTC  GAT  CGC  TGC  CGG  GAA  CTG  CGT  GAA  CAC  ATC  TTC      864
Ala  Ala  Val  Asp  Leu  Asp  Arg  Cys  Arg  Glu  Leu  Arg  Glu  His  Ile  Phe
                    275                      280                      285

AAC  TTC  AAG  CAG  CAT  CGT  CAG  CCC  CAG  CAC  TAT  GGT  CTG  ATC  GCG  GAA      912
Asn  Phe  Lys  Gln  His  Arg  Gln  Pro  Gln  His  Tyr  Gly  Leu  Ile  Ala  Glu
               290                      295                      300

CTC  TGAGGTTGCC  GAAAAGCATG  TGTGTCGTTG  TTCTCGGCGC  CTGGGTCACA                      965
Leu

TCCAGGCGCG  CCAGGGTGAC  GCTGGTGGAA  TAGTACCACG  ACCGCTTCAG  GGCGATCCGC              1025

AAGGAGATGC  GGGTCGCCGG  AGCGGCAAAG  CCCGACATTC  GTTTCGCACC  GACGGCCGTC              1085

GTGAACTCGA  CAGTCCGCGA  GAAGGGCGTA  TTGCGCGGCC  TGGACCTGTA  CGTGGAACTG              1145

TAGCCCATAT  ATAGATTTCC  AAAGAGTTTC  GGCGAGGCGC  GGCGCGCCTA  GCCCATGTG               1205

AGCGAGAACC  GTGCCCAGAT  CAAAGAATGA  GACCGACGCG  CCGGCCGCGG  CAAAGGATGA              1265

TCCTCAGGGT  CGGATCTATC  GCTCCGCCCT  GAAGCAGGAG  GGCGCACGCT  GGCTGCTGAC              1325

GGCGGAGGAA  GGGTTGCTGG  CAAAGCCCAA  GCCGCCCGGC  CTTGTTCCGG  CACTTGAGAA              1385

TGCGATCGCC  ATCGTCGATT  ACATCAACGG  TACACCGCCC  CATATCGCGT  CCCTGGCGGA              1445

GCTTTCAACG  ACGCTCGGGA  TATCCAAGAG  CCACTGTCAC  TCCATCCTCA  AGACGCTGAC              1505

GCATTTCGGC  TGGCTGAAAT  TCGACAATCG  CTCAAAGAGC  TACGAGCTGA  ATTC                    1559
```

( 2 ) INFORMATION FOR SEQ ID NO:58:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

```
Thr  Arg  Gln  Met  Ile  Leu  Ala  Val  Gly  Gln  Gln  Gly  Pro  Ile  Ala  Arg
 1               5                        10                       15

Ala  Glu  Thr  Arg  Glu  Gln  Val  Val  Arg  Leu  Leu  Asp  Met  Leu  Thr
              20                       25                       30

Lys  Ala  Ala  Ser  Arg  Gly  Ala  Asn  Phe  Ile  Val  Phe  Pro  Glu  Leu  Ala
               35                      40                       45

Leu  Thr  Thr  Phe  Phe  Pro  Arg  Trp  Tyr  Phe  Thr  Asp  Glu  Ala  Glu  Leu
      50                       55                       60

Asp  Ser  Phe  Tyr  Glu  Thr  Glu  Met  Pro  Gly  Pro  Val  Val  Arg  Pro  Leu
 65                       70                       75                       80

Phe  Glu  Lys  Ala  Ala  Glu  Leu  Gly  Ile  Gly  Phe  Asn  Leu  Gly  Tyr  Ala
                    85                       90                       95

Glu  Leu  Val  Val  Glu  Gly  Gly  Val  Lys  Arg  Arg  Phe  Asn  Thr  Ser  Ile
               100                      105                      110

Leu  Val  Asp  Lys  Ser  Gly  Lys  Ile  Val  Gly  Lys  Tyr  Arg  Lys  Ile  His
               115                      120                      125

Leu  Pro  Gly  His  Lys  Glu  Tyr  Glu  Ala  Tyr  Arg  Pro  Phe  Gln  His  Leu
      130                      135                      140

Glu  Lys  Arg  Tyr  Phe  Glu  Pro  Gly  Asp  Leu  Gly  Phe  Pro  Val  Tyr  Asp
145                      150                      155                      160

Val  Asp  Ala  Ala  Lys  Met  Gly  Met  Phe  Ile  Cys  Asn  Asp  Arg  Arg  Trp
                    165                      170                      175

Pro  Glu  Ala  Trp  Arg  Val  Met  Gly  Leu  Arg  Gly  Ala  Glu  Ile  Ile  Cys
```

-continued

```
                        180                                   185                                    190
Gly Gly Tyr Asn Thr Pro Thr His Asn Pro Glu Val Pro Gln His Asp
        195                     200                 205
His Leu Thr Ser Phe His His Leu Leu Ser Met Gln Ala Gly Ser Tyr
    210                 215                 220
Gln Asn Gly Ala Trp Ser Ala Ala Gly Lys Ala Gly Met Glu Glu
225                 230                 235                     240
Asn Cys Met Leu Leu Gly His Ser Cys Ile Val Ala Pro Thr Gly Glu
                245                 250                 255
Ile Val Ala Leu Thr Thr Thr Leu Glu Asp Glu Val Ile Thr Ala Ala
            260                 265                 270
Val Asp Leu Asp Arg Cys Arg Glu Leu Arg Glu His Ile Phe Asn Phe
        275                 280                 285
Lys Gln His Arg Gln Pro Gln His Tyr Gly Leu Ile Ala Glu Leu
        290                 295                 300
```

( 2 ) INFORMATION FOR SEQ ID NO:59:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD456

( i x ) FEATURE:
        ( A ) NAME/KEY: CDS
        ( B ) LOCATION: 233..1144

( x i ) SEQUENCE DESCRIPTION: SEQ ID NO:59:

```
GTCGACGGCG GGCTCGCGCG AGAGCTTGTC AAGCAGCGCA AATTCCGGTT CCGCTCCGGT        60

TGACAGATCA AAAATTTTAC GCCTGTTATT GTCGTGCTGC ATGTAATATT TCGTACTTTA       120

TGTAGAATTT GCATTGCGCC GCGAGTCACA AGCCGGTTT TCGGCGATGT GTTTCACAAC        180

GTTTTCCCGG CCGCTGGGCC GGACATCACC TAGGAAGGAG CAGAGGTTCA TG ACA          235
                                                         Thr
                                                          1

CGT CAG ATG ATA CTT GCA GTG GGA CAA CAA GGT CCG ATC GCG CGC GCG        283
Arg Gln Met Ile Leu Ala Val Gly Gln Gln Gly Pro Ile Ala Arg Ala
            5                   10                  15

GAG ACA CGC GAA CAG GTC GTC GTT CGT CTT CTC GAC ATG CTG ACG AAA        331
Glu Thr Arg Glu Gln Val Val Val Arg Leu Leu Asp Met Leu Thr Lys
        20                  25                  30

GCC GCG AGC CGG GGC GCG AAT TTC ATT GTC TTC CCC GAA CTC GCG CTT        379
Ala Ala Ser Arg Gly Ala Asn Phe Ile Val Phe Pro Glu Leu Ala Leu
    35                  40                  45

ACG ACC TTC TTC CCG CGC TGG TAT TTC ACC GAC GAG GCC GAG CTC GAT        427
Thr Thr Phe Phe Pro Arg Trp Tyr Phe Thr Asp Glu Ala Glu Leu Asp
50                  55                  60                  65

AGC TTC TAT GAG ACC GAA ATG CCC GGC CCG GTG GTC CGT CCA CTC TTT        475
Ser Phe Tyr Glu Thr Glu Met Pro Gly Pro Val Val Arg Pro Leu Phe
                70                  75                  80

GAG AAG GCC GCG GAA CTC GGG ATC GGC TTC AAT CTG GGC TAC GCT GAA        523
Glu Lys Ala Ala Glu Leu Gly Ile Gly Phe Asn Leu Gly Tyr Ala Glu
            85                  90                  95

CTC GTC GTC GAA GGC GGC GTC AAG CGT CGC TTC AAC ACG TCC ATT TTG        571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG        619
```

| | | | | | | | | | | | | | | | |
|---|---|---|---|---|---|---|---|---|---|---|---|---|---|---|---|
|Val|Asp|Lys|Ser|Gly|Lys|Ile|Val|Gly|Lys|Tyr|Arg|Lys|Ile|His|Leu|
| |115| | | |120| | | | |125| | | | | |

```
CCG GGT CAC AAG GAG TAC GAG GCC TAC CGG CCG TTC CAG CAT CTT GAA    667
Pro Gly His Lys Glu Tyr Glu Ala Tyr Arg Pro Phe Gln His Leu Glu
130             135                 140                 145

AAG CGT TAT TTC GAG CCG GGC GAT CTC GGC TTC CCG GTC TAT GAC GTC    715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT    763
Asp Ala Ala Lys Met Gly Met Phe Ile Cys Asn Asp Arg Arg Trp Pro
            165             170                 175

GAA GCC TGG CGG GTG ATG GGC CTC AGG GGC GCC GAG ATC ATC TGC GGC    811
Glu Ala Trp Arg Val Met Gly Leu Arg Gly Ala Glu Ile Ile Cys Gly
        180             185                 190

GGC TAC AAC ACG CCG ACC CAC AAT CCC CTT GTT CCC CAG CAC GAC CAC    859
Gly Tyr Asn Thr Pro Thr His Asn Pro Leu Val Pro Gln His Asp His
195             200                 205

CTG ACG TCC TTC CAC CAT CTC CTA TCG ATG CAG GCC GGG TCT TAT CAG    907
Leu Thr Ser Phe His His Leu Leu Ser Met Gln Ala Gly Ser Tyr Gln
210             215                 220                 225

AAC GGG GCC TGG TCC GCG GCC GCG GGC AAG TCA GGC ATG GAG GAG AAC    955
Asn Gly Ala Trp Ser Ala Ala Ala Gly Lys Ser Gly Met Glu Glu Asn
                230                 235                 240

TGC ATG CTG CTC GGC CAC TCC TGC ATC GTG GCG CCG ACC GGG GAA ATC   1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC   1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG   1099
Asp Leu Asp Arg Cys Arg Glu Leu Arg Glu His Ile Phe Asn Phe Lys
275             280                 285

CAG CAT CGT CAG CCC CAG CAC TAT GGT CTG ATC GCG GAA CTC TGAGGTTGCC 1151
Gln His Arg Gln Pro Gln His Tyr Gly Leu Ile Ala Glu Leu
290             295                 300

GAAAAGCATG TGTGTCGTTG TTCTCGGCGC CTGGGTCACA TCCAGGCGCG CCAGGGTGAC   1211

GCTGGTGGAA TAGTACCACG ACCGCTTCAG GGCGATCCGC AAGGAGATGC GGGTCGCCGG   1271

AGCGGCAAAG CCCGACATTC GTTTCGCACC GACGGCCGTC GTGAACTCGA CAGTCCGCGA   1331

GAAGGGCGTA TTGCGCGGCC TGGACCTGTA CGTGGAACTG TAGCCCATAT ATAGATTTCC   1391

AAAGAGTTTC GGCGAGGCGC GGCGCGCCTA GCCCCATGTG AGCGAGAACC GTGCCCAGAT   1451

CAAAGAATGA GACCGACGCG CCGGCCGCGG CAAAGGATGA TCCTCAGGGT CGGATCTATC   1511

GCTCCGCCCT GAAGCAGGAG GGCGCACGCT GGCTGCTGAC GGCGGAGGAA GGGTTGCTGG   1571

CAAAGCCCAA GCCGCCCGGC CTTGTTCCGG CACTTGAGAA TGCGATCGCC ATCGTCGATT   1631

ACATCAACGG TACACCGCCC CATATCGCGT CCCTGGCGGA GCTTTCAACG ACGCTCGGGA   1691

TATCCAAGAG CCACTGTCAC TCCATCCTCA AGACGCTGAC GCATTTCGGC TGGCTGAAAT   1751

TCGACAATCG CTCAAAGAGC TACGAGCTGA ATTC                               1785
```

(2) INFORMATION FOR SEQ ID NO:60:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:60:

| | | | | | | | | | | | | | | |
|---|---|---|---|---|---|---|---|---|---|---|---|---|---|---|
| Thr | Arg | Gln | Met | Ile | Leu | Ala | Val | Gly | Gln | Gly | Pro | Ile | Ala | Arg |
| 1 | | | | 5 | | | | | 10 | | | | | 15 |
| Ala | Glu | Thr | Arg | Glu | Gln | Val | Val | Arg | Leu | Leu | Asp | Met | Leu | Thr |
| | | | 20 | | | | 25 | | | | | 30 | | |
| Lys | Ala | Ala | Ser | Arg | Gly | Ala | Asn | Phe | Ile | Val | Phe | Pro | Glu | Leu | Ala |
| | | | 35 | | | | 40 | | | | | 45 | | |
| Leu | Thr | Thr | Phe | Phe | Pro | Arg | Trp | Tyr | Phe | Thr | Asp | Glu | Ala | Glu | Leu |
| | 50 | | | | | 55 | | | | | 60 | | | |
| Asp | Ser | Phe | Tyr | Glu | Thr | Glu | Met | Pro | Gly | Pro | Val | Val | Arg | Pro | Leu |
| 65 | | | | | 70 | | | | | 75 | | | | | 80 |
| Phe | Glu | Lys | Ala | Ala | Glu | Leu | Gly | Ile | Gly | Phe | Asn | Leu | Gly | Tyr | Ala |
| | | | | 85 | | | | | 90 | | | | | 95 | |
| Glu | Leu | Val | Val | Glu | Gly | Gly | Val | Lys | Arg | Arg | Phe | Asn | Thr | Ser | Ile |
| | | | 100 | | | | | 105 | | | | | 110 | | |
| Leu | Val | Asp | Lys | Ser | Gly | Lys | Ile | Val | Gly | Lys | Tyr | Arg | Lys | Ile | His |
| | | 115 | | | | | 120 | | | | | 125 | | | |
| Leu | Pro | Gly | His | Lys | Glu | Tyr | Glu | Ala | Tyr | Arg | Pro | Phe | Gln | His | Leu |
| | 130 | | | | | 135 | | | | | 140 | | | | |
| Glu | Lys | Arg | Tyr | Phe | Glu | Pro | Gly | Asp | Leu | Gly | Phe | Pro | Val | Tyr | Asp |
| 145 | | | | | 150 | | | | | 155 | | | | | 160 |
| Val | Asp | Ala | Ala | Lys | Met | Gly | Met | Phe | Ile | Cys | Asn | Asp | Arg | Arg | Trp |
| | | | | 165 | | | | | 170 | | | | | 175 | |
| Pro | Glu | Ala | Trp | Arg | Val | Met | Gly | Leu | Arg | Gly | Ala | Glu | Ile | Ile | Cys |
| | | | | 180 | | | | | 185 | | | | | 190 | |
| Gly | Gly | Tyr | Asn | Thr | Pro | Thr | His | Asn | Pro | Leu | Val | Pro | Gln | His | Asp |
| | | | 195 | | | | | 200 | | | | | 205 | | |
| His | Leu | Thr | Ser | Phe | His | His | Leu | Leu | Ser | Met | Gln | Ala | Gly | Ser | Tyr |
| | 210 | | | | | 215 | | | | | 220 | | | | |
| Gln | Asn | Gly | Ala | Trp | Ser | Ala | Ala | Ala | Gly | Lys | Ser | Gly | Met | Glu | Glu |
| 225 | | | | | 230 | | | | | 235 | | | | | 240 |
| Asn | Cys | Met | Leu | Leu | Gly | His | Ser | Cys | Ile | Val | Ala | Pro | Thr | Gly | Glu |
| | | | | 245 | | | | | 250 | | | | | 255 | |
| Ile | Val | Ala | Leu | Thr | Thr | Thr | Leu | Glu | Asp | Glu | Val | Ile | Thr | Ala | Ala |
| | | | | 260 | | | | | 265 | | | | | 270 | |
| Val | Asp | Leu | Asp | Arg | Cys | Arg | Glu | Leu | Arg | Glu | His | Ile | Phe | Asn | Phe |
| | | | 275 | | | | 280 | | | | | 285 | | | |
| Lys | Gln | His | Arg | Gln | Pro | Gln | His | Tyr | Gly | Leu | Ile | Ala | Glu | Leu | |
| | 290 | | | | | 295 | | | | | 300 | | | | |

( 2 ) INFORMATION FOR SEQ ID NO:61:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD468

( i x ) FEATURE:
        ( A ) NAME/KEY: CDS
        ( B ) LOCATION: 233..1144

( x i ) SEQUENCE DESCRIPTION: SEQ ID NO:61:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120
```

-continued

```
TGTAGAATTT GCATTGCGCC GCGAGTCACA AAGCCGGTTT TCGGCGATGT GTTTCACAAC         180

GTTTTCCCGG CCGCTGGGCC GGACATCACC TAGGAAGGAG CAGAGGTTCA TG ACA            235
                                                          Thr
                                                          1

CGT CAG ATG ATA CTT GCA GTG GGA CAA CAA GGT CCG ATC GCG CGC GCG         283
Arg Gln Met Ile Leu Ala Val Gly Gln Gln Gly Pro Ile Ala Arg Ala
             5                  10                  15

GAG ACA CGC GAA CAG GTC GTC GTT CGT CTT CTC GAC ATG CTG ACG AAA         331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT         379
Ala Ala Ser Arg Gly Ala Asn Phe Ile Val Phe Pro Glu Leu Ala Leu
     35                  40                  45

ACG ACC TTC TTC CCG CGC TGG CAT TTC ACC GAC GAG GCC GAG CTC GAT         427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT         475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA         523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG         571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG         619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA         667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC         715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT         763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC         811
Glu Ala Trp Arg Val Met Gly Leu Arg Gly Ala Glu Ile Ile Cys Gly
        180                 185                 190

GGC TAC AAC ACG CCG ACC CAC AAT CCC GCT GTT CCC CAG CAC GAC CAC         859
Gly Tyr Asn Thr Pro Thr His Asn Pro Ala Val Pro Gln His Asp His
    195                 200                 205

CTG ACG TCC TTC CAC CAT CTC CTA TCG ATG CAG GCC GGG TCT TAT CAG         907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC         955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC         1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC         1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG         1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC TGAGGTTGCC     1151
Gln His Arg Gln Pro Gln His Tyr Gly Leu Ile Ala Glu Leu
```

-continued

```
        290                      295                      300
GAAAAGCATG  TGTGTCGTTG  TTCTCGGCGC  CTGGGTCACA  TCCAGGCGCG  CCAGGGTGAC   1211

GCTGGTGGAA  TAGTACCACG  ACCGCTTCAG  GGCGATCCGC  AAGGAGATGC  GGGTCGCCGG   1271

AGCGGCAAAG  CCCGACATTC  GTTTCGCACC  GACGGCCGTC  GTGAACTCGA  CAGTCCGCGA   1331

GAAGGGCGTA  TTGCGCGGCC  TGGACCTGTA  CGTGGAACTG  TAGCCCATAT  ATAGATTTCC   1391

AAAGAGTTTC  GGCGAGGCGC  GGCGCGCCTA  GCCCCATGTG  AGCGAGAACC  GTGCCCAGAT   1451

CAAAGAATGA  GACCGACGCG  CCGGCCGCGG  CAAAGGATGA  TCCTCAGGGT  CGGATCTATC   1511

GCTCCGCCCT  GAAGCAGGAG  GGCGCACGCT  GGCTGCTGAC  GGCGGAGGAA  GGGTTGCTGG   1571

CAAAGCCCAA  GCCGCCCGGC  CTTGTTCCGG  CACTTGAGAA  TGCGATCGCC  ATCGTCGATT   1631

ACATCAACGG  TACACCGCCC  CATATCGCGT  CCCTGGCGGA  GCTTTCAACG  ACGCTCGGGA   1691

TATCCAAGAG  CCACTGTCAC  TCCATCCTCA  AGACGCTGAC  GCATTTCGGC  TGGCTGAAAT   1751

TCGACAATCG  CTCAAAGAGC  TACGAGCTGA  ATTC                                1785
```

( 2 ) INFORMATION FOR SEQ ID NO:62:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

```
Thr  Arg  Gln  Met  Ile  Leu  Ala  Val  Gly  Gln  Gln  Gly  Pro  Ile  Ala  Arg
 1                   5                        10                       15

Ala  Glu  Thr  Arg  Glu  Gln  Val  Val  Arg  Leu  Leu  Asp  Met  Leu  Thr
               20                       25                       30

Lys  Ala  Ala  Ser  Arg  Gly  Ala  Asn  Phe  Ile  Val  Phe  Pro  Glu  Leu  Ala
               35                       40                       45

Leu  Thr  Thr  Phe  Phe  Pro  Arg  Trp  His  Phe  Thr  Asp  Glu  Ala  Glu  Leu
          50                       55                       60

Asp  Ser  Phe  Tyr  Glu  Thr  Glu  Met  Pro  Gly  Pro  Val  Val  Arg  Pro  Leu
 65                       70                       75                       80

Phe  Glu  Lys  Ala  Ala  Glu  Leu  Gly  Ile  Gly  Phe  Asn  Leu  Gly  Tyr  Ala
                    85                       90                       95

Glu  Leu  Val  Val  Glu  Gly  Gly  Val  Lys  Arg  Arg  Phe  Asn  Thr  Ser  Ile
                   100                      105                      110

Leu  Val  Asp  Lys  Ser  Gly  Lys  Ile  Val  Gly  Lys  Tyr  Arg  Lys  Ile  His
              115                      120                      125

Leu  Pro  Gly  His  Lys  Glu  Tyr  Glu  Ala  Tyr  Arg  Pro  Phe  Gln  His  Leu
         130                      135                      140

Glu  Lys  Arg  Tyr  Phe  Glu  Pro  Gly  Asp  Leu  Gly  Phe  Pro  Val  Tyr  Asp
145                      150                      155                      160

Val  Asp  Ala  Ala  Lys  Met  Gly  Met  Phe  Ile  Cys  Asn  Asp  Arg  Arg  Trp
                    165                      170                      175

Pro  Glu  Ala  Trp  Arg  Val  Met  Gly  Leu  Arg  Gly  Ala  Glu  Ile  Ile  Cys
                    180                      185                      190

Gly  Gly  Tyr  Asn  Thr  Pro  Thr  His  Asn  Pro  Ala  Val  Pro  Gln  His  Asp
              195                      200                      205

His  Leu  Thr  Ser  Phe  His  His  Leu  Leu  Ser  Met  Gln  Ala  Gly  Ser  Tyr
         210                      215                      220

Gln  Asn  Gly  Ala  Trp  Ser  Ala  Ala  Ala  Gly  Lys  Val  Gly  Met  Glu  Glu
225                      230                      235                      240
```

| | | | | | | | | | | | | | | |
|---|---|---|---|---|---|---|---|---|---|---|---|---|---|---|
|Asn|Cys|Met|Leu|Leu|Gly|His|Ser|Cys|Ile|Val|Ala|Pro|Thr|Gly|Glu|
| | | |245| | | | |250| | | | |255| |
|Ile|Val|Ala|Leu|Thr|Thr|Thr|Leu|Glu|Asp|Glu|Val|Ile|Thr|Ala|Ala|
| | | |260| | | |265| | | | |270| | |
|Val|Asp|Leu|Asp|Arg|Cys|Arg|Glu|Leu|Arg|Glu|His|Ile|Phe|Asn|Phe|
| | |275| | | |280| | | | |285| | | |
|Lys|Gln|His|Arg|Gln|Pro|Gln|His|Tyr|Gly|Leu|Ile|Ala|Glu|Leu| |
| | |290| | | |295| | | | |300| | | |

( 2 ) INFORMATION FOR SEQ ID NO:63:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: JM109 pAD469

( i x ) FEATURE:
        ( A ) NAME/KEY: CDS
        ( B ) LOCATION: 233..1144

( x i ) SEQUENCE DESCRIPTION: SEQ ID NO:63:

```
GTCGACGGCG  GGCTCGCGCG  AGAGCTTGTC  AAGCAGCGCA  AATTCCGGTT  CCGCTCCGGT      60

TGACAGATCA  AAAATTTTAC  GCCTGTTATT  GTCGTGCTGC  ATGTAATATT  TCGTACTTTA     120

TGTAGAATTT  GCATTGCGCC  GCGAGTCACA  AAGCCGGTTT  TCGGCGATGT  GTTTCACAAC     180

GTTTTCCCGG  CCGCTGGGCC  GGACATCACC  TAGGAAGGAG  CAGAGGTTCA  TG  ACA        235
                                                               Thr
                                                                 1
```

| | | | | | | | | | | | | | | | |
|---|---|---|---|---|---|---|---|---|---|---|---|---|---|---|---|
|CGT|CAG|ATG|ATA|CTT|GCA|GTG|GGA|CAA|CAA|GGT|CCG|ATC|GCG|CGC|GCG|283|
|Arg|Gln|Met|Ile|Leu|Ala|Val|Gly|Gln|Gln|Gly|Pro|Ile|Ala|Arg|Ala| |
| | | | |5| | | | |10| | | | |15| | |

| | | | | | | | | | | | | | | | |
|---|---|---|---|---|---|---|---|---|---|---|---|---|---|---|---|
|GAG|ACA|CGC|GAA|CAG|GTC|GTC|GTT|CGT|CTT|CTC|GAC|ATG|CTG|ACG|AAA|331|
|Glu|Thr|Arg|Glu|Gln|Val|Val|Val|Arg|Leu|Leu|Asp|Met|Leu|Thr|Lys| |
| | |20| | | | |25| | | | |30| | | |

| | | | | | | | | | | | | | | | |
|---|---|---|---|---|---|---|---|---|---|---|---|---|---|---|---|
|GCC|GCG|AGC|CGG|GGC|GCG|AAT|TTC|ATT|GTC|TTC|CCC|GAA|CTC|GCG|CTT|379|
|Ala|Ala|Ser|Arg|Gly|Ala|Asn|Phe|Ile|Val|Phe|Pro|Glu|Leu|Ala|Leu| |
| |35| | | | |40| | | | |45| | | | |

| | | | | | | | | | | | | | | | |
|---|---|---|---|---|---|---|---|---|---|---|---|---|---|---|---|
|ACG|ACC|TTC|TTC|CCG|CGC|TGG|CAT|TTC|ACC|GAC|GAG|GCC|GAG|CTC|GAT|427|
|Thr|Thr|Phe|Phe|Pro|Arg|Trp|His|Phe|Thr|Asp|Glu|Ala|Glu|Leu|Asp|
|50| | | | |55| | | | |60| | | | |65| |

| | | | | | | | | | | | | | | | |
|---|---|---|---|---|---|---|---|---|---|---|---|---|---|---|---|
|AGC|TTC|TAT|GAG|ACC|GAA|ATG|CCC|GGC|CCG|GTG|GTC|CGT|CCA|CTC|TTT|475|
|Ser|Phe|Tyr|Glu|Thr|Glu|Met|Pro|Gly|Pro|Val|Val|Arg|Pro|Leu|Phe|
| | | |70| | | | |75| | | | |80| | |

| | | | | | | | | | | | | | | | |
|---|---|---|---|---|---|---|---|---|---|---|---|---|---|---|---|
|GAG|AAG|GCC|GCG|GAA|CTC|GGG|ATC|GGC|TTC|AAT|CTG|GGC|TAC|GCT|GAA|523|
|Glu|Lys|Ala|Ala|Glu|Leu|Gly|Ile|Gly|Phe|Asn|Leu|Gly|Tyr|Ala|Glu|
| | | |85| | | | |90| | | | |95| | |

| | | | | | | | | | | | | | | | |
|---|---|---|---|---|---|---|---|---|---|---|---|---|---|---|---|
|CTC|GTC|GTC|GAA|GGC|GGC|GTC|AAG|CGT|CGC|TTC|AAC|ACG|TCC|ATT|TTG|571|
|Leu|Val|Val|Glu|Gly|Gly|Val|Lys|Arg|Arg|Phe|Asn|Thr|Ser|Ile|Leu|
| | |100| | | | |105| | | | |110| | | |

| | | | | | | | | | | | | | | | |
|---|---|---|---|---|---|---|---|---|---|---|---|---|---|---|---|
|GTG|GAT|AAG|TCA|GGC|AAG|ATC|GTC|GGC|AAG|TAT|CGT|AAG|ATC|CAT|TTG|619|
|Val|Asp|Lys|Ser|Gly|Lys|Ile|Val|Gly|Lys|Tyr|Arg|Lys|Ile|His|Leu|
| |115| | | | |120| | | | |125| | | | |

| | | | | | | | | | | | | | | | |
|---|---|---|---|---|---|---|---|---|---|---|---|---|---|---|---|
|CCG|GGT|CAC|AAG|GAG|TAC|GAG|GCC|TAC|CGG|CCG|TTC|CAG|CAT|CTT|GAA|667|
|Pro|Gly|His|Lys|Glu|Tyr|Glu|Ala|Tyr|Arg|Pro|Phe|Gln|His|Leu|Glu|
|130| | | | |135| | | | |140| | | | |145|

| | | | | | | | | | | | | | | | |
|---|---|---|---|---|---|---|---|---|---|---|---|---|---|---|---|
|AAG|CGT|TAT|TTC|GAG|CCG|GGC|GAT|CTC|GGC|TTC|CCG|GTC|TAT|GAC|GTC|715|
|Lys|Arg|Tyr|Phe|Glu|Pro|Gly|Asp|Leu|Gly|Phe|Pro|Val|Tyr|Asp|Val|
| | |150| | | | |155| | | | |160| | | |

```
GAC  GCC  GCG  AAA  ATG  GGG  ATG  TTC  ATC  TGC  AAC  GAT  CGC  CGC  TGG  CCT      763
Asp  Ala  Ala  Lys  Met  Gly  Met  Phe  Ile  Cys  Asn  Asp  Arg  Arg  Trp  Pro
               165                      170                      175

GAA  GCC  TGG  CGG  GTG  ATG  GGC  CTC  AGG  GGC  GCC  GAG  ATC  ATC  TGC  GGC      811
Glu  Ala  Trp  Arg  Val  Met  Gly  Leu  Arg  Gly  Ala  Glu  Ile  Ile  Cys  Gly
               180                      185                      190

GGC  TAC  AAC  ACG  CCG  ACC  CAC  AAT  CCC  ATT  GTT  CCC  CAG  CAC  GAC  CAC      859
Gly  Tyr  Asn  Thr  Pro  Thr  His  Asn  Pro  Ile  Val  Pro  Gln  His  Asp  His
     195                      200                      205

CTG  ACG  TCC  TTC  CAC  CAT  CTC  CTA  TCG  ATG  CAG  GCC  GGG  TCT  TAT  CAG      907
Leu  Thr  Ser  Phe  His  His  Leu  Leu  Ser  Met  Gln  Ala  Gly  Ser  Tyr  Gln
210                 215                      220                           225

AAC  GGG  GCC  TGG  TCC  GCG  GCC  GCG  GGC  AAG  GTG  GGC  ATG  GAG  GAG  AAC      955
Asn  Gly  Ala  Trp  Ser  Ala  Ala  Ala  Gly  Lys  Val  Gly  Met  Glu  Glu  Asn
               230                      235                           240

TGC  ATG  CTG  CTC  GGC  CAC  TCC  TGC  ATC  GTG  GCG  CCG  ACC  GGG  GAA  ATC     1003
Cys  Met  Leu  Leu  Gly  His  Ser  Cys  Ile  Val  Ala  Pro  Thr  Gly  Glu  Ile
               245                      250                      255

GTC  GCT  CTC  ACT  ACG  ACG  CTG  GAA  GAC  GAG  GTG  ATC  ACC  GCC  GCC  GTC     1051
Val  Ala  Leu  Thr  Thr  Thr  Leu  Glu  Asp  Glu  Val  Ile  Thr  Ala  Ala  Val
               260                      265                      270

GAT  CTC  GAT  CGC  TGC  CGG  GAA  CTG  CGT  GAA  CAC  ATC  TTC  AAC  TTC  AAG     1099
Asp  Leu  Asp  Arg  Cys  Arg  Glu  Leu  Arg  Glu  His  Ile  Phe  Asn  Phe  Lys
     275                      280                      285

CAG  CAT  CGT  CAG  CCC  CAG  CAC  TAT  GGT  CTG  ATC  GCG  GAA  CTC  TGAGGTTGCC  1151
Gln  His  Arg  Gln  Pro  Gln  His  Tyr  Gly  Leu  Ile  Ala  Glu  Leu
290                 295                      300

GAAAAGCATG  TGTGTCGTTG  TTCTCGGCGC  CTGGGTCACA  TCCAGGCGCG  CCAGGGTGAC            1211

GCTGGTGGAA  TAGTACCACG  ACCGCTTCAG  GGCGATCCGC  AAGGAGATGC  GGGTCGCCGG            1271

AGCGGCAAAG  CCCGACATTC  GTTTCGCACC  GACGGCCGTC  GTGAACTCGA  CAGTCCGCGA            1331

GAAGGGCGTA  TTGCGCGGCC  TGGACCTGTA  CGTGGAACTG  TAGCCCATAT  ATAGATTTCC            1391

AAAGAGTTTC  GGCGAGGCGC  GGCGCGCCTA  GCCCCATGTG  AGCGAGAACC  GTGCCCAGAT            1451

CAAAGAATGA  GACCGACGCG  CCGGCCGCGG  CAAAGGATGA  TCCTCAGGGT  CGGATCTATC            1511

GCTCCGCCCT  GAAGCAGGAG  GGCGCACGCT  GGCTGCTGAC  GGCGGAGGAA  GGGTTGCTGG            1571

CAAAGCCCAA  GCCGCCGGCC  CTTGTTCCGG  CACTTGAGAA  TGCGATCGCC  ATCGTCGATT            1631

ACATCAACGG  TACACCGCCC  CATATCGCGT  CCCTGGCGGA  GCTTTCAACG  ACGCTCGGGA            1691

TATCCAAGAG  CCACTGTCAC  TCCATCCTCA  AGACGCTGAC  GCATTTCGGC  TGGCTGAAAT            1751

TCGACAATCG  CTCAAAGAGC  TACGAGCTGA  ATTC                                         1785
```

( 2 ) INFORMATION FOR SEQ ID NO:64:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:64:

```
Thr  Arg  Gln  Met  Ile  Leu  Ala  Val  Gly  Gln  Gln  Gly  Pro  Ile  Ala  Arg
 1                 5                      10                          15

Ala  Glu  Thr  Arg  Glu  Gln  Val  Val  Arg  Leu  Leu  Asp  Met  Leu  Thr
               20                      25                      30

Lys  Ala  Ala  Ser  Arg  Gly  Ala  Asn  Phe  Ile  Val  Phe  Pro  Glu  Leu  Ala
               35                      40                      45
```

| | | | | | | | | | | | | | | |
|---|---|---|---|---|---|---|---|---|---|---|---|---|---|---|
| Leu | Thr | Thr | Phe | Phe | Pro | Arg | Trp | His | Phe | Thr | Asp | Glu | Ala | Glu | Leu |
| | 50 | | | | 55 | | | | | 60 | | | | |
| Asp | Ser | Phe | Tyr | Glu | Thr | Glu | Met | Pro | Gly | Pro | Val | Val | Arg | Pro | Leu |
| 65 | | | | | 70 | | | | 75 | | | | | | 80 |
| Phe | Glu | Lys | Ala | Ala | Glu | Leu | Gly | Ile | Gly | Phe | Asn | Leu | Gly | Tyr | Ala |
| | | | | 85 | | | | | 90 | | | | | 95 | |
| Glu | Leu | Val | Val | Glu | Gly | Gly | Val | Lys | Arg | Arg | Phe | Asn | Thr | Ser | Ile |
| | | | 100 | | | | | 105 | | | | | 110 | | |
| Leu | Val | Asp | Lys | Ser | Gly | Lys | Ile | Val | Gly | Lys | Tyr | Arg | Lys | Ile | His |
| | | 115 | | | | | 120 | | | | | 125 | | | |
| Leu | Pro | Gly | His | Lys | Glu | Tyr | Glu | Ala | Tyr | Arg | Pro | Phe | Gln | His | Leu |
| | 130 | | | | | 135 | | | | | 140 | | | | |
| Glu | Lys | Arg | Tyr | Phe | Glu | Pro | Gly | Asp | Leu | Gly | Phe | Pro | Val | Tyr | Asp |
| 145 | | | | | 150 | | | | | 155 | | | | | 160 |
| Val | Asp | Ala | Ala | Lys | Met | Gly | Met | Phe | Ile | Cys | Asn | Asp | Arg | Arg | Trp |
| | | | | 165 | | | | | 170 | | | | | 175 | |
| Pro | Glu | Ala | Trp | Arg | Val | Met | Gly | Leu | Arg | Gly | Ala | Glu | Ile | Ile | Cys |
| | | | 180 | | | | | 185 | | | | | 190 | | |
| Gly | Gly | Tyr | Asn | Thr | Pro | Thr | His | Asn | Pro | Ile | Val | Pro | Gln | His | Asp |
| | | | 195 | | | | 200 | | | | | 205 | | | |
| His | Leu | Thr | Ser | Phe | His | His | Leu | Leu | Ser | Met | Gln | Ala | Gly | Ser | Tyr |
| | 210 | | | | | 215 | | | | | 220 | | | | |
| Gln | Asn | Gly | Ala | Trp | Ser | Ala | Ala | Ala | Gly | Lys | Val | Gly | Met | Glu | Glu |
| 225 | | | | | 230 | | | | | 235 | | | | | 240 |
| Asn | Cys | Met | Leu | Leu | Gly | His | Ser | Cys | Ile | Val | Ala | Pro | Thr | Gly | Glu |
| | | | | 245 | | | | | 250 | | | | | 255 | |
| Ile | Val | Ala | Leu | Thr | Thr | Thr | Leu | Glu | Asp | Glu | Val | Ile | Thr | Ala | Ala |
| | | | 260 | | | | | 265 | | | | | 270 | | |
| Val | Asp | Leu | Asp | Arg | Cys | Arg | Glu | Leu | Arg | Glu | His | Ile | Phe | Asn | Phe |
| | | 275 | | | | | 280 | | | | | 285 | | | |
| Lys | Gln | His | Arg | Gln | Pro | Gln | His | Tyr | Gly | Leu | Ile | Ala | Glu | Leu | |
| | 290 | | | | | 295 | | | | 300 | | | | | |

(2) INFORMATION FOR SEQ ID NO:65:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (vi) ORIGINAL SOURCE:
        (B) STRAIN: JM109 pAD470

(ix) FEATURE:
        (A) NAME/KEY: CDS
        (B) LOCATION: 233..1144

(xi) SEQUENCE DESCRIPTION: SEQ ID NO:65:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                         Thr
                                                          1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
         5                   10                  15
```

| | | | | | | | | | | | | | | | | |
|---|---|---|---|---|---|---|---|---|---|---|---|---|---|---|---|---|
| GAG | ACA | CGC | GAA | CAG | GTC | GTC | GTT | CGT | CTT | CTC | GAC | ATG | CTG | ACG | AAA | 331 |
| Glu | Thr | Arg | Glu | Gln | Val | Val | Val | Arg | Leu | Leu | Asp | Met | Leu | Thr | Lys | |
| | | 20 | | | | 25 | | | | | 30 | | | | | |
| GCC | GCG | AGC | CGG | GGC | GCG | AAT | TTC | ATT | GTC | TTC | CCC | GAA | CTC | GCG | CTT | 379 |
| Ala | Ala | Ser | Arg | Gly | Ala | Asn | Phe | Ile | Val | Phe | Pro | Glu | Leu | Ala | Leu | |
| | | 35 | | | | 40 | | | | 45 | | | | | | |
| ACG | ACC | TTC | TTC | CCG | CGC | TGG | CAT | TTC | ACC | GAC | GAG | GCC | GAG | CTC | GAT | 427 |
| Thr | Thr | Phe | Phe | Pro | Arg | Trp | His | Phe | Thr | Asp | Glu | Ala | Glu | Leu | Asp | |
| 50 | | | | | 55 | | | | | 60 | | | | | 65 | |
| AGC | TTC | TAT | GAG | ACC | GAA | ATG | CCC | GGC | CCG | GTG | GTC | CGT | CCA | CTC | TTT | 475 |
| Ser | Phe | Tyr | Glu | Thr | Glu | Met | Pro | Gly | Pro | Val | Val | Arg | Pro | Leu | Phe | |
| | | | | 70 | | | | | 75 | | | | | 80 | | |
| GAG | AAG | GCC | GCG | GAA | CTC | GGG | ATC | GGC | TTC | AAT | CTG | GGC | TAC | GCT | GAA | 523 |
| Glu | Lys | Ala | Ala | Glu | Leu | Gly | Ile | Gly | Phe | Asn | Leu | Gly | Tyr | Ala | Glu | |
| | | | 85 | | | | | 90 | | | | | 95 | | | |
| CTC | GTC | GTC | GAA | GGC | GGC | GTC | AAG | CGT | CGC | TTC | AAC | ACG | TCC | ATT | TTG | 571 |
| Leu | Val | Val | Glu | Gly | Gly | Val | Lys | Arg | Arg | Phe | Asn | Thr | Ser | Ile | Leu | |
| | | 100 | | | | | 105 | | | | | 110 | | | | |
| GTG | GAT | AAG | TCA | GGC | AAG | ATC | GTC | GGC | AAG | TAT | CGT | AAG | ATC | CAT | TTG | 619 |
| Val | Asp | Lys | Ser | Gly | Lys | Ile | Val | Gly | Lys | Tyr | Arg | Lys | Ile | His | Leu | |
| | 115 | | | | 120 | | | | | 125 | | | | | | |
| CCG | GGT | CAC | AAG | GAG | TAC | GAG | GCC | TAC | CGG | CCG | TTC | CAG | CAT | CTT | GAA | 667 |
| Pro | Gly | His | Lys | Glu | Tyr | Glu | Ala | Tyr | Arg | Pro | Phe | Gln | His | Leu | Glu | |
| 130 | | | | 135 | | | | | 140 | | | | | 145 | | |
| AAG | CGT | TAT | TTC | GAG | CCG | GGC | GAT | CTC | GGC | TTC | CCG | GTC | TAT | GAC | GTC | 715 |
| Lys | Arg | Tyr | Phe | Glu | Pro | Gly | Asp | Leu | Gly | Phe | Pro | Val | Tyr | Asp | Val | |
| | | | | 150 | | | | | 155 | | | | | 160 | | |
| GAC | GCC | GCG | AAA | ATG | GGG | ATG | TTC | ATC | TGC | AAC | GAT | CGC | CGC | TGG | CCT | 763 |
| Asp | Ala | Ala | Lys | Met | Gly | Met | Phe | Ile | Cys | Asn | Asp | Arg | Arg | Trp | Pro | |
| | | | 165 | | | | 170 | | | | | 175 | | | | |
| GAA | GCC | TGG | CGG | GTG | ATG | GGC | CTC | AGG | GGC | GCC | GAG | ATC | ATC | TGC | GGC | 811 |
| Glu | Ala | Trp | Arg | Val | Met | Gly | Leu | Arg | Gly | Ala | Glu | Ile | Ile | Cys | Gly | |
| | | 180 | | | | | 185 | | | | | 190 | | | | |
| GGC | TAC | AAC | ACG | CCG | ACC | CAC | AAT | CCC | CAT | GTT | CCC | CAG | CAC | GAC | CAC | 859 |
| Gly | Tyr | Asn | Thr | Pro | Thr | His | Asn | Pro | His | Val | Pro | Gln | His | Asp | His | |
| | 195 | | | | 200 | | | | | 205 | | | | | | |
| CTG | ACG | TCC | TTC | CAC | CAT | CTC | CTA | TCG | ATG | CAG | GCC | GGG | TCT | TAT | CAG | 907 |
| Leu | Thr | Ser | Phe | His | His | Leu | Leu | Ser | Met | Gln | Ala | Gly | Ser | Tyr | Gln | |
| 210 | | | | | 215 | | | | | 220 | | | | | 225 | |
| AAC | GGG | GCC | TGG | TCC | GCG | GCC | GCG | GGC | AAG | GTG | GGC | ATG | GAG | GAG | AAC | 955 |
| Asn | Gly | Ala | Trp | Ser | Ala | Ala | Ala | Gly | Lys | Val | Gly | Met | Glu | Glu | Asn | |
| | | | | 230 | | | | | 235 | | | | | 240 | | |
| TGC | ATG | CTG | CTC | GGC | CAC | TCC | TGC | ATC | GTG | GCG | CCG | ACC | GGG | GAA | ATC | 1003 |
| Cys | Met | Leu | Leu | Gly | His | Ser | Cys | Ile | Val | Ala | Pro | Thr | Gly | Glu | Ile | |
| | | | 245 | | | | 250 | | | | | 255 | | | | |
| GTC | GCT | CTC | ACT | ACG | ACG | CTG | GAA | GAC | GAG | GTG | ATC | ACC | GCC | GCC | GTC | 1051 |
| Val | Ala | Leu | Thr | Thr | Thr | Leu | Glu | Asp | Glu | Val | Ile | Thr | Ala | Ala | Val | |
| | | 260 | | | | 265 | | | | | 270 | | | | | |
| GAT | CTC | GAT | CGC | TGC | CGG | GAA | CTG | CGT | GAA | CAC | ATC | TTC | AAC | TTC | AAG | 1099 |
| Asp | Leu | Asp | Arg | Cys | Arg | Glu | Leu | Arg | Glu | His | Ile | Phe | Asn | Phe | Lys | |
| | 275 | | | | 280 | | | | | 285 | | | | | | |
| CAG | CAT | CGT | CAG | CCC | CAG | CAC | TAT | GGT | CTG | ATC | GCG | GAA | CTC | TGAGGTTGCC | | 1151 |
| Gln | His | Arg | Gln | Pro | Gln | His | Tyr | Gly | Leu | Ile | Ala | Glu | Leu | | | |
| 290 | | | | | 295 | | | | | 300 | | | | | | |

GAAAAGCATG TGTGTCGTTG TTCTCGGCGC CTGGGTCACA TCCAGGCGCG CCAGGGTGAC 1211

GCTGGTGGAA TAGTACCACG ACCGCTTCAG GGCGATCCGC AAGGAGATGC GGGTCGCCGG 1271

AGCGGCAAAG CCCGACATTC GTTTCGCACC GACGGCCGTC GTGAACTCGA CAGTCCGCGA 1331

GAAGGGCGTA TTGCGCGGCC TGGACCTGTA CGTGGAACTG TAGCCCATAT ATAGATTTCC 1391

-continued

```
AAAGAGTTTC GGCGAGGCGC GGCGCGCCTA GCCCCATGTG AGCGAGAACC GTGCCCAGAT    1451

CAAAGAATGA GACCGACGCG CCGGCCGCGG CAAAGGATGA TCCTCAGGGT CGGATCTATC    1511

GCTCCGCCCT GAAGCAGGAG GGCGCACGCT GGCTGCTGAC GGCGGAGGAA GGGTTGCTGG    1571

CAAAGCCCAA GCCGCCCGGC CTTGTTCCGG CACTTGAGAA TGCGATCGCC ATCGTCGATT    1631

ACATCAACGG TACACCGCCC CATATCGCGT CCCTGGCGGA GCTTTCAACG ACGCTCGGGA    1691

TATCCAAGAG CCACTGTCAC TCCATCCTCA AGACGCTGAC GCATTTCGGC TGGCTGAAAT    1751

TCGACAATCG CTCAAAGAGC TACGAGCTGA ATTC                                1785
```

( 2 ) INFORMATION FOR SEQ ID NO:66:

( i ) SEQUENCE CHARACTERISTICS:
    ( A ) LENGTH: 303 amino acids
    ( B ) TYPE: amino acid
    ( D ) TOPOLOGY: linear ( i i ) MOLECULE TYPE: protein ( x i ) SEQUENCE DESCRIPTION: SEQ ID NO:66:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
            35                  40                  45

Leu Thr Thr Phe Phe Pro Arg Trp His Phe Thr Asp Glu Ala Glu Leu
        50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro His Val Pro Gln His Asp
            195                 200                 205

His Leu Thr Ser Phe His His Leu Leu Ser Met Gln Ala Gly Ser Tyr
        210                 215                 220

Gln Asn Gly Ala Trp Ser Ala Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285
```

```
Lys  Gln  His  Arg  Gln  Pro  Gln  His  Tyr  Gly  Leu  Ile  Ala  Glu  Leu
     290                 295                      300
```

( 2 ) INFORMATION FOR SEQ ID NO:67:

( i ) SEQUENCE CHARACTERISTICS:
        ( A ) LENGTH: 926 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: HB101 pNT4553 (FERM BP- 4368)

( i x ) FEATURE:
        ( A ) NAME/KEY: CDS
        ( B ) LOCATION: 7..918

( x i ) SEQUENCE DESCRIPTION: SEQ ID NO:67:

```
CATATG  ACA  CGT  CAG  ATG  ATA  CTT  GCA  GTG  GGA  CAA  CAA  GGT  CCG  ATC     48
        Thr  Arg  Gln  Met  Ile  Leu  Ala  Val  Gly  Gln  Gln  Gly  Pro  Ile
         1                  5                       10

GCG  CGC  GCG  GAG  ACA  CGC  GAA  CAG  GTC  GTC  GTT  CGT  CTT  CTC  GAC  ATG    96
Ala  Arg  Ala  Glu  Thr  Arg  Glu  Gln  Val  Val  Val  Arg  Leu  Leu  Asp  Met
 15                 20                      25                           30

CTG  ACG  AAA  GCC  GCG  AGC  CGG  GGC  GCG  AAT  TTC  ATT  GTC  TTC  CCC  GAA   144
Leu  Thr  Lys  Ala  Ala  Ser  Arg  Gly  Ala  Asn  Phe  Ile  Val  Phe  Pro  Glu
                     35                      40                      45

CTC  GCG  CTT  ACG  ACC  TTC  TTC  CCG  CGC  TGG  TAT  TTC  ACC  GAC  GAG  GCC   192
Leu  Ala  Leu  Thr  Thr  Phe  Phe  Pro  Arg  Trp  Tyr  Phe  Thr  Asp  Glu  Ala
                50                       55                           60

GAG  CTC  GAT  AGC  TTC  TAT  GAG  ACC  GAA  ATG  CCC  GGC  CCG  GTG  GTC  CGT   240
Glu  Leu  Asp  Ser  Phe  Tyr  Glu  Thr  Glu  Met  Pro  Gly  Pro  Val  Val  Arg
      65                           70                       75

CCA  CTC  TTT  GAG  AAG  GCC  GCG  GAA  CTC  GGG  ATC  GGC  TTC  AAT  CTG  GGC   288
Pro  Leu  Phe  Glu  Lys  Ala  Ala  Glu  Leu  Gly  Ile  Gly  Phe  Asn  Leu  Gly
      80                      85                       90

TAC  GCT  GAA  CTC  GTC  GTC  GAA  GGC  GGC  GTC  AAG  CGT  CGC  TTC  AAC  ACG   336
Tyr  Ala  Glu  Leu  Val  Val  Glu  Gly  Gly  Val  Lys  Arg  Arg  Phe  Asn  Thr
 95                      100                     105                      110

TCC  ATT  TTG  GTG  GAT  AAG  TCA  GGC  AAG  ATC  GTC  GGC  AAG  TAT  CGT  AAG   384
Ser  Ile  Leu  Val  Asp  Lys  Ser  Gly  Lys  Ile  Val  Gly  Lys  Tyr  Arg  Lys
                     115                     120                      125

ATC  CAT  TTG  CCG  GGT  CAC  AAG  GAG  TAC  GAG  GCC  TAC  CGG  CCG  TTC  CAG   432
Ile  His  Leu  Pro  Gly  His  Lys  Glu  Tyr  Glu  Ala  Tyr  Arg  Pro  Phe  Gln
                130                      135                      140

CAT  CTT  GAA  AAG  CGT  TAT  TTC  GAG  CCG  GGC  GAT  CTC  GGC  TTC  CCG  GTC   480
His  Leu  Glu  Lys  Arg  Tyr  Phe  Glu  Pro  Gly  Asp  Leu  Gly  Phe  Pro  Val
           145                      150                      155

TAT  GAC  GTC  GAC  GCC  GCG  AAA  ATG  GGG  ATG  TTC  ATC  TGC  AAC  GAT  CGC   528
Tyr  Asp  Val  Asp  Ala  Ala  Lys  Met  Gly  Met  Phe  Ile  Cys  Asn  Asp  Arg
      160                      165                      170

CGC  TGG  CCT  GAA  GCC  TGG  CGG  GTG  ATG  GGC  CTC  AGG  GGC  GCC  GAG  ATC   576
Arg  Trp  Pro  Glu  Ala  Trp  Arg  Val  Met  Gly  Leu  Arg  Gly  Ala  Glu  Ile
175                      180                      185                      190

ATC  TGC  GGC  GGC  TAC  AAC  ACG  CCG  ACC  CAC  AAT  CCC  GAA  GTT  CCC  CAG   624
Ile  Cys  Gly  Gly  Tyr  Asn  Thr  Pro  Thr  His  Asn  Pro  Glu  Val  Pro  Gln
                     195                      200                      205

CAC  GAC  CAC  CTG  ACG  TCC  TTC  CAC  CAT  CTC  CTA  TCG  ATG  CAG  GCC  GGG   672
His  Asp  His  Leu  Thr  Ser  Phe  His  His  Leu  Leu  Ser  Met  Gln  Ala  Gly
                210                      215                      220

TCT  TAT  CAG  AAC  GGG  GCC  TGG  TCC  GCG  GCC  GCG  GGC  AAG  GCG  GGC  ATG   720
Ser  Tyr  Gln  Asn  Gly  Ala  Trp  Ser  Ala  Ala  Ala  Gly  Lys  Ala  Gly  Met
           225                      230                      235
```

| | | | | | | | | | | | | | | | |
|---|---|---|---|---|---|---|---|---|---|---|---|---|---|---|---|
| GAG | GAG | AAC | TGC | ATG | CTG | CTC | GGC | CAC | TCC | TGC | ATC | GTG | GCG | CCG | ACC | 768 |
| Glu | Glu | Asn | Cys | Met | Leu | Leu | Gly | His | Ser | Cys | Ile | Val | Ala | Pro | Thr |
| 240 | | | | | 245 | | | | | 250 | | | | | |
| GGG | GAA | ATC | GTC | GCT | CTC | ACT | ACG | ACG | CTG | GAA | GAC | GAG | GTG | ATC | ACC | 816 |
| Gly | Glu | Ile | Val | Ala | Leu | Thr | Thr | Thr | Leu | Glu | Asp | Glu | Val | Ile | Thr |
| 255 | | | | | 260 | | | | | 265 | | | | | 270 |
| GCC | GCC | GTC | GAT | CTC | GAT | CGC | TGC | CGG | GAA | CTG | CGT | GAA | CAC | ATC | TTC | 864 |
| Ala | Ala | Val | Asp | Leu | Asp | Arg | Cys | Arg | Glu | Leu | Arg | Glu | His | Ile | Phe |
| | | | | 275 | | | | | 280 | | | | | 285 | |
| AAC | TTC | AAG | CAG | CAT | CGT | CAG | CCC | CAG | CAC | TAT | GGT | CTG | ATC | GCG | GAA | 912 |
| Asn | Phe | Lys | Gln | His | Arg | Gln | Pro | Gln | His | Tyr | Gly | Leu | Ile | Ala | Glu |
| | | | 290 | | | | 295 | | | | | 300 | | | |
| CTC | TGAGGCTGCA | G | | | | | | | | | | | | | | 926 |
| Leu | | | | | | | | | | | | | | | |

( 2 ) INFORMATION FOR SEQ ID NO:68:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:68:

| | | | | | | | | | | | | | | |
|---|---|---|---|---|---|---|---|---|---|---|---|---|---|---|
| Thr | Arg | Gln | Met | Ile | Leu | Ala | Val | Gly | Gln | Gly | Pro | Ile | Ala | Arg |
| 1 | | | | 5 | | | | | 10 | | | | | 15 |
| Ala | Glu | Thr | Arg | Glu | Gln | Val | Val | Arg | Leu | Leu | Asp | Met | Leu | Thr |
| | | | 20 | | | | 25 | | | | | 30 | | |
| Lys | Ala | Ala | Ser | Arg | Gly | Ala | Asn | Phe | Ile | Val | Phe | Pro | Glu | Leu | Ala |
| | | | 35 | | | | 40 | | | | | 45 | | |
| Leu | Thr | Thr | Phe | Phe | Pro | Arg | Trp | Tyr | Phe | Thr | Asp | Glu | Ala | Glu | Leu |
| | 50 | | | | | 55 | | | | | 60 | | | | |
| Asp | Ser | Phe | Tyr | Glu | Thr | Glu | Met | Pro | Gly | Pro | Val | Val | Arg | Pro | Leu |
| 65 | | | | | 70 | | | | | 75 | | | | | 80 |
| Phe | Glu | Lys | Ala | Ala | Glu | Leu | Gly | Ile | Gly | Phe | Asn | Leu | Gly | Tyr | Ala |
| | | | | 85 | | | | | 90 | | | | | 95 | |
| Glu | Leu | Val | Val | Glu | Gly | Gly | Val | Lys | Arg | Arg | Phe | Asn | Thr | Ser | Ile |
| | | | 100 | | | | 105 | | | | | 110 | | | |
| Leu | Val | Asp | Lys | Ser | Gly | Lys | Ile | Val | Gly | Lys | Tyr | Arg | Lys | Ile | His |
| | | 115 | | | | 120 | | | | | 125 | | | | |
| Leu | Pro | Gly | His | Lys | Glu | Tyr | Glu | Ala | Tyr | Arg | Pro | Phe | Gln | His | Leu |
| | 130 | | | | | 135 | | | | | 140 | | | | |
| Glu | Lys | Arg | Tyr | Phe | Glu | Pro | Gly | Asp | Leu | Gly | Phe | Pro | Val | Tyr | Asp |
| 145 | | | | | 150 | | | | | 155 | | | | | 160 |
| Val | Asp | Ala | Ala | Lys | Met | Gly | Met | Phe | Ile | Cys | Asn | Asp | Arg | Arg | Trp |
| | | | | 165 | | | | | 170 | | | | | 175 | |
| Pro | Glu | Ala | Trp | Arg | Val | Met | Gly | Leu | Arg | Gly | Ala | Glu | Ile | Ile | Cys |
| | | | 180 | | | | 185 | | | | | 190 | | | |
| Gly | Gly | Tyr | Asn | Thr | Pro | Thr | His | Asn | Pro | Glu | Val | Pro | Gln | His | Asp |
| | | 195 | | | | 200 | | | | | 205 | | | | |
| His | Leu | Thr | Ser | Phe | His | His | Leu | Leu | Ser | Met | Gln | Ala | Gly | Ser | Tyr |
| | 210 | | | | | 215 | | | | | 220 | | | | |
| Gln | Asn | Gly | Ala | Trp | Ser | Ala | Ala | Ala | Gly | Lys | Ala | Gly | Met | Glu | Glu |
| 225 | | | | | 230 | | | | | 235 | | | | | 240 |
| Asn | Cys | Met | Leu | Leu | Gly | His | Ser | Cys | Ile | Val | Ala | Pro | Thr | Gly | Glu |
| | | | | 245 | | | | | 250 | | | | | 255 | |

| | | | | | | | | | | | | | | |
|---|---|---|---|---|---|---|---|---|---|---|---|---|---|---|
|Ile|Val|Ala|Leu|Thr|Thr|Thr|Leu|Glu|Asp|Glu|Val|Ile|Thr|Ala|Ala|
| | | |260| | | |265| | | |270| | | |
|Val|Asp|Leu|Asp|Arg|Cys|Arg|Glu|Leu|Arg|Glu|His|Ile|Phe|Asn|Phe|
| | | |275| | | |280| | | |285| | | |
|Lys|Gln|His|Arg|Gln|Pro|Gln|His|Tyr|Gly|Leu|Ile|Ala|Glu|Leu|
| | | |290| | | |295| | | |300| | | |

( 2 ) INFORMATION FOR SEQ ID NO:69:

( i ) SEQUENCE CHARACTERISTICS:
( A ) LENGTH: 1820 base pairs
( B ) TYPE: nucleic acid
( C ) STRANDEDNESS: double
( D ) TOPOLOGY: linear ( v i ) ORIGINAL SOURCE:
( B ) STRAIN: KNK 003A (FERM BP- 3181)

( i x ) FEATURE:
( A ) NAME/KEY: CDS
( B ) LOCATION: 701..1636

( x i ) SEQUENCE DESCRIPTION: SEQ ID NO:69:

```
GCATGCGCGG  GGAACTGAAG  AACTTGCAAG  ACGAACTCGG  CATTACCTTC  GTGCATGTAA      60

CCCATACCCA  GCCTGAGGCG  ATCGCGCTCG  CCGACATGGT  GGTTGTGATG  GATACGGGCC     120

GCATAGAGCA  GGCAGCGAGC  GCCAACGAAA  TCTACAACCG  GCCCGCGACG  CCCTATGTGG     180

CGCGCTTCAT  GGGCGGCCAA  AACGTGTTGA  CGGGGAGGGT  GGAGAGCATC  TCGCCCACCG     240

GCATGGTGCT  GAAAAGCGAA  AAGGGCGAGA  TCTTCAATGC  GCCTCTTACG  GGTGCTGCGC     300

CGAAGCTGGG  CGAACCCGTA  TCGATATCCA  TGCGCCGCGA  CCGCATCAGC  ATCAGCAAGC     360

CGCAAAACGG  CAAGGGCGCG  CAGCAGGCTG  ACGCGGTAAC  GGGTGTGGTC  GATTCCACGG     420

AATACCAGGG  CAGCTTCGTG  AAGGTCAGCA  TAGTGCTCGA  CGGTGGCGAG  ACCTTCGTCG     480

CAAACATGCC  CGACCATGAA  TTTTTCGCGG  AACCGGTGGA  TCACGGCGTC  CCGGTGGTCG     540

CCCGCTGGAA  ACCGGAGCAT  GTGCATGTCC  TGTCCAAGTC  TGACCGGGGC  GCCGACCACA     600

CCGAAATCTA  CCGCTTCCCT  GCAGGCGAAA  ATACCGTTTC  AATGGGCAAG  GGGCGGCAAA     660

CGGGGTTGAG  ACGACCCGGT  TTATCGAGGA  GGACGAGATG  ACA CGC ATC GTC AAT       715
                                              Thr Arg Ile Val Asn
                                                1               5
```

| GCA | GCC | GCC | GCG | CAG | ATG | GGG | CCC | ATC | AGC | CGG | TCC | GAA | ACG | CGC | AAG | 763 |
|---|---|---|---|---|---|---|---|---|---|---|---|---|---|---|---|---|
| Ala | Ala | Ala | Ala | Gln | Met | Gly | Pro | Ile | Ser | Arg | Ser | Glu | Thr | Arg | Lys | |
| | | | 10 | | | | | 15 | | | | | 20 | | | |

| GAT | ACG | GTC | CGG | CGC | CTG | ATC | GCG | CTC | ATG | CGC | GAG | GCG | AAG | GCC | CGC | 811 |
|---|---|---|---|---|---|---|---|---|---|---|---|---|---|---|---|---|
| Asp | Thr | Val | Arg | Arg | Leu | Ile | Ala | Leu | Met | Arg | Glu | Ala | Lys | Ala | Arg | |
| | | | 25 | | | | | 30 | | | | | 35 | | | |

| GGT | TCC | GAC | CTT | GTC | GTC | TTT | ACC | GAA | CTC | GCG | CTC | ACC | ACC | TTC | TTT | 859 |
|---|---|---|---|---|---|---|---|---|---|---|---|---|---|---|---|---|
| Gly | Ser | Asp | Leu | Val | Val | Phe | Thr | Glu | Leu | Ala | Leu | Thr | Thr | Phe | Phe | |
| | | | 40 | | | | | 45 | | | | | 50 | | | |

| CCC | CGC | TGG | GTG | ATC | GAG | GAC | GAA | GCT | GAG | CTC | GAC | AGC | TTC | TAC | GAG | 907 |
|---|---|---|---|---|---|---|---|---|---|---|---|---|---|---|---|---|
| Pro | Arg | Trp | Val | Ile | Glu | Asp | Glu | Ala | Glu | Leu | Asp | Ser | Phe | Tyr | Glu | |
| | | | 55 | | | | | 60 | | | | | 65 | | | |

| AAG | GAG | ATG | CCA | GGG | CCC | GAA | ACC | CAG | CCG | CTC | TTC | GAT | GAG | GCG | AAG | 955 |
|---|---|---|---|---|---|---|---|---|---|---|---|---|---|---|---|---|
| Lys | Glu | Met | Pro | Gly | Pro | Glu | Thr | Gln | Pro | Leu | Phe | Asp | Glu | Ala | Lys | |
| | | 70 | | | | 75 | | | | | 80 | | | | 85 | |

| CGC | TTG | GAG | ATC | GGC | TTC | TAT | CTC | GGT | TAT | GCC | GAG | CTG | GCG | GAG | GAG | 1003 |
|---|---|---|---|---|---|---|---|---|---|---|---|---|---|---|---|---|
| Arg | Leu | Glu | Ile | Gly | Phe | Tyr | Leu | Gly | Tyr | Ala | Glu | Leu | Ala | Glu | Glu | |
| | | | | 90 | | | | | 95 | | | | | 100 | | |

| GGC | GGC | AGG | AAG | CGG | CGC | TTC | AAC | ACC | TCT | ATC | CTT | GTG | GAC | CGC | AGC | 1051 |
|---|---|---|---|---|---|---|---|---|---|---|---|---|---|---|---|---|
| Gly | Gly | Arg | Lys | Arg | Arg | Phe | Asn | Thr | Ser | Ile | Leu | Val | Asp | Arg | Ser | |
| | | | 105 | | | | | 110 | | | | | 115 | | | |

| | | | | | | | | | | | | | | | | |
|---|---|---|---|---|---|---|---|---|---|---|---|---|---|---|---|---|
| GGC | CGG | ATC | GTC | GGC | AAG | TAC | CGC | AAG | GTG | CAC | CTG | CCC | GGG | CAC | AAA | 1099 |
| Gly | Arg | Ile | Val | Gly | Lys | Tyr | Arg | Lys | Val | His | Leu | Pro | Gly | His | Lys | |
| | | 120 | | | | | 125 | | | | | 130 | | | | |
| GAG | CCG | CAG | CCC | GGC | AGG | AAA | CAC | CAG | CAT | CTC | GAG | AAA | CGC | TAT | TTC | 1147 |
| Glu | Pro | Gln | Pro | Gly | Arg | Lys | His | Gln | His | Leu | Glu | Lys | Arg | Tyr | Phe | |
| | | 135 | | | | | 140 | | | | | 145 | | | | |
| GAG | CCC | GGC | GAT | CTC | GGC | TTC | GGT | GTC | TGG | CGC | GCC | TTC | GAC | GGC | GTA | 1195 |
| Glu | Pro | Gly | Asp | Leu | Gly | Phe | Gly | Val | Trp | Arg | Ala | Phe | Asp | Gly | Val | |
| 150 | | | | | 155 | | | | | 160 | | | | | 165 | |
| ATG | GGC | ATG | TGC | ATT | TGC | AAC | GAC | CGC | CGC | TGG | CCG | GAG | ACC | TAC | CGG | 1243 |
| Met | Gly | Met | Cys | Ile | Cys | Asn | Asp | Arg | Arg | Trp | Pro | Glu | Thr | Tyr | Arg | |
| | | | | 170 | | | | | 175 | | | | | 180 | | |
| GTC | ATG | GGC | TTG | CAG | GGA | GTG | GAG | ATG | GTC | ATG | CTG | GGC | TAC | AAC | ACG | 1291 |
| Val | Met | Gly | Leu | Gln | Gly | Val | Glu | Met | Val | Met | Leu | Gly | Tyr | Asn | Thr | |
| | | | | 185 | | | | | 190 | | | | | 195 | | |
| CCG | TAT | GAC | CAT | ACC | GGT | CAC | GAC | GAC | ATC | GAT | TCA | CTC | ACC | CAG | TTT | 1339 |
| Pro | Tyr | Asp | His | Thr | Gly | His | Asp | Asp | Ile | Asp | Ser | Leu | Thr | Gln | Phe | |
| | | | 200 | | | | | 205 | | | | | 210 | | | |
| CAC | AAT | CAT | CTC | TCC | ATG | CAG | GCG | GGC | GCC | TAC | CAG | AAT | TCG | ACC | TGG | 1387 |
| His | Asn | His | Leu | Ser | Met | Gln | Ala | Gly | Ala | Tyr | Gln | Asn | Ser | Thr | Trp | |
| | | 215 | | | | | 220 | | | | | 225 | | | | |
| GTG | ATC | GGC | ACC | GCC | AAA | TGC | GGC | ACC | GAG | GAG | GGC | TCC | AAA | ATG | GTG | 1435 |
| Val | Ile | Gly | Thr | Ala | Lys | Cys | Gly | Thr | Glu | Glu | Gly | Ser | Lys | Met | Val | |
| 230 | | | | | 235 | | | | | 240 | | | | | 245 | |
| GGG | CAG | AGC | GTG | ATC | GTT | GCG | CCC | TCG | GGC | GAG | ATC | GTC | GCT | ATG | GCC | 1483 |
| Gly | Gln | Ser | Val | Ile | Val | Ala | Pro | Ser | Gly | Glu | Ile | Val | Ala | Met | Ala | |
| | | | | 250 | | | | | 255 | | | | | 260 | | |
| TGC | ACG | ATC | GAG | GAC | GAG | ATC | ATC | ACC | GCA | CGC | TGC | GAT | CTC | GAC | ATG | 1531 |
| Cys | Thr | Ile | Glu | Asp | Glu | Ile | Ile | Thr | Ala | Arg | Cys | Asp | Leu | Asp | Met | |
| | | | | 265 | | | | | 270 | | | | | 275 | | |
| GGC | AAG | CGC | TAC | CGC | GAG | ACC | ATC | TTC | GAT | TTC | GCC | CGC | CAT | CGC | GAG | 1579 |
| Gly | Lys | Arg | Tyr | Arg | Glu | Thr | Ile | Phe | Asp | Phe | Ala | Arg | His | Arg | Glu | |
| | | 280 | | | | | 285 | | | | | 290 | | | | |
| CCC | GAC | GCC | TAT | CGC | CTG | ATC | GTC | GAA | CGC | AAA | GGG | GCT | GTG | CCG | CCG | 1627 |
| Pro | Asp | Ala | Tyr | Arg | Leu | Ile | Val | Glu | Arg | Lys | Gly | Ala | Val | Pro | Pro | |
| | | 295 | | | | | 300 | | | | | 305 | | | | |
| CCG | CAG | TGATCGGAAC | CTGAAAACGA | AATATCCCGC | CGGACGGTGG | GAAGGTGAAA | | | | | | | | | | 1683 |
| Pro | Gln | | | | | | | | | | | | | | | |
| 310 | | | | | | | | | | | | | | | | |

| | |
|---|---|
| GGAGGAGTCT CCATGACAAC AGTTATCAAG GGTGGAACAT CGTCGCCGCC GATCGCAGCT | 1743 |
| ATGAAGCCGA TATCCTGATC GAAGGCGAAA AGATCGCCCA GATCGGCAGG GATCTGCAGG | 1803 |
| GCGACAAGAT TGTCGAC | 1820 |

( 2 ) INFORMATION FOR SEQ ID NO:70:

( i ) SEQUENCE CHARACTERISTICS:
        ( A ) LENGTH: 311 amino acids
        ( B ) TYPE: amino acid
        ( D ) TOPOLOGY: linear ( i i ) MOLECULE TYPE: protein ( x i ) SEQUENCE DESCRIPTION: SEQ ID NO:70:

| | | | | | | | | | | | | | | |
|---|---|---|---|---|---|---|---|---|---|---|---|---|---|---|
| Thr | Arg | Ile | Val | Asn | Ala | Ala | Ala | Ala | Gln | Met | Gly | Pro | Ile | Ser | Arg |
| 1 | | | | 5 | | | | | 10 | | | | | 15 | |
| Ser | Glu | Thr | Arg | Lys | Asp | Thr | Val | Arg | Arg | Leu | Ile | Ala | Leu | Met | Arg |
| | | | 20 | | | | | 25 | | | | | 30 | | |
| Glu | Ala | Lys | Ala | Arg | Gly | Ser | Asp | Leu | Val | Val | Phe | Thr | Glu | Leu | Ala |
| | | 35 | | | | | 40 | | | | | 45 | | | |

-continued

| | | | | | | | | | | | | | | |
|---|---|---|---|---|---|---|---|---|---|---|---|---|---|---|
| Leu | Thr 50 | Thr | Phe | Phe | Pro | Arg 55 | Trp | Val | Ile | Glu | Asp 60 | Glu | Ala | Glu | Leu |
| Asp 65 | Ser | Phe | Tyr | Glu | Lys 70 | Glu | Met | Pro | Gly | Pro 75 | Glu | Thr | Gln | Pro | Leu 80 |
| Phe | Asp | Glu | Ala | Lys 85 | Arg | Leu | Glu | Ile | Gly 90 | Phe | Tyr | Leu | Gly | Tyr 95 | Ala |
| Glu | Leu | Ala | Glu 100 | Glu | Gly | Gly | Arg | Lys 105 | Arg | Arg | Phe | Asn | Thr 110 | Ser | Ile |
| Leu | Val | Asp 115 | Arg | Ser | Gly | Arg | Ile 120 | Val | Gly | Lys | Tyr | Arg 125 | Lys | Val | His |
| Leu | Pro 130 | Gly | His | Lys | Glu | Pro 135 | Gln | Pro | Gly | Arg | Lys 140 | His | Gln | His | Leu |
| Glu 145 | Lys | Arg | Tyr | Phe | Glu 150 | Pro | Gly | Asp | Leu | Gly 155 | Phe | Gly | Val | Trp | Arg 160 |
| Ala | Phe | Asp | Gly | Val 165 | Met | Gly | Met | Cys | Ile 170 | Cys | Asn | Asp | Arg | Arg 175 | Trp |
| Pro | Glu | Thr | Tyr 180 | Arg | Val | Met | Gly | Leu 185 | Gln | Gly | Val | Glu | Met 190 | Val | Met |
| Leu | Gly | Tyr 195 | Asn | Thr | Pro | Tyr | Asp 200 | His | Thr | Gly | His | Asp 205 | Asp | Ile | Asp |
| Ser | Leu 210 | Thr | Gln | Phe | His | Asn 215 | His | Leu | Ser | Met | Gln 220 | Ala | Gly | Ala | Tyr |
| Gln 225 | Asn | Ser | Thr | Trp | Val 230 | Ile | Gly | Thr | Ala | Lys 235 | Cys | Gly | Thr | Glu | Glu 240 |
| Gly | Ser | Lys | Met | Val 245 | Gly | Gln | Ser | Val | Ile 250 | Val | Ala | Pro | Ser | Gly 255 | Glu |
| Ile | Val | Ala | Met 260 | Ala | Cys | Thr | Ile | Glu 265 | Asp | Glu | Ile | Ile | Thr 270 | Ala | Arg |
| Cys | Asp | Leu 275 | Asp | Met | Gly | Lys | Arg 280 | Tyr | Arg | Glu | Thr | Ile 285 | Phe | Asp | Phe |
| Ala | Arg 290 | His | Arg | Glu | Pro | Asp 295 | Ala | Tyr | Arg | Leu | Ile 300 | Val | Glu | Arg | Lys |
| Gly 305 | Ala | Val | Pro | Pro | Pro 310 | Gln | | | | | | | | | |